(12) United States Patent
Oral et al.

(10) Patent No.: US 11,850,329 B2
(45) Date of Patent: Dec. 26, 2023

(54) METHODS OF MAKING A LAYERED CONSOLIDATED UHMWPE FOR USE AS A MEDICAL IMPLANT, AND PRODUCTS MADE BY THE METHODS

(71) Applicant: THE GENERAL HOSPITAL CORPORATION, Boston, MA (US)

(72) Inventors: Ebru Oral, Newton, MA (US); Orhun K. Muratoglu, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/222,398

(22) Filed: Apr. 5, 2021

(65) Prior Publication Data

US 2021/0228775 A1    Jul. 29, 2021

Related U.S. Application Data

(60) Continuation of application No. 16/229,400, filed on Dec. 21, 2018, now Pat. No. 10,967,100, which is a continuation of application No. 15/653,977, filed on Jul. 19, 2017, now abandoned, which is a division of application No. 14/584,519, filed on Dec. 29, 2014, now Pat. No. 9,731,047, which is a division of application No. 13/202,014, filed as application No. PCT/US2010/024935 on Feb. 22, 2010, now Pat. No. 8,933,145.

(60) Provisional application No. 61/154,134, filed on Feb. 20, 2009.

(51) Int. Cl.
| | |
|---|---|
| *C08F 2/46* | (2006.01) |
| *C08F 2/50* | (2006.01) |
| *C08G 61/04* | (2006.01) |
| *A61L 27/50* | (2006.01) |
| *C08J 3/20* | (2006.01) |
| *C08J 3/24* | (2006.01) |
| *C08J 3/28* | (2006.01) |
| *B65B 55/08* | (2006.01) |
| *B65B 55/10* | (2006.01) |
| *B65B 55/16* | (2006.01) |
| *B65B 55/18* | (2006.01) |
| *A61L 27/16* | (2006.01) |
| *A61L 29/04* | (2006.01) |
| *A61L 29/14* | (2006.01) |
| *A61L 31/04* | (2006.01) |
| *A61L 31/14* | (2006.01) |
| *C08K 5/134* | (2006.01) |

(52) U.S. Cl.
CPC .............. *A61L 27/50* (2013.01); *A61L 27/16* (2013.01); *A61L 27/505* (2013.01); *A61L 29/041* (2013.01); *A61L 29/14* (2013.01); *A61L 29/143* (2013.01); *A61L 31/048* (2013.01); *A61L 31/14* (2013.01); *A61L 31/143* (2013.01); *B65B 55/08* (2013.01); *B65B 55/10* (2013.01); *B65B 55/16* (2013.01); *B65B 55/18* (2013.01); *C08J 3/203* (2013.01); *C08J 3/247* (2013.01); *C08J 3/28* (2013.01); *C08K 5/134* (2013.01); *C08J 2323/06* (2013.01)

(58) Field of Classification Search
CPC ...... A61L 29/143; A61L 29/041; A61L 29/14; A61L 31/14; A61L 31/048; A61L 31/143; A61L 27/505; A61L 27/50; A61L 27/16; C08J 3/203; C08J 3/247; C08J 2323/06; C08K 5/134; C08L 23/06
USPC ................................ 522/75, 74, 71, 1; 520/1
See application file for complete search history.

(56) References Cited

U.S. PATENT DOCUMENTS

| | | | |
|---|---|---|---|
| 3,974,132 | A | 8/1976 | Valdiserri |
| 5,032,450 | A | 7/1991 | Rechlicz et al. |
| 5,096,654 | A | 3/1992 | Craggs et al. |
| 5,827,904 | A | 10/1998 | Hahn |
| 5,879,400 | A | 3/1999 | Merrill et al. |
| 6,165,220 | A | 12/2000 | McKellop et al. |
| 6,316,158 | B1 | 11/2001 | Saum et al. |
| 6,448,315 | B1 | 9/2002 | Lidgren et al. |
| 6,641,617 | B1 | 11/2003 | Merrill et al. |
| 6,852,772 | B2 | 2/2005 | Muratoglu et al. |
| 6,951,654 | B2 | 10/2005 | Malcolm et al. |
| 7,205,339 | B2 | 4/2007 | Muratoglu |
| 7,381,752 | B2 | 6/2008 | Muratoglu |
| 7,431,874 | B2 | 10/2008 | Muratoglu et al. |
| 7,790,779 | B2 | 9/2010 | Muratoglu |
| 7,833,452 | B2 | 11/2010 | Muratoglu et al. |
| 7,858,671 | B2 | 12/2010 | Merrill et al. |

(Continued)

FOREIGN PATENT DOCUMENTS

| | | |
|---|---|---|
| EP | 0881919 A1 | 12/1998 |
| EP | 1457172 A1 | 9/2004 |

(Continued)

OTHER PUBLICATIONS

Darquiche, Device-associated infections: a macroproblem that starts with microadherence. Clin Infect Dis. Nov. 1, 2001;33(9):1567-72.

(Continued)

*Primary Examiner* — Jessica Whiteley
(74) *Attorney, Agent, or Firm* — McCarter & English, LLP; John P. Isacson

(57) ABSTRACT

The present invention relates to methods for making wear and oxidation resistant polymeric materials by high temperature melting. The invention also provides methods of making medical implants containing cross-linked antioxidant-containing tough and ductile polymers and materials used therewith also are provided.

8 Claims, 87 Drawing Sheets

(56) References Cited

U.S. PATENT DOCUMENTS

| | | |
|---|---|---|
| 8,133,501 B2 | 3/2012 | Li et al. |
| 8,232,322 B2 | 7/2012 | East et al. |
| 8,420,000 B2 | 4/2013 | Muratoglu et al. |
| 8,425,815 B2 | 4/2013 | Muratoglu et al. |
| 8,461,225 B2 | 6/2013 | Muratoglu et al. |
| 8,529,937 B2 | 9/2013 | Brunner et al. |
| 8,530,057 B2 | 9/2013 | Muratoglu et al. |
| 8,569,395 B2 | 10/2013 | Muratoglu et al. |
| 8,858,979 B1 | 10/2014 | Desjardins et al. |
| 8,933,145 B2 | 1/2015 | Oral et al. |
| 9,168,683 B2 | 10/2015 | Muratoglu et al. |
| 9,220,811 B2 | 12/2015 | Overstreet et al. |
| 9,273,189 B2 | 3/2016 | Muratoglu et al. |
| 9,370,878 B2 | 6/2016 | Muratoglu et al. |
| 9,433,705 B2 | 9/2016 | Muratoglu et al. |
| 9,445,901 B2 | 9/2016 | Tunc et al. |
| 9,681,683 B2 | 6/2017 | Esposti et al. |
| 9,731,047 B2 | 8/2017 | Oral et al. |
| 9,937,278 B2 | 4/2018 | Steinberg et al. |
| 9,968,709 B2* | 5/2018 | Muratoglu ............ C08F 10/02 |
| 10,220,547 B2 | 3/2019 | Muratoglu et al. |
| 10,967,100 B2 | 4/2021 | Oral et al. |
| 10,981,302 B2 | 4/2021 | Muratoglu et al. |
| 2002/0064653 A1 | 5/2002 | Ladika |
| 2002/0107330 A1 | 8/2002 | Pinchuk et al. |
| 2004/0156879 A1* | 8/2004 | Muratoglu ............ B29C 43/003 424/423 |
| 2004/0180072 A1 | 9/2004 | Tunc et al. |
| 2005/0048121 A1 | 3/2005 | East et al. |
| 2005/0090571 A1 | 4/2005 | Mehta et al. |
| 2006/0064653 A1 | 3/2006 | Zhang et al. |
| 2007/0059334 A1 | 3/2007 | Abt et al. |
| 2007/0077268 A1 | 4/2007 | King et al. |
| 2007/0114702 A1 | 5/2007 | Muratoglu et al. |
| 2007/0141106 A1 | 6/2007 | Bonutti et al. |
| 2007/0213835 A1 | 9/2007 | Wimmer et al. |
| 2007/0265369 A1 | 11/2007 | Muratoglu |
| 2007/0267030 A1 | 11/2007 | Muratoglu et al. |
| 2007/0293647 A1 | 12/2007 | McKellop et al. |
| 2008/0215142 A1 | 9/2008 | Muratoglu et al. |
| 2008/0319137 A1 | 12/2008 | Rufner et al. |
| 2009/0030524 A1 | 1/2009 | Schroeder et al. |
| 2009/0118390 A1 | 5/2009 | Abt et al. |
| 2009/0181253 A1 | 7/2009 | Michalik et al. |
| 2009/0243159 A1 | 10/2009 | Sun |
| 2009/0263319 A1 | 10/2009 | Wohabrebbi et al. |
| 2010/0190882 A1 | 7/2010 | Muratoglu et al. |
| 2010/0292374 A1 | 11/2010 | Bellare |
| 2011/0039014 A1 | 2/2011 | King |
| 2011/0040381 A1 | 2/2011 | Kidd et al. |
| 2011/0070454 A1 | 3/2011 | Gregg et al. |
| 2012/0041094 A1 | 2/2012 | Oral et al. |
| 2012/0046380 A1 | 2/2012 | Morrison et al. |
| 2012/0052292 A1 | 3/2012 | Pulapura et al. |
| 2012/0267819 A1 | 10/2012 | Freedman |
| 2013/0203885 A1 | 8/2013 | Muratoglu et al. |
| 2014/0024736 A1 | 1/2014 | Thomas et al. |
| 2014/0098001 A1 | 4/2014 | Van Oosterbosch et al. |
| 2014/0175693 A1 | 6/2014 | Liu |
| 2015/0151866 A1 | 6/2015 | Oral et al. |
| 2015/0190545 A1 | 7/2015 | Oral |
| 2015/0290280 A1 | 10/2015 | Petrak et al. |
| 2015/0314038 A1 | 11/2015 | Oral et al. |
| 2016/0215117 A1 | 7/2016 | Muratoglu et al. |
| 2016/0250779 A1 | 9/2016 | Muratoglu et al. |
| 2017/0049934 A1* | 2/2017 | Muratoglu ............ B29C 43/18 |
| 2017/0137603 A1 | 5/2017 | Morrison et al. |
| 2017/0259467 A1* | 9/2017 | Muratoglu ............ A61L 27/505 |
| 2018/0161480 A1 | 6/2018 | Oral et al. |
| 2018/0318468 A1 | 11/2018 | Oral et al. |
| 2019/0134273 A1 | 5/2019 | Oral et al. |
| 2019/0160207 A1 | 5/2019 | Suhardi et al. |
| 2019/0255744 A1 | 8/2019 | Muratoglu et al. |

FOREIGN PATENT DOCUMENTS

| | | | |
|---|---|---|---|
| EP | 0881919 B1 | 8/2005 | |
| EP | 1779877 A1 | 5/2007 | |
| EP | 2384774 A2 | 11/2011 | |
| EP | 2833981 A2 | 2/2015 | |
| NO | 2002/048259 A2 | 6/2002 | |
| WO | 1997/029793 A1 | 8/1997 | |
| WO | 1997029793 A1 | 8/1997 | |
| WO | 1999/029793 A1 | 6/1999 | |
| WO | 1999029793 A1 | 6/1999 | |
| WO | 2001/005337 A1 | 1/2001 | |
| WO | 2001005337 A1 | 1/2001 | |
| WO | 2001/080778 A1 | 11/2001 | |
| WO | 2001080778 A1 | 11/2001 | |
| WO | 2002/00274 A1 | 1/2002 | |
| WO | 2002048259 A2 | 6/2002 | |
| WO | 2005/074619 A2 | 8/2005 | |
| WO | 2005074619 A2 | 8/2005 | |
| WO | 2005/110276 A1 | 11/2005 | |
| WO | 2005110276 A1 | 11/2005 | |
| WO | 2006/026040 A1 | 3/2006 | |
| WO | 2006026040 A1 | 3/2006 | |
| WO | 2007/024684 A2 | 3/2007 | |
| WO | 2007/024689 A2 | 3/2007 | |
| WO | 2007024684 A2 | 3/2007 | |
| WO | 2007024689 A2 | 3/2007 | |
| WO | 2007/056667 A2 | 5/2007 | |
| WO | 2007/139744 A2 | 12/2007 | |
| WO | 2008/092047 A1 | 7/2008 | |
| WO | 2008092047 A1 | 7/2008 | |
| WO | WO-2008092047 A1 * | 7/2008 | ............ A61L 27/16 |
| WO | 2008/109098 A2 | 9/2008 | |
| WO | 2010/096771 A2 | 8/2010 | |
| WO | 2010096771 A2 | 8/2010 | |
| WO | 2012/061499 A1 | 5/2012 | |
| WO | 2013/151950 A1 | 10/2013 | |
| WO | 2013/151960 A2 | 10/2013 | |
| WO | 2013151960 A2 | 10/2013 | |
| WO | 2013/170005 A1 | 11/2013 | |
| WO | 2015/057943 A2 | 4/2015 | |
| WO | 2015057943 A2 | 4/2015 | |
| WO | 2017/083476 A1 | 5/2017 | |
| WO | 2017/192347 A1 | 11/2017 | |
| WO | 2017192347 A1 | 11/2017 | |
| WO | 2019/046243 A2 | 3/2019 | |
| WO | 2019046243 A2 | 3/2019 | |

OTHER PUBLICATIONS

Suhardi et al., A Fully Functional Drug-Eluting Joint Implant. Nat Biomed Eng. 2017;1:0080.

Chen et al. "Photocrosslinking of Polyethylene. OI. Photoinitiators, Crosslinking Agent, and Reaction Kinetics" Nov. 1989, J. Polymer Science, Polymer Chemistry Ed. Interscience Publishers, NY NY, 27(12):4051-4075.

Evaluation of cross-linked UHMWPE with regards to its suitability as implant material for hip joint shells, pp. 1-91, Technical Univ. of Berlin, Plastics Research (Nov. 2003) (German) translation).

Evaluation of cross-linked UHMWPE with regards to its suitability as implant material for hip joint shells, pp. 1-91, Technical Univ. of Berlin, PlasticsResearch (Nov. 2003) (English translation).

International Search Report and Written Opinion for PCT/US2010/024935 dated Sep. 27, 2010.

International Search Report and Written Opinion for PCT/US2013/034887 dated Aug. 6, 2013.

International Search Report and Written Opinion for PCT/US2014/060865 dated Mar. 13, 2015.

International Search Report and Written Opinion for PCT/US2018/048256 dated Mar. 13, 2019.

Irganox 1010, Phenolic Primary Antioxidant for Processing and Long-Term Thermal Stabilization, Ciba Specialty Chemicals, Inc. (Aug. 1998).

Morshedian et al. "Polyethylene Cross-Linking by Two=Step Silane Method: A Review" 2009, Iranian Polymer Journal 18(2):103-128.

(56) References Cited

OTHER PUBLICATIONS

Atkinson et al. "Materials for Internal Prostheses: The Present Position and Possible Future Developments" 1980, Biomaterials 1(2):89-99 (abstract only).
Costa et al. Mechanism of Crosslinking and Oxidative Degradation UHMWPE handbook.
Kurtz "Chapter 16, Vitamin-E Blended UHMWPE Biomaterials" 2005, UHMWPE Handbook: Ultra high molecular weight polyethylene in total joint, vol. 11:235-250 (abstract only).
Oral et al. "Peroxide Cross-Linked UHMWPE Blended with Vitamin E" 2016, J. Biomed. Mater. Res., Part B 105(6):1379-1389.
Oral et al. "A Surface Crosslinked UHMWPE Stabilized by Vitamin E With Low Wear and High Fatigue Strength" 2010, Biomaterials 31(27):7051-7060.
Fang et al. "Processing and mechanical properties of HA/UHMWPE nanocomposite" 2006, Biomaterials 27:3701-3707.
U.S. Appl. No. 13/202,014, filed Oct. 31, 2011, U.S. Pat. No. 8,933,145, Issued.
U.S. Appl. No. 14/584,519, filed Dec. 29, 2014, U.S. Pat. No. 9,731,047, Issued.
U.S. Appl. No. 15/653,977, filed Jul. 19, 2017, 2018-0161480, Abandoned.
U.S. Appl. No. 16/229,400, filed Dec. 21, 2018, U.S. Pat. No. 10,967,100, Issued.
U.S. Appl. No. 14/389,852, filed Oct. 1, 2014, 2016-0215117, Published.
U.S. Appl. No. 15/774,860, filed May 9, 2018, 2018-0318468, Published.
Ajandouz et al., Effects of pH on Caramelization and Maillard Reaction Kinetics in Fructose-Lysine Model Systems. Journal of Food Science. 2001;66(7):926-931.
Atkinson et al., Materials for internal prostheses: the present position and possible future developments. Biomaterials. Apr. 1980;1(2):89-99.
Bourne, Prophylactic use of antibiotic bone cement: an emerging standard—in the affirmative. J Arthroplasty. Jun. 2004;19(4 Suppl 1):69-72.
Bragdon et al., A new pin-on-disk wear testing method for simulating wear of polyethylene on cobalt-chrome alloy in total hip arthroplasty. J Arthroplasty. Aug. 2001;16(5):658-65.
Chen et al., Photocrosslinking of Polyethylene. I. Photoinitiators, Crosslinking Agent, and Reaction Kinetics. Journal of Polymer Science Part A: Polymer Chemistry Edition. 1989;27(12):4051-4075.
Costa et al., Mechanisms of Crosslinking, Oxidative Degradation and Stabilization of UHMWPE. UHMWPE Biomaterials Handbook, Second Edition. Chapter 21, pp. 309-323, (2009).
Darouiche, Device-associated infections: a macroproblem that starts with microadherence. Clin Infect Dis. Nov. 1, 2001;33(9):1567-72.
De Kok et al., Reactivity of Peptides in the Maillard Reaction. Thermally Generated Flavors, Maillard, Microwave, and Extrusion Processes. American Chemical Society. Chapter 13, pp. 158-179, Nov. 30, 1993.
Eichner et al., Detection of Amadori Compounds in Heated Foods. Thermally Generated Flavors, Maillard, Microwave, and Extrusion Processes. American Chemical Society. Chapter 15, pp. 42-54, Nov. 30, 1993.
Fang et al., Processing and mechanical properties of HA/UHMWPE nanocomposites. Biomaterials. Jul. 2006;27(20):3701-7.
Gogia et al., Local antibiotic therapy in osteomyelitis. Semin Plast Surg. May 2009;23(2):100-7.
Irganox 1010, Phenolic Primary Antioxidant for Processing and Long-Term Thermal Stabilization, Ciba Specialty Chemicals, Inc. 2 pages, Aug. 1998.
John, Plastics Research, Evaluation of cross-linked UHMWPE with regards to its suitability as implant material for hip joint shells. Manfred H. Wagner. Polymer Technology/Plastics Technical Center, Berlin. 155 pages, Nov. 2003.
Kurtz et al., Vitamin-E Blended UHMWPE Biomaterials. UHMWPE Biomaterials Handbook, Third Edition, Ultra High Molecular Weight Polyethylene in Total Joint Replacement and Medical Devices. pp. 293-306, (2016).
Maillard et al., Chimie Organique. Comptes Rendus Hebdomadaires Des Seances de L'Academie des Sciences. Jan. 8, 1912;154(2):66-68.
Morshedian et al., Polyethylene Cross-linking by Two-step Silane Method: A Review. Iranian Polymer Journal. 2009;18(2):103-128.
Mortin et al., Rapid bactericidal activity of daptomycin against methicillin-resistant and methicillin-susceptible *Staphylococcus aureus* peritonitis in mice as measured with bioluminescent bacteria. Antimicrob Agents Chemother. May 2007;51(5):1787-94.
Muratoglu et al., Gradient crosslinking of UHMWPE using irradiation in molten state for total joint arthroplasty. Biomaterials. Feb. 2002;23(3):717-24.
Oral et al., A surface crosslinked UHMWPE stabilized by vitamin E with low wear and high fatigue strength. Biomaterials. Sep. 2010;31(27):7051-60.
Oral et al., Peroxide cross-linked UHMWPE blended with vitamin E. J Biomed Mater Res B Appl Biomater. Aug. 2017;105(6):1379-1389.
R.T. Vanderbilt Company Inc., Comprehensive Varox Peroxide Accelerator Product Guide. www.rtvanderbilt.com, 31 pages, Apr. 18, 2012.
R.T. Vanderbilt Company Inc., Varox DBPH Liquid, Peroxide Accelerator, 2,5-dimethyl-2,5-di(t-butylperoxy)hexane. Chemicals Technical Data Sheet. 2 pages, Apr. 18, 2011.
Spellberg et al., Systemic antibiotic therapy for chronic osteomyelitis in adults. Clin Infect Dis. Feb. 1, 2012;54(3):393-407.
Stevens et al., An articulated antibiotic spacer used for infected total knee arthroplasty: a comparative in vitro elution study of Simplex and Palacos bone cements. J Orthop Res. Jan. 2005;23(1):27-33.
Buhardi et al., A Fully Functional Drug-Eluting Joint Implant. Nat Biomed Eng. 2017;1:0080.
Van De Belt et al., Infection of orthopedic implants and the use of antibiotic-loaded bone cements. A review. Acta Orthop Scand. Dec. 2001;72(6):557-71.
Van De Belt et al., Surface roughness, porosity and wettability of gentamicin-loaded bone cements and their antibiotic release. Biomaterials. Oct. 2000;21(19):1981-7.
International Search Report and Written Opinion for Application No. PCT/US2010/024935, dated Sep. 27, 2010, 13 pages.
International Search Report and Written Opinion for Application No. PCT/US2013/034887, dated Sep. 26, 2013, 6 pages.
International Search Report and Written Opinion for Application No. PCT/US2014/060865, dated Mar. 13, 2015, 12 pages.
International Search Report and Written Opinion for Application No. PCT/US2016/061256, dated Feb. 9, 2017, 10 pages.
International Search Report and Written Opinion for Application No. PCT/US2017/029789, dated Jul. 31, 2017, 9 pages.
International Search Report and Written Opinion for Application No. PCT/US2018/048256, dated Mar. 13, 2019, 16 pages.
International Search Report and Written Opinion for Application No. PCT/US2019/060904, dated Jan. 28, 2020, 6 pages.
International Search Report and Written Opinion for Application No. PCT/US2020/024497, dated Jul. 2, 2020, 22 pages.

* cited by examiner

| PERIPHERY SHIELD CROSS-SECTIONS | | CORE SHIELD CROSS-SECTIONS | |
|---|---|---|---|
| FIG. 22A |  | FIG. 22H |  |
| FIG. 22B |  | FIG. 22I |  |
| FIG. 22C |  | FIG. 22J | 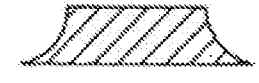 |
| FIG. 22D |  | FIG. 22K | 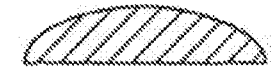 |
| FIG. 22E |  | FIG. 22L | 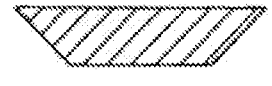 |
| FIG. 22F |  | FIG. 22M | 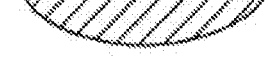 |
| FIG. 22G |  | FIG. 22N | 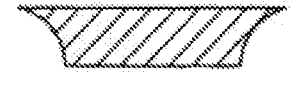 |

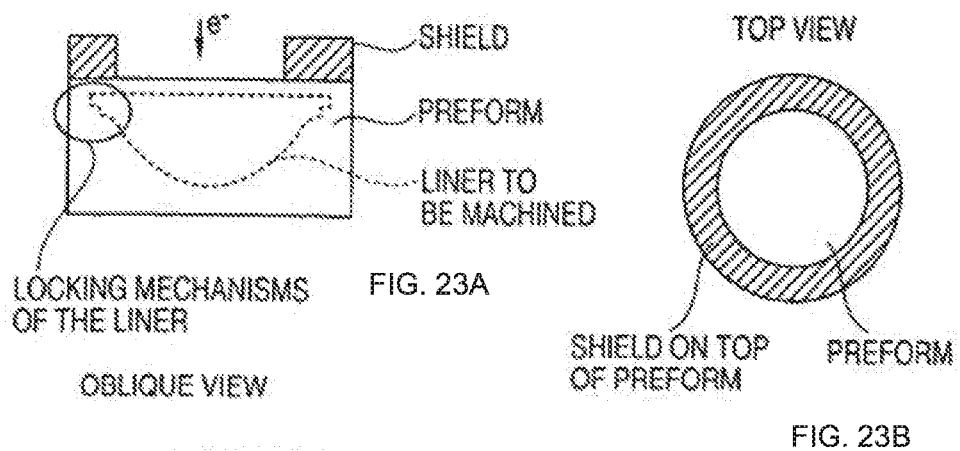
FIG. 23A
FIG. 23B
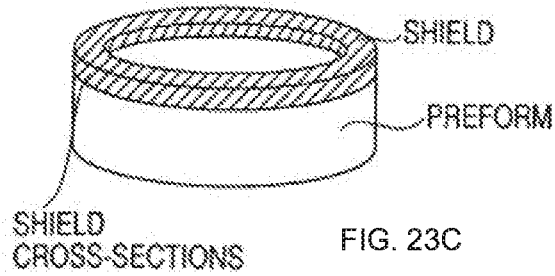
FIG. 23C
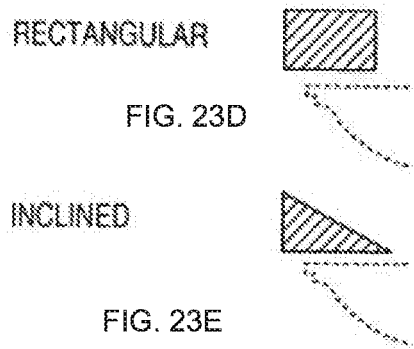
FIG. 23D
FIG. 23E
FIG. 23F

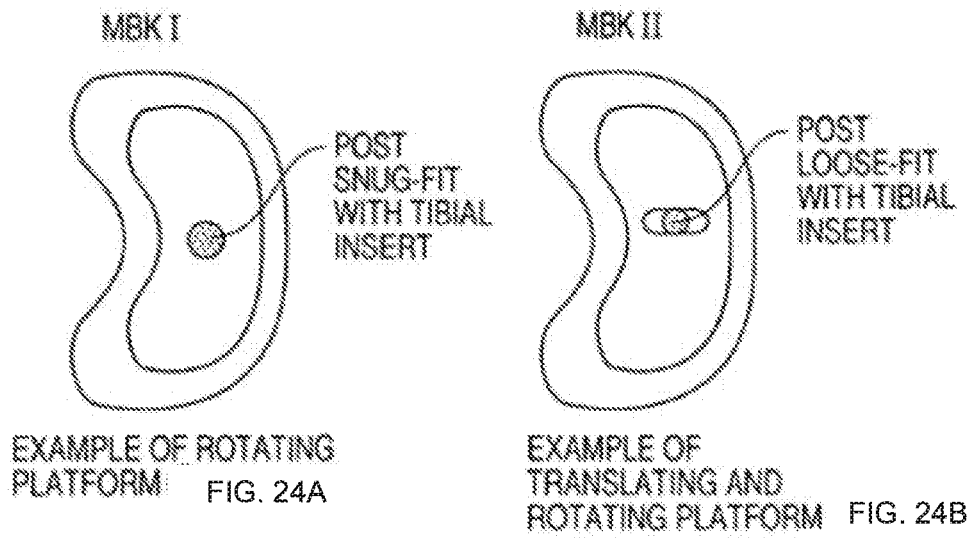
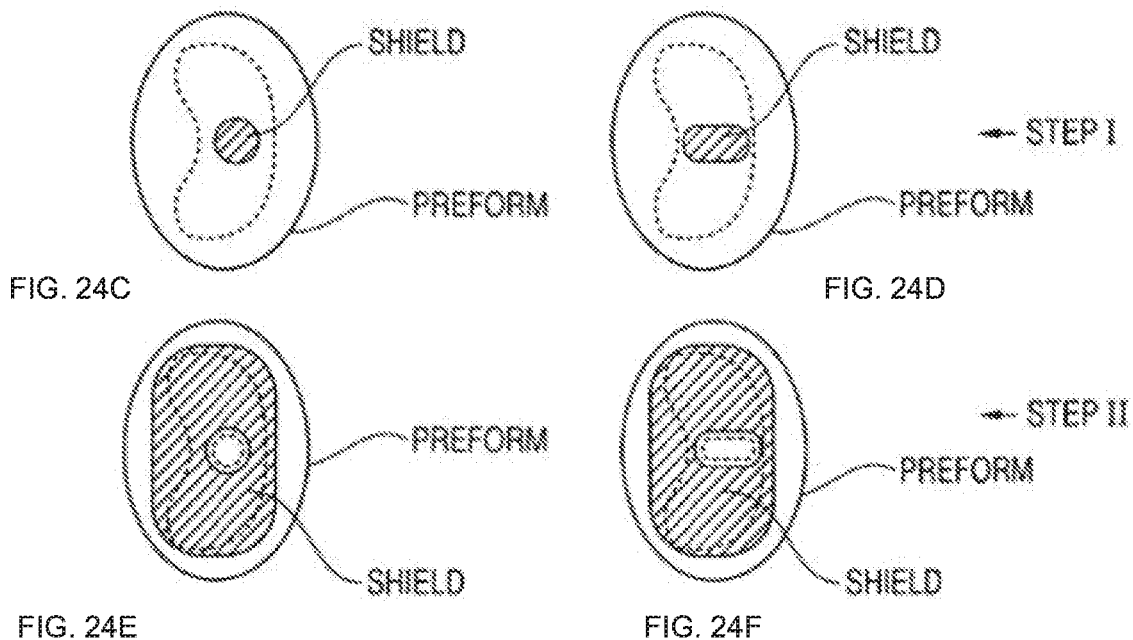

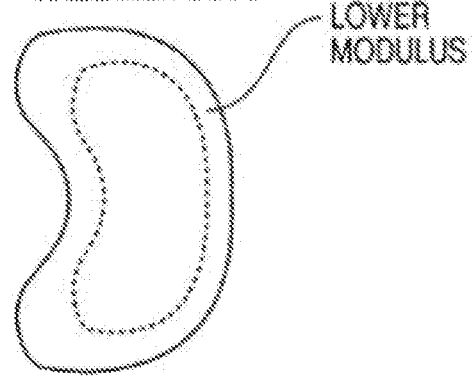
FIG. 25A  TOP VIEW
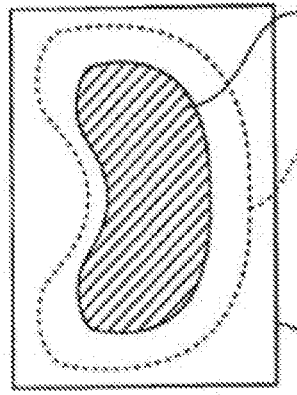
FIG. 25B  STEP I
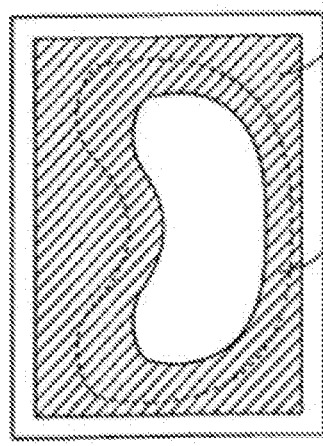
FIG. 25C  STEP II

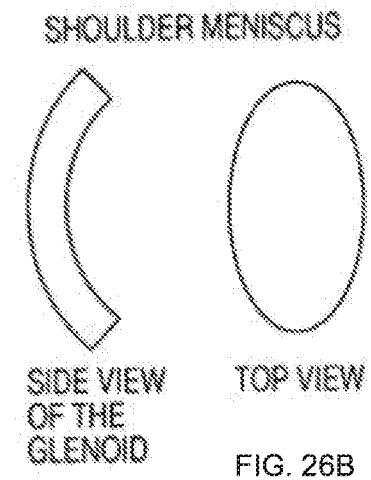
FIG. 26A SIDE VIEW OF THE GLENOID / FIG. 26B TOP VIEW — SHOULDER MENISCUS
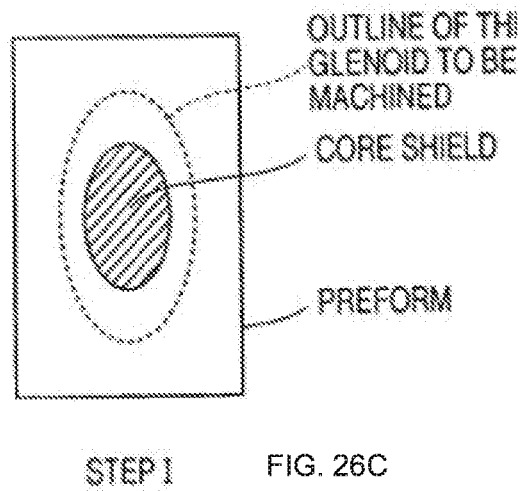
FIG. 26C STEP I — OUTLINE OF THE GLENOID TO BE MACHINED, CORE SHIELD, PREFORM
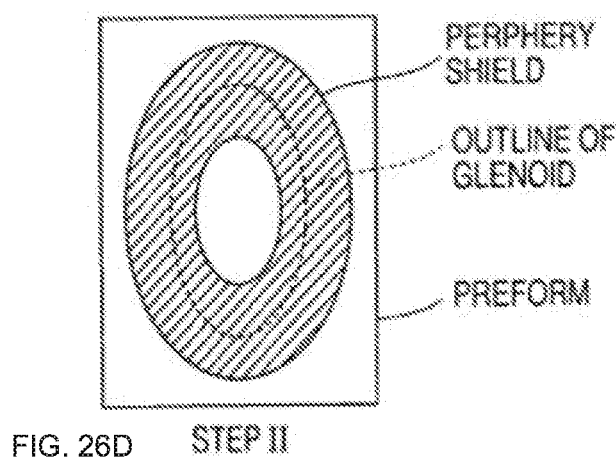
FIG. 26D STEP II — PERIPHERY SHIELD, OUTLINE OF GLENOID, PREFORM

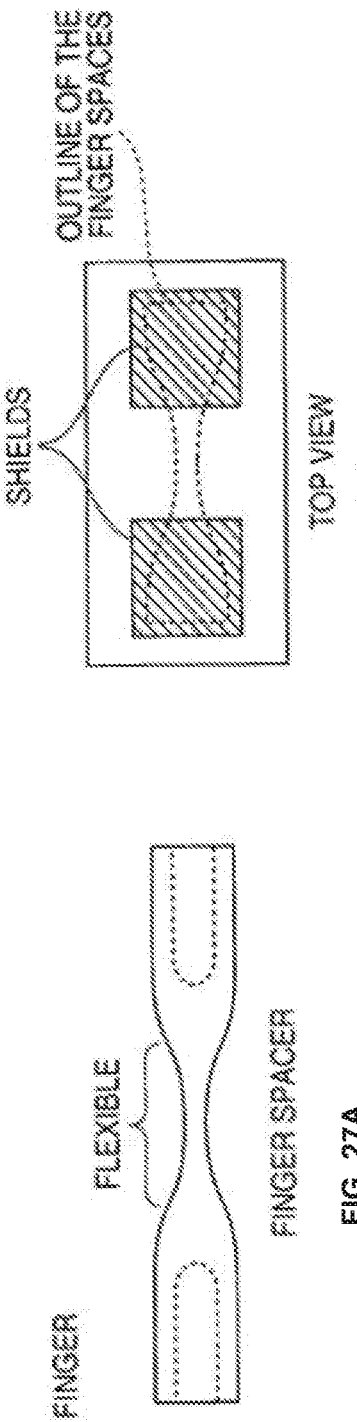
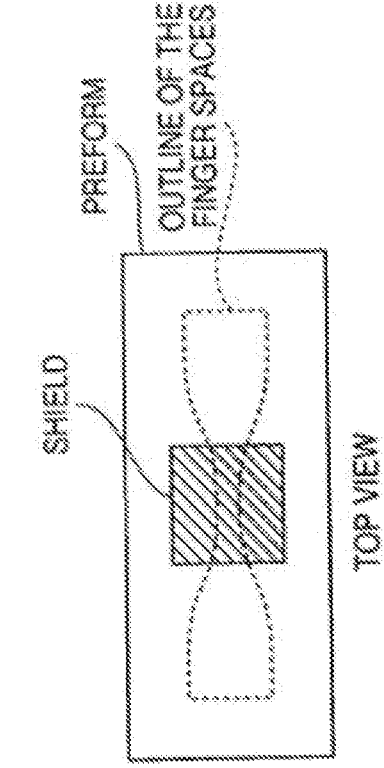
FIG. 27A FIG. 27B FIG. 27C

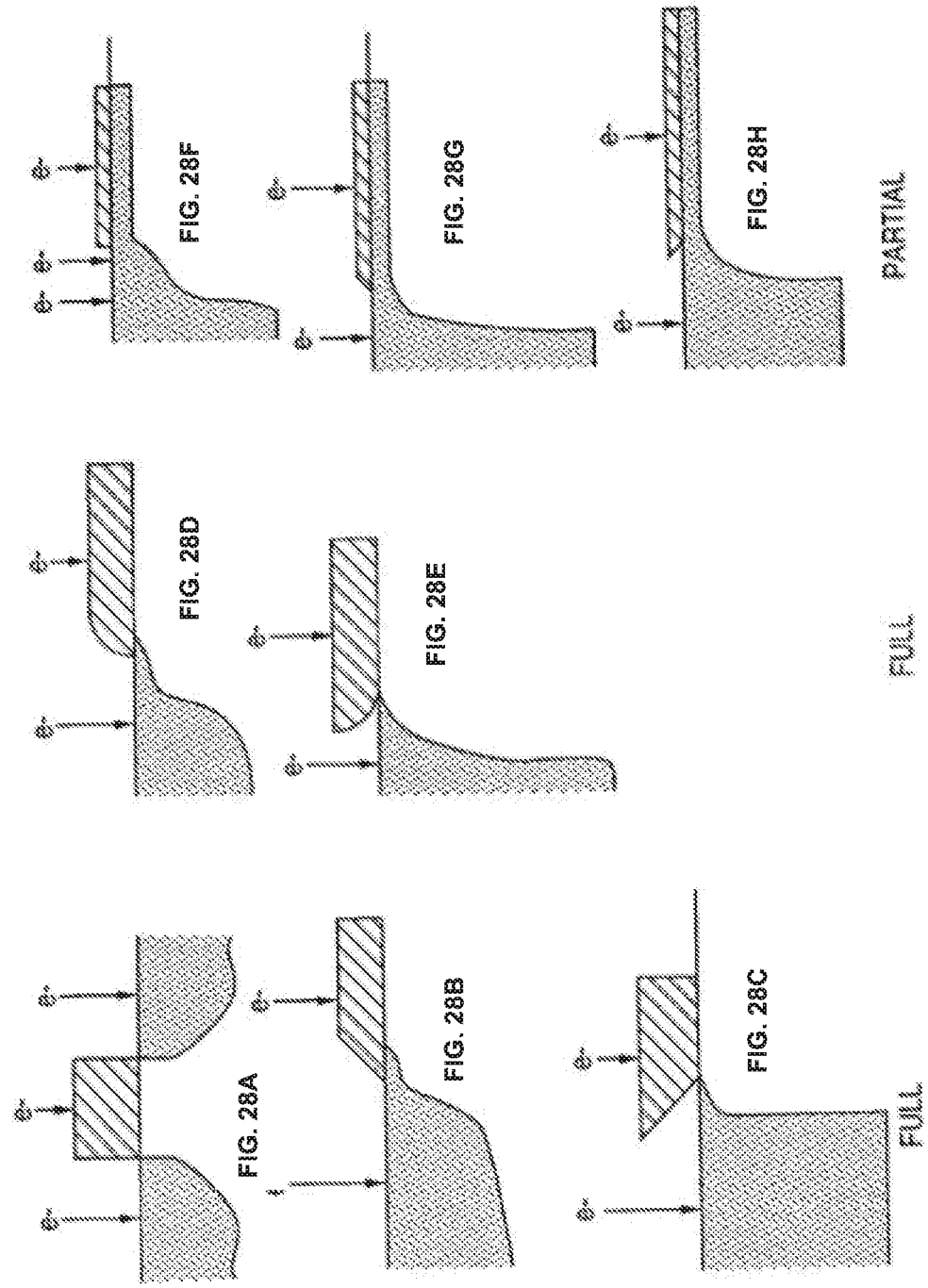

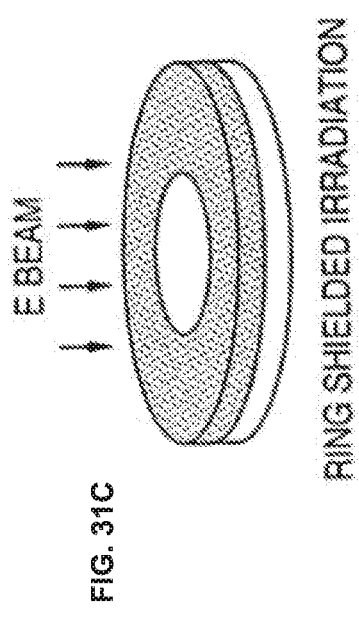
FIG. 31C RING SHIELDED IRRADIATION
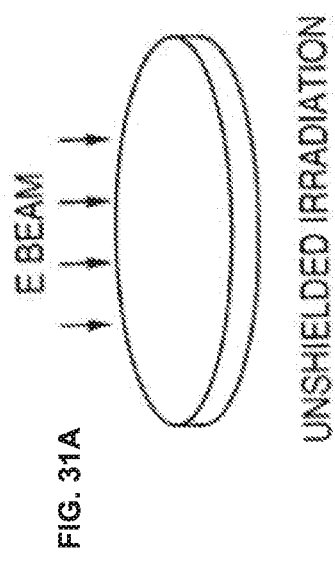
FIG. 31A UNSHIELDED IRRADIATION
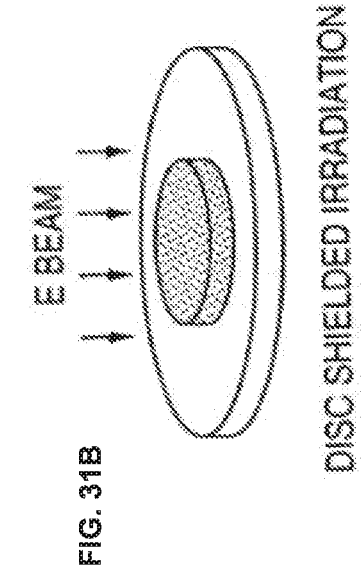
FIG. 31B DISC SHIELDED IRRADIATION

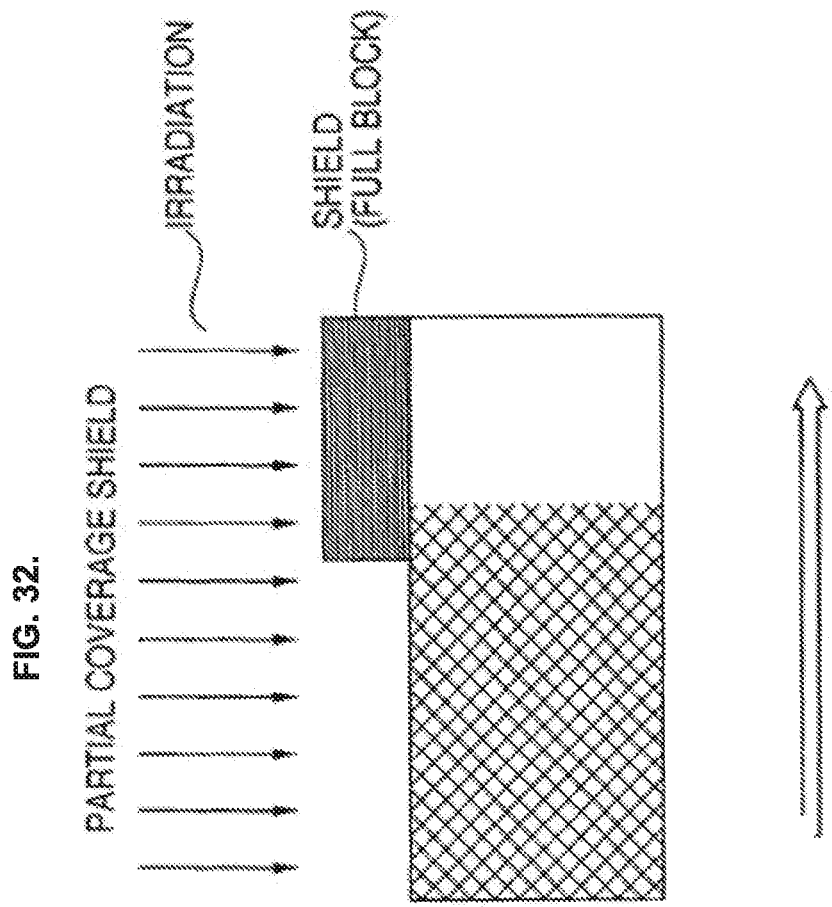
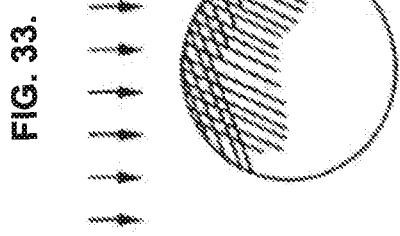
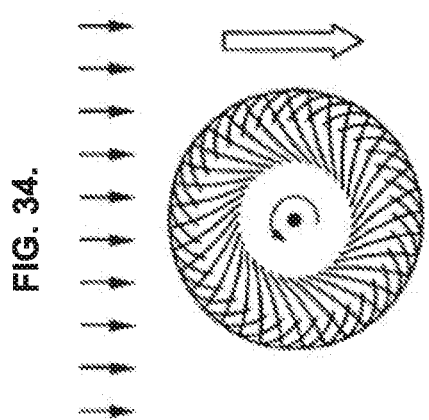

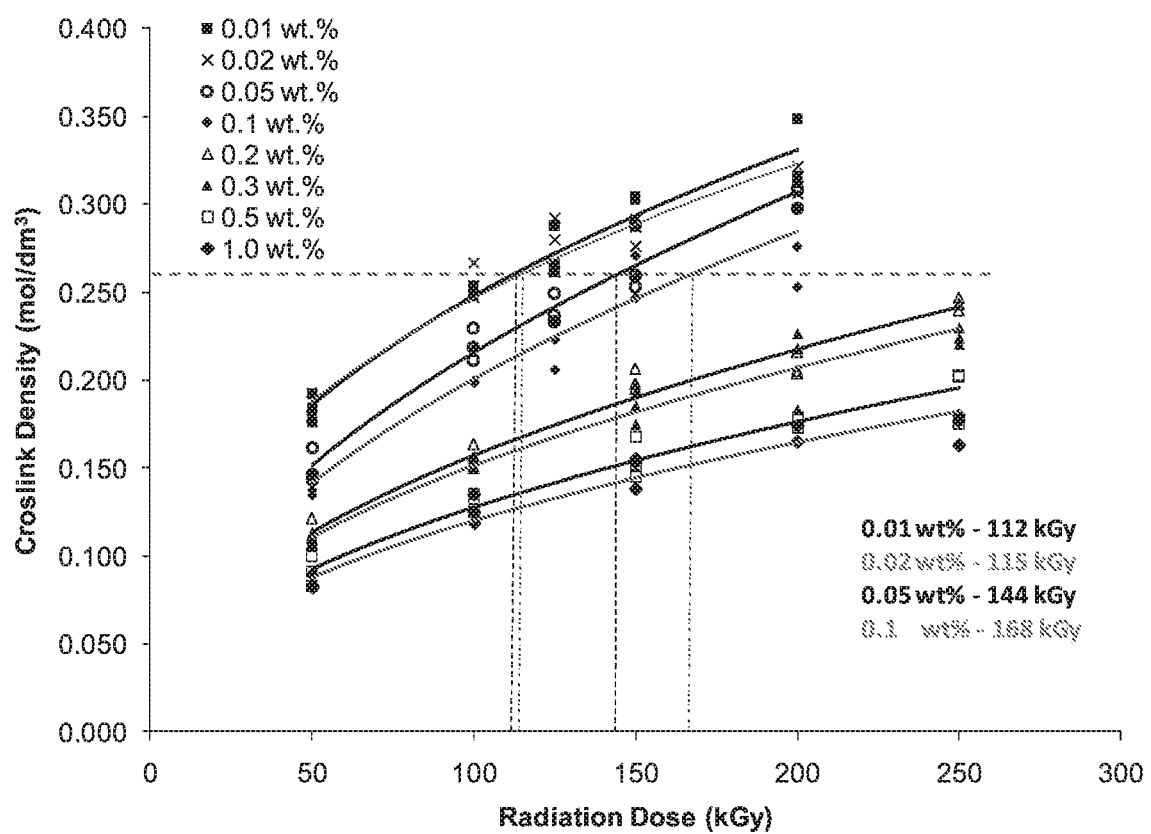

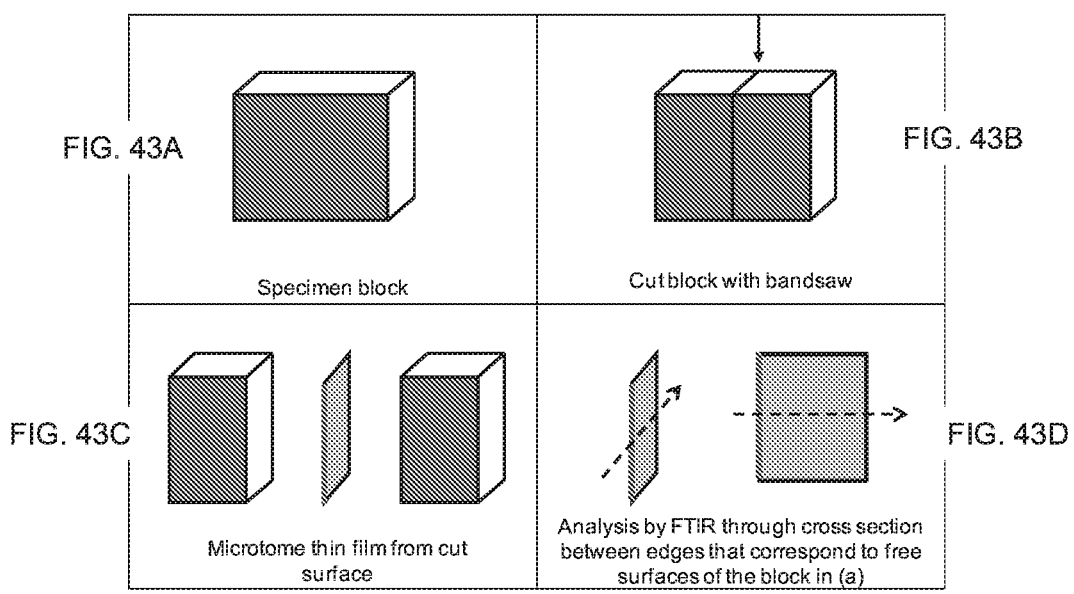

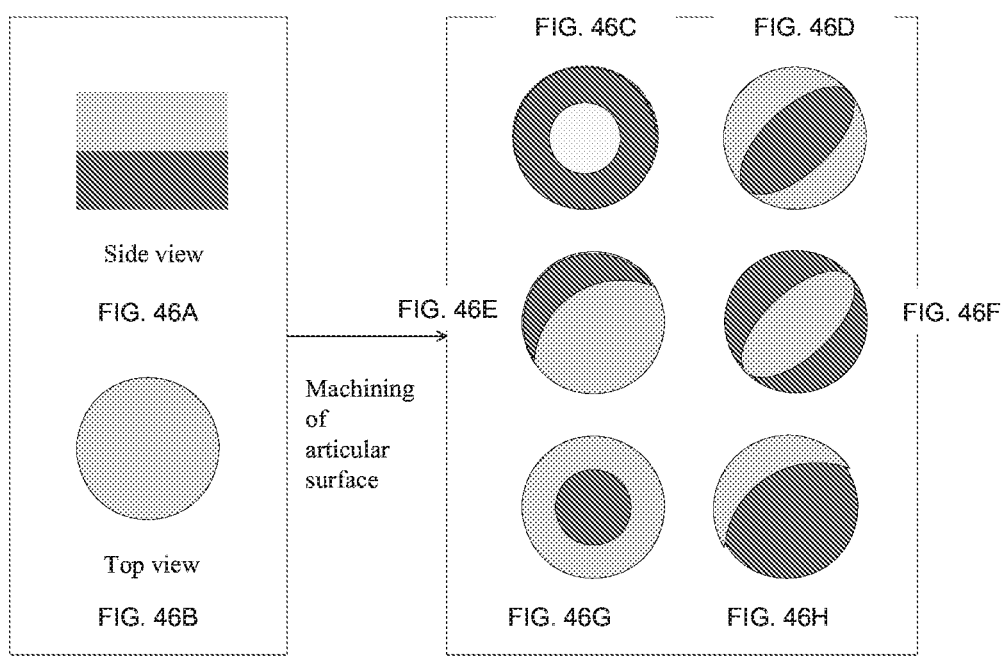

Side

Top

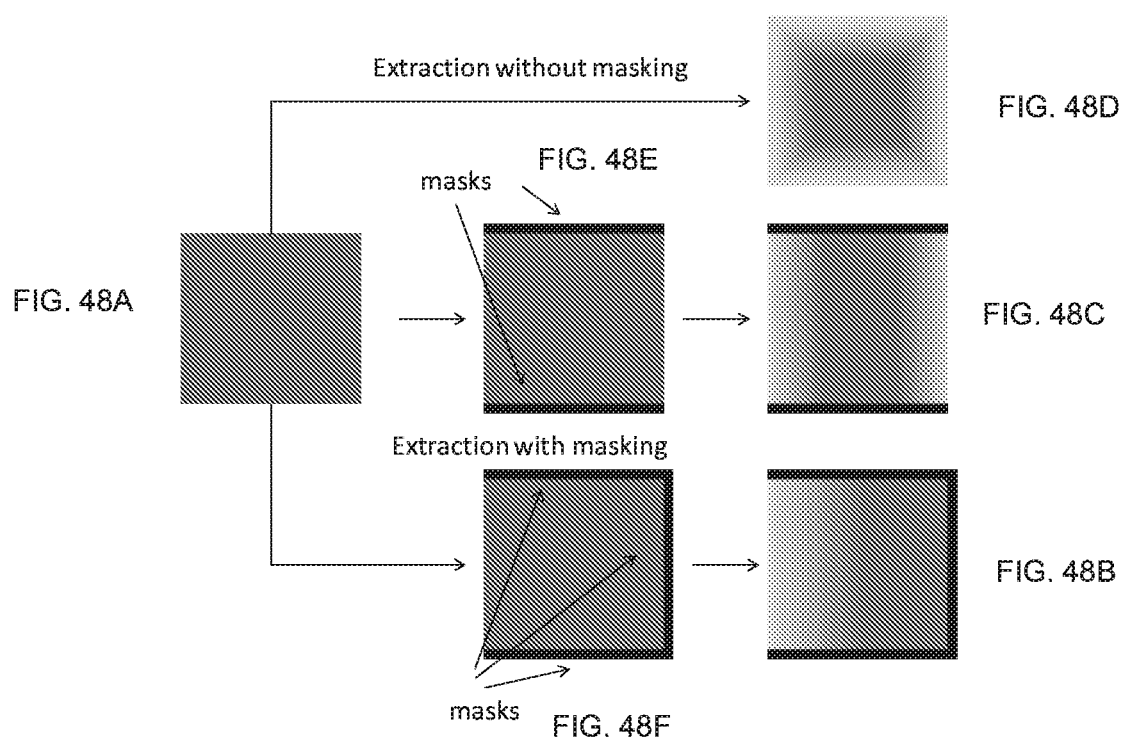

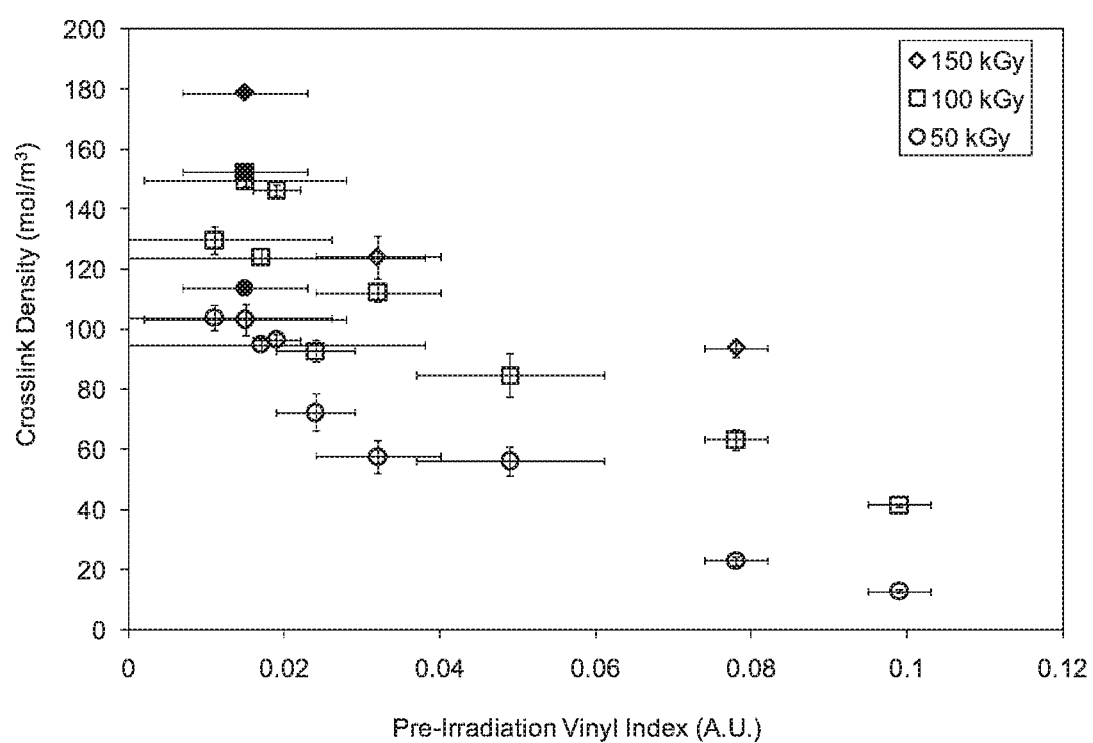

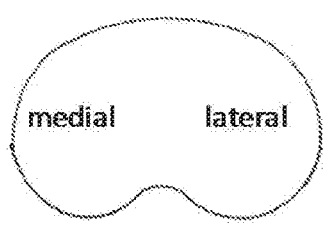
FIG. 67A Generic tibial insert – top view (medial, lateral)
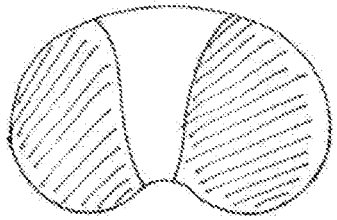
FIG. 67B
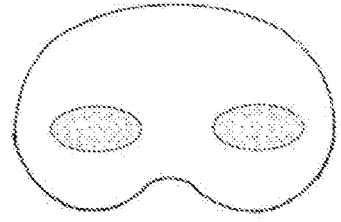
FIG. 67C
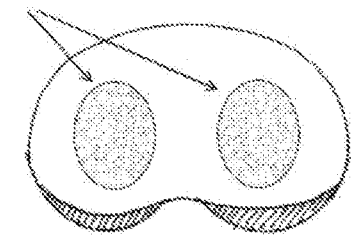
Regions with low concentrations of antioxidant
FIG. 67D
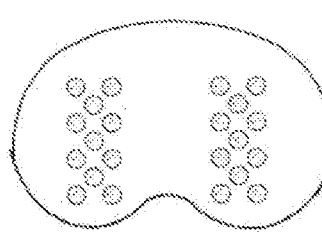
FIG. 67E
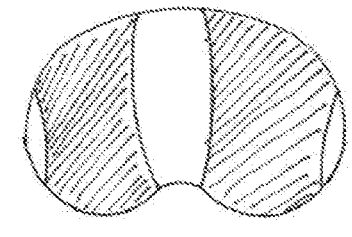
FIG. 67F Generic acetabular liner – crosssectional view α= 1° through 180°
α=90°
α=90° through 180°

β=0° through 90°
β=0° through 10°
β=0° through 5°

γ=0° - 110°

Generic acetabular liner – top view

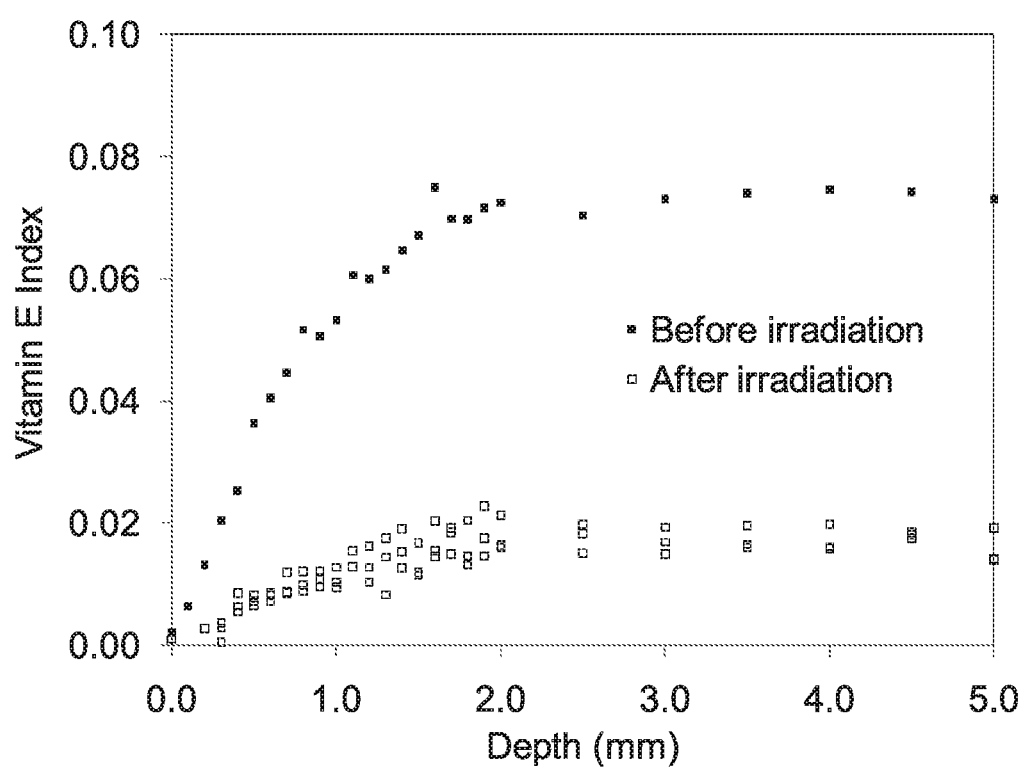

METHODS OF MAKING A LAYERED CONSOLIDATED UHMWPE FOR USE AS A MEDICAL IMPLANT, AND PRODUCTS MADE BY THE METHODS

CROSS-REFERENCE TO RELATED APPLICATIONS

This application is a continuation application of U.S. application Ser. No. 16/229,400 filed Dec. 21, 2018, which is a continuation application of U.S. application Ser. No. 15/653,977 filed Jul. 19, 2017, which is a divisional application of U.S. application Ser. No. 14/584,519 filed Dec. 29, 2014, now U.S. Pat. No. 9,731,047 issued on Aug. 15, 2017, which is a divisional application of U.S. application Ser. No. 13/202,014 filed Oct. 31, 2011, now U.S. Pat. No. 8,933,145 issued on Jan. 13, 2015, which is a § 371 National Stage Application of international application No. PCT/US2010/024935 filed Feb. 22, 2010, which claims the priority benefit of U.S. Provisional Application No. 61/154,314 filed Feb. 20, 2009, the disclosures of which are incorporated by reference in their entireties.

FIELD OF THE INVENTION

The present invention relates to methods for making wear resistant polymeric materials. Methods of making medical implants containing antioxidant-containing wear resistant polymers and materials used therewith also are provided. Wear resistant polymeric materials and medical implants containing such materials are also provided.

BACKGROUND OF THE INVENTION

It is advantageous to have tough and ductile polymeric materials, for example, Ultrahigh Molecular Weight Polyethylene (UHMWPB), for total joint implants without sacrificing oxidative stability and wear resistance. Wear resistance can be improved by cross-linking. However, crosslinking reduces the toughness and ductility of the material. Therefore, it is desirable to have a method to increase toughness and ductility of wear and oxidation resistant polymeric material.

Various methods of making cross-linked polymeric materials are known in the field. Saum et al (U.S. Pat. No. 6,316,158) described melting and subsequent radiation crosslinking of UHMWPE to increase ductility substantially through an increase in elongation at break. However, Saum et al. suggested not to using antioxidants in this process. The UHMWPE preform material used by Saum et al. does not contain antioxidants, as they believed that the presence of antioxidant may cause adverse effects in medical applications.

This application describes methods and approaches not found in the field for making cross-linked, wear and oxidation resistant, tough and ductile polymers, and materials used therein.

SUMMARY OF THE INVENTION

The present invention relates generally to methods for making cross-linked, wear and oxidation resistant polymeric materials. Methods of making medical implants containing cross-linked and antioxidant-containing polymers, and materials obtainable thereby, and materials used therewith, also are provided. More specifically, the invention relates to methods of making cross-linked, wear and oxidation resistant, tough and ductile polymeric materials by high temperature melting. Also, the invention relates to methods of making crosslinked, wear and oxidation resistant polymeric materials with a gradient of antioxidants and/or a gradient in crosslink density.

In one embodiment, the invention provides methods of making a wear resistant polymeric material comprising the steps of: i) irradiating a starting material by ionizing radiation, wherein the starting material is a polymeric material or a mixture of polymeric materials, wherein the polymeric material is blended or doped with at least one antioxidant or already has a gradient of antioxidants); ii) heating the irradiated starting material to a temperature of about 200° C. or more; iii) continue heating the irradiated material following irradiation; and iv) cooling the heated polymeric material, thereby forming a wear resistant polymeric material.

In one embodiment, the invention provides methods of making a wear resistant polymeric material comprising the steps of: i) irradiating a starting material by ionizing radiation, wherein the starting material is a polymeric material or a mixture of polymeric materials, wherein the polymeric material is blended or doped with at least one antioxidant or already has a gradient of antioxidants); ii) heating the irradiated starting material to a temperature of about 120° C. or more; iii) continue heating the irradiated material following irradiation; and iv) cooling the heated polymeric material, thereby forming a wear resistant polymeric material.

In another embodiment, the invention provides methods of making a wear resistant polymeric material comprising the steps of: i) irradiating a starting material by ionizing radiation, wherein the starting material is a polymeric material or a mixture of polymeric materials, wherein the polymeric material is blended or doped with at least one antioxidant or already has a gradient of antioxidant; ii) heating the irradiated starting material to a temperature of about 200° C. or more; iii) continue heating the irradiated material following irradiation; iv) cooling the heated and irradiated polymeric material; and v) doping the irradiated polymeric material with at least one antioxidant, thereby forming a wear resistant polymeric material.

In another embodiment, the invention provides methods of making a wear resistant polymeric material comprising the steps of: i) heating a starting material to a temperature of about 200° C. or more, wherein the starting material is a polymeric material or a mixture of polymeric materials, wherein the polymeric material is blended or doped with at least one antioxidant or already has a gradient of antioxidant; ii) continue heating the starting material; iii) irradiating the heated starting material by ionizing radiation; and iv) cooling the irradiated material, thereby forming a wear resistant polymeric material.

In another embodiment, the invention provides methods of making a wear resistant polymeric material comprising the steps of: i) heating a starting material to a temperature of about 200° C. or more, wherein the starting material is a polymeric material or a mixture of polymeric materials, wherein the polymeric material is blended or doped with at least one antioxidant or already has a gradient of antioxidant; ii) continue heating the starting material; iii) cooling the heated material; iv) irradiating the material by ionizing radiation; v) heating the irradiated material to a temperature above or below the melting point of the polymeric material; and vi) cooling the heated and irradiated material from v), thereby forming a wear resistant polymeric material.

In another embodiment, the invention provides methods of making a wear resistant polymeric material comprising the steps of: i) heating a starting material to a temperature of about 200° C. or more, wherein the starting material is a polymeric material or a mixture of polymeric materials, wherein the polymeric material is blended or doped with at least one antioxidant or already has a gradient of antioxidant; ii) continue heating the starting material; iii) cooling the heated material; iv) irradiating the material by ionizing radiation; and v) doping the irradiated polymeric material with at least one antioxidant, thereby forming a wear resistant polymeric material.

In another embodiment, the invention provides methods of making a wear resistant polymeric material comprising the steps of: i) heating a starting material to a temperature of about 200° C. or more, wherein the starting material is a polymeric material or a mixture of polymeric materials, wherein the polymeric material is blended or doped with at least one antioxidant or already has a gradient of antioxidant; ii) continue heating the starting material; iii) cooling the heated material; iv) irradiating the material by ionizing radiation; v) doping the irradiated polymeric material with at least one antioxidant; vi) heating the antioxidant-doped and irradiated material to a temperature above or below the melting point of the polymeric material; and vii) cooling the heated and irradiated material from vi), thereby forming a wear resistant polymeric material.

In another embodiment, the invention provides methods of making a wear resistant polymeric material comprising the steps of: i) irradiating a starting material by ionizing radiation, wherein the starting material is a polymeric material or a mixture of polymeric materials, wherein the polymeric material is blended or doped with at least one antioxidant or having a already has of antioxidant; ii) heating the irradiated starting material to a temperature of about 200° C. or more; iii) continue heating the irradiated material following irradiation; iv) cooling the heated polymeric material; v) irradiating the material by ionizing radiation; and vi) doping the irradiated polymeric material with at least one antioxidant, thereby forming a wear resistant polymeric material.

In another embodiment, the invention provides methods of making a wear resistant polymeric material, wherein the starting material is obtained by a method comprising the steps of: i) blending one or more polymeric materials; ii) heating the polymeric blend to a temperature of about 200° C. or more; and iii) cooling and consolidating the polymeric blend.

In another embodiment, the invention provides methods of making a wear resistant polymeric material, wherein the starting material is obtained by a method comprising the steps of: i) blending one or more polymeric materials with at least one antioxidant; ii) heating the antioxidant-polymeric blend to a temperature of about 200° C. or more; and iii) cooling and consolidating the polymeric blend.

In another embodiment, the invention provides methods of making a wear resistant polymeric material, wherein the wear resistant polymeric material is cross-linked.

In another embodiment, the invention provides methods of making a wear resistant polymeric material, wherein the heating is continued for at least for one minute, 10 minutes, 20 minutes, 30 minutes, one hour, two hours, five hours, ten hours, 24 hours, or more.

In another embodiment, the invention provides methods of making a wear resistant polymeric material, wherein the starting material is heated to a temperature between about 200° C. and about 500° C. or more.

In another embodiment, the invention provides methods of making a wear resistant polymeric material, wherein the starting irradiated material is heated to a temperature between about 200° C. and about 500° C. or more.

In another embodiment, the invention provides methods of making a wear resistant polymeric material, wherein the starting material is heated to a temperature of about 200° C., about 220° C., about 250° C., about 280° C., about 300° C., about 320° C., about 350° C., about 380° C., about 400° C., about 420° C., about 450° C., about 480° C. and about 500° C. or more.

In another embodiment, the invention provides methods of making a wear resistant polymeric material, wherein the starting material is heated to a temperature of about 300° C. for about five hours.

In another embodiment, the invention provides methods of making a wear resistant polymeric material, wherein the heating is carried out in an inert environment.

In another embodiment, the invention provides methods of making a wear resistant polymeric material, wherein the polymeric material is UHMWPE resin, powder, or flake.

In another embodiment, the invention provides methods of making a wear resistant polymeric material, wherein the polymeric material is compression molded to a second surface prior to high temperature melting, thereby making an interlocked hybrid material, and wherein the second surface is a porous metal.

In another embodiment, the invention provides methods of making a wear resistant polymeric material, wherein the doping is carried out by soaking the polymeric material or medical implant in the antioxidant for about 0.1 hours to about 72 hours, for example, the antioxidant is vitamin E.

In another embodiment, the invention provides methods of making a wear resistant polymeric material, wherein the polymeric is selected from a group consisting of a low-density polyethylene, high-density polyethylene, linear low-density polyethylene, ultra-high molecular weight polyethylene (UHMWPE), or a mixture thereof.

In another embodiment, the invention provides methods of making a wear resistant polymeric material, wherein the irradiation is carried out in an atmosphere containing between about 1% and about 22% oxygen.

In another embodiment, the invention provides methods of making a wear resistant polymeric material, wherein the irradiation is carried out in an inert atmosphere, and wherein the atmosphere contains gases selected from the group consisting of nitrogen, argon, helium, neon, or the like, and a combination thereof.

In another embodiment, the invention provides methods of making a wear resistant polymeric material, wherein the radiation dose is between about 25 and about 1000 kGy, for example, preferably, the radiation dose is about 65 kGy, about 75 kGy, or about 100 kGy.

In another embodiment, the invention provides methods of making a wear resistant polymeric material, wherein reduction of free radicals in the cross-linked polymeric material is achieved by heating the polymeric material in contact with a non-oxidizing medium, wherein the non-oxidizing medium is an inert gas, an inert fluid, or a polyunsaturated hydrocarbon selected from the group consisting of acetylenic hydrocarbons such as acetylene; conjugated or unconjugated olefinic hydrocarbons such as butadiene and (meth)acrylate monomers; and sulphur monochloride with chloro-tri-fluoroethylene (CTFE) or acetylene.

In another embodiment, the invention provides methods of making a wear resistant polymeric material, wherein the polymeric material is irradiated at a temperature of about 40° C., about 75° C., about 100° C., about 110° C., about 120° C., about 130° C., about 135° C., about 140° C., about 145° C., about 150° C., about 155° C., about 160° C., about 165° C., about 170° C., about 175° C., about 180° C., about 185° C., about 190° C., or about 195° C.

In another embodiment, the invention provides medical devices comprising the polymeric material made according to any of methods disclosed herein.

In another embodiment, the invention provides medical devices comprising a cross-linked polymeric material made according to any of methods disclosed herein.

In another embodiment, the invention provides medical devices comprising a polymeric material with a gradient of crosslink density made according to any of methods disclosed herein.

In another embodiment, the invention provides medical devices comprising a tough, and ductile polymeric material made according to any of methods disclosed herein.

In another embodiment, the invention provides medical devices comprising a cross-linked, wear and oxidation resistant, tough, and ductile polymeric material made according to any of methods disclosed herein.

According to one aspect of the invention, the medical device is contacted, diffused, or homogenized with one or more antioxidants in a supercritical fluid, for example, $CO_2$.

According to one aspect of the invention, the medical device is selected from the group consisting of acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polymeric posts, intervertebral discs, interpositional devices for any joint, sutures, tendons, heart valves, stents, and vascular grafts.

According to another aspect of the invention, the medical device is a non-permanent medical device, wherein the non-permanent medical device is selected from the group consisting of a catheter, a balloon catheter, a tubing, an intravenous tubing, and a suture.

According to another aspect of the invention, the medical device is packaged and sterilized by ionizing radiation or gas sterilization, thereby forming a sterile, highly cross-linked, oxidatively stable medical device.

According to one aspect of the invention, the doping is carried out by soaking the polymeric material or the medical implant in one or more antioxidants) or their solutions, preferably, for about 5 minutes to about 100 hours or more, more preferably, for about an hour, about 30 minutes, 2, 3, 4, 5, 6, 7, 8, 9, 10, 11, 12, 13, 14, 15, or about 16 hours, and/or the antioxidant is heated to about 120° C. and the doping is carried out at about 120° C., and/or the antioxidant is warmed to about room temperature and the doping is carried out at room temperature or at a temperature between room temperature and the peak melting temperature of the polymeric material or less than about 137° C., and/or the cross-linked polymeric material is heated at a temperature below the melt of the cross-linked polymeric material. Depending upon the polymeric material selected, heat treatment, homogenization and other temperatures are determined in view of melting temperatures of the selected polymeric material.

According to another aspect of the invention, the doping is carried out by soaking the polymeric material or medical implant in the antioxidant, preferably, for about 5 minutes to about 100 hours or more, more preferably, for about an hour, about 30 minutes, 2, 3, 4, 5, 6, 7, 8, 9, 10, 11, 12, 13, 14, 15, or about 16 hours, and/or the doping is carried out at a temperature above the melting point of the polymeric material. For example, the doping is carried out at a temperature of about 140° C., about 145° C., about 150° C., about 155° C., about 160° C., about 165° C., about 170° C., about 175° C., about 180° C., about 185° C., about 190° C., about 195° C., about 200° C., about 250° C., about 280° C., about 300° C., about 320° C., about 350° C., about 380° C., about 400° C., or more.

According to another aspect of the invention, the polymeric material is a polypropylene, a polyamide, a polyether ketone, or a mixture thereof; wherein the polyolefin is selected from a group consisting of a low-density polyethylene, high-density polyethylene, linear low-density polyethylene, ultra-high molecular weight polyethylene (UHMWPE), or a mixture thereof; and wherein the polymeric material is polymeric resin, including powder, flakes, particles, or the like, or a mixture thereof or a consolidated resin.

In one embodiment, the antioxidant-doped or antioxidant-blended polymeric material is homogenized at a temperature below or above the melting point of the polymeric material for about an hour to several days.

In another embodiment of the invention, the oxidation-resistant cross-linked medical implant preform is further homogenized following the irradiation step by heating to a temperature below or above the melt to allow diffusion of one or more antioxidants.

In another embodiment of the invention, the antioxidant-doped polymeric material, the oxidation-resistant medical implant preform, or the medical implant preform is homogenized before and/or after irradiation, by thermally annealing at a temperature below or above the melting point of the polymeric material.

In another embodiment, the invention provides methods of making a wear resistant polymeric material comprising the steps of: i) irradiating a starting material by ionizing radiation, wherein the starting material is a mixture of polymeric materials, wherein the polymeric material has a gradient of antioxidants containing Irganox® 1010-rich surface regions and vitamin E-rich bulk regions; thereby forming a wear resistant polymeric material.

In another embodiment, the invention provides methods of making a wear resistant polymeric material comprising the steps of: i) irradiating a starting material by ionizing radiation, wherein the starting material is a mixture of polymeric materials, wherein the polymeric material has a gradient of antioxidants containing Irganox® 1010-rich surface regions and vitamin E-rich bulk regions; ii) heating the irradiated starting material; iii) continue heating the irradiated material following irradiation; and iv) cooling the heated polymeric material, thereby forming a wear resistant polymeric material.

In another embodiment, the invention provides methods of making a wear resistant polymeric material comprising the steps of: irradiating a starting material by ionizing radiation at an elevated temperature below the melt, wherein the starting material is a mixture of UHMWPE and an antioxidant from the Irganox® family; thereby forming a wear resistant polymeric material.

In another embodiment, the invention provides medical implants made by layered molding of wear resistant polymeric materials, wherein the polymeric material is made by a process comprising the steps of: i) irradiating a starting material by ionizing radiation, wherein the starting material is a polymeric material or a mixture of polymeric materials, wherein the polymeric material is blended or doped with at least one antioxidant or already has a gradient of antioxidant, wherein the articular surfaces of the polymeric material contain one or more antioxidants from Irganox® family and the bulk regions of the polymeric material contain at least one antioxidant from the Irganox® family and/or another antioxidant; thereby forming a wear resistant polymeric material.

In another embodiment, the invention provides medical implants made by layered molding of wear resistant polymeric materials, wherein the polymeric material is made by a process comprising the steps of: i) irradiating a starting material by ionizing radiation, wherein the starting material is a polymeric material or a mixture of polymeric materials, wherein the polymeric material is blended or doped with at least one antioxidant or already has a gradient of antioxidant, wherein the articular surfaces of the polymeric material contain one or more antioxidants from Irganox® family and the bulk regions of the polymeric material contain at least one antioxidant from the Irganox® family and/or another antioxidant; ii) heating the irradiated starting material to a temperature of about 120° C. or more; iii) continue heating the irradiated material following irradiation; and iv) cooling the heated polymeric material, thereby forming a wear resistant polymeric material.

In another embodiment, the invention provides medical implants made by layered molding of wear resistant polymeric materials, wherein the polymeric material is made by a process comprising the steps of: i) irradiating a starting material by ionizing radiation, wherein the starting material is a polymeric material or a mixture of polymeric materials, wherein the polymeric material is blended or doped with at least one antioxidant or already has a gradient of antioxidant, wherein the articular surfaces of the polymeric material contain one or more antioxidants from Irganox® family and the bulk regions of the polymeric material contain at least one antioxidant from the Irganox® family and/or another antioxidant; ii) heating the irradiated starting material to a temperature of about 200° C. or more; iii) continue heating the irradiated material following irradiation; and iv) cooling the heated polymeric material, thereby forming a wear resistant polymeric material.

In another embodiment, the invention provides medical implants comprising wear resistant polymeric materials, wherein the polymeric material is made by a process comprising irradiating a starting material by ionizing radiation, wherein the starting material is a polymeric material or a mixture of polymeric materials, wherein the polymeric material is blended or doped with at least one antioxidant or already has a gradient of antioxidant, wherein the articular surfaces of the polymeric material contain one or more antioxidants from Irganox® family and the bulk region of the polymeric material contain a different antioxidant and one or more antioxidants from the Irganox® family.

According to one aspect of the invention, the polymeric material is irradiated at a temperature of about 40° C., about 75° C., about 100° C., about 110° C., about 120° C., about 130° C., about 135° C., about 140° C., about 145° C., about 150° C., about 155° C., about 160° C., about 165° C., about 170° C., about 175° C., about 180° C., about 185° C., about 190° C., or about 195° C.

According to an aspect of the invention, heating after irradiation is used to homogenize the concentration of at least one antioxidant through the polymeric material or medical implant. Heating is done below, at or above the melting point of the polymeric material or specifically by high temperature melting. A benefit of the heating process can be that the concentration of residual free radicals is reduced.

According to another aspect of the invention, the heating is continued for at least for one minute, 10 minutes, 20 minutes, 30 minutes, one hour, two hours, five hours, ten hours, 24 hours, or more.

According to another aspect of the invention, the radiation dose is about 25, about 50, about 60, about 65, about 75, about 100, about 125, about 150, about 175, or about 200 kGy.

According to another aspect of the invention, the Irganox® is Irganox® 1010.

According to another aspect of the invention, the Irganox® concentration is between 0.0001 and 50%; between 0.01 and 1%; between 0.01 and 0.1%; or 0.01, 0.02, 0.03, 0.04, 0.05, 0.06, 0.07, 0.08, 0.09% or 0.1%.

According to another aspect of the invention, the antioxidant concentration is between 0.0001 and 50%; between 0.01 and 5%; between 0.1 and 5%; 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, or 5%.

According to another aspect of the invention, the bulk antioxidant is tocopherol, vitamin-E, or Irganox®.

According to another aspect of the invention, the bulk antioxidant is a mixture of different Irganoxes; or a mixture of different tocopherols and Irganoxes.

According to another aspect of the invention, the Irganox® containing articular surface is about between 0.001 and 5 mm; about 1, 1.2, 1.4, 1.6, 1.8, 2, 2.2, 2.4, 2.6, 2.8, 3, 3.5, 4, or 5 mm in thickness.

According to another aspect of the invention, the Irganox® containing articular and backside surfaces are of equal thickness or different thicknesses.

According to another aspect of the invention, the polymeric material is melted after irradiation, machined after irradiation to form a preform, and the perform is annealed after irradiation, wherein the annealing is carried out before machining the polymeric material.

In another embodiment, the invention provides methods of making a medical implant comprising a polymeric material, wherein the polymeric material is irradiated at a temperature of about 100° C. or about 120° C., wherein the polymeric material is machined to form the medical implant, and wherein the polymeric material is packaged and sterilized.

In another embodiment, the invention provides methods of making a wear resistant polymeric material comprising the steps of: i) irradiating a starting material by ionizing radiation, wherein the starting material is a polymeric material or a mixture of polymeric materials, wherein the polymeric material is blended with one or more antioxidant of Irganox® family and with or without vitamin E; ii) mechanically deforming the antioxidant-blended and irradiated polymeric material at an elevated temperature below the melting point; iii) heating the antioxidant-blended irradiated starting material to a temperature that is below or above the melting point of the polymeric material; and iv) cooling the heated polymeric material, thereby forming a wear resistant polymeric material.

In another embodiment, the invention provides methods of making a wear resistant polymeric material, wherein the starting material is obtained by a method comprising the steps of: i) blending one or more polymeric materials; and ii) consolidating the blend by compression molding as a single layer or as multiple layers containing different concentrations and/or types of one or more antioxidants.

In another embodiment, the invention provides methods of making a wear resistant polymeric material, wherein the starting material is obtained by a method comprising the steps of: i) blending one or more polymeric materials with at least one antioxidant; and ii) consolidating the blend by compression molding as a single layer or as multiple layers containing different concentrations and/or of one or more antioxidants.

In another embodiment, the invention provides methods of making a wear resistant polymeric material, wherein the polymeric material is irradiated and mechanically deformed, wherein the mechanically deformed crosslinked material is heated to a temperature of about 130° C., about 135° C., about 150° C., or about 180° C.

In another embodiment, the invention provides methods of making a wear resistant polymeric material, wherein the mechanical deformation is carried out to a compression ratio of about 2.0 at temperature that is below the melting point of the polymeric material.

Unless otherwise defined, all technical and scientific terms used herein in their various grammatical forms have the same meaning as commonly understood by one of ordinary skill in the art to which this invention belongs. Although methods and materials similar to those described herein can be used in the practice or testing of the present invention, the preferred methods and materials are described below. In case of conflict, the present specification, including definitions, will control. In addition, the materials, methods, and examples are illustrative only and are not limiting.

Further features, objects, and advantages of the present invention are apparent in the claims and the detailed description that follows. It should be understood, however, that the detailed description and the specific examples, while indicating preferred aspects of the invention, are given by way of illustration only, since various changes and modifications within the spirit and scope of the invention will become apparent to those skilled in the art from this detailed description.

These and other aspects of the invention will become apparent to the skilled artisan in view of the teachings contained herein.

The invention is further disclosed and exemplified by reference to the text and drawings that follow.

BRIEF DESCRIPTION OF THE DRAWINGS

FIG. 1 illustrates an example of the initial (0) process step of making wear resistant polymeric materials or medical devices.

FIG. 2 illustrates examples (1 to 3) of processes, steps and conditions of various methods of making wear resistant polymeric materials or medical devices.

FIG. 3 illustrates examples (4 to 6) of processes, steps and conditions of various methods of making wear resistant polymeric materials or medical devices.

FIG. 4 illustrates examples (7 to 9) of processes, steps and conditions of various methods of making wear resistant polymeric materials or medical devices.

FIG. 5 illustrates examples (10 to 12) of processes, steps and conditions of various methods of making wear resistant polymeric materials or medical devices.

FIG. 6 illustrates examples (13 to 15) of processes, steps and conditions of various methods of making wear resistant polymeric materials or medical devices.

FIG. 7 illustrates examples (16 to 18) of processes, steps and conditions of various methods of making wear resistant polymeric materials or medical devices.

FIG. 8 illustrates examples (19 to 26) of processes, steps and conditions of various methods of making wear resistant polymeric materials or medical devices.

FIG. 9 illustrates examples (27 to 30) of processes, steps and conditions of various methods of making wear resistant polymeric materials or medical devices.

FIG. 10 illustrates examples (31 to 35) of processes, steps and conditions of various methods of making wear resistant polymeric materials or medical devices.

FIG. 11 illustrates examples (36 to 38) of processes, steps and conditions of various methods of making wear resistant polymeric materials or medical devices.

FIG. 12 illustrates examples (39 to 41) of processes, steps and conditions of various methods of making wear resistant polymeric materials or medical devices.

FIG. 13A shows the direction of radiation beam; FIG. 13B shows shielded UHMWPE construct under a radiation beam.

FIG. 14A shows a UHMWPE construct; FIG. 14B shows a UHMWPE construct cut in half.

FIG. 18A shows the direction of radiation beam; FIG. 18B shows aluminum partial shielded UHMWPE construct under a radiation beam.

FIG. 19A shows a UHMWPE construct; FIG. 19B shows a UHMWPE construct cut in half; and FIG. 19C depicts bisected UHMWPE construct for microtoming and Infra-red analysis.

FIGS. 22A-22N depict various exemplary shield geometries (FIG. 22 A-G periphery shield cross-sections and FIG. 22 H-N core shield cross-sections), which can be used in various arrangements according to the invention, such as in FIGS. 31A-31C. FIG. 22A shows a geometric shape of a periphery shield cross-section, FIG. 22B shows another geometric shape of a periphery shield cross-section, FIG. 22C shows another geometric shape of a periphery shield cross-section, FIG. 22D shows another geometric shape of a periphery shield cross-section, FIG. 22E shows another geometric shape of a periphery shield cross-section, FIG. 22F shows another geometric shape of a periphery shield cross-section, FIG. 22G shows another geometric shape of a periphery shield cross-section, FIG. 22H shows a geometric shape of a core shield cross-section, FIG. 22I shows another geometric shape of a core shield cross-section, FIG. 22J shows another geometric shape of a core shield cross-section, FIG. 22K shows another geometric shape of a core shield cross-section, FIG. 22L shows another geometric shape of a core shield cross-section, FIG. 22M shows another geometric shape of a core shield cross-section, and FIG. 22N shows another geometric shape of a core shield cross-section.

FIGS. 23A-23F depict the use of the present invention in the fabrication of an acetabular liner of a hip prosthesis. FIG. 23A. Shows Irradiation of a shielded liner, FIG. 23B. Shows top view of a shielded preform; FIG. 23C. Depicts a shielded preform with cross-sections; FIG. 23D. Rectangular shield; FIG. 23E. Inclined shield; FIG. 23F. Curved shield.

FIGS. 24A-24F depict the use of the present invention in the fabrication of a mobile bearing knee prosthesis (such as a rotating platform knee). FIG. 24A depicts a rotating platform, FIG. 24B depicts a translating and rotating platform, FIG. 24C depicts Step-1 of a rotating platform, 24D depicts Step-I of a translating and rotating platform, FIG. 24E depicts Step-II of a rotating platform, and FIG. 24F depicts Step-II of a translating and rotating platform.

FIGS. 25A-25C depict the use of the present invention in the fabrication of a knee meniscus prosthesis. FIG. 25A: Top view, FIG. 25B: Step I, and FIG. 25C Step II.

FIGS. 26A-26D depict the use of the present invention in the fabrication of a shoulder meniscus prosthesis. FIG. 26A: Side view, FIG. 26B: Top view, FIG. 26C: Step I, and FIG. 26D: Step n.

FIGS. 27A-27C depict the use of the present invention in the fabrication of a spacer for a finger joint. FIG. 27A: Finger Spacer, FIG. 27B: Top view Step I, and FIG. 27C: Top view Step n.

FIGS. 28A-28H depict exemplary shield edge geometries and the resultant irradiation penetration envelopes. One set of illustrations shows shields that fully block the radiation from the covered area, while the other set of illustrations shows shields that partially block the radiation from the covered area. FIG. 28A depicts a shield edge geometry that frilly blocking the radiation from the covered area, FIG. 28B depicts another shield edge geometry that fully blocking the radiation from the covered area, FIG. 28C depicts another shield edge geometry that frilly blocking the radiation from the covered area, FIG. 28D depicts another shield edge geometry that fully blocking the radiation from the covered area, FIG. 28E depicts another shield edge geometry that frilly blocking the radiation from the covered area, FIG. 28F depicts a shield edge geometry that partially blocking the radiation from the covered area, FIG. 28G depicts another shield edge geometry that partially blocking the radiation from the covered area, and FIG. 28H depicts another shield edge geometry that partially blocking the radiation from the covered area.

FIG. 29A: without shield and FIG. 29B: with shield.

FIGS. 31A-31C illustrate the irradiation of a polymer preform using both a ring-shaped and disc-shaped shield in sequence. FIG. 31A: Unshielded Irradiation, FIG. 31B: Disc shielded Irradiation, and FIG. 31C: Ring shielded Irradiation.

FIG. 32 illustrates an embodiment of partial coverage shielding as described herein.

FIG. 33 illustrates an embodiment of complete coverage shielding as described herein.

FIG. 34 illustrates another embodiment of complete coverage shielding as described herein.

FIG. 41C illustrates cross-link density as a function of radiation dose in UHMWPE blends of Irganox® 1035. The dashed lines indicate the radiation dose required to obtain a cross-link density of 0.260 mol/dm$^3$; the crosslink density of 100-kGy irradiated virgin UHMWPE. The numbers at the right side of the graph are the radiation dose values required to obtain this level of crosslinking in Irganox® 1035 blended UHMWPE as a function of concentration.

FIGS. 43A-3D illustrate thin-section preparation from specimen block for FTIR analysis. (FIG. 43A) Specimen block, (FIG. 43B) cut block with band saw, (FIG. 43C) microtome thin film from cut surface, and (FIG. 43D) analysis by FTIR through cross section.

FIGS. 46A-46H show schematic examples of obtaining preferentially surface cross-linked regions by machining after layered molding. Darker color shows regions with higher antioxidant concentration blended into the polymer. FIG. 46 shows side view (FIG. 46A) and top view (FIG.

46B), the surface is machined such that the articular surface is concave and the outside part of the surface is machined down to the UHMWPE containing high antioxidant concentration (FIG. 46C). Alternatively, the surface can have a contour after machining such that part of the surface contains more than another part (FIG. 46A-H). FIG. 46D shows a contour after machining, FIG. 46E shows another contour after machining, FIG. 46F shows another contour after machining, FIG. 46G shows another contour after machining, and FIG. 46H shows another contour after machining.

FIG. 47A shows that there can be more than two layers having different concentrations of at least one antioxidant. Alternatively, the blends are layered in such a way to allow for high concentration regions within the low concentration regions (FIG. 47B and FIG. 47C). FIG. 47B shows an example of blended layers with high concentration regions within the low concentration regions. FIG. 47C shows another example of blended layers with high concentration regions within the low concentration regions. FIG. 47D, FIG. 47E and FIG. 47F show top view of FIG. 47A, FIG. 47B and FIG. 47C, respectively.

FIGS. 48A-48F show schematic description of masking during extraction. Darker color shows regions with higher antioxidant concentration in the polymer. FIG. 48A: antioxidant blend of UHMWPE, FIG. 48B-FIG. 48C: UHMWPE after extraction with masking, and FIG. 48D: UHMWPE after extraction without masking. FIG. 48E and FIG. 48F are masks used during the extraction.

FIG. 62A shows the ultimate tensile strength (UTS), FIG. 62B shows the tensile work-to-failure (WF), FIG. 62C shows the IZOD impact strength, and FIG. 62D shows the change in the wear rate of UHMWPE.

FIG. 65 shows the effect of the initial vinyl index before irradiation on the crosslink density of irradiated high temperature melted UHMWPEs. The solid symbols represent irradiated and melted UHMWPE without high temperature melting (CISM). The open symbols are irradiated UHMWPEs with prior high temperature melting.

FIGS. 67A-67F depict schematic of a generic tibial insert with regions containing different concentrations of antioxidant. For example, the shaded regions contain Irganox® 1010 at a low concentration such as 0.05 wt % and the other regions contain higher concentration of antioxidant such as 1 wt % vitamin E. FIG. 67 depicts top (articular surface) views of a generic tibial insert showing different concentrations of antioxidants in different regions. FIG. 67A shows top view of medial and lateral regions, FIG. 67B shows a generic tibial insert with regions containing different concentrations of antioxidant, FIG. 67C shows another generic tibial insert with regions containing different concentrations of antioxidant, FIG. 67D shows another generic tibial insert with regions containing different concentrations of antioxidant, FIG. 67E shows another generic tibial insert with regions containing different concentrations of antioxidant, and FIG. 67F shows another generic tibial insert with regions containing different concentrations of antioxidant.

FIG. 69A: Before irradiation and FIG. 69B: after irradiation.

FIG. 70A, FIG. 70B, and FIG. 70C show vitamin E concentration profiles of 0.5 wt % vitamin E-blended UHMWPE as a function of depth away from the surface after extraction and irradiation, respectively (FIG. 70A); the wear rate as a function of depth away from the surface of 0.5 wt % vitamin E-blended UHMWPE after extraction and 150 kGy irradiation (FIG. 70B); and the wear rate as a function of depth away from the surface of 1 wt % vitamin E-blended UHMWPE after extraction and 150, 200, 250 and 300 kGy irradiation (FIG. 70C).

DETAILED DESCRIPTION OF THE INVENTION

Figure 1:
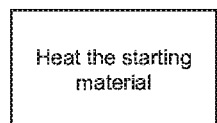
FIGS. 1 through 12 illustrate examples (0 to 41) of processes, steps and conditions of various methods of making wear resistant polymeric materials or medical devices.

The present invention provides methods for making cross-linked, wear and oxidation resistant polymeric materials. The invention pertains to methods of making medical implants containing cross-linked and antioxidant-containing tough and ductile polymers, and materials obtainable thereby and used therewith also are provided.

This application describes that the use of antioxidants, such as vitamin-E, increases the ductility of UHMWPE even further by acting as a plasticizing agent. Also, the application discloses that the presence of an antioxidant delays and/or prevents chain scissioning that can occur during high temperature melting.

High Temperature Melting

The invention pertains to use the high temperature melting (HTM) in combination with radiation crosslinking and/or high pressure crystallization in various sequences as outlined herein (see for example, in FIGS. 1-12). One object of the invention is to achieving a UHMWPE with low wear, high oxidation resistance, and high toughness/ductility.

Although not bound by any theory, it is believed that at high temperatures two processes could affect the morphology and properties of UHMWPE: One is the increased self-diffusion of chain entanglements across the granule boundaries and the other is the chain scissioning, which in turn would help self-diffusion. Inter-chain diffusion can increase entanglements in the amorphous phase of UHMWPE, which can lead to increased elongation. Inter-chain diffusion is increased effectively above the melting point of the crystals where the mobility of all chains is increased and the crystalline phase is not present to inhibit mobility. Above the melting point of the crystals, increasing temperature increases kinetic energy of the amorphous chains, resulting in more effective diffusion. Therefore, effective entanglement of the chains in the amorphous phases can be obtained by increasing temperature and also by increasing the time allowed for inter-chain diffusion. This is also true for diffusion across the grain boundaries, which may increase the strength of the material considerably.

Un-crosslinked UHMWPE has shape memory when molten at typical processing temperature, for example 150° C., for a moderate amount of time. This is because the diffusion of the ultra-high molecular weight chains of the polymer is very slow and it is energetically favorable to assume for the chains (and crystals) mostly the same configuration during cooling and re-crystallization. However, the more diffusion is allowed for the chains, that is the higher the melting temperature and the longer the melting time, shape memory will be hindered and the polymer will not re-crystallize in the same configuration and to the same crystallinity level.

Radiation crosslinking reduces wear of UHMWPE, but residual free radicals remain in UHMWPE, resulting in long-term oxidation. The incorporation of an antioxidant such as vitamin E in UHMWPE can stabilize these residual free radicals and render the cross-linked UHMWPE oxidatively stable without the need for quenching the free radicals. According to one aspect of the invention, the antioxidant is incorporated in UHMWPE powder and molded or extruded together, and/or the antioxidant is diffused into already molded or extruded parts before or after radiation crosslinking.

One approach to reduce free radicals in radiation cross-linked UHMWPE is to anneal below the melting point. Annealing below the melting point is desirable because melting the crystals completely in the presence of the cross-links reduces the mechanical strength of the material through a decrease in crystallinity. Annealing below the melting point can be done at an elevated temperature more effectively by increasing the pressure. This is because the melting point of cross-linked UHMWPE increases with increasing pressure. For example, it is observed that 100-kGy irradiated UHMWPE is not completely molten at 150° C. under 10,000 psi of hydrostatic pressure, whereas its melting point at ambient pressure is approximately 140° C.

Another approach is to completely melt the crystals by annealing above the melting point. Depending on the pre-melting crystallinity and the crosslink density of the network, which dictate the mobility of the chains, increasing the temperature during melting can increase the elongation, leading to higher toughness.

Yet, another approach to eliminate free radicals as well as increasing strength of the cross-linked UHMWPE is high pressure crystallization and high pressure annealing. UHMWPE exhibits a hexagonal crystal phase at high temperatures and pressures (above about 210 MPa and about 160° C.) where crystals can grow to a larger extent and overall crystallinity can be increased. The polymer can be crystallized from the melt by first melting then increasing the pressure to a level such that extended chain growth is observed. The second approach (high pressure annealing) is to pressurize and heat in such a manner that the hexagonal phase is achieved through the solid phases (orthorhombic, monoclinic or transient hexagonal) rather than the melt. In both of these approaches, the free radicals are reduced or eliminated due to the mobility induced in the crystals due to the phase transformation. In a similar manner, deformation of the crystalline material in the solid state by mechanical loading can also result in mobility in the crystals and reduction or elimination in free radicals.

Extended chain crystal formation in UHMWPE can result in a UHMWPE with higher crystallinity and mechanical strength. Increasing the elongation of a highly crystalline, high strength UHMWPE is also desirable. This can be achieved by increasing the elongation of UHMWPE prior to high pressure crystallization.

Controlling the cross-link density and cross-link density distribution is possible by irradiation at different temperatures. For example, irradiation in the melt state can result in homogenous distribution of cross-links in contrast to irradiation below the melting point, where cross-links are not formed in the crystalline regions and only the amorphous content is cross-linked. Similarly, one can use a spatially variable anti-crosslinking agent concentration such as that of vitamin E during irradiation to tailor the crosslink density distribution.

In one embodiment, virgin polymeric material or a blend of the polymeric material with an antioxidant such as vitamin E is melted above the melting point at a high temperature for a period of time (FIG. 1 at 0).

Figure 2:
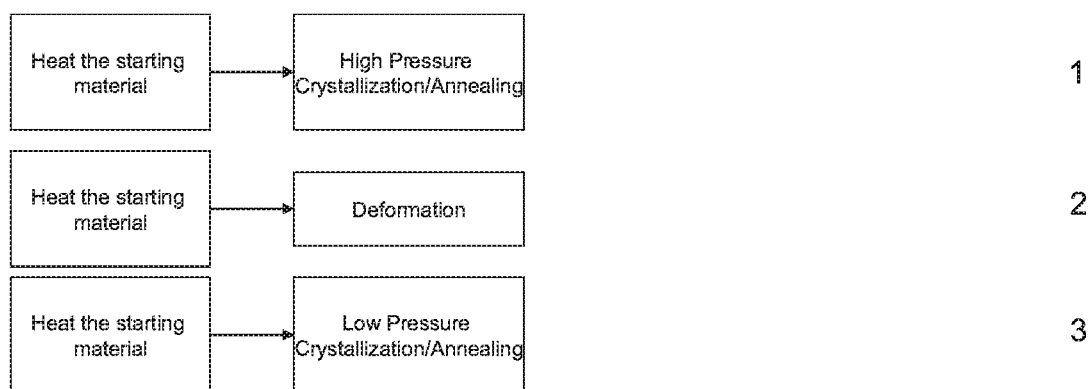
Figure 3:
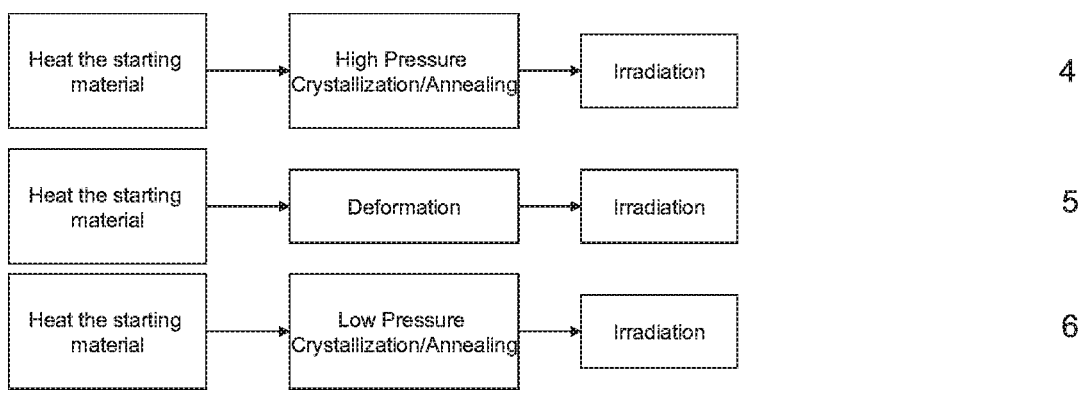
Figure 4:
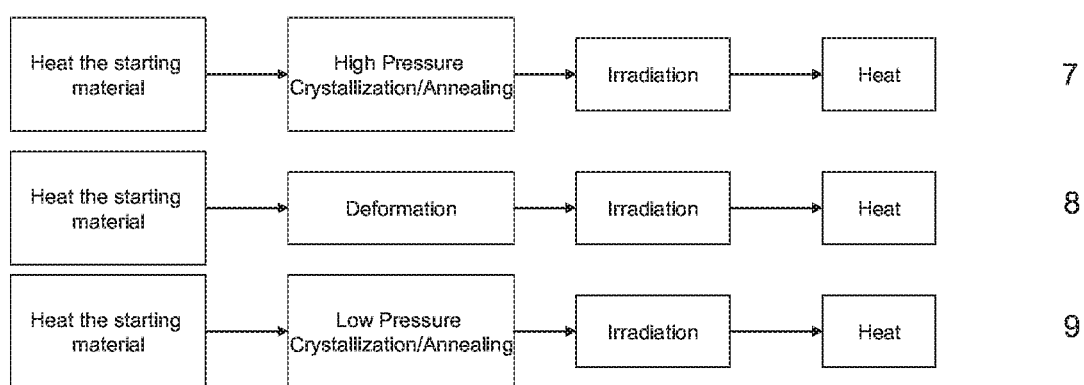
Figure 6:
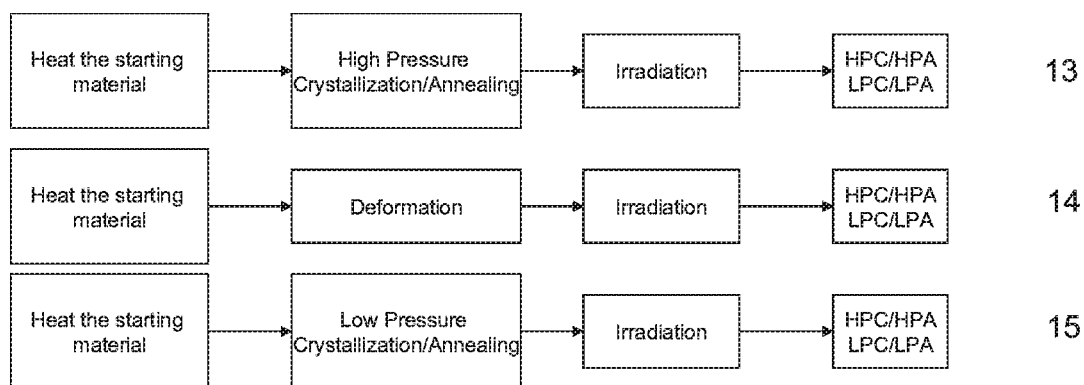

In another embodiment, virgin polymeric material or a blend of the polymeric material with an antioxidant such as vitamin E is melted above the melting point at a high temperature for a prolonged period of time. Further, this high elongation material is pressure crystallized under low or high pressure to obtain a highly crystalline material with high elongation. Then, this highly crystalline material with improved elongation may be cross-linked by irradiation or chemical means (FIG. 2 at 1 and 3, and FIG. 3 at 4). After radiation cross-linking, the material can be heated to below or above the melting point or above the melting point at a high temperature for a prolonged period of time (FIG. 4 at 7 and 9). Alternatively, after cross-linking, it can be pressure crystallized or annealed (FIG. 6 at 13 and 15).

In another embodiment, the starting material is a blend of polymeric material with a lower molecular weight polymer blend such that the effective molecular weight between cross-links is reduced and the crosslink density is increased compared to virgin UHMWPE at the same radiation dose. In another embodiment, the starting material is a blend of UHMWPE with a lower molecular weight polymer blend such that the resultant UHMWPE is more lubricious and the coefficient of friction of UHMWPE against CoCr is lower than that of virgin UHMWPE.

In another embodiment, melting a virgin polymeric material or a blend of the polymeric material with an antioxidant such as vitamin E above the melting point at a high temperature for a prolonged period time is used to increase the elongation. This UHMWPE is deformed under load biaxially or uniaxially to obtain a highly oriented polymer (FIG. 2 at 2). Then, this material can be radiation crosslinked (FIG. 3 at 5 and 6). After cross-linking, the material can be heated to below or above the melting point or above the melting point at a high temperature for a prolonged period of time (FIG. 4 at 8). Alternatively, after cross-linking, it can be pressure crystallized or annealed (FIG. 6 at 14).

Figure 5:
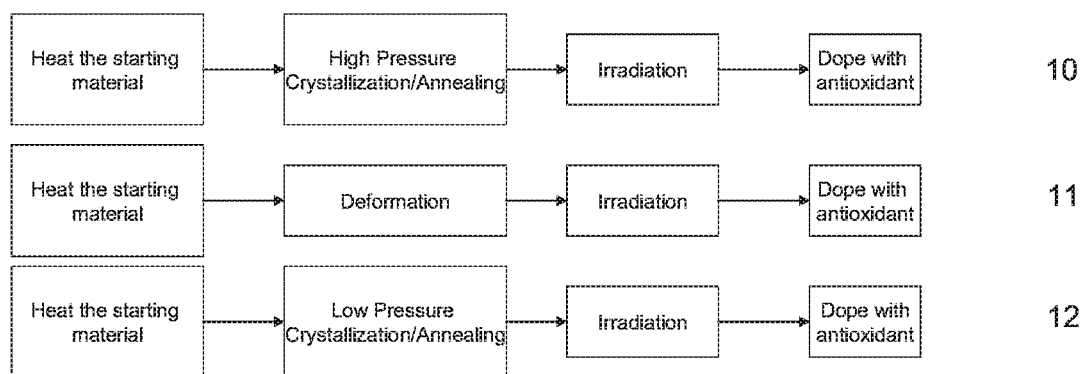

In another embodiment, melting a blend of polymeric material with an antioxidant such as vitamin E above the melting point at a high temperature for a prolonged period time is used to increase the elongation. The material is then pressure crystallized or annealed. Then, it is cross-linked by radiation or chemical means. Finally, it is diffused an antioxidant such as vitamin E by doping followed optionally by homogenization of the antioxidant at elevated temperature (FIG. 5 at and 12).

In another embodiment, melting a virgin polymeric material or a blend of the polymeric material with an antioxidant such as vitamin E above the melting point at a high temperature for a prolonged period of time is used to increase the elongation. This UHMWPE is deformed under load biaxially or uniaxially to obtain a highly oriented polymer. Then, this material is radiation crosslinked. Finally, it is diffused an antioxidant such as vitamin E by doping followed optionally by homogenization of the antioxidant at elevated temperature (FIG. 5 at 11).

Figure 7:
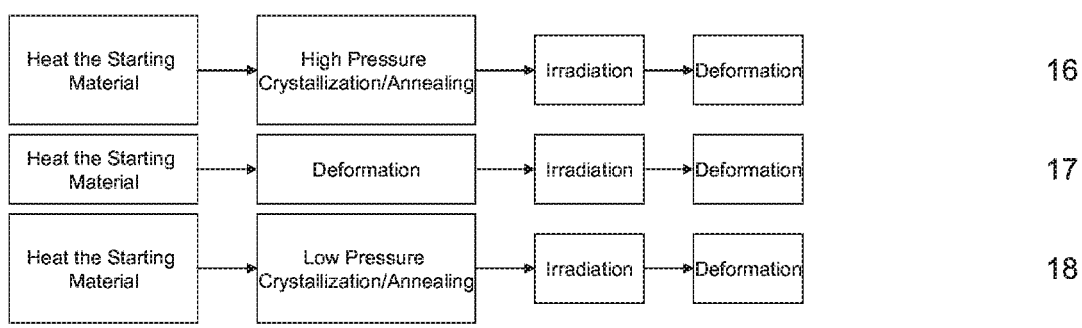
Figure 8:
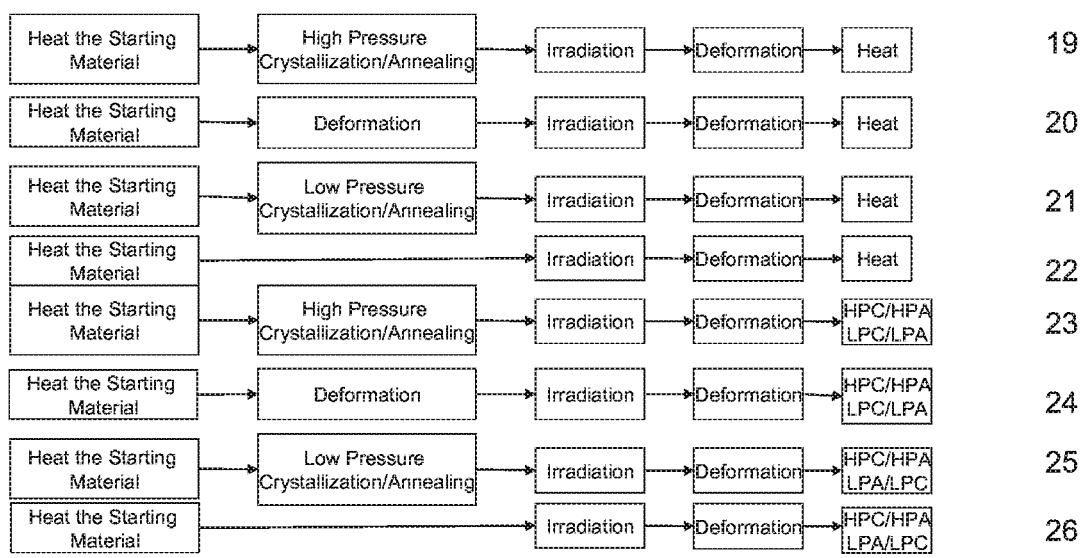

In one embodiment, virgin polymeric material or a blend of the polymeric material with an antioxidant such as vitamin E is melted above the melting point at a high temperature for a prolonged period of time. Further, this high elongation material is pressure crystallized under low or high pressure to obtain a highly crystalline material with high elongation. Then, this highly crystalline material with improved elongation may be cross-linked by irradiation or chemical means. After radiation cross-linking, the material is deformed under load biaxially or uniaxially to obtain a highly oriented polymer (FIG. 7 at 16 and 18). The material may further be heated below or above the melting point or above the melting point at a high temperature (FIG. 8 at 19 and 21). Alternatively, it may be pressure crystallized at low or high pressure (FIG. 8 at 23).

In one embodiment, virgin polymeric material or a blend of the polymeric material with an antioxidant such as vitamin E is melted above the melting point at a high temperature for a prolonged period of time. This UHMWPE is deformed under load biaxially or uniaxially to obtain a highly oriented polymer. Further, it is cross-linked by radiation or chemical means. It may further be deformed under load biaxially or uniaxially (FIG. 7 at 17). After deformation, it may be heated below or above the melting point or above the melting point at a high temperature (FIG. 8 at 20). Alternatively, it may be pressure crystallized at low or high pressure (FIG. 8 at 24).

In one embodiment, virgin polymeric material or a blend of the polymeric material with an antioxidant such as vitamin E is melted above the melting point at a high temperature for a prolonged period of time. This material is further cross-linked by radiation or chemical means. It may further be deformed under load biaxially or uniaxially. After deformation, it may be heated below or above the melting point or above the melting point at a high temperature (FIG. 8 at 22). Alternatively, after deformation, it may be pressure crystallized at low or high pressure (FIG. 8 at 26).

Figure 9:
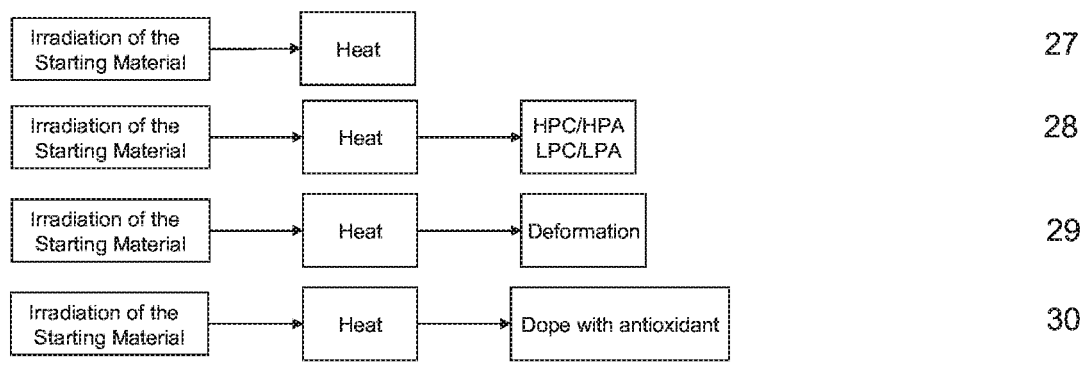

In one embodiment, a virgin polymeric material or a blend of the polymeric material with an antioxidant such as vitamin E is cross-linked by radiation or chemical means. It is then heated above the melting point at a high temperature for a prolonged period of time (FIG. 9 at 27). This material may further be pressure crystallized at high or low pressure (FIG. 9 at 28). Alternatively, after melting, it may be deformed under load biaxially or uniaxially (FIG. 9 at 29). Alternatively, it may be diffused with an antioxidant by doping followed optionally by homogenization of the antioxidant by annealing at elevated temperature (FIG. 9 at 30).

Figure 10:
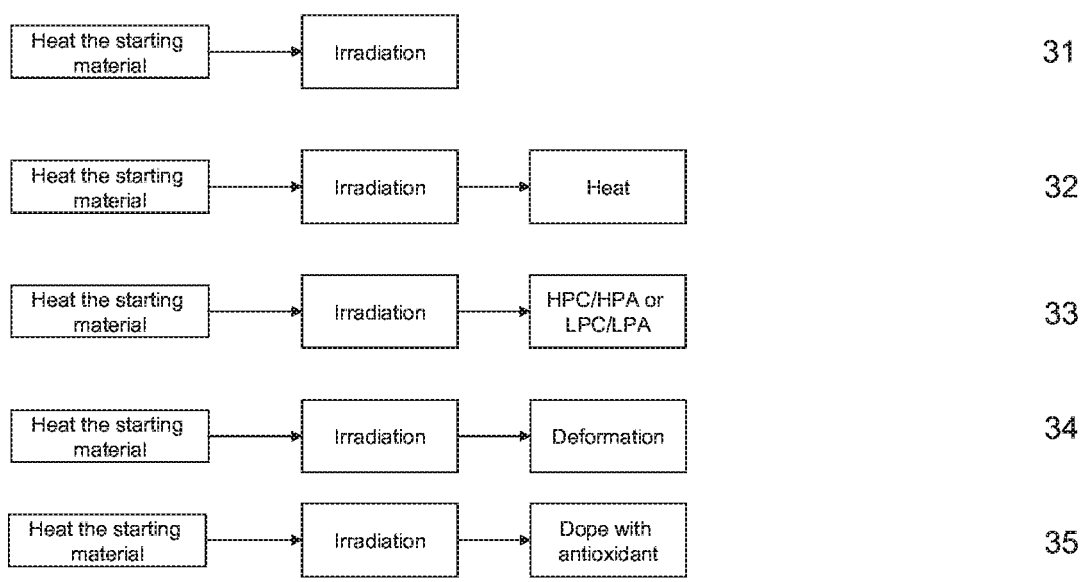

In one embodiment, a virgin polymeric material or a blend of the polymeric material with an antioxidant such as vitamin E is melted above the melting point at a high temperature for a prolonged period of time. Then, this material is cross-linked by radiation or chemical means (FIG. at 31). The material can be further heated below or above the melting point or above the melting point at a high temperature (FIG. 10 at 32). Alternatively, after cross-linking, it can be pressure crystallized at low or high pressure (FIG. 10 at 33). Alternatively, after cross-linking, it can be deformed under load uniaxially or biaxially (FIG. 10 at 34). An antioxidant such as vitamin E may be diffused into the cross-linked UHMWPE by doping in antioxidant followed optionally by homogenization of the antioxidant at elevated temperature FIG. 10 at (35).

Figure 11:
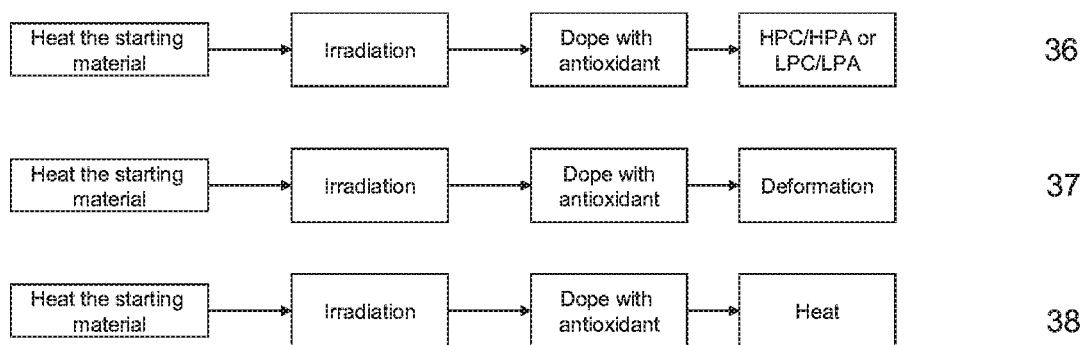

In one embodiment, melting a virgin polymeric material or a blend of the polymeric material with an antioxidant such as vitamin E above the melting point at a high temperature for a prolonged period time is used to increase the elongation. The material is then cross-linked by radiation or chemical means. An antioxidant such as vitamin E can be diffused into this material by doping optionally followed by homogenization at elevated temperature. The strength of this material is then improved by high pressure crystallization or annealing (FIG. 11 at 36).

In one embodiment, melting a virgin polymeric material or a blend of the polymeric material with an antioxidant such as vitamin E above the melting point at a high temperature for a prolonged period time is used to increase the elongation. The material is then cross-linked by radiation or chemical means. An antioxidant such as vitamin E can be diffused into this material by doping optionally followed by homogenization at elevated temperature. The material can further be deformed under load uniaxially or biaxially (FIG. 11 at 37).

In one embodiment, melting a virgin polymeric material or a blend of the polymeric material with an antioxidant such as vitamin E above the melting point at a high temperature for a prolonged period time is used to increase the elongation. The material is then cross-linked by radiation or chemical means. An antioxidant such as vitamin E can be diffused into this material by doping optionally followed by homogenization at elevated temperature. It can further be heated below or above the melting point or above the melting point at a high temperature (FIG. 11 at 38).

Figure 12:
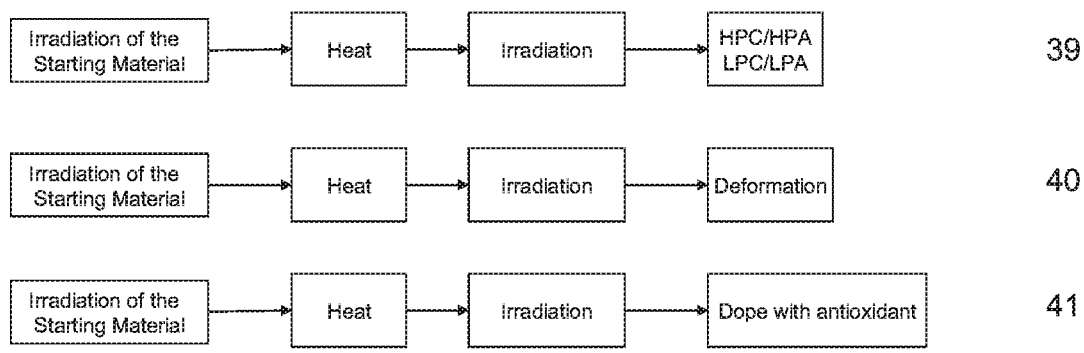

In one embodiment virgin polymeric material or a blend of the polymeric material with an antioxidant such as vitamin E is cross-linked by radiation or chemical means. This material is then heated below or above the melting point or above the melting point at a high temperature. It can be further cross-linked by radiation or chemical means. Finally, it is pressure crystallized at high or low pressure (FIG. 12 at 39).

In one embodiment, a virgin polymeric material or a blend of the polymeric material with an antioxidant such as vitamin E is cross-linked by radiation or chemical means. This material is then heated below or above the melting point or above the melting point at a high temperature. It can be further cross-linked by radiation or chemical means. Finally, it is deformed under load uniaxially or biaxially (FIG. 12 at 40).

In one embodiment, a virgin polymeric material or a blend of the polymeric material with an antioxidant such as vitamin E is cross-linked by radiation or chemical means. This material is then heated below or above the melting point or above the melting point at a high temperature. It can be further cross-linked by radiation or chemical means. Finally, it is diffused with an antioxidant such as vitamin E by doping optionally followed by homogenization at an elevated temperature (FIG. 12 at 41).

Controlling Crosslink Density Distribution

In one embodiment, a blend of the polymeric material with a spatially controlled concentration of blend is used as starting material. For example, UHMWPE powders containing different amount of vitamin E can be consolidated such that some parts of the consolidated UHMWPE contains more vitamin E than other parts. When this material is irradiated, the crosslink density, thus the wear rate and mechanical properties of these different parts can be different. This is due to vitamin E inhibiting cross-linking in UHMWPE with increasing concentration. Alternatively, UHMWPE can be molded with a spatially controlled concentration of a second component such as low molecular weight polyethylene. When this material is irradiated, the crosslink density, thus the wear rate and mechanical properties of these different parts can be different. Alternatively, spatially controlled distribution of one or more free radical scavenger/antioxidant other than vitamin E is used.

In another embodiment, gradient crosslinking in UHMWPE can be used by using shields against irradiation in a desired pattern. Alternatively, a chemical crosslinking species can be used in only part of the UHMWPE for the same purpose.

Melting at high temperature for prolonged periods of time enhances the diffusion of polymer chains in polyethylene and other high molecular weight polymers, increasing the strength of the polymer through increased entanglements. At the same time, increasing temperature increases degradation of the polymer chains through chain scissioning and this decreases the mechanical properties of the material. Therefore, these two factors are in competition in terms of the strength of the polymer.

Wear resistance in UHMWPE as a joint bearing surface has directly related to reduced plastic deformation. Cross-linking by radiation or chemical means decreases the plastic deformation and decreases the wear. This is because wear fibrils are a result of the orientation of polymer fibrils in the principal direction of motion and their weakening and fracture in the transverse directions. Wear is then caused by multidirectional motion.

By high temperature melting and increasing the entanglements between chains, wear resistance can be increased. Therefore, radiation/chemical crosslinking can be used in conjunction with high temperature melting to increase the wear resistance of UHMWPE as a bearing surface. However, when a high temperature melted UHMWPE is irradiated, it is not oxidation resistant and the free radicals have to stabilized or eliminated for oxidative stability.

The oxidation resistance of radiation cross-linked UHMWPE is crucial in its performance as a bearing surface as oxidation deteriorates its mechanical and wear properties in vivo over a long period of time. Oxidation is largely thought to be related to residual free radicals trapped in the crystalline regions of the polymer, their migration to the crystalline/amorphous interface and their reaction with diffused oxygen. Oxidation may also be related to other free radical generating mechanisms such as the material coming into contact with a free radical inducing medium or chains scission through static, dynamic or cyclic deformation. The safest way of protecting against these free radicals is the introduction of an antioxidant such as vitamin E into UHMWPE before or after cross-linking.

An antioxidant with a lipophilic structure can also act as a plasticizing agent in addition to protecting the material against oxidation. Then, it would be advantageous to incorporate the antioxidant in the polymer to improve mechanical properties as well.

In the case of high temperature melting, it is herein demonstrated that chain scission dominates as temperature is increased. The inclusion of an antioxidant/free radical scavenger can decrease the breakdown of the material and also affect its cross-linking ability with subsequent processing steps.

Antioxidants/free radical scavengers/anti-crosslinking agents can be chosen from but not limited to glutathione, lipoic acid, vitamins such as ascorbic acid (vitamin C), vitamin B, vitamin D, vitamin-E, tocopherols (synthetic or natural, alpha-, gamma-, delta-), acetate vitamin esters, water soluble tocopherol derivatives, tocotrienols, water soluble tocotrienol derivatives; melatonin, carotenoids including various carotenes, lutein, pycnogenol, glycosides, trehalose, polyphenols and flavonoids, quercetin, lycopene, lutein, selenium, nitric oxide, curcuminoids, 2-hydroxytetronic acid; cannabinoids, synthetic antioxidants such as tertiary butyl hydroquinone, 6-amino-3-pyrodinoles, butylated hydroxyanisole, butylated hydroxytoluene, ethoxyquin, tannins, propyl gallate, other gallates, Aquanox family; Irganox® and Irganox® B families including Irganox® 1010, Irganox® 1076, Irganox® 1330, Irganox® 1035; Irgafos® family; phenolic compounds with different chain lengths, and different number of OH groups; enzymes with antioxidant properties such as superoxide dismutase, herbal or plant extracts with antioxidant properties such as St. John's Wort, green tea extract, grape seed extract, rosemary, oregano extract, mixtures, derivatives, analogues or conjugated forms of these. They can be primary antioxidants with reactive OH or NH groups such as hindered phenols or secondary aromatic amines, they can be secondary antioxidants such as organophosphorus compounds or thiosynergists, they can be multifunctional antioxidants, hydroxylamines, or carbon centered radical scavengers such as lactones or acrylated bis-phenols. The antioxidants can be selected individually or used in any combination. Also, antioxidants can be used in conjunction with hydroperoxide decomposers.

In an embodiment, the polymer blend is irradiated at a dose rate of about 1 to 1000 kGy per pass. The irradiation dose rates that can be reached with electron beam are much higher than those with gamma irradiation. Electron beam dose rate are typically on the order of 1 to several hundred kGy per pass with each pass taking anywhere between a few seconds to a few minutes. E-beam irradiation is performed by passing the UHMWPE under the beam. In each pass a quantifiable dose is applied. The dose/pass could be the entire desired dose or a fraction thereof. In some embodiments the decision for the dose/pass is made to avoid overheating (for instance complete melting) of UHMWPE. In others the dose/pass is determined based on the desired properties that one targets. The dose/pass could be 1/10, 1/9, 1/8, 1/7, 1/6, 1/5 etc. . . . of the total desired dose level. Also the dose received at each pass during an irradiation run need not to be equal each other; any combination of dose/pass values could be used to reach the total target dose. The same approach is used with gamma irradiation, which involves passing UHMWPE in front of the gamma source.

The polymer blend is brought to a certain initial temperature and irradiated. The dose rate is high enough to cause radiation generated heating (including adiabatic and partially adiabatic) of the polymer. The temperature of the sample during irradiation depends on the starting temperature and the radiation dose level used. Following equation, which assumes purely radiation generated heating (including adiabatic and partially adiabatic) conditions, can be used to estimate the temperature:

$$D = \Delta H_{m,i}(T_i) + c_p \Delta T,\qquad \text{EQ1:}$$

where D is the radiation dose level absorbed by the sample, $T_i$ is the instantaneous temperature of the sample, $\Delta T$ ($=T_i-T_o$) is the difference between the instantaneous temperature ($T_i$) of the sample and the initial temperature ($T_o$) of the sample, $\Delta H_{m,i}(T_i)$ is the melting enthalpy of the crystals that melt below the instantaneous temperature of the sample, and $c_p$ is the specific heat of the polymer. This equation assumes purely radiation generated heating (including adiabatic and partially adiabatic) conditions; while there will be some heat loss to the surroundings near the surface of the irradiated sample, the bulk of the sample will more closely follow the temperature predicted by this equation, especially at high dose rates, and thus is a practical approximation. If a certain temperature is desired during irradiation, the equation is used to determine the irradiation parameters. In this embodiment the radiation dose level can be above 1 kGy. More preferably it can be 25 kGy, 50 kGy, 100 kGy, 150 kGy, 200 kGy or above. The dose rate can be about 1, 10, 25, 75, 100, 150, 200, or more kGy per pass or any dose rate in-between. The initial temperature can be below room temperature (RT), RT, above RT, about 40, 50, 75, 100, 110, 125, 130, 135° C. or more or any temperature thereabout or therebetween. The irradiation can be carried out with e-beam, gamma, or x-rays. The latter two has lower dose rates than e-beam; therefore e-beam is more practical to reach high dose rates.

In another embodiment, the polymer blend is irradiated with gamma or e-beam followed by annealing or melting to recombine the free radicals trapped in the crystalline domains. When the irradiation is carried out at low temperatures and/or low dose rates, the cross-link density is lower than it is after the irradiated polymer blend is annealed below the melting point or melted.

In certain embodiments, it is not desired to completely melt the polymer blend during the irradiation step. For example, with a required high dose level (higher than 100 kGy) to reach a desired cross-link density, the polymer blend could be subjected to radiation generated (including adiabatic and partially adiabatic) melting and result in complete melting of the blend. Post-irradiation melting reduces the crystallinity of the sample, which in turn reduces mechanical properties of the blend. One can prevent complete melting of the blend during irradiation by keeping the dose rate low to minimize radiation generated heating (including adiabatic and partially adiabatic), reduce the initial temperature, and/or reduce the radiation dose. In certain embodiments the polymer blend may require a higher initial temperature; in such cases one can use low radiation dose rate to reduce the extent of melting by radiation generated heating.

In another embodiment, irradiation is carried out in multiple steps so as to reduce the extent of radiation generated heating (including adiabatic and partially adiabatic) of the polymer blend. For instance, the polymer blend is irradiated in multiple passes under or near the radiation source (such as e-beam, gamma, or x-rays). The time between the passes can be adjusted to allow the polymer blend to cool down to the desired irradiation temperature. In some embodiments it is desirable to heat the sample between irradiation passes.

In another embodiment, the initial temperature of the polymer sample is adjusted such that the temperature of the polymer blend is increased to its peak melting point during irradiation.

DSC testing of warm irradiated blends typically exhibit three melting peaks on their first heat and two melting peaks on their second heat. The area under the highest melting peak of the first heat can be used to determine the extent of melting in the polymer during warm irradiation.

In another embodiment, crystallinity of a blend of a polymeric material with at least one antioxidant is increased through, for example high pressure crystallization. The highly crystalline blend is then irradiated. The crystalline domains contain little or no antioxidant, as a result, the bee radicals formed in the crystalline domains are viable for recombination and cross-linking reactions. To allow the recombination of the free radicals in the crystalline domains the blend is irradiated with a high enough dose rate to partially melt the polymer. Alternatively, the irradiation is carried out at an elevated temperature to partially melt the polymer. Another approach is to post-irradiation anneal or melt the polymer to allow the free radicals in the crystalline domains to recombine with each other. These approaches result in an improved cross-linking efficiency for the blend. A post-irradiation homogenization step may be necessary to diffuse at least one antioxidant from antioxidant-rich regions to antioxidant-poor regions.

In another embodiment, a polymer/antioxidant blend is mixed with virgin polymer flakes and consolidated. The consolidation cycle is kept as short as possible and at the lowest possible temperature to minimize bleeding of the antioxidant from the antioxidant blended flakes into virgin flakes. The consolidated polymer is then irradiated and subsequently homogenized to allow diffusion of antioxidant from antioxidant-rich regions to antioxidant-poor regions.

Alternatively, the antioxidant doped flakes could be subjected to an annealing cycle to diffuse the antioxidant to deeper into individual flakes and minimize its presence as a surface coating. This also reduces the extent of antioxidant bleeding across from the doped flakes to virgin flakes during consolidation and/or irradiation.

The invention provides various methods to improve the oxidative stability of irradiated antioxidant-containing polymers. In an embodiment, the invention provides methods to improve oxidative stability of polymers by heat treatment (such as annealing) of irradiated polymer-antioxidant blend to reduce the concentration of the residual free radicals through recombination reactions resulting in cross-linking and/or through reaction of the residual free radicals with the antioxidant. The latter is likely to take place by the abstraction of a hydrogen atom from the antioxidant molecules to the polymer, thus eliminating the residual free radical on the polymer backbone. Hence heat treatment (such as annealing) of an irradiated polymer in the presence of an antioxidant is more effective in reducing the concentration of residual free radicals than heat treatment (such as annealing) of an irradiated polymer in the absence of an antioxidant.

In another embodiment, invention provides methods to improve oxidative stability of polymers by diffusing more antioxidant into the irradiated polymer-antioxidant blend. The antioxidant diffusion methods have been described by Muratoglu et al. (see, e.g., US 2004/0156879; U.S. application Ser. No. 11/465,544, filed Aug. 18, 2006; PCT/US2006/032329 Published as WO 2007/024689, which are incorporated herein by reference).

In another embodiment, invention provides methods to improve oxidative stability of polymers by extracting antioxidants and creating a gradient of antioxidant concentration. The antioxidant extraction methods have been described in WO 2008/092047, the methodologies of which are hereby incorporated by reference.

In another embodiment, invention provides methods to improve oxidative stability of polymers by mechanically deforming the irradiated antioxidant-containing polymers to reduce or eliminate the residual free radicals. Mechanical deformation methods have been described by Muratoglu et al. (see, e.g., US 2004/0156879; US 2005/0124718; and PCT/US05/003305 published as WO 2005/074619), which are incorporated herein by reference.

The present invention also describes methods that allow reduction in the concentration of residual free radical in irradiated polymer, even to undetectable levels, without heating the material above its melting point. This method involves subjecting an irradiated sample to a mechanical deformation that is below the melting point of the polymer. The deformation temperature could be as high as about 135° C., for example, for UHMWPE. The deformation causes motion in the crystalline lattice, which permits recombination of free radicals previously trapped in the lattice through cross-linking with adjacent chains or formation of trans-vinylene unsaturations along the back-bone of the same chain. If the deformation is of sufficiently small amplitude, plastic flow can be avoided. The percent crystallinity should not be compromised as a result. Additionally, it is possible to perform the mechanical deformation on machined components without loss in mechanical tolerance. The material resulting horn the present invention is a cross-linked polymeric material that has reduced concentration of residuals free radical, and preferably substantially no detectable free radicals, while not substantially compromising the crystallinity and modulus.

The present invention further describes that the deformation can be of large magnitude, for example, a compression ratio of 2 in a channel die. The deformation can provide enough plastic deformation to mobilize the residual free radicals that are trapped in the crystalline phase. It also can induce orientation in the polymer that can provide anisotropic mechanical properties, which can be useful in implant fabrication. If not desired, the polymer orientation can be removed with an additional step of heating at an increased temperature below or above the melting point.

According to another aspect of the invention, a high strain deformation can be imposed on the irradiated component. In this fashion, free radicals trapped in the crystalline domains likely can react with free radicals in adjacent crystalline planes as the planes pass by each other during the deformation-induced flow. High frequency oscillation, such as ultrasonic frequencies, can be used to cause motion in the crystalline lattice. This deformation can be performed at elevated temperatures that is below the melting point of the polymeric material, and with or without the presence of a sensitizing gas. The energy introduced by the ultrasound yields crystalline plasticity without an increase in overall temperature.

The present invention also provides methods of further heating following free radical elimination below melting point of the polymeric material. According to one aspect of the invention, elimination of free radicals below the melt is achieved either by the sensitizing gas methods and/or the mechanical deformation methods. Further heating of cross-linked polymer containing reduced or no detectable residual free radicals is done for various reasons, for example:

1. Mechanical deformation, if large in magnitude (for example, a compression ratio of two during channel die deformation), will induce molecular orientation, which may not be desirable for certain applications, for example, acetabular liners. Accordingly, for mechanical deformation:
    a) Thermal treatment below the melting point (for example, less than about 137° C. for UHMWPE) is utilized to reduce the amount of orientation and also to reduce some of the thermal stresses that can persist following the mechanical deformation at an elevated temperature and cooling down. Following heating, it is desirable to cool down the polymer at slow enough cooling rate (for example, at about 10° C./hour) so as to minimize thermal stresses. If under a given circumstance, annealing below the melting point is not sufficient to achieve reduction in orientation and/or removal of thermal stresses, one can heat the polymeric material to above its melting point.

b) Thermal treatment above the melting point (for example, more than about 137° C. for UHMWPE) can be utilized to eliminate the crystalline matter and allow the polymeric chains to relax to a low energy, high entropy state. This relaxation leads to the reduction of orientation in the polymer and substantially reduces thermal stresses. Cooling down to room temperature is then carried out at a slow enough cooling rate (for example, at about 10° C./hour) so as to minimize thermal stresses.

2. The contact before, during, and/or after irradiation with a sensitizing environment to yield a polymeric material with no substantial reduction in its crystallinity when compared to the reduction in crystallinity that otherwise occurs following irradiation and subsequent or concurrent melting. The crystallinity of polymeric material contacted with a sensitizing environment and the crystallinity of radiation treated polymeric material is reduced by heating the polymer above the melting point (for example, more than about 137° C. for UHMWPE). Cooling down to room temperature is then carried out at a slow enough cooling rate (for example, at about 10° C./hour) so as to minimize thermal stresses.

As described herein, it is demonstrated that mechanical deformation can eliminate residual free radicals in a radiation cross-linked UHMWPE. The invention also provides that one can first deform UHMWPE to a new shape either at solid- or at molten-state, for example, by compression. According to a process of the invention, mechanical deformation of UHMWPE when conducted at a molten-state, the polymer is crystallized under load to maintain the new deformed shape. Following the deformation step, the deformed UHMWPE sample is irradiated below the melting point to cross-link, which generates residual free radicals. To reduce these free radicals to as low as undetectable levels, the irradiated polymer specimen is heated to a temperature below the melting point of the deformed and irradiated polymeric material (for example, up to about 135° C. for UHMWPE) to allow for the shape memory to partially recover the original shape. Generally, it is expected to recover about 80-90% of the original shape. During this recovery, the crystals undergo motion, which can help the free radical recombination and elimination. The above process is termed as a 'reverse-IBMA'. The reverse-IBM A (reverse-irradiation below the melt and mechanical annealing) technology can be a suitable process in terms of bringing the technology to large-scale production of UHMWPE-based medical devices.

The consolidated polymeric materials according to any of the methods described herein can be irradiated at room temperature or at an elevated temperature below or above the melting point of the polymeric material.

In certain embodiments of the present invention any of the method steps disclosed herein, including blending, mixing, consolidating, quenching, irradiating, annealing, mechanically deforming, doping, homogenizing, heating, melting, and packaging of the finished product, such as a medical implant, can be carried out in presence of a sensitizing gas and/or liquid or a mixture thereof, inert gas, air, vacuum, and/or a supercritical fluid.

The consolidated and irradiation cross-linked polymeric materials according to any of the methods described herein can be further doped with an antioxidant.

The consolidated and irradiation cross-linked polymeric materials according to any of the methods described herein can be further doped with an antioxidant and homogenized at a temperature below or above the melting point of the polymeric material.

In another embodiment, the invention provides a partially or entirely highly cross-linked, oxidatively stable highly crystalline medical device, made by any of the above methods.

In another embodiment, the invention provides a partially or entirely highly cross-linked, oxidatively stable highly crystalline medical device, wherein the polymeric material is machined subsequently after the consolidation, irradiation, heating and/or annealing or the quenching step.

In another embodiment, the invention provides a highly cross-linked, oxidatively stable highly crystalline medical device.

According to an aspect of the invention, the limitations of antioxidant diffusion in polymeric material are overcome by shortening the diffusion path of antioxidant necessary after irradiation. This is achieved by creating a polymeric article that has higher antioxidant concentration in the bulk (generally the interior regions) and lower antioxidant concentration on the surface (exterior regions). When this polymeric article is irradiated, the antioxidant rich regions in the bulk, in which wear reduction through cross-linking is not necessary, have a lower final cross-link density than they would have in the absence or lessened presence of antioxidant. On the other hand, the surface contains either no antioxidant or lower concentrations of antioxidant. Therefore, the surface is cross-linked during irradiation to levels similar to material irradiated in the absence of antioxidant and the wear rate is reduced. Cross-linking is only needed on and near the articular surfaces to improve the wear resistance of the implant. Although the surface and the bulk of a polymeric material generally refer to exterior regions and the interior regions, respectively, there generally is no discrete boundary between these two regions. The regions are more of a gradient-like transition, can differ based upon the size and shape of the object and the resin used.

Irradiation of UHMWPE with antioxidant/anti-crosslinking agents such as vitamin E reduces the cross-linking efficiency of polymeric material and also reduces the antioxidant potency of the antioxidants). Still, in some embodiments, there is enough antioxidant in the bulk such that after the irradiation step(s) there is still enough antioxidant potency to prevent oxidation in the bulk of the polymeric material. Thus, after irradiation, the polymeric article is oxidation-resistant in the bulk and is highly cross-linked on the surface. However, the surface may still contain unstabilized free radicals that can oxidize without enough antioxidant and reduce the mechanical properties of the article. Alternatively, even if a gradient vitamin E/antioxidant concentration is not present, some antioxidant may be used up during the processing steps such as heating or irradiation and oxidative stability may be decreased or compromised. To prevent oxidation on the antioxidant-poor surface region, the article can be irradiated at an elevated temperature below or above the melting point to reduce the concentration of residual free radicals. Or the irradiated article can be treated by using one or more of the following methods:

(1) doping with α-tocopherol through diffusion at an elevated temperature below or above the melting point of the irradiated polymeric material followed optionally by homogenization;
(2) mechanically deforming of the UHMWPE followed by heating below or above the melting point of the article;
(3) high pressure crystallization or high pressure annealing of the article; and
(4) further heat treating the article below or above the melting point.

After one or more of these treatments, the free radicals are stabilized or practically eliminated (reduced to undetectable or insignificant levels) in the article.

Another added benefit of this invention is that the α-tocopherol doping can be carried out at elevated temperatures to shorten the diffusion time.

All of the embodiments are described with α-tocopherol as the antioxidant but any other antioxidant/free radical scavenger or mixtures of antioxidants/free radical scavengers also can be used.

According to one embodiment, the polymeric material is an article having a shape of an implant, a preform that can be machined to an implant shape, or any other shape.

In one embodiment, the polymeric article is prepared with antioxidant/anti-crosslinking agent-rich and antioxidant/anti-crosslinking agent-poor regions where the antioxidant/anti-crosslinking agent-poor regions are located at one or more of the surface (exterior regions) and the antioxidant/anti-crosslinking agent-rich regions are in the bulk (generally the interior regions).

An advantage of starting with antioxidant/anti-crosslinking agent-rich and antioxidant/anti-crosslinking agent-poor regions in the polymeric article is that the radiation cross-linking is primarily be limited to the antioxidant/anti-crosslinking agent-poor regions (in most embodiments the articular surfaces) and therefore the reduction in the mechanical properties of the implant due to cross-linking is minimized.

In another embodiment, the consolidated polymeric material is fabricated through direct compression molding (DCM). The DCM mold is filled with a combination of polyethylene resin, powder, or flake containing α-tocopherol and with virgin polyethylene resin, powder, or flake, which is without antioxidant/anti-crosslinking agent. The mold is then heated and pressurized to complete the DCM process. The concentration of antioxidant/anti-crosslinking agent in the initial antioxidant/anti-crosslinking agent-containing resin, powder, or flake may be sufficiently high to retain its (their) efficiency throughout the DCM process, and any subsequent irradiation and cleaning steps. In the antioxidant/anti-crosslinking agent-poor regions, the total concentration of antioxidant/anti-crosslinking agent is between about 0.0005 wt % and about 20 wt % or higher, preferably between about 0.005 wt % and about 5.0 wt %, preferably about 0.05 wt %, or preferably about 0.1 wt %. In the antioxidant/anti-crosslinking agent-rich regions, the total concentration of antioxidant/anti-crosslinking agent is between about 0.0005 wt % and about 20 wt % or higher, preferably between about 0.005 wt % and about 5.0 wt %, preferably about 1 wt %, or preferably about 2 wt %. The DCM mold is filled with either or both of the resins, powders, or flakes to tailor the distribution of the antioxidant/anti-crosslinking agent in the consolidated polymeric article. One issue is the diffusion of antioxidant/anti-crosslinking agent from the blended resin, powder, or flake regions to the virgin resin, powder, or flake regions, especially during consolidation where high temperatures and durations are typical. Any such diffusion would reduce the efficiency of subsequent cross-linking in the affected virgin resin, powder, or flake regions. One can control the diffusion process by tailoring the distribution of antioxidant/anti-crosslinking agent, by optimizing the type and content of antioxidant/anti-crosslinking agent in the rich and poor regions of the blended polymer, by reducing the temperature of consolidation, and/or reducing the time of consolidation.

In some embodiments, the antioxidant/anti-crosslinking agent-rich region is predominantly confined to the core of the polymeric article and the antioxidant/anti-crosslinking agent-poor polymeric material is predominantly confined to the outer shell whereby the thickness of the α-tocopherol-poor region is between about 0.01 mm and 20 mm, more preferably between about 1 mm and 5 mm, or more preferably about 3 mm.

In some embodiments, the outer layer is limited to only one or more faces of the polymeric article. For example a polymeric article is made through DCM process by compression molding two layers of polyethylene resin, powder, or flake, one containing 0.3 or 0.5 wt % α-tocopherol and one virgin with no α-tocopherol. The order in which the two resins, powders, or flakes are placed into the mold determines which faces of the polymeric article are α-tocopherol poor and the thickness of the α-tocopherol-poor region is determined by the amount of virgin resin, powder, or flake used. This polymeric article is subsequently irradiated, doped with α-tocopherol, homogenized, machined on one or more of the faces to shape a polymeric implant, packaged and sterilized. Alternatively, the polymeric article containing antioxidant/anti-crosslinking agent-rich and antioxidant/anti-crosslinking agent-poor regions is irradiated, then homogenized, machined on one or more of the faces to shape a medical implant, packaged and sterilized.

In some embodiments, the antioxidant/anti-crosslinking agent-rich region is molded from a blend of antioxidant/anti-crosslinking agent-containing resin, powder, or flake and virgin polyethylene resin, powder, or flake.

In some embodiments, the resin, powder, or flake containing antioxidant/anti-crosslinking agent and the virgin polyethylene resin, powder, or flake are dry-mixed prior to molding, thereby creating a distribution of antioxidant/anti-crosslinking agent-rich and antioxidant/anti-crosslinking agent-poor regions throughout the polymeric article.

In some embodiments, the antioxidant/anti-crosslinking agent-poor polymeric region is confined to the articular bearing surface of the implant.

In some embodiments, the resin, powder, or flake containing antioxidant/anti-crosslinking agent undergoes partial or complete consolidation prior to the DCM process. This preformed piece of antioxidant/anti-crosslinking agent-containing polymeric material allows more precise control over the spatial distribution of antioxidant/anti-crosslinking agent in the finished part. For example, the partially or completely consolidated resin, powder, or flake is placed in a mold surrounded by virgin resin, powder, or flake and further consolidated, creating a polymeric article with an antioxidant/anti-crosslinking agent-poor region on the outer shell and antioxidant/anti-crosslinking agent-rich region in the bulk of the polymeric article.

In another embodiment a polymeric component is fabricated through DCM as described above with spatially-controlled antioxidant/anti-crosslinking agent-rich and anti-oxidant/anti-crosslinking agent-poor regions. This component is subsequently treated by e-beam irradiation. E-beam irradiation is known to have a gradient cross-linking effect in the direction of the irradiation, but this is not always optimized in components which have curved surfaces, such as acetabular cups, where the cross-linking is different at different points on the articulating surface. The spatial distribution of antioxidant/anti-crosslinking agent-rich regions is used in conjunction with e-beam irradiation to create uniform surface cross-linking which gradually decreases to minimal cross-linking in the bulk. After irradiation, the polymeric component is doped with at least one antioxidant. This component is cross-linked and stabilized at the surface and transitions to the uncross-linked and stabilized material with increasing depth from the surface.

In some embodiments the antioxidant/anti-crosslinking agent/polymeric material blended resin, powder, or flake mixture has a very high antioxidant/anti-crosslinking agent concentration such that when this resin, powder, or flake mixture is consolidated with neat resin, powder, or flake there is a steep gradient of antioxidant/anti-crosslinking agent across the interface. The consolidated piece is then irradiated to cross-link the polymer preferably in the antioxidant/anti-crosslinking agent-poor region. Subsequently, the piece is heated to drive diffusion of at least one antioxidant from the antioxidant-rich bulk region to the antioxidant-poor surface region.

In some embodiments, a vitamin-E-polymeric material (for example, UHMWPE) blend and antioxidant/anti-crosslinking agent-poor polymeric resin, powder, or flake are molded together to create an interface. The quantities of the blend and/or the virgin resins are tailored to obtain a desired antioxidant/anti-crosslinking agent-poor polymeric material thickness. Alternatively, the molded piece/material is machined to obtain the desired thickness of the antioxidant/anti-crosslinking agent-poor polymeric layer. The machined-molded piece/material is irradiated followed by:
Either doping with vitamin E and homogenized below the melting point of the polymeric material,
or heated below the melt without doping to reduce the free radicals to as low as undetectable levels (for example, for different durations),
or heated below the melt for long enough duration, to diffuse the bulk antioxidant from the blend layer into the antioxidant-poor layer (for example, for different durations, different blend compositions are used to accelerate the diffusion from the blend region to the antioxidant-poor region),
or heated to a temperature above the melting point to reduce free radicals to as low as undetectable levels and/or improve toughness,
or high pressure crystallized/annealed, thereby forming a medical implant and/or device. The medical device can be used at this stage or can be machined further to obtain a net shaped implant. The device/implant also can be packaged and sterilized.

In another embodiment, the thickness of the antioxidant/anti-crosslinking agent-poor surface is determined by the final toughness of the polymeric material with a gradient crosslink density. For example, a polymeric material with a crosslinked surface layer thickness of 1 mm in a 6 mm-thick polymeric material has higher toughness that one with a crosslinked surface layer thickness of 2 mm.

A low threshold in the initial concentration profile of the antioxidant/anti-crosslinking agent in the consolidated polymeric material is determined below which the regions are designated as surface layers and a high threshold above which the regions are designated as bulk layers. These two thresholds can be the same or they can be different. In the case where they are different, the regions with values between these two thresholds are designated as the gradient interface.

Similarly, after radiation crosslinking, a low threshold in the crosslink density or wear rate profile is determined below which the regions are designated as low crosslinking and a high threshold is determined above which the regions are designated as highly crosslinked. The regions with values between these two thresholds are designated as the crosslink gradient.

In another embodiment, the antioxidant-doped or -blended polymeric material is homogenized at a temperature below the melting point of the polymeric material for a desired period of time, for example, the antioxidant-doped or -blended polymeric material is homogenized for about an hour to several days to one week or more than one week at room temperature to about 135° C. to 137° C. (for example for UHMWPE). Preferably, the homogenization is carried out above room temperature, preferably at about 90° C. to about 135° C., more preferably about 80° C. to about 100° C., more preferably about 120° C. to about 125° C., most preferably about 130° C.

In another embodiment, the antioxidant-doped or -blended polymeric material is homogenized at a temperature above the melting point of the polymeric material for a desired period of time, for example, the antioxidant-doped or -blended polymeric material is homogenized for about an hour to several days to one week or more than one week at room temperature to about 300° C. Preferably, the homogenization is carried out at about 140° C. to about 350° C., more preferably about 170° C. to about 300° C., more preferably about 280° C. to about 300° C., most preferably about 300° C.

A purpose of homogenization is to make the concentration profile of at least one additive throughout the interior of a consolidated polymeric material more spatially uniform. After doping of the polymeric material is completed, the consolidated polymeric material is removed from the bath of antioxidant and wiped thoroughly to remove excess antioxidant from the surfaces of the polymeric material. The polymeric material is kept in an inert atmosphere (nitrogen, argon, and/or the like) or in air during the homogenization process. The homogenization also can be performed in a chamber with supercritical fluids, such as carbon dioxide or the like.

In another embodiment, the DCM process is conducted with a metal piece that becomes an integral part of the consolidated polymeric article. For example, a combination of antioxidant/anti-crosslinking agent-containing polyethylene resin, powder, or flake and an antioxidant/anti-crosslinking agent-poor polyethylene resin, powder, or flake is direct compression molded into a metallic acetabular cup or a tibial base plate. The porous tibial metal base plate is placed in the mold, antioxidant/anti-crosslinking agent-rich polymeric resin, powder, or flake is added on top and then antioxidant/anti-crosslinking agent-poor polymeric resin, powder, or flake is added last, for example. After consolidation and irradiation, doping of the article with at least one antioxidant is optionally carried out to further stabilize the free radicals. Prior to the DCM consolidation, the pores of the metal piece can be filled with a waxy or plaster substance through half the thickness to achieve polyethylene interlocking through the other unfilled half of the metallic piece. The pore filler is maintained through the irradiation and subsequent antioxidant doping steps to prevent infusion of antioxidant in to the pores of the metal. In some embodiments, the article is machined after doping to shape an implant.

In another embodiment, there are more than one metal pieces integral to the polymeric article.

In another embodiment, one or some or all of the metal pieces integral to the polymeric article is a porous metal piece that allows bone in-growth when implanted into the human body.

In some embodiments, one or some or all of the metal pieces integral to the polymeric article is a non-porous metal piece.

In one embodiment, the consolidated polymeric article is irradiated using ionizing radiation such as gamma, electron-beam, or x-ray to a dose level between about 1 and about 10,000 kGy, preferably about 25 to about 250 kGy, preferably about 50 to about 150 kGy, preferably about 65 kGy, preferably about 85 kGy, or preferably about 100 kGy, or preferably about 150 kGy.

In another embodiment, the irradiated polymeric article is doped with at least one antioxidant by placing the article in an antioxidant bath at room temperature or at an elevated temperature for a given amount of time.

In another embodiment, the doped polymeric article is heated below the melting point of the polymeric article.

In one embodiment, the metal mesh of the implant is sealed using a sealant to prevent or reduce the infusion of antioxidant into the pores of the mesh during the selective doping of the implant. Preferably, the sealant is water soluble. But other sealants are also used. The final cleaning step that the implant is subjected to also removes the sealant. Alternatively, an additional sealant removal step is used. Such sealants as water, saline, aqueous solutions of water soluble polymers such as poly-vinyl alcohol, water soluble waxes, plaster of Paris, or others are used. In addition, a photoresist like SU-8, or other, may be cured within the pores of the porous metal component. Following processing, the sealant may be removed via an acid etch or a plasma etch.

In another embodiment, the polyethylene-porous metal mono-block is doped so that the polymeric material is fully immersed in antioxidant or antioxidant solution but the porous metal is either completely above the antioxidant solution surface or only partially immersed during doping. This reduces infusion of antioxidant into the pores of the metal mesh.

In yet another embodiment, the doped polymeric article is machined to form a medical implant. In some embodiments, the machining is carried out on sides with no metallic piece if at least one is present.

In many embodiments, the medical devices are packaged and sterilized.

In another aspect of the invention, the medical device is cleaned before packaging and sterilization.

In other embodiments, the antioxidant/anti-crosslinking agent, such as vitamin E, concentration profiles in device/implant components can be controlled in several different ways, following various processing steps and in different orders, for example:

I. Blending the antioxidant/anti-crosslinking agent and polyethylene resin, powder, or flakes, consolidating the blend, machining of implants, radiation cross-linking (at a temperature below the melting point of the polymeric material), and doping with at least one antioxidant;

II. Blending the antioxidant/anti-crosslinking agent and polyethylene resin, powder, or flakes, consolidating the blend, machining of implants, radiation cross-linking (at a temperature below the melting point of the polymeric material), doping with at least one antioxidant and homogenizing;

III. Blending the antioxidant/anti-crosslinking agent and polyethylene resin, powder, or flakes, consolidating the blend, machining of implants, radiation cross-linking (at a temperature below the melting point of the polymeric material), doping with at least one antioxidant and homogenizing, extracting/eluting out the excess antioxidant or at least a portion of the antioxidant;

IV. Blending the antioxidant/anti-crosslinking agent and polyethylene resin, powder, or flakes, consolidating the blend, machining of preforms, radiation cross-linking (at a temperature below the melting point of the polymeric material), doping with at least one antioxidant, machining of devices and implants;

V. Blending the antioxidant/anti-crosslinking agent and polyethylene resin, powder, or flakes, consolidating the blend, machining of preforms, radiation cross-linking (at a temperature below the melting point of the polymeric material), doping with at least one antioxidant and homogenizing, machining of devices and implants;

VI. Blending the antioxidant/anti-crosslinking agent and polyethylene resin, powder, or flakes, consolidating the blend, machining of preforms, radiation cross-linking (at a temperature below the melting point of the polymeric material), doping with at least one antioxidant and homogenizing, machining of implants, extraction of antioxidant;

VII. Radiation cross-linking of consolidated polymeric material (at a temperature below the melting point of the polymeric material), machining implant, doping with at least one antioxidant, extracting/eluting out the excess antioxidant or at least a portion of the antioxidant;

VIII. Radiation cross-linking of consolidated polymeric material (at a temperature below the melting point of the polymeric material), machining implants, doping with at least one antioxidant and homogenizing, extracting/eluting out the excess antioxidant or at least a portion of the antioxidant;

IX. Radiation cross-linking of consolidated polymeric material (at a temperature below the melting point of the polymeric material), machining preforms, doping with at least one antioxidant, extraction of the antioxidant, machining of devices and implants;

X. Radiation cross-linking of consolidated polymeric material (at a temperature below the melting point of the polymeric material), machining preforms, doping with at least one antioxidant and homogenizing, extracting/eluting out the excess antioxidant or at least a portion of the antioxidant, machining of devices and implants;

XI. Radiation cross-linking of consolidated polymeric material (at a temperature below the melting point of the polymeric material), machining preforms, doping with at least one antioxidant, machining of implants, extracting/eluting out the excess antioxidant or at least a portion of the antioxidant; and/or XII. Radiation cross-linking of consolidated polymeric material (at a temperature below the melting point of the polymeric material), machining preforms, doping with at least one antioxidant and homogenizing, machining of implants, homogenizing, extracting/eluting out the excess antioxidant or at least a portion of the antioxidant;

XIII. Blending the antioxidant/anti-crosslinking agent and polyethylene resin, powder, or flakes, consolidating the blend, radiation cross-linking, and machining of devices and implants;

XIV. Blending the antioxidant/anti-crosslinking agent and polyethylene resin, powder, or flakes, consolidating the blend, radiation cross-linking, machining of implants and doping with at least one antioxidant;

XV. Blending the antioxidant/anti-crosslinking agent and polyethylene resin, powder, or flakes, consolidating the blend, radiation cross-linking, doping with at least one antioxidant and machining of devices and implants;

XVI. Blending the antioxidant/anti-crosslinking agent and polyethylene resin, powder, or flakes, consolidating the blend, radiation cross-linking, machining of devices and implants, doping with at least one antioxidant and homogenizing;

XVII. Blending the antioxidant/anti-crosslinking agent and polyethylene resin, powder, or flakes, consolidating the blend, radiation cross-linking, doping with at least one antioxidant, homogenizing and machining of devices and implants;

XVIII. Blending the antioxidant/anti-crosslinking agent and polyethylene resin, powder, or flakes, consolidating the blend, partially extracting/eluting out antioxidant/anti-crosslinking agent; radiation cross-linking;

XIX. Blending the antioxidant/anti-crosslinking agent and polyethylene resin, powder, or flakes, consolidating the blend, machining of implants, partially extracting/eluting out antioxidant/anti-crosslinking agent; radiation cross-linking;

XX. Blending the antioxidant/anti-crosslinking agent and polyethylene resin, powder, or flakes, consolidating the blend, partially extracting/eluting out antioxidant/anti-crosslinking agent; machining of devices and implants and radiation cross-linking;

XXI. Blending the antioxidant/anti-crosslinking agent and polyethylene resin, powder, or flakes, consolidating the blend, partially extracting/eluting out antioxidant/anti-crosslinking agent; machining of implants, radiation cross-linking, doping with at least one antioxidant;

XXII. Blending the antioxidant/anti-crosslinking agent and polyethylene resin, powder, or flakes, consolidating the blend, partially extracting/eluting out antioxidant/anti-crosslinking agent; machining of devices and implants, radiation cross-linking, homogenizing;

XXIII. Blending the antioxidant/anti-crosslinking agent and polyethylene resin, powder, or flakes, consolidating the blend, partially extracting/eluting out antioxidant/anti-crosslinking agent; machining of devices and implants, radiation cross-linking, doping with at least one antioxidant and homogenizing;

XXIV. Blending the antioxidant/anti-crosslinking agent and polyethylene resin, powder, or flakes, consolidating the blend directly as devices and implants, and radiation cross-linking;

XXV. Blending the antioxidant/anti-crosslinking agent and polyethylene resin, powder, or flakes, consolidating the blend directly as devices and implants, partially extracting/eluting out antioxidant/anti-crosslinking agent and radiation cross-linking;

XXVI. Blending the antioxidant/anti-crosslinking agent and polyethylene resin, powder, or flakes, consolidating the blend directly as devices and implants, radiation cross-linking and homogenizing;

XXVII. Blending the antioxidant/anti-crosslinking agent and polyethylene resin, powder, or flakes, consolidating the blend directly as devices and implants, partially extracting/eluting out antioxidant/anti-crosslinking agent, radiation cross-linking and homogenizing.

In another embodiment, all of the above processes are further followed by cleaning, packaging and sterilization (gamma irradiation, e-beam irradiation, ethylene oxide or gas plasma sterilization).

Methods and Sequence of Irradiation:

The selective, controlled manipulation of polymers and polymer alloys using radiation chemistry can, in another aspect, be achieved by the selection of the method by which the polymer is irradiated. The particular method of irradiation employed, either alone or in combination with other aspects of the invention, such as the polymer or polymer alloy chosen, contribute to the overall properties of the irradiated polymer.

Gamma irradiation or electron radiation may be used. In general, gamma irradiation results in a higher radiation penetration depth than electron irradiation. Gamma irradiation, however, generally provides low radiation dose rate and requires a longer duration of time, which can result in more in-depth and extensive oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance less than 10 minutes. The penetration of the electron beam depends on the beam energy measured by million electron-volts (MeV). Most polymers exhibit a density of about 1 g/cm$^3$, which leads to the penetration of about 1 cm with a beam energy of 2-3 MeV and about 4 cm with a beam energy of 10 MeV. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

According to certain embodiments, the cross-linked polymeric material can have a melt history, meaning that the polymeric material is melted concurrently with or subsequent to irradiation for cross-linking. According to other embodiments, the cross-linked polymeric material has no such melt history.

Various irradiation methods including IMS, CIR, CISM (a.k.a. CIR-SM), WIR, and WIAM are defined and described in greater detail below for cross-linked polymeric materials with a melt history, that is irradiated with concurrent or subsequent melting:

(i) Irradiation in the Molten State (IMS):

Melt-irradiation (MIR), or irradiation in the molten state ("IMS"), is described in detail in U.S. Pat. No. 5,879,400. In the IMS process, the polymer to be irradiated is heated to at or above its melting point. Then, the polymer is irradiated. Following irradiation, the polymer is cooled.

Prior to irradiation, the polymer is heated to at or above its melting temperature and maintained at this temperature for a time sufficient to allow the polymer chains to achieve an entangled state. A sufficient time period may range, for example, from about 5 minutes to about 3 hours or to about 24 hours.

The temperature of melt-irradiation for a given polymer depends on the DSC (measured at a heating rate of 10° C./min during the first heating cycle) peak melting temperature ("PMT") for that polymer. In general, the irradiation temperature in the IMS process is at least about 2° C. higher than the PMT, more preferably between about 2° C. and about 20° C. higher than the PMT, and most preferably between about 5° C. and about 10° C. higher than the PMT.

Exemplary ranges of acceptable total dosages are disclosed in greater detail in U.S. Pat. Nos. 5,879,400, and 6,641,617, and International Application WO 97/29793. For example, preferably a total dose of about or greater than 1 MRad is used. More preferably, a total dose of greater than about 10 Mrad is used.

In electron beam IMS, some energy deposited by the electrons is converted to heat. This primarily depends on how well the sample is thermally insulated during the irradiation. With good thermal insulation, most of the heat generated is not lost to the surroundings and leads to the radiation generated heating (including adiabatic and partially adiabatic) of the polymer to a higher temperature than the irradiation temperature. The heating could also be induced by using a high enough dose rate to minimize the heat loss to the surroundings. In some circumstance, heating may be detrimental to the sample that is being irradiated. Gaseous by-products, such as hydrogen gas when the polymer is irradiated, are formed during the irradiation. During irradiation, if the heating is rapid and high enough to cause rapid expansion of the gaseous by-products, and thereby not allowing them to diffuse out of the polymer, the polymer may cavitate. The cavitation is not desirable in that it leads to the formation of defects (such as air pockets, cracks) in the structure that could in turn adversely affect the mechanical properties of the polymer and in vivo performance of the device made thereof.

The temperature rise depends on the dose level, level of insulation, and/or dose rate. The dose level used in the irradiation stage is determined based on the desired properties. In general, the thermal insulation is used to avoid cooling of the polymer and maintaining the temperature of the polymer at the desired irradiation temperature. Therefore, the temperature rise can be controlled by determining an upper dose rate for the irradiation.

In embodiments of the present invention in which electron radiation is utilized, the energy of the electrons can be varied to alter the depth of penetration of the electrons, thereby controlling the degree of cross-linking following irradiation. The range of suitable electron energies is disclosed in greater detail in U.S. Pat. Nos. 5,879,400, 6,641,617, and International Application WO 97/29793. In one embodiment, the energy is about 0.5 MeV to about 12 MeV. In another embodiment the energy is about 1 MeV to 10 MeV. In another embodiment, the energy is about 10 MeV.

(ii) Cold Irradiation (CIR):

Cold irradiation is described in detail in U.S. Pat. Nos. 6,641,617, 6,852,772, and WO 97/29793. In the cold irradiation process, a polymer is provided at room temperature or below room temperature. Preferably, the temperature of the polymer is about 20° C. Then, the polymer is irradiated. In one embodiment of cold irradiation, the polymer may be irradiated at a high enough total dose and/or at a fast enough dose rate to generate enough heat in the polymer to result in at least a partial melting of the crystals of the polymer.

Gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depths, but requires less time and, therefore, reduces the risk of extensive oxidation. Accordingly, gamma irradiation or electron irradiation may be used based upon the depth of penetration preferred, time limitations and tolerable oxidation levels.

The total dose of irradiation may be selected as a parameter in controlling the properties of the irradiated polymer. In particular, the dose of irradiation can be varied to control the degree of cross-linking in the irradiated polymer. The preferred dose level depends on the molecular weight of the polymer and the desired properties that can be achieved following irradiation. In general, increasing the dose level with CIR leads to an increase in wear resistance.

Exemplary ranges of acceptable total dosages are disclosed in greater detail in U.S. Pat. Nos. 6,641,617 and 6,852,772, International Application WO 97/29793, and in the embodiments below. In one embodiment, the total dose is about 0.5 MRad to about 1,000 Mrad. In another embodiment, the total dose is about 1 MRad to about 100 MRad. In yet another embodiment, the total dose is about 4 MRad to about 30 MRad. In still other embodiments, the total dose is about 20 MRad or about 15 MRad.

If electron radiation is utilized, the energy of the electrons also is a parameter that can be varied to tailor the properties of the irradiated polymer. In particular, differing electron energies results in different depths of penetration of the electrons into the polymer. The practical electron energies range from about 0.1 MeV to 16 MeV giving approximate iso-dose penetration levels of 0.5 mm to 8 cm, respectively. A preferred electron energy for maximum penetration is about 10 MeV, which is commercially available through vendors such as Studer (Daniken, Switzerland) or E-Beam Services (New Jersey, USA). The lower electron energies may be preferred for embodiments where a surface layer of the polymer is preferentially cross-linked with gradient in cross-link density as a function of distance away from the surface.

(iii) Warm Irradiation (WIR):

Warm irradiation is described in detail in U.S. Pat. No. 6,641,617 and WO 97/29793. In the warm irradiation process, a polymer is provided at a temperature above room temperature and below the melting temperature of the polymer. Then, the polymer is irradiated. In one embodiment of warm irradiation, it has been termed "warm irradiation adiabatic melting" or "WIAM." In a theoretical sense, adiabatic means an absence of heat transfer to the surroundings. In a practical sense, which applies here, such heating can be achieved by the combination of insulation, irradiation dose rates and irradiation time periods, as disclosed herein and in the documents cited herein. However, there are situations where irradiation causes heating, but there is still a loss of energy to the surroundings. Also, not all warm irradiation refers to an adiabatic. Warm irradiation also can have non-adiabatic or partially (such as about 10-75% of the heat generated is lost to the surroundings) adiabatic heating. In all embodiments of WIR, the polymer may be irradiated at a high enough total dose and/or a high enough dose rate to generate enough heat in the polymer to result in at least a partial melting of the crystals of the polymer, meaning some but not all molecules transition from the crystalline to the amorphous state.

The polymer may be provided at any temperature below its melting point but preferably above room temperature. The temperature selection depends on the specific heat and the enthalpy of melting of the polymer and the total dose level used. The equation provided in U.S. Pat. No. 6,641,617 and International Application WO 97/29793 may be used to calculate the preferred temperature range with the criterion that the final temperature of polymer maybe below or above the melting point. Preheating of the polymer to the desired temperature may be done in an inert (such as under nitrogen, argon, neon, or helium, or the like, or a combination thereof) or non-inert environment (such as air).

In general terms, the pre-irradiation heating temperature of the polymer can be adjusted based on the peak melting temperature (PMT) measure on the DSC at a heating rate of 10° C./min during the first heat. In one embodiment the polymer is heated to about 20° C. to about PMT. In another embodiment, the polymer is pre-heated to about 90° C. In another embodiment, the polymer is heated to about 100° C. In another embodiment, the polymer is pre-heated to about 30° C. below PMT and 2° C. below PMT. In another embodiment, the polymer is pre-heated to about 12° C. below PMT. The polymer can be pre-heated to up to 300° C. before irradiation and cooled down to initial irradiation temperature.

In the WIAM embodiment of WIR, the temperature of the polymer following irradiation is at or above the melting temperature of the polymer. Exemplary ranges of acceptable temperatures following irradiation are disclosed in greater detail in U.S. Pat. No. 6,641,617 and International Application WO 97/29793. In one embodiment, the temperature following irradiation is about room temperature to PMT, or about 40° C. to PMT, or about 100° C. to PMT, or about 110° C. to PMT, or about 120° C. to PMT, or about PMT to about 200° C. These temperature ranges depend on the polymer's PMT and is much higher with reduced level of hydration. In another embodiment, the temperature following irradiation is about 145° C. to about 190° C. In yet another embodiment, the temperature following irradiation is about 145° C. to about 190° C. In still another embodiment, the temperature following irradiation is about 150° C.

In WIR, gamma irradiation or electron radiation may be used. In general, gamma irradiation results in a higher dose penetration depth than electron irradiation. Gamma irradiation, however, generally requires a longer duration of time, which can result in more in-depth oxidation, particularly if the gamma irradiation is carried out in air. Oxidation can be reduced or prevented by carrying out the gamma irradiation in an inert gas, such as nitrogen, argon, neon, or helium, or under vacuum. Electron irradiation, in general, results in more limited dose penetration depths, but requires less time and, therefore, reduces the risk of extensive oxidation. Accordingly, gamma irradiation or electron irradiation may be used based upon the depth of penetration preferred, time limitations and tolerable oxidation levels. In the WIAM embodiment of WIR, electron radiation is used.

The total dose of irradiation may also be selected as a parameter in controlling the properties of the irradiated polymer. In particular, the dose of irradiation can be varied to control the degree of cross-linking in the irradiated polymer. Exemplary ranges of acceptable total dosages are disclosed in greater detail in U.S. Pat. No. 6,641,617 and International Application WO 97/29793.

The dose rate of irradiation also may be varied to achieve a desired result. The dose rate is a prominent variable in the WIAM process. The preferred dose rate of irradiation would be to administer the total desired dose level in one pass under the electron-beam. One also can deliver the total dose level with multiple passes under the beam, delivering a (equal or unequal) portion of the total dose at each time. This would lead to a lower effective dose rate.

Ranges of acceptable dose rates are exemplified in greater detail in U.S. Pat. No. 6,641,617 and International Application WO 97/29793. In general, the dose rates vary between 0.5 Mrad/pass and 50 Mrad/pass. The upper limit of the dose rate depends on the resistance of the polymer to cavitation/cracking induced by the irradiation.

If electron radiation is utilized, the energy of the electrons also is a parameter that can be varied to tailor the properties of the irradiated polymer. In particular, differing electron energies result in different depths of penetration of the electrons into the polymer. The practical electron energies range from about 0.1 MeV to 16 MeV giving approximate iso-dose penetration levels of 0.5 mm to 8 cm, respectively. The preferred electron energy for maximum penetration is about 10 MeV, which is commercially available through vendors such as Studer (Daniken, Switzerland) or E-Beam Services New Jersey, USA). The lower electron energies may be preferred for embodiments where a surface layer of the polymer is preferentially cross-linked with gradient in cross-link density as a function of distance away from the surface.

(iv) Subsequent Heating—Substantial Reduction of Detectable Residual Free Radicals:

Depending on the polymer or polymer alloy used, and whether the polymer was irradiated below its melting point, there may be residual free radicals left in the material following the irradiation process. A polymer irradiated below its melting point with ionizing radiation contains cross-links as well as long-lived trapped free radicals. Some of the free radicals generated during irradiation become trapped in the crystalline regions and/or at crystalline lamellae surfaces leading to oxidation-induced instabilities in the long-term (see Kashiwabara, H. S. Shimada, and Y. Hori, *Radiat. Phys. Chem.*, 1991, 37(1): p. 43-46; Jahan, M. S. and C. Wang, *Journal of Biomedical Materials Research*, 1991, 25: p. 1005-1017; Sutula, L. C., et al., *Clinical Orthopedic Related Research*, 1995, 3129: p. 1681-1689). The elimination of these residual, trapped free radicals through heating can be, therefore, desirable in precluding long-term oxidative instability of the polymer. Jahan M. S. and C. Wang, *Journal of Biomedical Materials Research*, 1991, 25: p. 1005-1017; Sutula, L. C., et al., *Clinical Orthopedic Related Research*, 1995, 319: p. 28-4. For polymer blends with antioxidants, it may also be desirable to reduce residual free radicals to preserve the efficiency and activity of the antioxidant(s).

Residual free radicals may be reduced by heating the polymer above the melting point of the polymer used. The heating allows the residual free radicals to recombine with each other. If for a given system the preform does not have substantially any detectable residual free radicals following irradiation, then a later heating step may be omitted. Also, if for a given system the concentration of the residual free radicals is low enough to not lead to degradation of device performance, the heating step may be omitted.

The reduction of free radicals to the point where there are substantially no detectable free radicals can be achieved by heating the polymer to above the melting point. The heating provides the molecules with sufficient mobility so as to eliminate the constraints derived from the crystals of the polymer, thereby allowing essentially all of the residual free radicals to recombine. Preferably, the polymer is heated to a temperature between the peak melting temperature (PMT) and degradation temperature ($T_d$) of the polymer, more preferably between about 3° C. above PMT and $T_d$, more preferably between about 10° C. above PMT and 340° C., more preferably between about 10° C. and 12° C. above PMT and most preferably about 15° C. above PMT. The elongation of the polymeric materials may be increased when heated to about 300° C.

In certain embodiments, there may be an acceptable level of residual free radicals in which case, the post-irradiation annealing also can be carried out below the melting point of the polymer, the effects of such free radicals can be minimized or eliminated by an antioxidant.

(v) Sequential Irradiation:

The polymer is irradiated with either gamma or e-beam radiation in a sequential manner. With e-beam the irradiation is carried out with multiple passes under the beam and with gamma radiation the irradiation is carried out in multiple passes through the gamma source. Optionally, the polymer is thermally treated in between each or some of the irradiation passes. The thermal treatment can be heating below the melting point or at the melting point of the polymer. The irradiation at any of the steps can be warm irradiation, cold irradiation, or melt irradiation, or any combination thereof. For example the polymer is irradiated with 30 kGy at each step of the cross-linking and it is first heated to about 120° C. and then annealed at about 120° C. for about 5 hours after each irradiation cycle.

(vi) Blending and Doping:

As stated above, the cross-linked polymeric material can optionally have a melt history, meaning it is melted before, concurrent with or subsequent to irradiation. The polymeric material can be blended with an antioxidant prior to consolidation and irradiation. Also, the consolidated polymeric material can be doped with an antioxidant prior to or after irradiation, and optionally can have been melted before, concurrent with or subsequent to irradiation. Furthermore, a polymeric material can both be blended with an antioxidant prior to consolidation and doped with an antioxidant after consolidation (before or after irradiation and optional melting). The polymeric material can be subjected to extraction at different times during the process, and can be extracted multiple times as well.

The polymeric material can be blended with any of the antioxidants, including alpha-ocopherol (such as vitamin E), delta-tocopherol; propyl, octyl, or dedocyl gallates; lactic, citric, ascorbic, tartaric acids, and organic acids, and their salts; orthophosphates; tocopherol acetate; lycopene; or a combination thereof. Other possible antioxidants are given under the definition of 'antioxidant'.

High temperature melting of UHMWPE can serve several different purposes. One is the transformation of the crystalline regions to amorphous such that when an irradiated material is recrystallized, the residual free radicals in the crystalline regions have been eliminated. Another purpose is the increase in chain entanglement, increasing the ductility of the melted material. A third is the creation of increased chain ends (as observed by increased vinyl index), creating cross-linkable moieties in the material. Interestingly, when a high temperature melted UHMWPE is subsequently irradiated, the cross-link density is decreased compared to a non-high temperature melted and irradiated UHMWPE but the wear rate is lower. Unlike melting below 200° C., where the duration of melting has little or no effect on mechanical or subsequent radiation cross-linking properties, high temperature melting above 200° C. results in strong time- and temperature-dependence of the resultant properties. In addition, the cross-link density of the prior or subsequently irradiated UHMWPE is dependent on the temperature and duration of the high temperature melting. Since high temperature melting can change the morphology of the polymer and the distribution of entanglements and cross-links, high temperature melting after high pressure crystallization can also result in a different material than melting below 200° C.

The resulting properties of high temperature melted UHMWPE is also dependent on the environment of the melting process, i.e. contact with air when the material is above 200° C. changes the properties dramatically. The inclusion of an antioxidant is preferred during high temperature melting and can hinder some of the effects of air exposure on the mechanical and wear properties.

In addition, the effect of a free radical scavenger/antioxidant together with high temperature melting has various effects on prior or subsequently irradiated UHMWPE. For example, vitamin E hinders radiation cross-linking as a function of concentration when present in UHMWPE during irradiation, and the wear rate of this UHMWPE is increased when compared to UHMWPE irradiated without vitamin E. In contrast, high temperature melting decreases the wear rate of irradiated UHMWPE despite a decrease in cross-link density. Therefore, combinations of vitamin E and high temperature melting processes before and after radiation cross-linking can be optimized to result in a variety of materials with low wear and high ductility. Also, spatial control of a non-uniform vitamin E concentration or a non-uniform high temperature melting profile can result in a material with non-uniform cross-linking, ductility, wear resistance and toughness and can be tailored according to the application.

Definitions and Other Embodiments

The term "toughness" of a material refers to its ability to distribute an applied stress such that failure does not occur until there are very high stresses. It is quantified by the area under the stress-strain curve of a material. For example, a higher work-to-failure, which is the area under the engineering stress-strain curve obtained from tensile mechanical testing is attributed directly to increased toughness. For example, toughness also refers to impact toughness, which is the work-to-failure as measured by impact testing. In the examples, this is demonstrated by IZOD impact testing according to ASTM F648.

"Ductility" refers to the ability of a material to plastically deform under stress. Ductility can be quantified as the total energy absorbed by plastic deformation; i.e. the area under the curve of the plastic segment of the engineering stress-strain curve. In the examples, increased elongation to break is attributed to increased ductility since the yield strength of these materials are relatively similar.

"Antioxidant" refers to what is known in the art as (see, for example, WO 01/80778, U.S. Pat. No. 6,448,315). Alpha- and delta-tocopherol; propyl, octyl, or dedocyl gallates; lactic, citric, ascorbic, tartaric acids, and organic acids, and their salts; orthophosphates, lycopene, tocopherol acetate are generally known form of antioxidants. Antioxidants are also referred as free radical scavengers, include: glutathione, lipoic acid, vitamins such as ascorbic acid (vitamin C), vitamin B, vitamin D, vitamin-E, tocopherols (synthetic or natural, alpha-, gamma-, delta-), acetate vitamin esters, water soluble tocopherol derivatives, tocotrienols, water soluble tocotrienol derivatives; melatonin, carotenoids, including various carotenes, lutein, pycnogenol, glycosides, trehalose, polyphenols and flavonoids, quercetin, lycopene, lutein, selenium, nitric oxide, curcuminoids, 2-hydroxytetronic acid; cannabinoids, synthetic antioxidants such as tertiary butyl hydroquinone, 6-amino-3-pyrodinoles, butylated hydroxyanisole, butylated hydroxytoluene, ethoxyquin, tannins, propyl gallate, other gallates, Aquanox family; Irganox® and Irganox® B families including Irganox® 1010, Irganox® 1076, Irganox® 1330; Irgafos® family including Irgafos® 168; phenolic compounds with different chain lengths, and different number of OH groups; enzymes with antioxidant properties such as superoxide dismutase, herbal or plant extracts with antioxidant properties such as St. John's Wort, green tea extract, grape seed extract, rosemary, oregano extract, mixtures, derivatives, analogues or conjugated forms of these. Antioxidants/free radical scavengers can be primary antioxidants with reactive OH or NH groups such as hindered phenols or secondary aromatic amines, they can be secondary antioxidants such as organophosphorus compounds or thiosynergists, they can be multifunctional antioxidants, hydroxylamines, or carbon centered radical scavengers such as lactones or acrylated bis-phenols. The antioxidants can be selected individually or used in any combination.

Irganox®, as described herein refers to a family of antioxidants manufactured by Ciba Specialty Chemicals. Different antioxidants are given numbers following the Irganox® name, such as Irganox® 1010, Irganox® 1035, Irganox® 1076, Irganox® 1098, etc. Irgafos® refers to a family of processing stabilizers manufactured by Ciba Specialty Chemicals. Irganox® family has been expanded to include blends of different antioxidants with each other and with stabilizers from different families such as the Irgafos family. These have been given different initials after the Irganox® name, for instance, the Irganox® HP family are synergistic combinations of phenolic antioxidants, secondary phosphate stabilizers and the lactone Irganox® HP-136. Similarly, there are Irganox® B (blends), Irganox® L (aminic), Irganox® E (with vitamin E), Irganox® ML, Irganox® MD families. Herein we discuss these antioxidants and stabilizers by their tradenames, but other chemicals with equivalent chemical structure and activity can be used. Addition, these chemicals can be used individually or in mixtures of ant composition. Some of the chemical structures and chemical names of the antioxidants in the Irganox® family are listed in Table 23.

"Anti-crosslinking agent" is a chemical compound which reduces the resultant cross-link density as a result of cross-linking processes in the polymer such as ionizing radiation exposure when it is blended with the polymer. Anti-crosslinking agents can be antioxidants as well. They can act when they are present in the polymer at any concentration or they may be activated when they are present at a threshold concentration or they may act only when activated by an additional additive.

"Supercritical fluid" refers to what is known in the art, for example, supercritical propane, acetylene, carbon dioxide ($CO_2$). In this connection the critical temperature is that temperature above which a gas cannot be liquefied by pressure alone. The pressure under which a substance may exist as a gas in equilibrium with the liquid at the critical temperature is the critical pressure. Supercritical fluid condition generally means that the fluid is subjected to such a temperature and such a pressure that a supercritical fluid and thereby a supercritical fluid mixture is obtained, the temperature being above the supercritical temperature, which for $CO_2$ is 31.3° C., and the pressure being above the supercritical pressure, which for $CO_2$ is 73.8 bar. More specifically, supercritical condition refers to a condition of a mixture, for example, UHMWPE with an antioxidant, at an elevated temperature and pressure, when a supercritical fluid mixture is formed; and then evaporate $CO_2$ from the mixture, UHMWPE doped with an antioxidant is obtained (see, for example, U.S. Pat. No. 6,448,315 and WO 02/26464). Other supercritical fluids can be chosen from the group of water, chloroform, nitric oxide, elementary gasses such as argon, nitrogen, organic compounds such as acetic acid, benzene, ethanol, ethylene oxide, methanol, methyl ethyl ketone, monolefins such as ethylene, propylene, or paraffins such as ethane, methane, propane, n-butane, n-heptane. A co-solvent or a mixture of fluids can be used.

The term "compression molding" as referred herein related generally to what is known in the art and specifically relates to high temperature molding polymeric material wherein polymeric material is in any physical state, including resin, powder, or flake form, is compressed into a slab form or mold of a medical implant, for example, a tibial insert, an acetabular liner, a glenoid liner, a patella, or an unicompartmental insert, an interpositional device for any joint can be machined.

The term "layered molding" refers to consolidating a polymeric material by compression molding one or more of its resin forms, which may be in the form of flakes, powder, pellets or the like or consolidated forms in layers such that there are distinct regions in the consolidated form containing different concentrations of constituents. These resin forms include blends of the polymeric material with other polymers in their resin forms and other chemicals such as antioxidants. The antioxidants could be blended with the polymeric material in solid, liquid, or solution form. Examples of such layered molded polymeric material are shown in FIGS. 42A, 46A-46G, 47A-47C, 68A-68H and 69A-69B.

Whenever a layered-molded UHMWPE is described in the examples below and is used in any of the embodiments it can be fabricated by:
1. layered molding of UHMPWE resin powder or its antioxidant/anti-crosslinking agent blends where
   a. one or more layers contain no antioxidant or anti-crosslinking agent and one or more layers contain one or more additives, antioxidants and/or anti-crosslinking agents, or
   b. one or more layers contain one or more antioxidants and/or anti-crosslinking agents and one or more layers contain one or more antioxidants and/or anti-crosslinking agents where in the concentration of at least one antioxidant/anti-crosslinking agent is higher in one layer than another, or
   c. at least one layer contains an antioxidant from the Irganox® family and another contains vitamin E, or
   d. at least one layer contains Irganox® 1010 and another contains vitamin E, or
   e. at least one layer contains Irganox® 1010 and a second contains Irganox® 1010 at a higher concentration;
2. molding together of previously molded layers of UHMWPE containing different or identical concentration of antioxidants/anti-crosslinking agents where
   a. one or more layers contain no antioxidant or anti-crosslinking agent and one or more layers contain one or more additives, antioxidants and/or anti-crosslinking agents, or b. one or more layers contain one or more antioxidants and/or anti-crosslinking agents and one or more layers contain one or more antioxidants and/or anti-crosslinking agents where in the concentration of at least one antioxidant/anti-crosslinking agent is higher in one layer than another, or c. at least one layer contains an antioxidant from the Irganox® family and another contains vitamin E, or d. at least one layer contains Irganox® 1010 and another contains vitamin E, or e. at least one layer contains Irganox® 1010 and a second contains Irganox® 1010 at a higher concentration; and/or 3. molding of UHMWPE resin powder with or without antioxidant/anti-crosslinking agent on to a at least one previously molded UHMWPE with or without antioxidant/anti-crosslinking agent where a. one or more layers contain no antioxidant or anti-crosslinking agent and one or more layers contain one or more additives, antioxidants and/or anti-crosslinking agents, or b. one or more layers contain one or more antioxidants and/or anti-crosslinking agents and one or more layers contain one or more antioxidants and/or anti-crosslinking agents where in the concentration of at least one antioxidant/anti-crosslinking agent is higher in one layer than another, or c. at least one layer contains an antioxidant from the Irganox® family and another contains vitamin E, or d. at least one layer contains Irganox® 1010 and another contains vitamin E, or e. at least one layer contains Irganox® 1010 and a second contains Irganox® 1010 at a higher concentration.

Layered molding can be done using parallel plates or any plate/mold geometry which directly result in an implant or implant preform, i.e. direct compression molding. It can also be done such that the polymeric material is directly layered compression molded onto a second surface, for example a porous metal to result in an implant or implant preform. An implant preform is a material, which after slight modification such as machining results in an implant. Preforms are generally oversized versions of implants, where machining from the surfaces gives the final implant surfaces.

The molding process generally involves
(i) heating the layers to be molded,
(ii) pressurizing them together while heated,
(iii) keeping at temperature and pressure, and
(iv) cooling down and releasing pressure.

The order of cooling and pressure release can be used interchangeably. In some embodiments the cooling and pressure release my follow varying rates independent form each other.

The layers to be molded can be heated in water, air, inert gas or any environment containing a mixture of gases or supercritical fluids before pressurization. The layers can be pressurized individually at room temperature or at an elevated temperature below the melting point or above the melting point before being molded together. The temperature at which the layers are pre-heated can be the same or different from the molding temperature. The temperature can be gradually increased from pre-heat to mold temperature with or without pressure. The pressure to which the layers are exposed before molding can be gradually increased or increased and maintained at the same level.

During molding, different regions of the mold can be heated to different temperatures. The temperature and pressure can be maintained during molding for 1 second up to 1000 hours or longer.

During cool-down under pressure, the pressure can be maintained at the molding pressure or increased or decreased. The cooling rate can be 0.0001° C./minute to 120° C./minute or higher. The cooling rate can be different for different regions of the mold. After cooling down to about room temperature, the mold can be kept under pressure for 1 second to 1000 hours. Or the pressure can be released partially or completely at an elevated temperature.

The term "direct compression molding" (DCM) as referred herein related generally to what is known in the art and specifically relates to molding applicable in polyethylene-based devices, for example, medical implants wherein polyethylene in any physical state, including resin, powder, or flake form, is compressed to solid support, for example, a metallic back, metallic mesh, or metal surface containing grooves, undercuts, or cutouts. The compression molding also includes high temperature compression molding of polyethylene at various states, including resin, powder, flakes and particles, to make a component of a medical implant, for example, a tibial insert, an acetabular liner, a glenoid liner, a patella, an interpositional device for any joint or an unicompartmental insert.

The term "Mechanical deformation" refers to a deformation taking place below the melting point of the material, essentially 'cold-working' the material. The deformation modes include uniaxial, channel flow, uniaxial compression, biaxial compression, oscillatory compression, tension, uniaxial tension, biaxial tension, ultra-sonic oscillation, bending, plane stress compression (channel die), torsion or a combination of any of the above. The deformation could be static or dynamic. The dynamic deformation can be a combination of the deformation modes in small or large amplitude oscillatory fashion. Ultrasonic frequencies can be used. All deformations can be performed in the presence of sensitizing gases and/or at elevated temperatures.

The term "deformed state" refers to a state of the polymeric material following a deformation process, such as a mechanical deformation, as described herein, at solid or at melt. Following the deformation process, deformed polymeric material at a solid state or at melt is be allowed to solidify/crystallize while still maintains the deformed shape or the newly acquired deformed state.

"IBMA" refers to irradiation below the melt and mechanical annealing. "IBMA" was formerly referred to as "CIMA" (Cold Irradiation and Mechanically Annealed).

The term "mechanically interlocked" refers generally to interlocking of polymeric material and the counterface, that are produced by various methods, including compression molding, heat and irradiation, thereby forming an interlocking interface, resulting into a 'shape memory' of the interlocked polymeric material. Components of a device having such an interlocking interface can be referred to as a "hybrid material". Medical implants having such a hybrid material contain a substantially sterile interface.

The term "substantially sterile" refers to a condition of an object, for example, an interface or a hybrid material or a medical implant containing interface(s), wherein the interface is sufficiently sterile to be medically acceptable, i.e., will not cause an infection or require revision surgery.

"Metallic mesh" refers to a porous metallic surface of various pore sizes, for example, 0.1-3 mm. The porous surface can be obtained through several different methods, for example, sintering of metallic powder with a binder that is subsequently removed to leave behind a porous surface; sintering of short metallic fibers of diameter 0.1-3 mm; or sintering of different size metallic meshes on top of each other to provide an open continuous pore structure.

"Bone cement" refers to what is known in the art as an adhesive used in bonding medical devices to bone. Typically, bone cement is made out of polymethylmethacrylate (PMMA). Bone cement can also be made out of calcium phosphate.

"High temperature compression molding" refers to the compression molding of polymeric material in any form, for example, resin, powder, flakes or particles, to impart new geometry under pressure and temperature. During the high temperature (above the melting point of polymeric material) compression molding, polymeric material is heated to above its melting point, pressurized into a mold of desired shape and allowed to cool down under pressure to maintain a desired shape.

"Shape memory" refers to what is known in the art as the property of polymeric material, for example, an UHMWPE, that attains a preferred high entropy shape when melted. The preferred high entropy shape is achieved when the resin, powder, or flake is consolidated through compression molding.

The phrase "substantially no detectable residual free radicals" refers to a state of a polymeric component, wherein enough free radicals are eliminated to avoid oxidative degradation, which can be evaluated by electron spin resonance (ESR). The phrase "detectable residual free radicals" refers to the lowest level of free radicals detectable by ESR or more. The lowest level of free radicals detectable with state-of-the-art instruments is about $10^{14}$ spins/gram and thus the term "detectable" refers to a detection limit of about $10^{14}$ spins/gram by ESR. Thus, the term 'undetectable' refers to values below this limit.

The terms "about" or "approximately" in the context of numerical values and ranges refers to values or ranges that approximate or are close to the recited values or ranges such that the invention can perform as intended, such as utilizing a method parameter (e.g., time, dose, dose rate/level, and temperature), having a desired degree of cross-linking and/or a desired lack of or quenching of free radicals, as is apparent to the skilled person from the teachings contained herein. This is due, at least in part, to the varying properties of polymer compositions. Thus, these terms encompass values beyond those resulting from systematic error. These terms make explicit what is implicit, as known to the person skilled in the art.

All ranges set forth herein in the summary and description of the invention include all numbers or values thereabout or therebetween of the numbers of the range. The ranges of the invention expressly denominate and set forth all integers, decimals and fractional values in the range. For example, the radiation dose can be about 50 kGy, about 65 kGy, about 75 kGy, about 100 kGy, about 200 kGy, about 300 kGy, about 400 kGy, about 500 kGy, about 600 kGy, about 700 kGy, about 800 kGy, about 900 kGy, or about 1000 kGy, or above 1000 kGy, or any integer, decimal or fractional value thereabout or therebetween.

"Polymeric materials" or "polymer" include polyethylene, for example, Ultra-high molecular weight polyethylene (UHMWPE) refers to linear non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHMWPE starting material, prior to any irradiation. See U.S. Pat. No. 5,879,400, PCT/US99/16070, filed on Jul. 16, 1999, and PCT/US97/02220, filed Feb. 11, 1997. The term "polyethylene article" or "polymeric article" or "polymer" generally refers to articles comprising any "polymeric material" disclosed herein.

"Polymeric materials" or "polymer" also include hydrogels, such as poly (vinyl alcohol), poly (acrylamide), poly (acrylic acid), polyethylene glycol), blends thereof, or interpenetrating networks thereof, which can absorb water such that water constitutes at least 1 to 10,000% of their original weight, typically 100 wt % of their original weight or 99% or less of their weight after equilibration in water.

"Polymeric material" or "polymer" can be in the form of resin, flakes, powder, consolidated stock, implant, and can contain additives such as antioxidants). The "polymeric material" or "polymer" also can be a blend of one or more of different resin, flakes or powder containing different concentrations of an additive such as an antioxidant. The blending of resin, flakes or powder can be achieved by the blending techniques known in the art. The "polymeric material" also can be a consolidated stock of these blends.

"Blending" generally refers to mixing of a polyolefin in its pre-consolidated form with an additive. If both constituents are solid, blending can be done dry or by using a third component such as a liquid to mediate the mixing of the two components, after which the liquid is removed by evaporating ('solvent blending'). If the additive is liquid, for example α-tocopherol, then the solid can be mixed with large quantities of liquid, then diluted down to desired concentrations with the solid polymer to obtain uniformity in the blend. In the case where an additive is also an antioxidant, for example vitamin E, or α-tocopherol, then blended polymeric material is also antioxidant-doped. Polymeric material, as used herein, also applies to blends of a polyolefin and a plasticizing agent, for example a blend of UHMWPE resin powder blended with α-tocopherol and consolidated. Polymeric material, as used herein, also applies to blends of an additive, a polyolefin and a plasticizing agent, for example UHMWPE soaked in α-tocopherol.

In one embodiment UHMWPE flakes are blended with α-tocopherol; preferably the UHMWPE/α-tocopherol blend is heated to diffuse the α-tocopherol into the flakes. The UHMWPE/α-tocopherol blend is further blended with virgin UHMWPE flakes to obtain a blend of UHMWPE flakes where some flakes are poor in α-tocopherol and others are rich in α-tocopherol. This blend is then consolidated and irradiated. During irradiation the α-tocopherol poor regions are more highly cross-linked than the α-tocopherol poor regions. Following irradiation the blend is homogenized to diffuse α-tocopherol from the α-tocopherol rich to α-tocopherol poor regions and achieve oxidative stability throughout the polymer.

The products and processes of this invention also apply to various types of polymeric materials, for example, any polypropylene, any polyamide, any polyether ketone, or any polyolefin, including high-density-polyethylene, low-density-polyethylene, linear-low-density-polyethylene, ultra-high molecular weight polyethylene (UHMWPE), copolymers or mixtures thereof. The products and processes of this invention also apply to various types of hydrogels, for example, poly(vinyl alcohol), polyethylene glycol), polyethylene oxide), poly(acrylic acid), polymethacrylic acid), polyacrylamide), copolymers or mixtures thereof, or copolymers or mixtures of these with any polyolefin. Polymeric materials, as used herein, also applies to polyethylene of various forms, for example, resin, powder, flakes, particles, powder, or a mixture thereof, or a consolidated form derived from any of the above. Polymeric materials, as used herein, also applies to hydrogels of various forms, for example, film, extrudate, flakes, particles, powder, or a mixture thereof, or a consolidated form derived from any of the above.

Blending of additives in the polymeric material resin can be done by:
1. Dissolving an antioxidant/anti-crosslinking agent in a solvent or a mixture of solvents,
2. Mixing the polymer resin with the antioxidant/anti-crosslinking agent solution,
3. Drying the solvent by evaporation, optionally using elevated temperature or vacuum.

Solvents can be chosen from organic solvents such as acetic acid, acetone, acetonitrile, benzene, butanols, butanone, carbon tetrachloride, chlorobenzene, chloroform, cyclohexane, 1,2-dicholoethane, diethyl ether, diethylene glycol, diethylene glycol diethyl ether, 1,2-dimethoxyethane, dimethyl ether, dimethylformamide, dimethyl sulfoxide, dioxane, ethanol, ethyl acetate, ethylene glycol, glycerin, heptane, hexane, methanol, pentane, propanols, pyridine, tetrahydrofuran, toluene, xylene or they can be aqueous solvents. Aqueous solvents can be pure water or solution of other compounds such as acids, salts, or bases in water. They can be aqueous solutions of surfactants (generally amphiphilic compounds) such as fatty acids. They can also be inorganic nonaqueous solvents such as liquid alumina. Solvent can also be a supercritical fluid such as supercritical carbon dioxide.

The solvent is typically selected depending on the solubility of the antioxidants/anti-crosslinking agents desired to be blended into the polymer. The polymer resin can optionally dissolve in the same solvent. Different antioxidants/anti-crosslinking agents can be dissolved in different solvents and mixed together before mixing in the polymer or can be separately mixed with the polymer powder. In each case more than one solvent can be used. Dissolution of the antioxidants/anti-crosslinking agents can be enhanced or enabled by raising the temperature or pressure or raising the temperature and pressure such that the solvent is in the supercritical state.

The term "additive" refers to any material that can be added to a base polymer in less than 50 v/v %. This material can be organic or inorganic material with a molecular weight less than that of the base polymer. An additive can impart different properties to the polymeric material, for example, it can be a plasticizing agent, a nucleating agent, or an antioxidant.

The term "plasticizing agent" refers to what is known in the art, a material with a molecular weight less than that of the base polymer, for example vitamin E ($\alpha$-tocopherol) in unirradiated or cross-linked ultrahigh molecular weight polyethylene or low molecular weight polyethylene in high molecular weight polyethylene, in both cases ultrahigh molecular weight polyethylene being the base polymer. The plasticizing agent is typically added to the base polymer in less than about 20 weight percent. The plasticizing agent generally increases flexibility and softens the polymeric material.

The term "plasticization" or "plasticizing" refers to the properties that a plasticizing agent imparts on the polymeric material to which it has been contacted with. These properties may include but are not limited to increased elongation at break, reduced stiffness and increased ductility.

A "nucleating agent" refers to an additive known in the art, an organic or inorganic material with a molecular weight less than that of the base polymer, which increases the rate of crystallization in the polymeric material. Typically, organocaiboxylic acid salts, for example calcium carbonate, are good nucleation agents for polyolefins. Also, nucleating agents are typically used in small concentrations such as 0.5 wt %.

"Cross-linking Polymeric Materials" refers to polymeric materials, for example, UHMWPE can be cross-linked by a variety of approaches, including those employing cross-linking chemicals (such as peroxides and/or silane) and/or irradiation. Preferred approaches for cross-linking employ irradiation. Cross-linked UHMWPE also can be obtained through cold irradiation, warm irradiation, or melt irradiation according to the teachings of U.S. Pat. Nos. 5,879,400, 6,641,617, and PCT/US97/02220.

"Consolidated polymeric material refers" to a solid, consolidated bar stock, solid material machined from stock, or semi-solid form of polymeric material derived from any forms as described herein, for example, resin, powder, flakes, particles, or a mixture thereof, that can be consolidated. The consolidated polymeric material also can be in the form of a slab, block, solid bar stock, machined component, film, tube, balloon, preform, implant, finished medical device or unfinished device.

By "crystallinity" is meant the fraction of the polymer that is crystalline. The crystallinity is calculated by knowing the weight of the sample (weight in grams), the heat absorbed by the sample in melting (E, in J/g) and the heat of melting of polyethylene crystals ($\Delta H$=291 J/g), and using the following equation according to ASTM F2625 and the like or their successors:

$$\% \text{ Crystallinity} = E/w \cdot \Delta H$$

By tensile "elastic modulus" is meant the ratio of the nominal stress to corresponding strain for strains as determined using the standard test ASTM 638 M III and the like or their successors.

The term "non-permanent device" refers to what is known in the art as a device that is intended for implantation in the body for a period of time shorter than several months. Some non-permanent devices could be in the body for a few seconds to several minutes, while other may be implanted for days, weeks, or up to several months. Non-permanent devices include catheters, tubing, intravenous tubing, and sutures, for example.

"Pharmaceutical compound", as described herein, refers to a drug in the form of a powder, suspension, emulsion, particle, film, cake, or molded form. The drug can be free-standing or incorporated as a component of a medical device.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

The term "interface" in this invention is defined as the niche in medical devices formed when an implant is in a configuration where a component is in contact with another piece (such as a metallic or a non-metallic component), which forms an interface between the polymer and the metal or another polymeric material. For example, interfaces of polymer-polymer or polymer-metal are in medical prosthesis, such as orthopedic joints and bone replacement parts, for example, hip, knee, elbow or ankle replacements.

Medical implants containing factory-assembled pieces that are in close contact with the polyethylene form interfaces. In most cases, the interfaces are not readily accessible to ethylene oxide gas or the gas plasma during a gas sterilization process.

"Irradiation", in one aspect of the invention, the type of radiation, preferably ionizing, is used. According to another aspect of the invention, a dose of ionizing radiation ranging from about kGy to about 1000 kGy is used. The radiation dose can be about 25 kGy, about 50 kGy, about 65 kGy, about 75 kGy, about 100 kGy, about 150, kGy, about 200 kGy, about 300 kGy, about 400 kGy, about 500 kGy, about 600 kGy, about 700 kGy, about 800 kGy, about 900 kGy, or about 1000 kGy, or above 1000 kGy, or any value thereabout or therebetween. Preferably, the radiation dose can be between about 25 kGy and about 150 kGy or between about 50 kGy and about 100 kGy. These types of radiation, including gamma, x-ray, and/or electron beam, kills or inactivates bacteria, viruses, or other microbial agents potentially contaminating medical implants, including the interfaces, thereby achieving product sterility. The irradiation, which may be electron or gamma irradiation, in accordance with the present invention can be carried out in air atmosphere containing oxygen, wherein the oxygen concentration in the atmosphere is at least 1%, 2%, 4%, or up to about 22%, or any value thereabout or therebetween. In another aspect, the irradiation can be carried out in an inert atmosphere, wherein the atmosphere contains gas selected from the group consisting of nitrogen, argon, helium, neon, or the like, or a combination thereof. The irradiation also can be carried out in a sensitizing gas such as acetylene or mixture or a sensitizing gas with an inert gas or inert gases. The irradiation also can be carried out in a vacuum. The irradiation can also be carried out at room temperature, or at between room temperature and the melting point of the polymeric material, or at above the melting point of the polymeric material. The irradiation can be carried out at any temperature or at any dose rate using e-beam, gamma, and/or x-ray. The irradiation temperature can be below or above the melting point of the polymer. The polymer can be first heated and then irradiated. Alternatively, the heat generated by the beam, i.e., radiation generated heating (including adiabatic and partially adiabatic) can increase the temperature of the polymer. Subsequent to the irradiation step the polymer can be heated to melt or heated to a temperature below its melting point for annealing. These post-irradiation thermal treatments can be carried out in air, inert gas and/or in vacuum. Also the irradiation can be carried out in small increments of radiation dose and in some embodiments these sequences of incremental irradiation can be interrupted with a thermal treatment. The sequential irradiation can be carried out with about 1, 10, 20, 30, 40, 50, 100 kGy, or higher radiation dose increments. Between each or some of the increments the polymer can be thermally treated by melting and/or annealing steps. The thermal treatment after irradiation is mostly to reduce or to eliminate the residual free radicals in the polymers created by irradiation, and/or eliminate the crystalline matter, and/or help in the removal of any extractables that may be present in the polymer.

In accordance with a preferred feature of this invention, the irradiation may be carried out in a sensitizing atmosphere. This may comprise a gaseous substance which is of sufficiently small molecular size to diffuse into the polymer and which, on irradiation, acts as a polyfunctional grafting moiety. Examples include substituted or unsubstituted polyunsaturated hydrocarbons; for example, acetylenic hydrocarbons such as acetylene; conjugated or unconjugated olefinic hydrocarbons such as butadiene and (meth)acrylate monomers; sulphur monochloride, with chloro-tri-fluoroethylene (CTFE) or acetylene being particularly preferred. By "gaseous" is meant herein that the sensitizing atmosphere is in the gas phase, either above or below its critical temperature, at the irradiation temperature.

If electron radiation is used, the energy of the electrons also is a parameter that can be varied to tailor the properties of the irradiated polymer. In particular, differing electron energies result in different depths of penetration of the electrons into the polymer. The practical electron energies range from about 0.1 MeV to 16 MeV giving approximate iso-dose penetration levels of 0.5 mm to 8 cm, respectively. The preferred electron energy for maximum penetration is about 10 MeV, which is commercially available through vendors such as Studer (Daniken, Switzerland) or E-Beam Services New Jersey, USA). The lower electron energies may be preferred for embodiments where a surface layer of the polymer is preferentially cross-linked with gradient in cross-link density as a function of distance away from the surface.

The term "dose rate" refers to a rate at which the radiation is carried out. Dose rate can be controlled in a number of ways. One way is by changing the power of the e-beam, scan width, conveyor speed, and/or the distance between the sample and the scan horn. Another way is by carrying out the irradiation in multiple passes with, if desired, cooling or heating steps in-between. With gamma and x-ray radiations the dose rate is controlled by how close the sample is to the radiation source, how intense is the source, the speed at which the sample passes by the source.

Gamma irradiation, however, generally provides low radiation dose rate and requires a longer duration of time, which can result in more in-depth oxidation, particularly if the gamma irradiation is carried out in air. Electron irradiation, in general, results in a mote limited dose penetration depth, but requires less time and, therefore, reduces the risk of extensive oxidation if the irradiation is carried out in air. In addition if the desired dose levels are high, for instance 20 Mrad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 Mrad melt-irradiation can be completed in for instance less than 10 minutes. The penetration of the electron beam depends on the beam energy measured by million electron-volts (MeV). Most polymers exhibit a density of about 1 g/cm$^3$, which leads to the penetration of about 1 cm with a beam energy of 2-3 MeV and about 4 cm with a beam energy of 10 MeV. The penetration of e-beam is known to increase slightly with increased irradiation temperatures. If electron irradiation is preferred, the desired depth of penetration can be adjusted based on the beam energy. Accordingly, gamma irradiation or electron irradiation may be used based upon the depth of penetration preferred, time limitations and tolerable oxidation levels.

Ranges of acceptable dose rates are exemplified in International Application WO 97/29793. In general, the dose rates vary between 0.5 Mrad/pass and 50 Mrad/pass. The upper limit of the dose rate depends on the resistance of the polymer to cavitation/cracking induced by the irradiation.

If electron radiation is utilized, the energy of the electrons also is a parameter that can be varied to tailor the properties of the irradiated polymer. In particular, differing electron energies result in different depths of penetration of the electrons into the polymer. The practical electron energies range from about 0.1 MeV to 16 MeV giving approximate iso-dose penetration levels of 0.5 mm to 8 cm, respectively. The preferred electron energy for maximum penetration is about 10 MeV, which is commercially available through vendors such as Studer (Daniken, Switzerland) or E-Beam Services New Jersey, USA). The lower electron energies may be preferred for embodiments where a surface layer of the polymer is preferentially cross-linked with gradient in cross-link density as a function of distance away from the surface.

In accordance with another aspect of the invention, the polymeric preform also has a gradient of cross-link density in a direction perpendicular to the direction of irradiation, wherein a part of the polymeric preform was preferentially shielded to partially block radiation during irradiation in order to provide the gradient of cross-link density, wherein the preferential shielding is used where a gradient of cross-link density is desired and the gradient of cross-link density is in a direction perpendicular to the direction of irradiation on the preferentially shielded polymeric preform, such as is disclosed in U.S. Pat. No. 7,205,339, the methodologies of which are hereby incorporated by reference.

Various methods of preferential shielding according to the invention are described in more details in the following illustrative examples. Although the examples may represent only selected embodiments of the invention, it should be understood that the following examples are illustrative and not limiting.

Preferential Shielding:

The selective, controlled manipulation of polymers using radiation chemistry can, in another aspect, be achieved by preferential irradiation shielding. By using a shield or shields made of selected materials, selected thicknesses, selected geometry's, selected areas and utilization of the shields in a selected order, the overall properties of the irradiated polymer may be controlled and tailored to achieve a desired result, particularly in view of alterations that can be made in the type of irradiation, the irradiation dose, dose rate and exposure time and temperature, as well as the methodology used (for example, IMS, WIR, CIR, CIR-SM and WIAM). Shielded irradiation can be used in conjunction with other methods such as varying the concentration profile of an antioxidant/anti-crosslinking agent in the polymeric material to control crosslink density distribution.

a. Shield Material

The irradiation shield may be made from any material that will at least shield in part polymer from the irradiation. Exemplary materials include ceramics, metals, and glass. Suitable ceramics include alumina and zirconia. Suitable metals include aluminum, lead, iron, and steel. Polymers also may be used as shields.

b. Shield Geometry's and Order

An irradiation shield may be provided in any shape, cross-section, or thickness.

It is well known in the art that the thickness of the shield will contribute to the ability of the material to shield the irradiation. Accordingly, the thickness of the shield can be selected depending upon the extent of shielding that is desired in the shielded portion. In this manner, the depth of irradiation penetration can be controlled, or a total shielding of irradiation of the covered areas can be achieved. The iso-dose penetration (defined as the depth at which the dose equals that at the e-beam incidence surface) and the dose-depth penetration profile depend on the energy of the electrons used.

The irradiation of materials with electrons leads to the well known built-up of absorbed dose level as a function of distance away from the electron beam incidence surface. This built-up of the absorbed dose is due to the generation of secondary electrons following the collision of the incident electrons with the atoms of the host material. The collisions generate more electrons at the expense of loosing kinetic energy while increasing the effective absorbed dose level as the electron flux travels into the material. At a critical depth, the kinetic energy loss reaches a level where the electron flux slows down and leads to an abrupt decay in the absorbed dose level. The depth at which the absorbed dose level is equal to that at the surface is called the iso-dose penetration depth. This penetration increases with the increasing energy of the incident electrons. Provided herein are two methods of determining the iso-dose penetration of 10 MeV electrons into UHMWPE, namely dosimetry and determination of trans-vinlyene unsaturations.

Thus, effect of irradiation and shielding can be controlled through the materials used in the shield, the thickness of the shield (constant or variable), the extent to which the shield covers the area of the material being irradiated (full or partial), the order of shielding and irradiation, the type and extent of irradiation, and polymer selection.

c. Complete Coverage Shielding

UHMWPE (GUR 1050) was covered by aluminum shield of varying thicknesses (1, 3, 5, 7, 9, 11, 13, 15 mm) and irradiated either at room temperature or at 125° C. The irradiation was carried out at E-Beam Services (Cranbury, N.J.) using the 10/50 Impela linear electron accelerator operated at 10 MeV and 50 kW. To determine the penetration profile of the effects of e-beam, spatial variation in the trans-vinylene content in the irradiated UHMWPE specimens was determined. The GUR 1050 UHMWPE has no detectable trans-vinylene unsaturations. The ionizing radiation, e-beam in the present case, leads to the formation of trans-vinylene unsaturations, the content of which varies linearly with absorbed radiation dose.

Figure 13A:
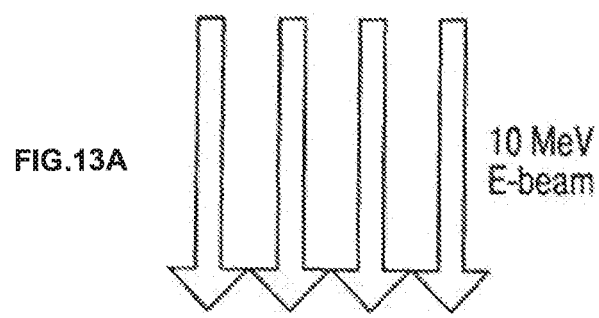
FIGS. 13A-13B depict a schematic of a complete coverage shield covering a UHMWPE construct.
Figure 13B:
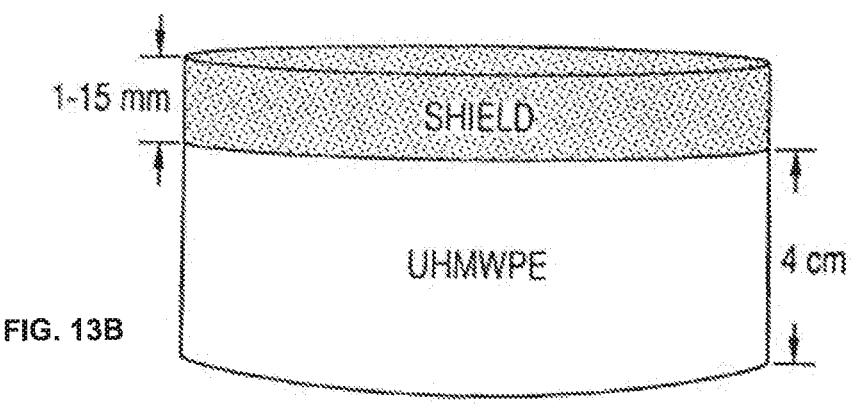
Figure 14A:
FIGS. 14A-14B depict the construct of FIGS. 13A-13B that has been bisected for microtoming.
Figure 14B:
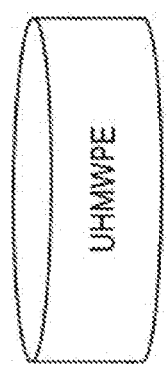
Figure 14C:
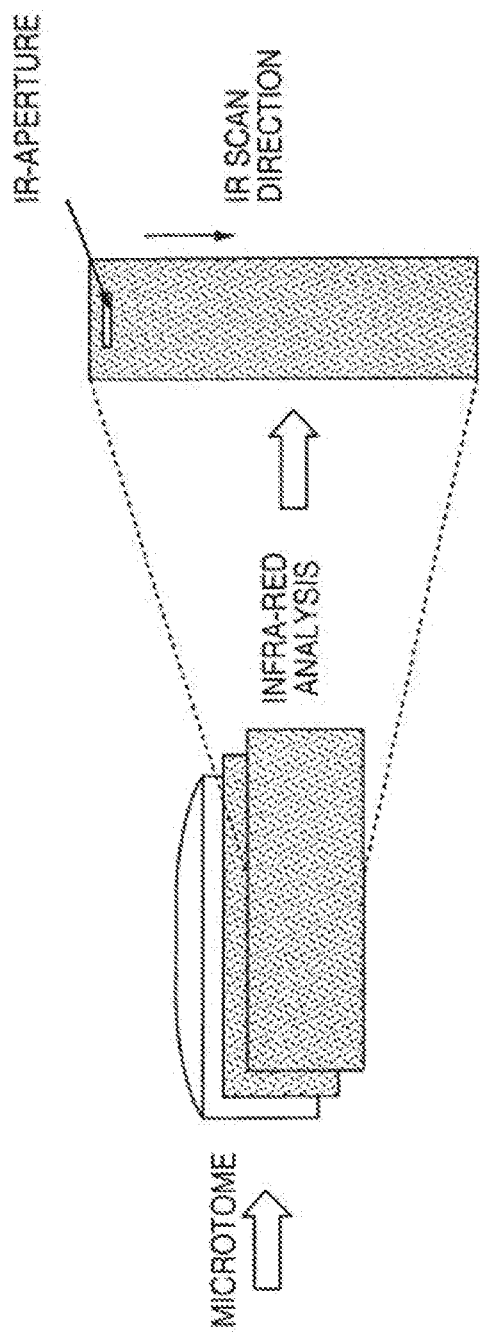
FIG. 14C depicts bisected UHMWPE construct for microtoming and Infra-red analysis.

FIGS. 13A-13B show a schematic of the shield/UHMWPE construct. Following irradiation, the irradiated UHMWPE construct was machined in half and microtomed as shown in FIGS. 14A-14C. The microtomed thin section was then analyzed using a BioRad UMA 500 infra-red microscope with an aperture size of 100 µm by 50 µm as a function of depth away from the shield/UHMWPE interface at 1 mm increments. Each individual infra-red spectra was then analyzed by normalizing the area under the trans-vinylene vibration at 965 cm$^{-1}$ to die that under the 1900 cm$^{-1}$ after subtracting the respective baselines. The value obtained, that is the trans-vinylene index (TVI), is directly proportional to the absorbed radiation dose level.

The following equation was used:

$$TVI = \frac{\int_{950}^{980} A(w)dw - B_1}{\int_{1850}^{1985} A(w)dw - B_2}$$

$$B_1 = \frac{[A(980) + A(950)](980 - 950)}{2}$$

$$B_2 = \frac{[A(1850) + A(1985)](1985 - 1880)}{2}$$

where A(w) is the infra-red absorbance measured at wave number, w, $B_1$ is the area under the baseline of the trans-vinylene vibration and $B_2$ is that of the baseline under the reference (1900 cm$^{-1}$) vibration.

Figure 15:
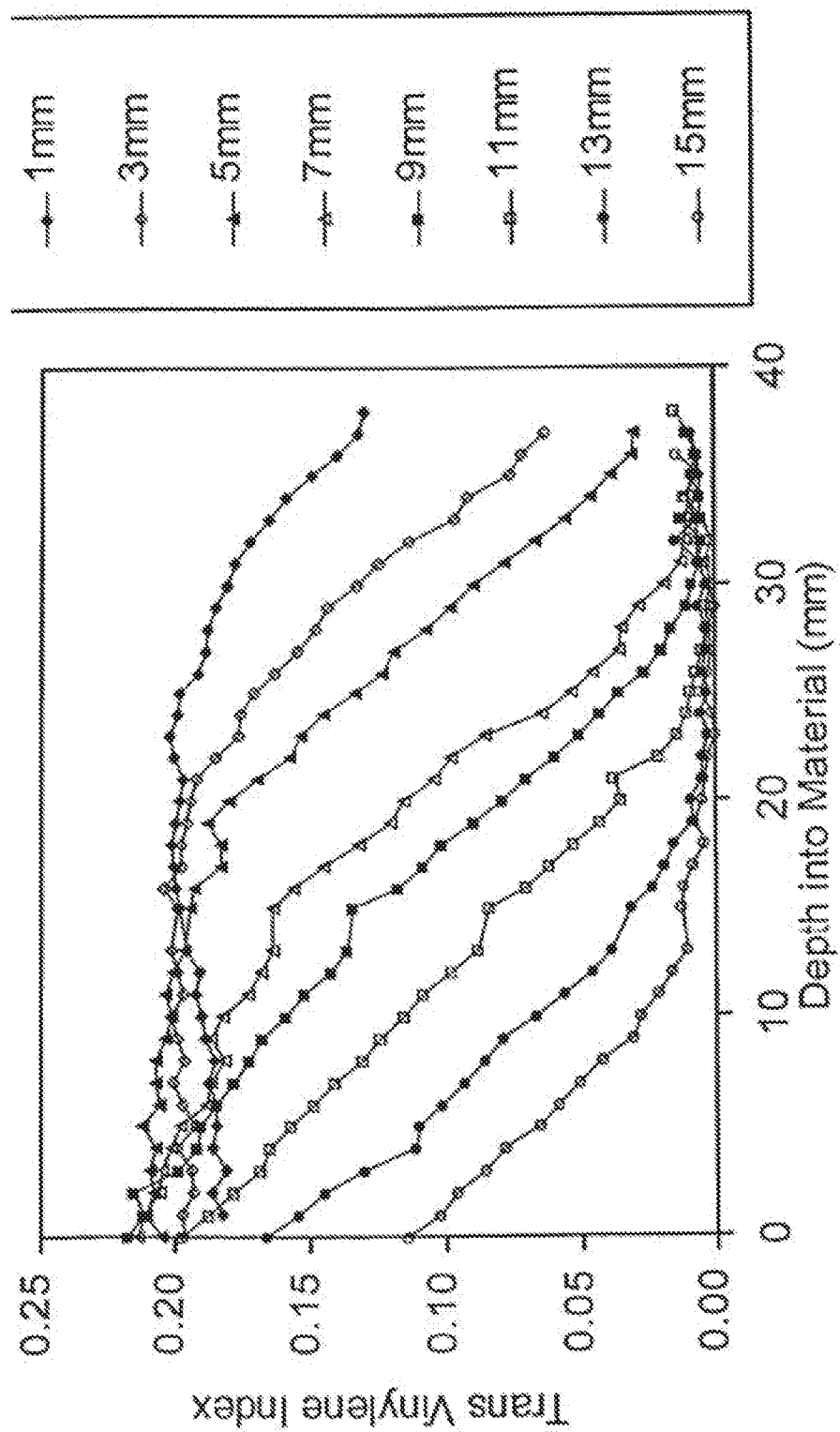
FIG. 15 shows the variation of the trans vinylene index as a function of distance for UHMWPE irradiated at room temperature.
Figure 16:
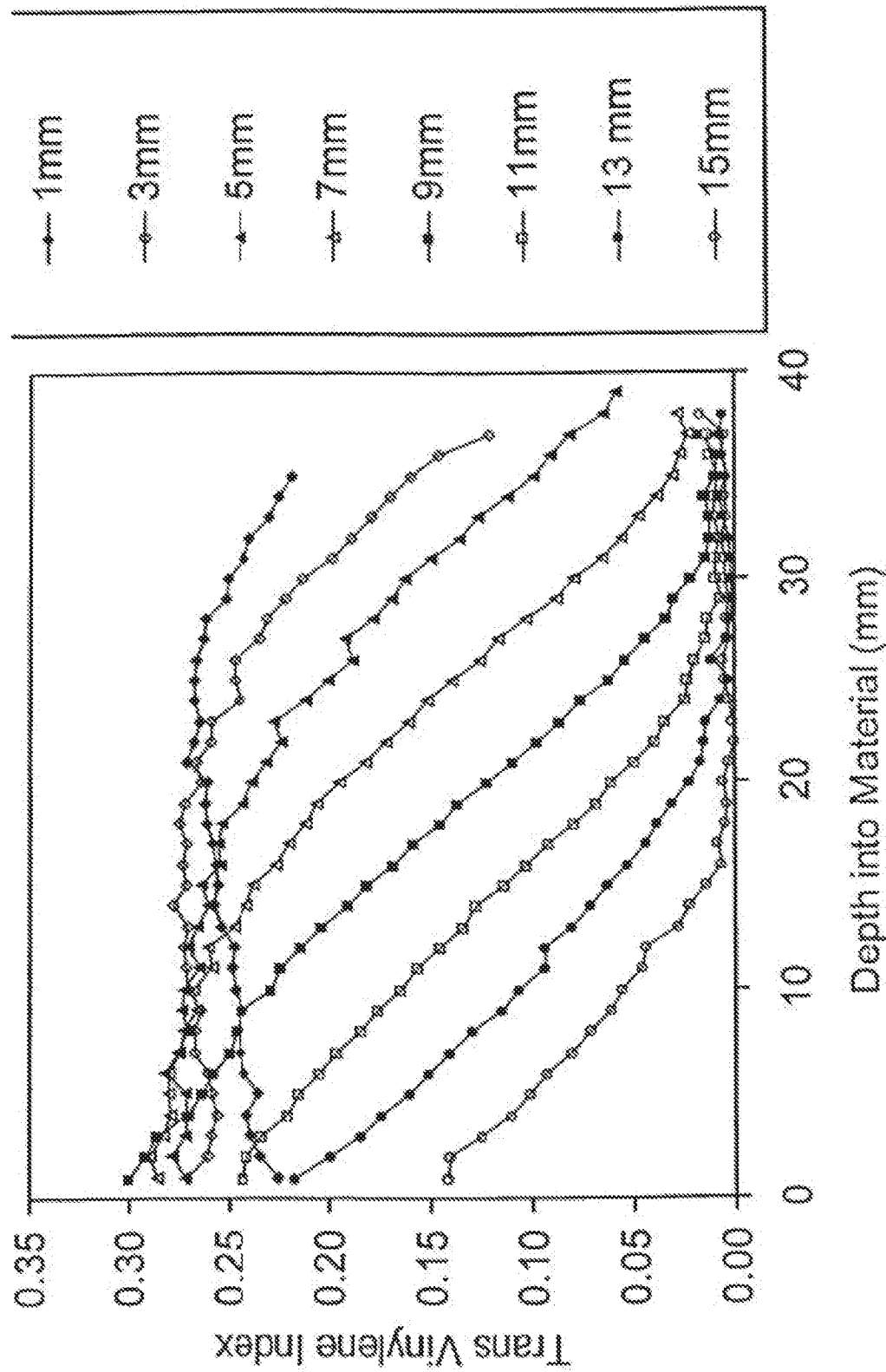
FIG. 16 shows the variation of the trans vinylene index as a function of distance for UHMWPE irradiated at 125° C.
Figure 17:
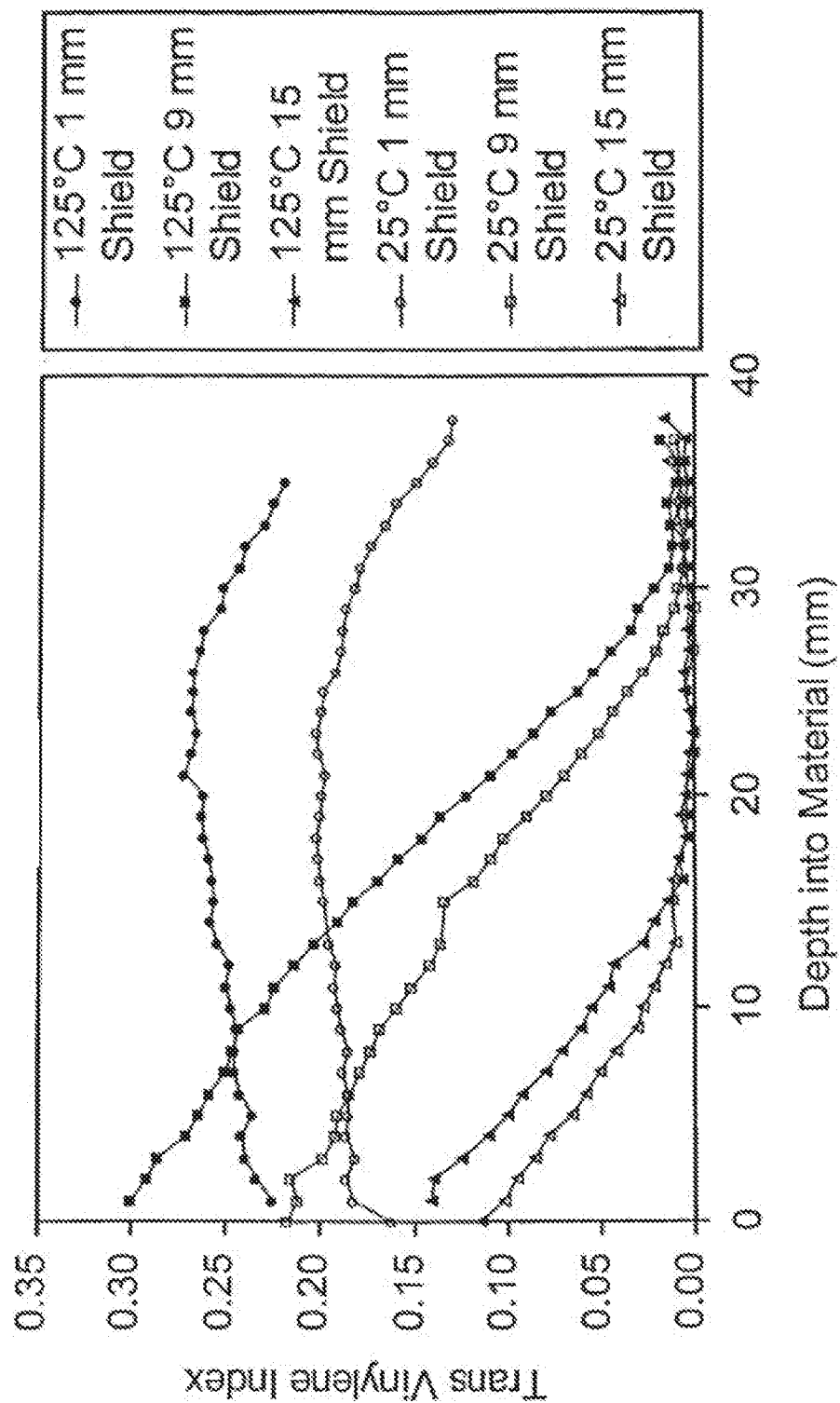
FIG. 17 shows the variation of the trans vinylene index as a function of distance for UHMWPE irradiated at 2 different temperature (25° C. and 125° C.) and different complete (that is, full) coverage shield thicknesses (1 mm, 9 mm, and 15 mm).

FIG. 15 shows the variation of TVI in room temperature irradiated UHMWPE as a function of distance away from the shield/UHMWPE interface for different shield thicknesses. FIG. 16 shows the same for the UHMWPE that was irradiated at 125° C. The FIGS. clearly show that the penetration of the effects of e-beam can be controlled by placing an aluminum shield and by varying its thickness. The temperature at which the irradiation is being carried can also be used to change the profile of the beam penetration. This is illustrated in FIG. 17 where the variation in TVI with depth is presented for three different shield thicknesses (1, 9, and 15 mm) and two irradiation temperatures (25° C. and 125° C.).

d. Partial Coverage Shielding

Figures 18A, 18B:
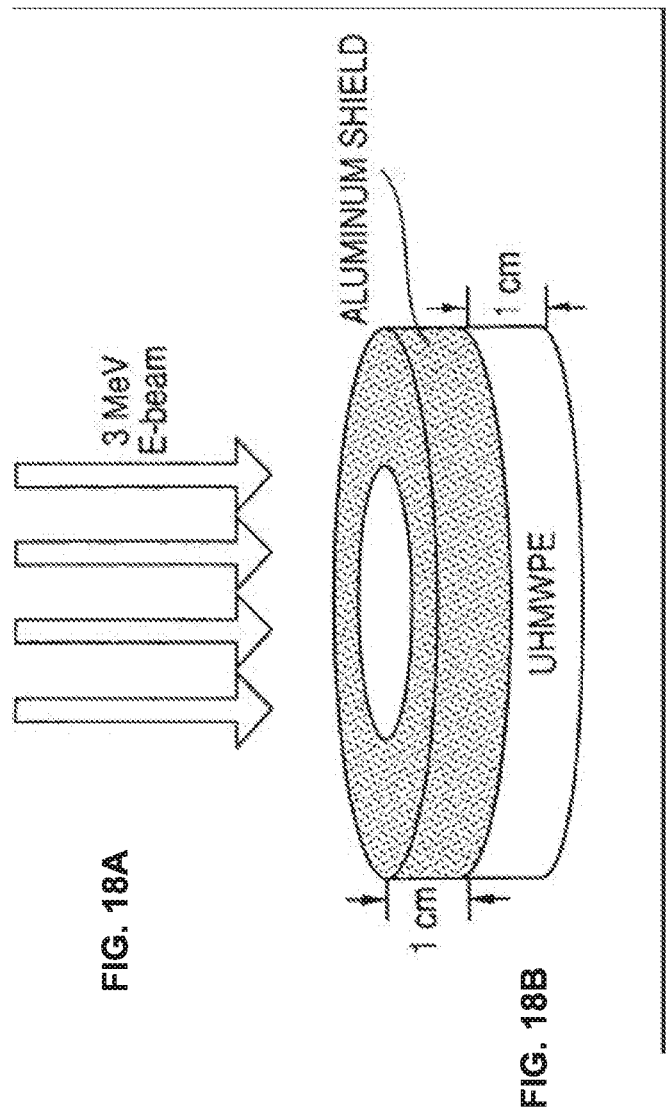
FIGS. 18A-18B depict a UHMWPE construct covered with a 1 cm thick aluminum partial shield (hole in center).

UHMWPE (GUR 1050) was covered by a 1 cm thick aluminum shield with a round opening in the center, as shown in FIGS. 18A-18B. The UHMWPE/shield construct was then irradiated at 150° C. using the Van de Graaf generator at the High Voltage Research Laboratories of Massachusetts Institute of Technology (Cambridge, Mass.). This partial shielding scheme should lead to the irradiation of the central part of the UHMWPE cylinder. To confirm this, the spatial distribution of the effects of e-beam was determined by measuring the content of trans-vinylene unsaturations as a function of distance away from the side-wall to the center of the UHMWPE disc in the direction perpendicular to the e-beam incidence direction.

The GUR 1050 UHMWPE has no detectable trans-vinylene unsaturations. The ionizing radiation, e-beam in the present case, leads to the formation of trans-vinylene unsaturations, the content of which varies linearly with absorbed radiation dose.

Figure 19A:
FIGS. 19A-19C depict the construct of FIGS. 18A-18B that has been bisected for microtoming.
Figure 19B:
Figure 19C:
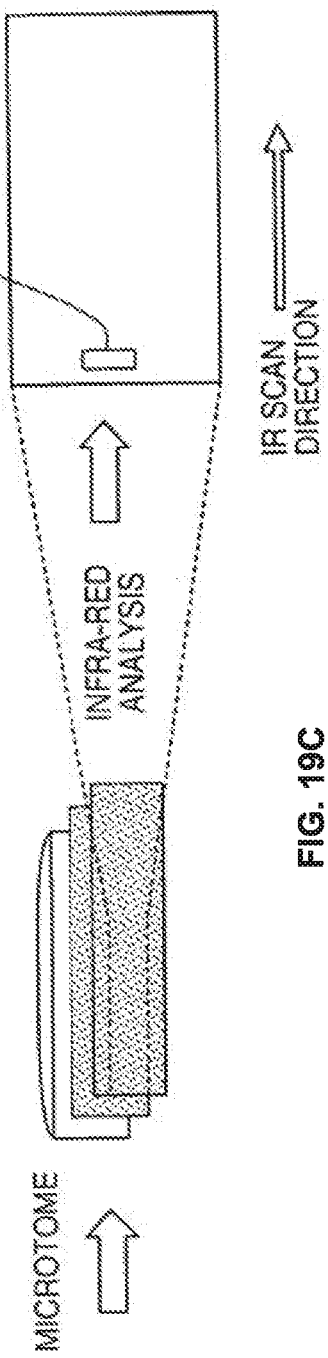

Following irradiation, the irradiated UHMWPE cylinder was machined in half and microtomed as shown in FIGS. 19A-19C. The microtomed thin section was then analyzed using a BioRad UMA 500 infra-red microscope with an aperture size of 100 μm by 50 μm as a function of depth away from the sidewall to the center of the irradiated UHMWPE disk at 1 mm increments. Each individual infra-red spectra was then analyzed by normalizing the area under the trans-vinylene vibration at 965 cm$^{-1}$ to the that under the 1900 cm$^{-1}$ after subtracting the respective baselines. The value obtained, that is the trans-vinylene index (TVI), is directly proportional to the absorbed radiation dose level.

The following equation was used:

$$TVI = \frac{\int_{950}^{980} A(w)dw - B_1}{\int_{1850}^{1985} A(w)dw - B_2}$$

$$B_1 = \frac{[A(980) + A(950)](980 - 950)}{2}$$

$$B_2 = \frac{[A(1850) + A(1985)](1985 - 1880)}{2}$$

where A(w) is the infra-red absorbance measured at wave number, w, $B_1$ is the area under the baseline of the trans-vinylene vibration and $B_2$ is that of the baseline under the reference (1900 cm$^{-1}$) vibration.

Figure 20:
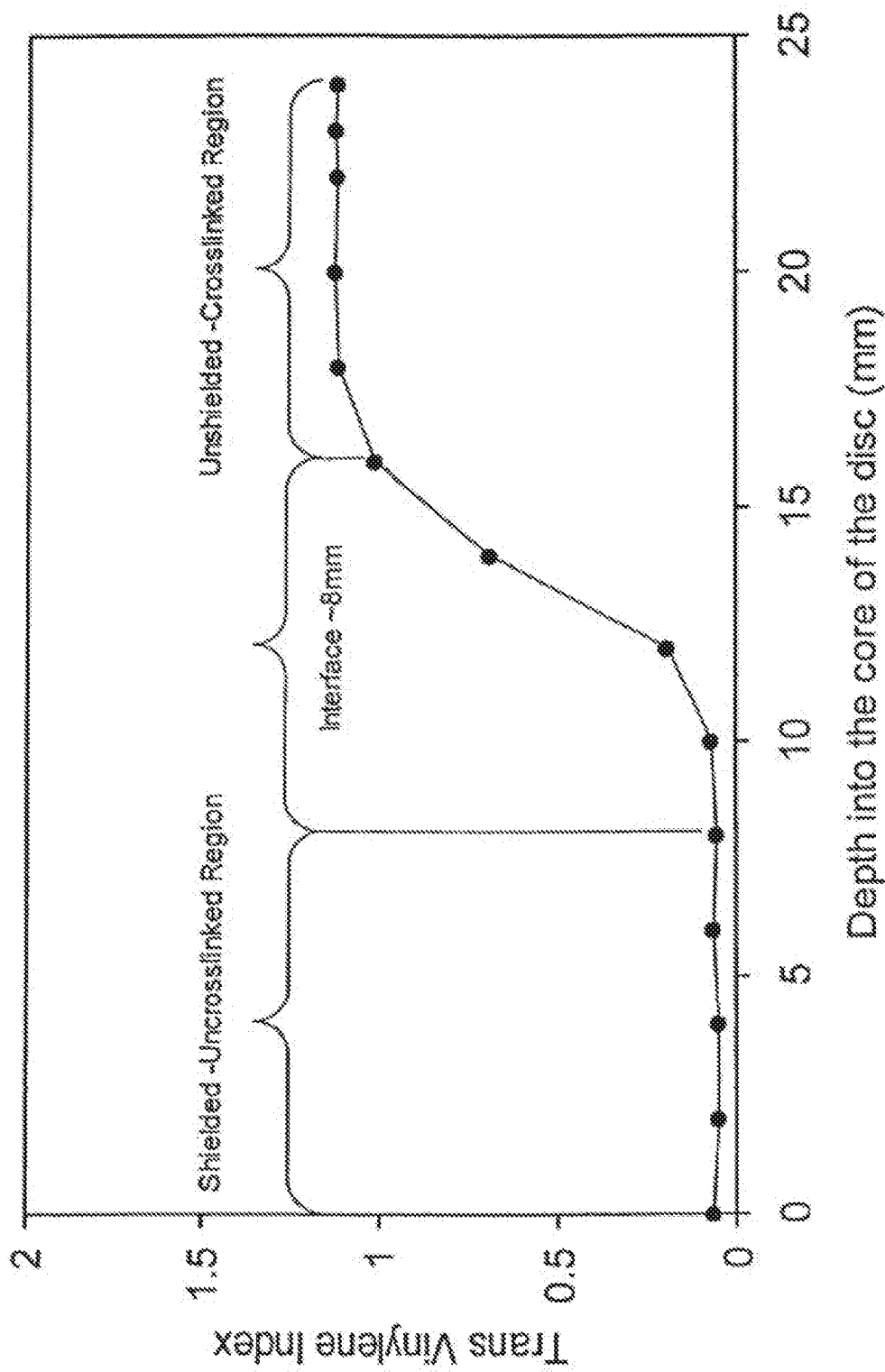
FIG. 20 shows the variation of the trans vinylene index as a function of distance for irradiated UHMWPE.

FIG. 20 shows the variation of TVI in the irradiated UHMWPE as a function of distance away from the sidewall of the shielded and irradiated UHMWPE. Under the shielded region, the TVI level was near zero; while the value under the unshielded region increased, indicating the presence of radiation in this region.

Figures 21A, 21B:
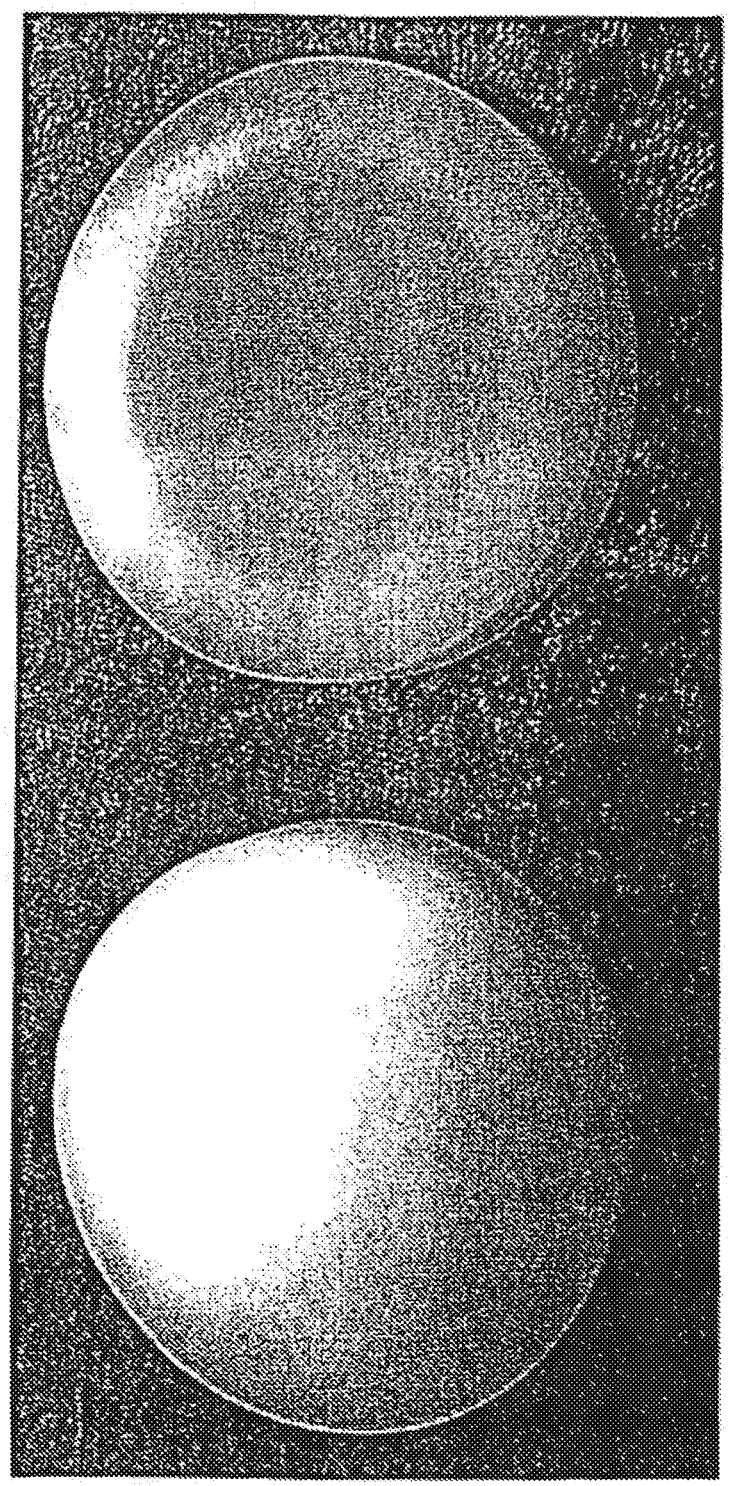
FIGS. 21A-21B compare unradiated UHMWPE (FIG. 21A) to the partially-shield UHMWPE (FIG. 21B) according to FIGS. 18A-18B.

The effect of irradiation with a disc shaped shield on UHMWPE also is illustrated in FIGS. 21A-21B where an unirradiated UHMWPE (FIG. 21A) and shield-irradiated UHMWPE (FIG. 21B) are shown. When the irradiation is carried out above the melting point of UHMWPE, which is the case here, the crystallinity decreases significantly and melt-irradiated UHMWPE becomes more transparent. This transparency is apparent in FIG. 21B, in the region where the shield was not covering the UHMWPE disc. The decrease in the crystallinity is also associated with a decrease in modulus. Therefore, one can use the procedure described here to manufacture different shaped UHMWPE with regions of lower modulus for specific medical applications.

The shape and cross-section of the shield also plays an important role in determining the properties of the irradiated polymer. Any shape and cross-section shield, or combination of shapes and cross-sections, may be utilized to achieve a desired cross-link depth and pattern.

Figure 29B:
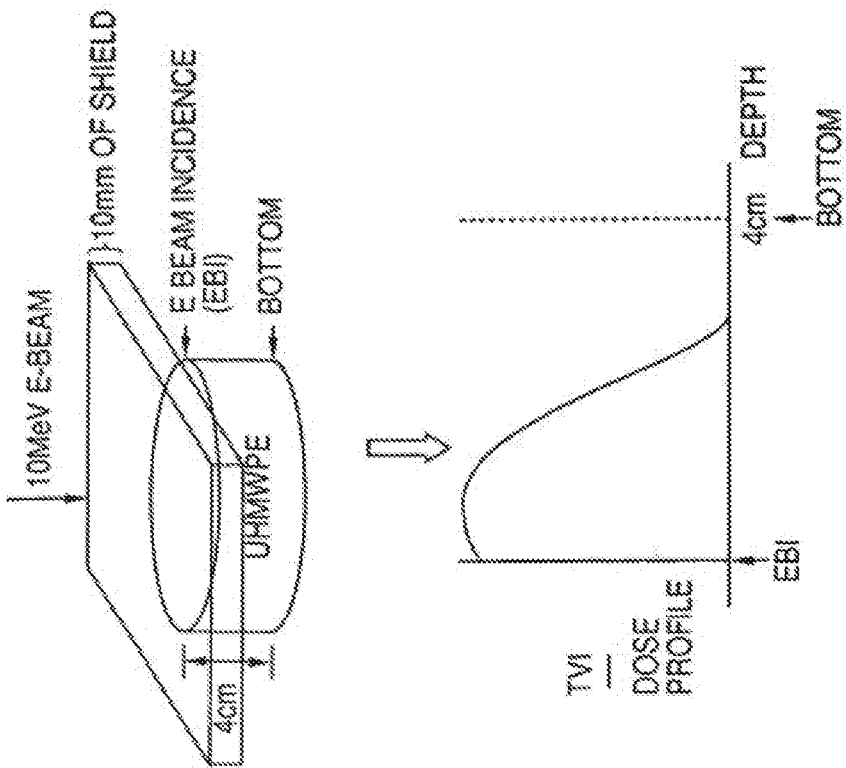
FIGS. 29A-29B are illustrations of the effect of a radiation shield on the depth of penetration of electron radiation at 10 MeV.
Figure 29A:
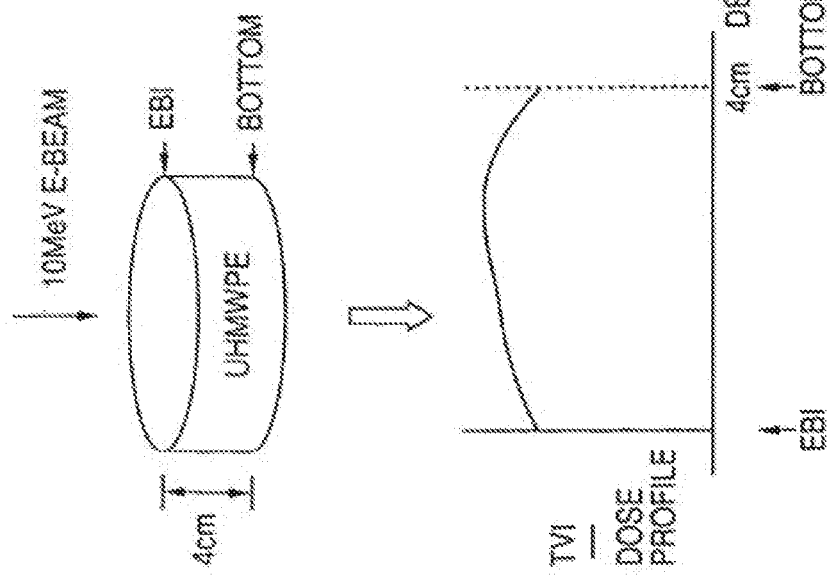
Figure 30:
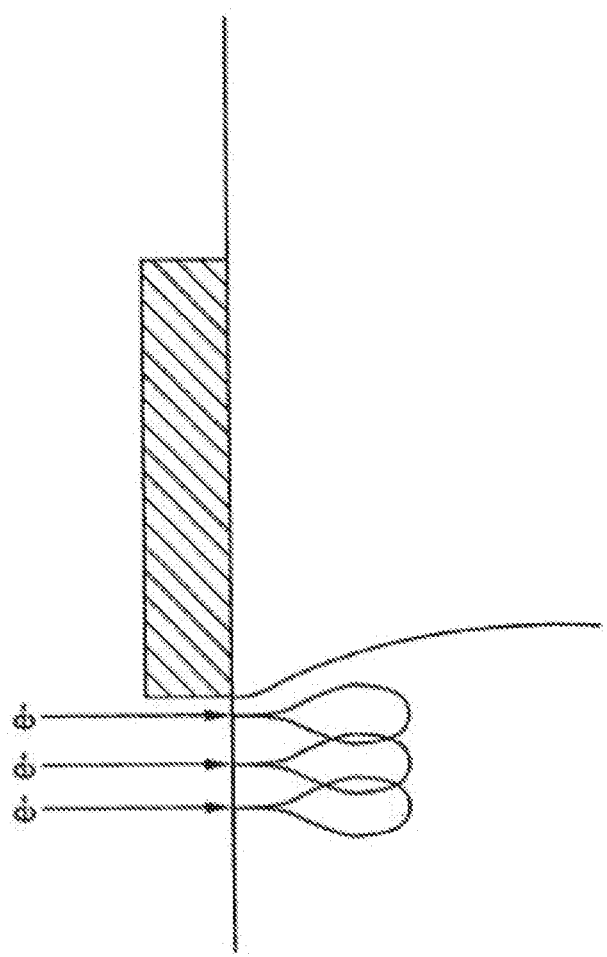
FIG. 30 is a depiction of the "teardrop" electron penetration envelope signature left by electron radiation as it travels through a polymer.

FIGS. 28A-28H illustrate some exemplary shield edge geometry's and the hypothesized irradiation penetration envelopes resulting therefrom are shown in FIG. 30. In particular, depiction (FIG. 28A) show a rectangular cross-section. The cross-link pattern, when there is a full blocking of irradiation, leaves most of the area under the shield uncross-linked. However, there is a portion of the polymer under each edge of the shield that is cross-linked due to the electron penetration envelope. This pattern is the result of the "teardrop" signature left by electron radiation as it travels through the polymer. This signature is depicted in FIG. 30. FIGS. 29A-29B illustrate the effect of an irradiation shield on the depth of penetration of electron radiation at 10 MeV.

Depictions (FIG. 28B), (FIG. 28C), (FIG. 28G) and (FIG. 28H) illustrate an inclined or declined cross-section and the resultant cross-linking pattern. Depictions (FIG. 28D) and (FIG. 28E) illustrate a curved cross-section and the resultant cross-linking pattern. Other cross-sections are attainable according to the teachings contained herein.

Illustrative examples of suitable shield geometry's, cross-sections, and the use of shielding in sequence are shown in FIGS. 22A-22I, 23A-23E, 24A-24F, 25A-25C, 26A-26D, 27A-27C, and 31A-31C. FIGS. 31A-31C, for example, illustrates the irradiation of a polymer preform using both a ring-shaped and disc-shaped shield in sequence. Using a combination of ring and discs shields is an exemplary method of using shielding to impart different properties to the core and periphery of a polymer preform.

e. Complete Coverage vs. Partial Coverage Shielding

"Complete" coverage shielding, denoting the use of a shield that covers the entire surface of the polymer being irradiated, is characterized by a cross-linking gradient parallel to the direction of irradiation. That is, due to the shield (including, for example, a portion of the polymer itself), there will be differences in the degree of cross-linking, resulting in a gradient ranging from extensively cross-linked to non-cross-linked, in the plane of the preform that is parallel to the vector that defines the direction of the radiation from the source to the preform. Examples of complete coverage shielding are shown in FIGS. 29A-29B, 33 and 34. In FIG. 33, the surface of the polymer is designed to be of sufficient thickness to act as a shield for the irradiation from the inner portion of the polymer. In other embodiments, other shields may be placed on or over the surface of the polymer such that the depth of penetration of irradiation, as the resulting cross-linking, is affected. FIG. 34 shows a particular embodiment of complete coverage shielding in which the preform is rotated along an axis passing through the interior of the preform. As FIG. 34 shows, this embodiment results in a gradient of cross-linking parallel to the vector that defines the direction of the radiation from the source to the preform and in which outer portion of the preform are more extensively cross-linked relative to the inner portion.

"Partial" coverage shielding, denoting the use of a shield that does not cover the entire surface of the polymer being irradiated, is characterized by a cross-linking gradient perpendicular to direction of irradiation. That is, due to the shield, there will be differences in the degree of cross-linking, ranging from extensively cross-linked to non-cross-linked, in the plane of the preform that is perpendicular to the vector that defines the direction of the radiation from the source to the preform. FIG. 32. Due to propagation of the electrons in the irradiated preform, a degree of cross-linking will occur under the outer edges of the shield, which are schematically depicted as tear drops in FIG. 30. Thus, where differential shielding has been performed, a gradient of fuller cross-linking to comparatively lesser cross-linking or no crosslinking will be observed in the plane represented by the directional arrow in (see FIG. 32). Thus, cross-linking will be greatest in the unshielded areas, begin to decrease at the interface of the shield and an unshielded (or lesser shielded) edge, and decrease further, or be absent altogether (depending upon the thickness and consistency of the shield), at the inner portions under the shielded area.

Gradient of Antioxidant/Anti-Crosslinking Agent Distribution:

A gradient concentration refers in general to a gradient distribution of an additive concentration throughout or a portion of a polymeric preform. A gradient concentration of antioxidant/anti-crosslinking agent refers to a gradient of antioxidant/anti-crosslinking agent distribution throughout or a portion of a polymeric preform. The gradient of antioxidant distribution can be continuous or non-continuous throughout or within a portion of the polymeric preform. Such as, a polymeric preform containing layers of consolidated UHMWPE and the preform has a gradient of antioxidant distribution uniform throughout the preform or the gradient of antioxidant distribution varies from one layer to another. A gradient concentration of the antioxidant can be limited or directed to an interface or a layer of polymeric material within a polymeric preform where there is a gradient of antioxidant distribution within a defined region.

A gradient of cross-link density and a gradient concentration of antioxidant also can be obtained by extraction methods, such as disclosed in WO 2008/092047, the methodologies of which are hereby incorporated by reference.

The terms "extraction" or "elution" of antioxidant from antioxidant containing consolidated polymeric material refers to partial or complete removal of the antioxidant, for example, vitamin E, from the consolidated polymeric material by various processes disclosed herein. For example, the extraction or elution of antioxidant can be done with a compatible solvent that dissolves the antioxidant contained in the consolidated polymeric material. Such solvents include, but not limited to, a hydrophobic solvent, such as hexane, heptane, or a longer chain alkane; an alcohol such as ethanol, any member of the propanol or butanol family or a longer chain alcohol; or an aqueous solution in which an antioxidant, such as vitamin E is soluble. Such a solvent also can be made by using an emulsifying agent such as Tween 20, Tween 80, fatty acids, other surfactants or ethanol. The extraction or elution of antioxidant from antioxidant containing consolidated polymeric material is generally done prior to placement and/or implantation of the polymeric material, or a medical implant comprising the antioxidant containing consolidated polymeric material, into the body.

Extraction of α-tocopherol from a polyethylene at a temperature below the melting temperature of the polyethylene can be achieved by placing the polyethylene in an open or in a sealed chamber. A solvent or an aqueous solution also can be added in order to extract the α-tocopherol from polyethylene. The chamber is then heated below the melting point of the polyethylene, preferably between about room temperature to near the melting point, more preferably about 100° C. to about 137° C., more preferably about 120° C., or more preferably about 130° C. If a sealed chamber is used, there will be an increase in pressure during heating. Because the polyethylene is cross-linked, only the crystalline regions melt. The chemical cross-links between chains remain intact and allow the polyethylene to maintain its shape throughout the process despite surpassing its melting temperature. Increasing pressure increases the melting temperature of the polymeric material. In this case, homogenization below the melt is performed under pressure above 137° C., for example at about 145° C.

Extraction of α-tocopherol from a polyethylene at a temperature above the melting temperature of the polyethylene can be achieved by placing the polyethylene in an open or in a sealed chamber. A solvent or an aqueous solution also can be added in order to extract the α-tocopherol from polyethylene. The chamber is then heated above the melting point of the polyethylene, preferably between about 137° C. to about 400° C., more preferably about 137° C. to about 200° C., more preferably about 137° C., or more preferably about 160° C. If a sealed chamber is used, there will be an increase in pressure during heating. Because the polyethylene is cross-linked, only the crystalline regions melt. The chemical cross-links between chains remain intact and allow the polyethylene to maintain its shape throughout the process despite surpassing its melting temperature. Since crystallites pose a hindrance to diffusion of α-tocopherol in polyethylene, increasing the temperature above the melting point should increase the rate of extraction of α-tocopherol. Increasing pressure increases the melting temperature of the polymeric material.

"Metal Piece", in accordance with the invention, the piece forming an interface with polymeric material is, for example, a metal. The metal piece in functional relation with polymeric material, according to the present invention, can be made of a cobalt chrome alloy, stainless steel, titanium, titanium alloy or nickel cobalt alloy, for example.

"Non-metallic Piece", in accordance with the invention, the piece forming an interface with polymeric material is, for example, a non-metal. The non-metal piece in functional relation with polymeric material, according to the present invention, can be made of ceramic material, for example.

The term "inert atmosphere" refers to an environment having no more than 1% oxygen and more preferably, an oxidant-free condition that allows free radicals in polymeric materials to form cross links without oxidation during a process of sterilization. An inert atmosphere is used to avoid $O_2$, which would otherwise oxidize the medical device comprising a polymeric material, such as UHMWPE. Inert atmospheric conditions such as nitrogen, argon, helium, or neon are used for sterilizing polymeric medical implants by ionizing radiation.

Inert atmospheric conditions such as nitrogen, argon, helium, neon, or vacuum are also used for sterilizing interfaces of polymeric-metallic and/or polymeric-polymeric in medical implants by ionizing radiation.

Inert atmospheric conditions also refer to an inert gas, inert fluid, or inert liquid medium, such as nitrogen gas or silicon oil.

"Anoxic environment" refers to an environment containing gas, such as nitrogen, with less than 21%-22% oxygen, preferably with less than 2% oxygen. The oxygen concentration in an anoxic environment also can be at least about 1%, 2%, 4%, 6%, 8%, 10%, 12% 14%, 16%, 18%, 20%, or up to about 22%, or any value thereabout or therebetween.

The term "vacuum" refers to an environment having no appreciable amount of gas, which otherwise would allow free radicals in polymeric materials to form cross links without oxidation during a process of sterilization. A vacuum is used to avoid $O_2$, which would otherwise oxidize the medical device comprising a polymeric material, such as UHMWPE. A vacuum condition can be used for sterilizing polymeric medical implants by ionizing radiation.

A vacuum condition can be created using a commercially available vacuum pump. A vacuum condition also can be used when sterilizing interfaces of polymeric-metallic and/or polymeric-polymeric in medical implants by ionizing radiation.

A "sensitizing environment" or "sensitizing atmosphere" refers to a mixture of gases and/or liquids (at room temperature) that contain sensitizing gaseous and/or liquid components) that can react with residual free radicals to assist in the recombination of the residual free radicals. The gases maybe acetylene, chloro-trifluoro ethylene (CTFE), ethylene, or like. The gases or the mixtures of gases thereof may contain noble gases such as nitrogen, argon, neon and like. Other gases such as, carbon dioxide or carbon monoxide may also be present in the mixture. In applications where the surface of a treated material is machined away during the device manufacture, the gas blend could also contain oxidizing gases such as oxygen. The sensitizing environment can be dienes with different number of carbons, or mixtures of liquids and/or gases thereof. An example of a sensitizing liquid component is octadiene or other dienes, which can be mixed with other sensitizing liquids and/or non-sensitizing liquids such as a hexane or a heptane. A sensitizing environment can include a sensitizing gas, such as acetylene, ethylene, or a similar gas or mixture of gases, or a sensitizing liquid, for example, a diene. The environment is heated to a temperature ranging from room temperature to a temperature below the melting point of the material.

In certain embodiments of the present invention in which the sensitizing gases and/or liquids or a mixture thereof, inert gas, air, vacuum, and/or a supercritical fluid can be present at any of the method steps disclosed herein, including blending, mixing, consolidating, quenching, irradiating, annealing, mechanically deforming, doping, homogenizing, heating, melting, and packaging of the finished product, such as a medical implant.

"Residual free radicals" refers to free radicals that are generated when a polymer is exposed to ionizing radiation such as gamma or e-beam irradiation. While some of the free radicals recombine with each other to from cross-links, some become trapped in crystalline domains. The trapped free radicals are also known as residual free radicals.

According to one aspect of the invention, the levels of residual free radicals in the polymer generated during an ionizing radiation (such as gamma or electron beam) is preferably determined using electron spin resonance and treated appropriately to reduce the free radicals.

"Sterilization", one aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from about 25-70 kGy, or by gas sterilization with ethylene oxide or gas plasma.

Another aspect of the present invention discloses a process of sterilization of medical implants containing polymeric material, such as cross-linked UHMWPE. The process comprises sterilizing the medical implants by ionizing sterilization with gamma or electron beam radiation, for example, at a dose level ranging from 25-200 kGy. The dose level of sterilization is higher than standard levels used in irradiation. This is to allow cross-linking or further cross-linking of the medical implants during sterilization.

One aspect of the present invention discloses a process of increasing the uniformity of the antioxidant following doping in polymeric component of a medical implant during the manufacturing process by heating for a time period depending on the melting temperature of the polymeric material. For example, the preferred temperature is about 137° C. or less. Another aspect of the invention discloses a heating step that can be carried in the air, in an atmosphere, containing oxygen, wherein the oxygen concentration is at least about 1%, 2%, 4%, or up to about 22%, or any value thereabout or therebetween. In another aspect, the invention discloses a heating step that can be carried while the implant is in contact with an inert atmosphere, wherein the inert atmosphere contains gas selected from the group consisting of nitrogen, argon, helium, neon, or the like, or a combination thereof. In another aspect, the invention discloses a heating step that can be carried while the implant is in contact with a non-oxidizing medium, such as an inert fluid medium, wherein the medium contains no more than about 1% oxygen. In another aspect, the invention discloses a heating step that can be carried while the implant is in a vacuum.

The term "radiation generated heat" refers to the heat generated as a result of conversion of some of the energies deposited by the electrons or gamma rays to heat during an irradiation process. Radiation generated heating, which includes adiabatic and partially adiabatic heating, primarily depends on how well the sample is thermally insulated during the irradiation. With good thermal insulation, most of the heat generated is not lost to the surroundings and leads to the radiation generated heating (adiabatic and partially adiabatic) of the polymer to a higher temperature than the irradiation temperature. The heating also could be induced by using a high enough dose rate to minimize the heat loss to the surroundings. The radiation generated heating (including adiabatic and partially adiabatic) depends on a number of processing parameters such as dose rate, initial temperature of the sample, absorbed radiation dose, and the like. Radiation generated heating (including adiabatic and partially adiabatic) is a result of the conversion of the radiation dose to heat in the irradiated sample. If the temperature of the sample is high enough during melting, radiation generated heating (including adiabatic and partially adiabatic) results in melting of the crystals. Even when the initial temperature of the polymer is low, for example, near room temperature or 40° C., the radiation generated heating (including adiabatic and partially adiabatic) can be high enough to increase the temperature of the polymer during irradiation. If the initial temperature and radiation dose are too high, radiation generated heating (including adiabatic and partially adiabatic) may result in complete melting of the polymer.

It should be noted that in theoretical thermodynamics, "adiabatic heating" refers to an absence of heat transfer to the surroundings. In the practice, such as in the creation of new polymeric materials, "adiabatic heating" refers to situations where a sufficient majority of thermal energy is imparted on the starting material and is not transferred to the surroundings. Such can be achieved by the combination of insulation, irradiation dose rates and irradiation time periods, as disclosed herein and in the documents cited herein. Thus, what may approach adiabatic heating in the theoretical sense achieves it in the practical sense. However, not all warm irradiation refers to an "adiabatic heating." Warm irradiation also can have non-adiabatic or partially (such as 10-75% of the heat generated are lost to the surroundings) adiabatic heating.

In an aspect of this invention, room temperature irradiation refers that the polymeric material is at ambient temperature is not heated by an external heating element before or during irradiation. However, the irradiation itself may heat up the polymeric material. In some cases the radiation dose is lower, which only results in minor rise in temperature in the polymeric material, and in some other cases the radiation dose is higher, which results in large increases in temperature in the polymeric material. Similarly the dose rate also plays an important role in the heating of the polymeric material during irradiation. At low dose rate the temperature rise is smaller while with larger dose rates the radiation imparted heating becomes more adiabatic and leads to larger increases in the temperature of the polymeric material. In any of these cases, as long as there is no other heating source other than radiation itself, the process is considered as room temperature irradiation.

In another aspect of this invention, there is described the heating method of implants to increase the uniformity of the antioxidant. The medical device comprising a polymeric raw material, such as UHMWPE, is generally heated to a temperature of about 137° C. or less following the step of doping with the antioxidant. The medical device is kept heated in the inert medium until the desired uniformity of the antioxidant is reached.

The term "below melting point" or "below the melt" refers to a temperature below the melting point of a polymeric material, for example, polyethylene such as UHMWPE. The term "below melting point" or "below the melt" refers to a temperature less than about 145° C., which may vary depending on the melting temperature of the polymeric material, for example, about 145° C., 140° C. or 135° C., which again depends on the properties of the polymeric material being treated, for example, molecular weight averages and ranges, batch variations, etc. The melting temperature is typically measured using a differential scanning calorimeter (DSC) at a heating rate of 10° C. per minute. The peak melting temperature thus measured is referred to as melting point, also referred as transition range in temperature from crystalline to amorphous phase, and occurs, for example, at approximately 137° C. for some grades of UHMWPE. It may be desirable to conduct a melting study on the starting polymeric material in order to determine the melting temperature and to decide upon an irradiation and annealing temperature. Generally, the melting temperature of polymeric material is increased when the polymeric material is under pressure.

The term "heating" refers to thermal treatment of the polymer at or to a desired heating temperature. In one aspect, heating can be carried out at a rate of about 10° C. per minute to the desired heating temperature. In another aspect, the heating can be carried out at the desired heating temperature for desired period of time. In other words, heated polymers can be continued to heat at the desired temperature, below or above the melt, for a desired period of time. Heating time at or to a desired heating temperature can be at least 1 minute to 48 hours to several weeks long. In one aspect the heating time is about 1 hour to about 24 hours. In another aspect, the heating can be carried out for any time period as set forth herein, before or after irradiation. Heating temperature refers to the thermal condition for heating in accordance with the invention. Heating can be performed at any time in a process, including during, before and/or after irradiation. Heating can be done with a heating element. Other sources of energy include the environment and irradiation.

The term "high temperature melting" refers to thermal treatment of the polymer or a starting material to a temperature between about 200° C. and about 500° C. or more, for example, temperature of about 200° C., about 250° C., about 280° C., about 300° C., about 320° C., about 350° C., about 380° C., about 400° C., about 420° C., about 450° C., about 480° C. or more. Heating time at "high temperature melting" can be at least 30 minutes to 48 hours to several weeks long. In one aspect the "high temperature melting" time is continued for about 1 minute to about 48 hours or more. For example, the heating is continued for at least for one minute, 10 minutes, 20 minutes, 30 minutes, one hour, two hours, five hours, ten hours, 24 hours, or more.

The term "annealing" refers to heating or a thermal treatment condition of the polymers in accordance with the invention. Annealing generally refers to continued heating the polymers at a desired temperature below its peak melting point for a desired period of time. Annealing time can be at least 1 minute to several weeks long. In one aspect the annealing time is about 4 hours to about 48 hours, preferably 24 to 48 hours and more preferably about 24 hours. "Annealing temperature" refers to the thermal condition for annealing in accordance with the invention. Annealing can be performed at any time in a process, including during, before and/or after irradiation.

In certain embodiments of the present invention in which annealing can be carried out, for example, in an inert gas, e.g., nitrogen, argon or helium, in a vacuum, in air, and/or in a sensitizing atmosphere, for example, acetylene.

The term "contacted" includes physical proximity with or touching such that the sensitizing agent can perform its intended function. Preferably, a polymeric composition or preform is sufficiently contacted such that it is soaked in the sensitizing agent, which ensures that the contact is sufficient. Soaking is defined as placing the sample in a specific environment for a sufficient period of time at an appropriate temperature, for example, soaking the sample in a solution of an antioxidant. The environment is heated to a temperature ranging from room temperature to a temperature below the melting point of the material. The contact period ranges from at least about 1 minute to several weeks and the duration depending on the temperature of the environment.

The term "non-oxidizing" refers to a state of polymeric material having an oxidation index (A. U.) of less than about 0.5, according to ASTM F2102 or equivalent, following aging polymeric materials for 5 weeks in air at 80° C. oven. Thus, a non-oxidizing cross-linked polymeric material generally shows an oxidation index (A. U.) of less than about 0.5 after the aging period.

The term "oxidatively stable" or "oxidative stability" or "oxidation-resistant" refers a state of polymeric material having an oxidation index (A. U.) of less than about 0.1 following aging polymeric materials for 5 weeks in air at 80° C. oven. Thus, a oxidatively stable or oxidation-resistant cross-linked polymeric material generally shows an oxidation index (A. U.) of less than about 0.1 after the aging period.

The term "surface" of a polymeric material refers generally to the exterior region of the material having a thickness of about 1.0 µm to about 2 cm, preferably about 1.0 mm to about 5 mm, more preferably about 2 mm of a polymeric material or a polymeric sample or a medical device comprising polymeric material.

The term "bulk" of a polymeric material refers generally to an interior region of the material having a thickness of about 1.0 µm to about 2 cm, preferably about 1.0 mm to about 5 mm, more preferably about 2 mm, from the surface of the polymeric material to the center of the polymeric material. However, the bulk may include selected sides or faces of the polymeric material including any selected surface, which may be contacted with a higher concentration of antioxidant.

Although the terms "surface" and "bulk" of a polymeric material generally refer to exterior regions and the interior regions, respectively, there generally is no discrete boundary between the two regions. But, rather the regions are more of a gradient-like transition. These can differ based upon the size and shape of the object and the resin used.

The term "doping" refers to a general process known in the art (see, for example, U.S. Pat. Nos. 6,448,315 and 5,827,904). In this connection, doping generally refers to contacting a polymeric material with an antioxidant under certain conditions, as set forth herein, for example, doping UHMWPE with an antioxidant under supercritical conditions.

In certain embodiments of the present invention in which doping of antioxidant is carried out at a temperature above the melting point of the polymeric material, the antioxidant-doped polymeric material can be further heated above the melt or annealed to eliminate residual free radicals after irradiation. Melt-irradiation of polymeric material in presence of an antioxidant, such as vitamin E, can change the distribution of the vitamin E concentration and also can change the mechanical properties of the polymeric material. These changes can be induced by changes in crystallinity and/or by the plasticization effect of vitamin E at certain concentrations.

According to one embodiment, the surface of the polymeric material is contacted with little or no antioxidant and bulk of the polymeric material is contacted with a higher concentration of at least one antioxidant.

According to another embodiment, the surface of the polymeric material is contacted with no antioxidant and bulk of the polymeric material is contacted with a higher concentration of at least one antioxidant.

According to one embodiment, the bulk of the polymeric material is contacted with little or no antioxidant and surface of the polymeric material is contacted with a higher concentration of antioxidant.

According to another embodiment, the bulk of the polymeric material is contacted with no antioxidant and surface of the polymeric material is contacted with a higher concentration of antioxidant.

According to another embodiment, the surface of the polymeric material and the bulk of the polymeric material are contacted with the same concentration of antioxidant.

According to one embodiment, the surface of the polymeric material may contain from about 0 wt % to about 50 wt % antioxidant, preferably about 0.001 wt % to about 10 wt %, preferably between about 0.01 wt % to about 0.5 wt %, more preferably about 0.2 wt %. According to another embodiment, the bulk of the polymeric material may contain from about 0 wt % to about 50 wt %, preferably about 0.001 wt % to about 10 wt %, preferably between about 0.01 wt % to about 0.5 wt %, more preferably about 0.2 wt %, preferably between about 0.2 wt % and about 1% wt %, preferably about 0.5 wt %.

According to one embodiment, the antioxidant/anti-cross-linking agent-poor regions of the polymeric material may contain a total additive concentration from about 0 wt % to about 50 wt % antioxidant, preferably about 0.001 wt % to about 10 wt %, preferably between about 0.01 wt % to about 0.5 wt %, more preferably about 0.05 wt %. According to another embodiment, the antioxidant/anti-crosslinking agent-rich regions of the polymeric material may contain from about 0 wt % to about 50 wt %, preferably about 0.001 wt % to about 10 wt %, preferably between about 0.01 wt % to about 5 wt %, preferably between about 0.2 wt % and about 5% wt %, preferably about 1 wt %.

According to another embodiment, the antioxidant concentration in the polymeric material can be about 1 ppm to about 10,000 ppm, preferably about 100 ppm, about 500 ppm, about 1000 ppm, about 2000 ppm, about 3000 ppm, about 5000 ppm, or to any value thereabout or therebetween.

According to another embodiment, the radiation dose is adjusted depending on the concentration of the antioxidant to achieve a desired cross-link density. At higher antioxidant concentrations, generally a higher dose level is required in order to reach the same cross-link density.

According to another embodiment, the surface of the polymeric material and the bulk of the polymeric material contain the same concentration of antioxidants).

More specifically, consolidated polymeric material can be doped with an antioxidant by soaking the material in a solution of the antioxidant. This allows the antioxidant to diffuse into the polymer. For instance, the material can be soaked in 100% antioxidant. The material also can be soaked in an antioxidant solution where a carrier solvent can be used to dilute the antioxidant concentration. To increase the depth of diffusion of the antioxidant, the material can be doped for longer durations, at higher temperatures, at higher pressures, and/or in presence of a supercritical fluid. This can be performed sequentially for different antioxidants or doping can be done with more than one antioxidant at a time.

The antioxidant can be diffused to a depth of about 5 mm or more from the surface, for example, to a depth of about 3-5 mm, about 1-3 mm, or to any depth thereabout or therebetween.

The doping process can involve soaking of a polymeric material, medical implant or device with an antioxidant, such as vitamin E, for about half an hour up to several days, preferably for about one hour to 24 hours, more preferably for one hour to 16 hours. The antioxidant can be at room temperature or heated up to about 137° C. and the doping can be carried out at room temperature or at a temperature up to about 137° C. Preferably the antioxidant solution is heated to a temperature between about 100° C. and 135° C. or between about 110° C. and 130° C., and the doping is carried out at a temperature between about 100° C. and 135° C. or between about 110° C. and 130° C. More preferably, the antioxidant solution is heated to about 120° C. and the doping is carried out at about 120° C.

Doping with α-tocopherol through diffusion at a temperature above the melting point of the irradiated polymeric material (for example, at a temperature above 137° C. for UHMWPE) can be carried out under reduced pressure, ambient pressure, elevated pressure, and/or in a sealed chamber, for about 0.1 hours up to several days, preferably for about 0.5 hours to 6 hours or more, more preferably for about 1 hour to 5 hours. The antioxidant can be at a temperature of about 137° C. to about 400° C., more preferably about 137° C. to about 200° C., more preferably about 137° C. to about 160° C.

The doping and/or the irradiation steps can be followed by an additional step of homogenization. The term "homogenization" refers to a heating step in air or in anoxic environment to improve the spatial uniformity of the antioxidant concentration within the polymeric material, medical implant or device. Homogenization also can be carried out before and/or after the irradiation step. The heating may be carried out above or below or at the peak melting point. Antioxidant-doped or -blended polymeric material can be homogenized at a temperature below or above or at the peak melting point of the polymeric material for a desired period of time, for example, the antioxidant-doped or -blended polymeric material can be homogenized for about an hour to several days at room temperature to about 400° C. Preferably, the homogenization is carried out at 90° C. to 180° C., more preferably 100° C. to 137° C., more preferably 120° C. to 135° C., most preferably 130° C. Homogenization is preferably carried out for about one hour to several days to two weeks or more, more preferably about 12 hours to 300 hours or more, more preferably about 280 hours, or more preferably about 200 hours. More preferably, the homogenization is carried out at about 130° C. for about 36 hours or at about 120° C. for about 24 hours. The polymeric material, medical implant or device is kept in an inert atmosphere (nitrogen, argon, and/or the like), under vacuum, or in air during the homogenization process. The homogenization also can be performed in a chamber with supercritical fluids such as carbon dioxide or the like. The pressure of the supercritical fluid can be about 1000 to about 3000 psi or more, more preferably about 1500 psi. It is also known that pressurization increases the melting point of UHMWPE. A temperature higher than 137° C. can be used for homogenization below the melting point if applied pressure has increased the melting point of UHMWPE beyond 137° C.

Homogenization enhances the diffusion of the antioxidant from antioxidant-rich regions to antioxidant poor regions. The diffusion is generally faster at higher temperatures. At a temperature above the melting point the hindrance of diffusion from the crystalline domains is eliminated and the homogenization occurs faster. Melt-homogenization and subsequent recrystallization may reduce the mechanical properties mostly due to a decline in the crystallinity of the polymer. This may be acceptable or even desirable for certain applications. For example, applications where the decline in mechanical properties is not desirable the homogenization can be carried out below the melting point. Alternatively, below or above the melt homogenized samples may be subjected to high pressure crystallization to further improve their mechanical properties.

The polymeric material, medical implant or device is kept in an inert atmosphere (nitrogen, argon, neon, and/or the like), under vacuum, or in air during the homogenization process. The homogenization also can be performed in a chamber with supercritical fluids such as carbon dioxide or the like. The pressure of the supercritical fluid can be 1000 to 3000 psi or more, more preferably about 1500 psi. The homogenization can be performed before and/or after and/or during the diffusion of the antioxidant.

In one embodiment, the invention discloses:
1. Starting material can be: Homopolymer, UHMWPE, other polyolefins, copolymers etc.; Blended with vitamin E; Doped with vitamin E; Blended with antioxidants; Doped with antioxidants; Blended of polymers; Gradients of antioxidant etc., and the like.
2. Heating include: Annealing below melt, Melting, and/or Melting at 300° C. (melt above the peak melting point in the respective medium); and all of the above in water, steam, air, inert, sensitizing gas, reduced oxygen environment, in antioxidant, in antioxidant solutions, or supercritical fluid(s).
3. Post-Irradiation treatments include: Heating (anneal or melt or melt at 300° C.), Doping with antioxidant, High pressure crystallization (HPC), High pressure annealing (HPA), Deformation, and/or Low pressure annealing (LPA), and Low pressure crystallization (LPC).
4. Sterilization by methods including: Gamma, e-beam, x-ray, Gas plasma, and Ethylene oxide.

In another embodiment, the invention discloses:
1. Heating of the Starting Material and Pressurize, cool under pressure.
2. Heating of the Starting Material then HPC, HPA, Deformation, LPA, or LPC followed by Irradiation, and optionally followed by Post-Irradiation Treatments.
3. Irradiation of the Starting Material then heat and optionally followed by post-irradiation treatments (for example, HPC).
4. Heat the Starting Material then Irradiation, and optionally followed by Post-Irradiation Treatments.

Each composition and aspects, and each method and aspects, which are described above can be combined with another in various manners consistent with the teachings contained herein. According to the embodiments and aspects of the inventions, all methods and the steps in each method can be applied in any order and repeated as many times in a manner consistent with the teachings contained herein.

The invention is further described by the following examples, which do not limit the invention in any manner.

EXAMPLES

VITAMIN E: Vitamin E (Acros™ 99% D-α-Tocopherol, Fisher Brand), was used in the experiments described herein, unless otherwise specified. The vitamin E used is very light yellow in color and is a viscous fluid at room temperature. Its melting point is 2-3° C.

DETERMINATION OF VITAMIN E INDEX (A.U.): Fourier transform infrared spectroscopy (FTIR) is used to quantify the Vitamin E content in the UHMWPE. The FTIR, in other words also known as infra-red microscopy, is used to quantify the Vitamin E content by measuring the vitamin E index, which is a dimensionless parameter.

The absorption peak associated with the alpha-tocopherol is located at 1265 cm-1, which is then normalized with a methylene peak at 1895 cm-1. This ratio is reported as a vitamin E index.

The sample is prepared by microtoming a slice between 100 and 200 micrometers thick through the thickness of the sample. The section must be microtomed orthogonally to the scan direction to prevent spreading the alpha-tocopherol in the through-thickness direction. The slice is mounted on the translating stage of a FTIR microscope, and FTIR spectra are collected a specified intervals from the surface into the bulk of the sample.

The vitamin E index can be converted into an absolute concentration by comparing the index to a calibration curve prepared from UHMWPE sections containing known amounts of Vitamin E.

Example 1. High Temperature Melting of UHMWPE Followed by High Pressure Crystallization (HPC)

Slab compression molded (CM) and ram extruded (RE) blocks of UHMWPE (GUR1050, Orthoplastics, Lancashire, UK) were placed each in a stainless steel pouch, which was closed but not sealed. The pouch was placed in contact with the platens of a molding press (3895, Carver, Wabash, Ind.). Argon gas was constantly purged through the pouch while the platens were heated. The sample was brought to 300° C. and kept at this temperature under argon purge for 5 hours. Then, it was cooled under argon purge to about room temperature by shutting the heater off. The cooled samples were then placed in a pressure chamber in water. The chamber was sealed and the temperature was increased to 180° C. The sample was kept at about 10,000 psi and 180° C. for 5 hours. The, the chamber was pressurized to 45,000 psi by pumping water and the sample was kept at approximately 45,000 psi and 180° C. for at least 5 hours. Then, the chamber was cooled while maintaining pressure to below the melting point of UHMWPE at ambient pressure, i.e. approximately 137° C., more often to room temperature. Then, the pressure was released and the sample was taken out of the chamber. Thin sections (3.2 mm-thick) were machined from the high temperature melted and high temperature melted and subsequently high pressure crystallized UHMWPE.

Control samples were untreated CM and RE UHMWPE and high pressure crystallized (HPC) CM and RE UHMWPEs without prior high temperature melting.

Tensile mechanical properties were tested using Type V dog-bone-shaped samples stamped out of these thin sections at 10 mm/min according to ASTM D-638. The elongation-to-break (EAB) was measured using a laser extensometer. The work-to-failure (WF) was calculated as the area under the engineering stress-strain curve. The IZOD single-notch impact tests were done according to ASTM F648 (Orthoplastics, Lancashire, UK).

TABLE 1

Mechanical properties of high temperature melted and high pressure crystallized UHMWPE

| | UTS (MPa) | EAB (%) | E (GPa) | YS (MPa) | IZOD Impact Strength (kJ/m$^2$) | Work to failure (kJ/m$^2$) |
|---|---|---|---|---|---|---|
| Slab compression molded (CM) UHMWPE | | | | | | |
| Untreated | 51 ± 3 | 442 ± 20 | 1.3 ± 0.3 | 22 ± 1 | 127 ± 7 | 2995 ± 267 |
| HPC | 60 ± 2 | 359 ± 11 | NA | 24 ± 1 | | |
| HTM | 47 ± 4 | 654 ± 36 | 2.4 ± 0.6 | 22 ± 1 | 148 ± 3 | 4294 ± 296 |
| HTM HPC | 43 ± 2 | 543 ± 53 | 4.3 ± 1.6 | 25 ± 1 | | 3283 ± 832 |
| Ram extruded (RE) UHMWPE | | | | | | |
| Untreated | 53 ± 6 | 391 ± 42 | 1.1 ± 0.6 | 20 ± 1 | | |
| HPC | 61 ± 6 | 323 ± 23 | 5.5 ± 1.0 | 25 ± 1 | | |
| HTM | 44 ± 2 | 484 ± 42 | 2.5 ± 0.6 | 23 ± 1 | | |
| HTM HPC | 53 ± 2 | 537 ± 5 | 4.5 ± 0.5 | 30 ± 1 | | |

TABLE 2

Crystallinity ($X_c$), peak melting point (PMT) of HTM and HTM HPC UHMWPE compared to control UHMWPEs.

| | $X_c$ (%) | PMT (° C.) |
|---|---|---|
| Slab compression molded (CM) UHMWPE | | |
| Untreated | 53 ± 3 | 135.1 ± 0.0 |
| HPC | 72 ± 4 | 144.3 ± 0.6 |
| HTM | 56 ± 1 | 134.9 ± 0.2 |
| HTM HPC | 67 ± 1 | 138.8 ± 0.7 |
| Ram extruded (RE) UHMWPE | | |
| Untreated | 51 ± 4 | 135.1 ± 0.1 |
| HPC | 68 ± 3 | 146.4 ± 0.7 |
| HTM | 62 ± 1 | 135.0 ± 0.1 |
| HTM HPC | 80 ± 1 | 144.3 ± 0.7 |

Crystallinity (n=3 each) was measured by differential scanning calorimetry from −20° C. to 180° C. at a heating rate of 10° C./min. The crystallinity was determined by normalizing the enthalpy of fusion by the enthalpy of fusion of 100% crystalline polyethylene; 291 J/g.

Sets of data were compared using Student t-test with unequal variance. Statistical significance was attributed for $p<0.05$.

The tensile mechanical properties of untreated UHMWPE, high temperature melted (HTM) UHMWPE, and high temperature melted, high pressure crystallized (HTM HPC) UHMWPE are shown in Table 1. The results showed that melting UHMWPE at 300° C. increased elongation significantly. The crystallinity was also increased (Table 2), resulting in a tough material with improved elongation. High pressure crystallization following melting at 300° C. increased crystallinity and peak melting point substantially for both ram extruded and compression molded UHMWPE, resulting in a highly crystalline UHMWPE (Table 2) with substantially improved elongation. In addition, the modulus of melted and high pressure crystallized UHMWPE was less than non-melted high pressure crystallized UHMWPE.

Example 2. High Temperature Melting of UHMWPE Followed by HPC and Irradiation

Slab compression molded (CM) and ram extruded (RE) blocks of virgin UHMWPE and 0.15 wt % vitamin E-blended, compression molded UHMWPE are placed each in a stainless steel pouch, which is closed but not sealed. The pouch is placed in contact with the platens of a molding press. Argon gas is constantly purged through the pouch while the platens are heated. The sample is brought to 300° C. and kept at this temperature under argon purge for 5 hours. Then, it is cooled under argon purge to about room temperature. The cooled samples are then placed in a pressure chamber in water. The chamber is sealed and the temperature is increased to 180° C. The sample is kept at about 10,000 psi and 180° C. for 5 hours. The, the chamber is pressurized to 45,000 psi by pumping water and the sample is kept at approximately 45,000 psi and 180° C. for at least 5 hours. Then, the chamber is cooled while maintaining pressure to below the melting point of UHMWPE at ambient pressure, i.e. approximately 137° C., more often to room temperature. Then, the pressure is released and the sample is taken out of the chamber. Then, high temperature melted and subsequently high pressure crystallized UHMWPE is irradiated at 25, 50, 100 and 150 kGy by electron beam irradiation.

Example 3. High Temperature Melting of Highly Cross-Linked UHMWPE

Slab compression molded GUR1050 UHMWPE that had been irradiated to 100-kGy was used. Approximately 4 cm-thick blocks were placed in pre-heated inert gas convection oven (LLD1-16N-3, Despatch Inc., MN) at 300 or 320° C. The samples were kept at temperature under nitrogen flow for 1, 5 or 12 hours, after which the samples were cooled under nitrogen flow to below approximately 60° C. before taking the samples out of the oven.

Tensile testing was performed on dog-bones (Type V, ASTM D-638) stamped out of 3.2 mm-thick sections machined from high temperature melted UHMWPEs. Testing was performed at 10 mm/min (MTS Insight, Eden Prairie, Minn.). Elongation to break (EAB) was determined by using a laser extensometer. Work to failure was determined as the area under the engineering stress-strain curves. The IZOD single-notch impact tests were done according to ASTM F648 (Orthoplastics, Lancashire, UK). Ultimate tensile strength (UTS) and elastic modulus (E) were also measured.

Wear rates were determined by pin-on-disc wear testing on a custom-designed bidirectional wear tester (see Bragdon C R, O'Connor D O, Lowenstein J D, Jasty M, Biggs S A, Harris W H. A new pin-on-disc wear testing method for simulating wear of polyethylene on cobalt-chrome alloy in total hip arthroplasty. *Journal of Arthroplasty* 2001: 41(2): 795-808). Testing was performed in undiluted, preserved bovine serum at 2 Hz for 2 million cycles (MC) with gravimetric assessment of wear at approximately every 500,000 cycles. Wear rate was determined as a linear regression of weight loss as a function of number of cycles from 0.5 to 2 MC.

Thin sections (150 µm-thick) were microtomed and analyzed using Fourier Transform Infrared Spectroscopy (FTIR). A vinyl index was calculated using the area under 880-920 $cm^{-1}$ and normalizing it to the area under 1895 $cm^{-1}$.

TABLE 3

High temperature melting (HTM) and elongation of unirradiated UHMWPE as a function of increasing melting time.

| | UTS (MPa) | EAB (%) | E (GPa) | YS (MPa) | Wear rate (mg/MC) | IZOD impact strength (kJ/m²) |
|---|---|---|---|---|---|---|
| No irr. | 59 ± 5 | 401 ± 15 | 1.3 ± 0.3 | 21 ± 1 | −10.2 ± 0.9 | 127 ± 7 |
| No irr., 300° C., 1 hr | 49 ± 1 | 541 ± 19 | 1.2 ± 0.2 | 19 ± 1 | | 90 ± 3 |
| No irr., 300° C., 5 hr | 58 ± 5 | 720 ± 14 | 1.6 ± 0.3 | 22 ± 1 | | 148 ± 3 |
| No irr., 300° C., 12 hr | 52 ± 2 | 889 ± 26 | 1.6 ± 0.2 | 21 ± 1 | | 118 ± 6 |
| No irr., 320° C., 1 hr | 60 ± 3 | 809 ± 44 | 1.6 ± 0.2 | 22 ± 1 | | 67 ± 13 |
| No irr., 320° C., 5 hr | 44 ± 4 | 922 ± 217 | 2.6 ± 0.5 | 21 ± 2 | | 134 ± 1 |

TABLE 4

High temperature melting (HTM) and the elongation of 100-kGy irradiated UHMWPE as a function of increasing melting time.

| | UTS (MPa) | EAB (%) | E (GPa) | YS (MPa) | Wear rate (mg/MC) | IZOD impact strength (kJ/m²) |
|---|---|---|---|---|---|---|
| 100-kGy | 50 ± 4 | 244 ± 19 | | 24 ± 1 | −2.3 ± 0.2 | 74 ± 2 |
| 100-kGy, 300° C., 1 hr | 42 ± 1 | 386 ± 19 | 1.8 ± 0.2 | 19 ± 1 | −2.7 ± 1.0 | 149 ± 5 |
| 100-kGy, 300° C., 5 hr | 44 ± 3 | 527 ± 29 | 1.7 ± 0.1 | 20 ± 1 | | 102 ± 7 |
| 100-kGy, 300° C., 12 hr | 42 ± 5 | 601 ± 60 | 1.8 ± 0.3 | 19 ± 0 | −5.9 ± 1.4 | 99 ± 6 |
| 100-kGy, 320° C., 1 hr | 42 ± 2 | 587 ± 22 | 2.3 ± 0.2 | 21 ± 0 | | 97 ± 5 |
| 100-kGy, 320° C., 5 hr | 41 ± 2 | 872 ± 25 | 3.1 ± 0.2 | 21 ± 0 | | 33 ± 4 |

High temperature melting (HTM) increased the elongation of both unirradiated and 100-kGy irradiated UHMWPE both compared to untreated UHMWPE and as a function of increasing melting time (Table 3 and Table 4). The crystallinity of unirradiated UHMWPEs melted at 300° C. did not change with increasing melting time, but the vinyl index, which is an indicator of increased chain ends, increased (Table 5). Crystallinity of both unirradiated and 100-kGy irradiated UHMWPEs high temperature melted at 320° C. were substantially higher than those melted at 300° C. (Table 5 and Table 6). The vinyl index of irradiated UHMWPE was higher after high temperature melting when compared to unirradiated UHMWPE.

There are two mechanisms expected to be prevalent in high temperature melted UHMWPEs; the first is the increased self-diffusion of polymer chains across grain boundaries at the high temperature, the other is increased chain scissioning due to degradation at high temperature. It is possible that the high crystallinity accompanying high vinyl indices in some samples is due to the recrystallization of broken chains. However, shorter time melting of unirradiated UHMWPE resulted in both high UTS due to increased diffusion/entanglement of chains, higher elongation to break, higher work to failure without the detriment of increased chain scission, for example 300° C. for 5 hours and 320° C. for 1 hr.

TABLE 5

Properties of high temperature melted UHMWPEs.

| | Crystallinity (%) | Peak melting point (° C.) | Vinyl index | Cross-link density (mol/m$^3$) | Wear rate (mg/MC) |
|---|---|---|---|---|---|
| No irr. | | | | | 10.2 ± 0.9 |
| No irr., 300° C., 1 hr | 56 ± 1 | 134 ± 0 | 0.02 | — | |
| No irr., 300° C., 5 hr | 57 ± 2 | 135 ± 0 | 0.04 | — | |
| No irr., 300° C., 12 hr | 57 ± 1 | 135 ± 0 | 0.06 | — | |
| No irr., 320° C., 1 hr | 63 ± 2 | 134 ± 0 | 0.05 | — | |
| No irr., 320° C., 5 hr | 69 ± 1 | 133 ± 0 | 0.09 | — | |

TABLE 6

Properties of 100-kGy irradiated and high temperature melted UHMWPEs.

| | Crystallinity (%) | Peak melting point (° C.) | Vinyl index | Cross-link density (mol/m$^3$) | Wear rate (mg/MC) |
|---|---|---|---|---|---|
| 100-kGy | | | | | 2.29 ± 1.0 |
| 100-kGy, 300° C., 1 hr | 45 ± 1 | 132 ± 0 | 0.02 | 109 ± 3 | 2.74 ± 1.0 |
| 100-kGy, 300° C., 5 hr | 55 ± 1 | 130 ± 0 | 0.06 | 54 ± 1 | |
| 100-kGy, 300° C., 12 hr | 54 ± 0 | 132 ± 0 | 0.07 | 45 ± 2 | 5.86 ± 1.4 |
| 100-kGy, 320° C., 1 hr | 58 ± 0 | 132 ± 0 | 0.09 | 45 ± 2 | |
| 100-kGy, 320° C., 5 hr | 60 ± 1 | 131 ± 0 | 0.12 | 20 ± 0 | |

Figure 35:
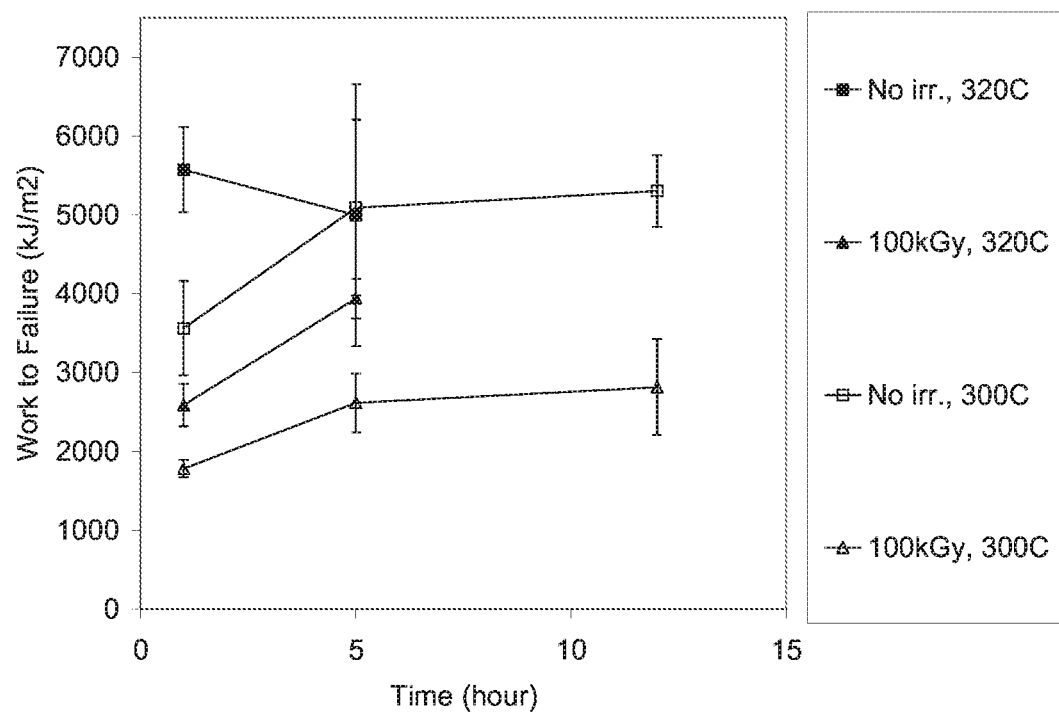
FIG. 35 shows work-to-failure of unirradiated and 100-kGy irradiated UHMWPE melted at 300 and 320° C. as a function of time.

The work-to-failure, an indicator of plasticity, increased as a function of time at melting temperature (FIG. 35). This suggested that there is a balance between chain diffusion and polymer degradation, which allows the properties to improve for a period of time at the high melting temperature.

Figure 36:
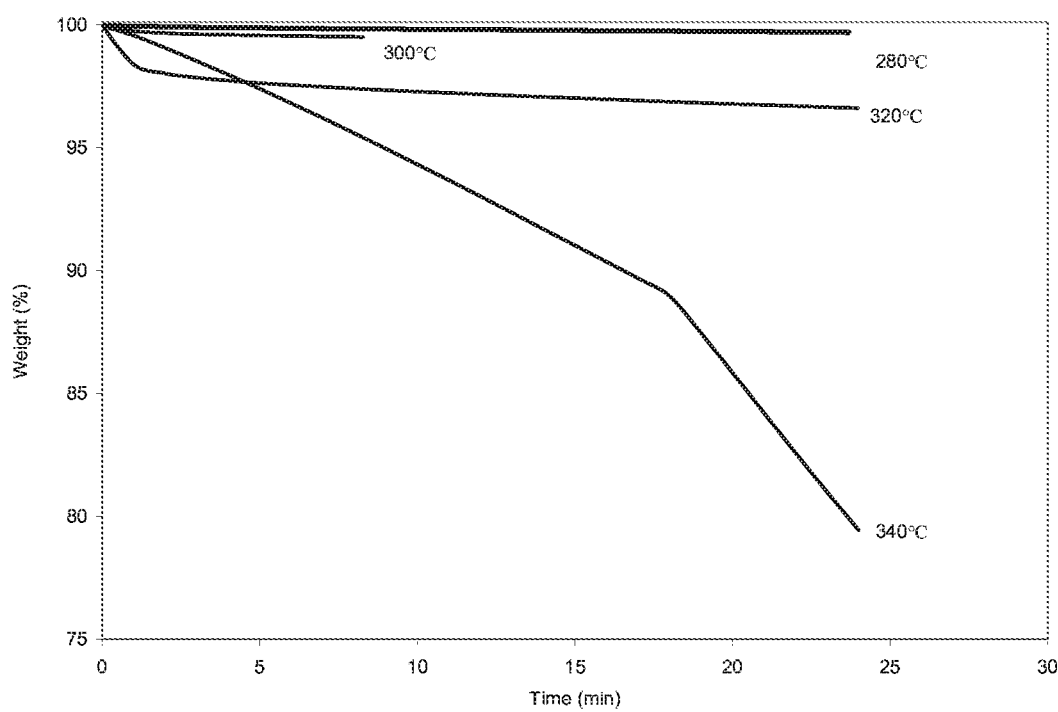
FIG. 36 shows weight loss of unirradiated UHMWPE melted at 280, 300, 320, and 340° C. as a function of time.
Figure 37:
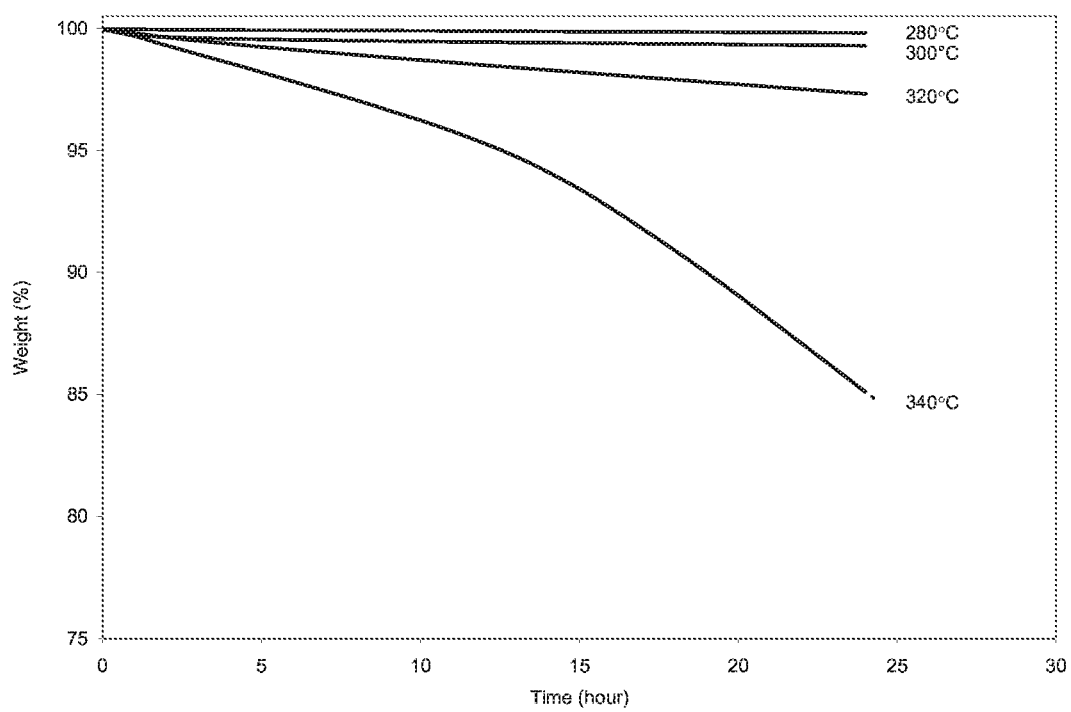
FIG. 37 shows weight loss of 65-kGy irradiated UHMWPE melted at 280, 300, 320, and 340° C. as a function of time.
Figure 38:
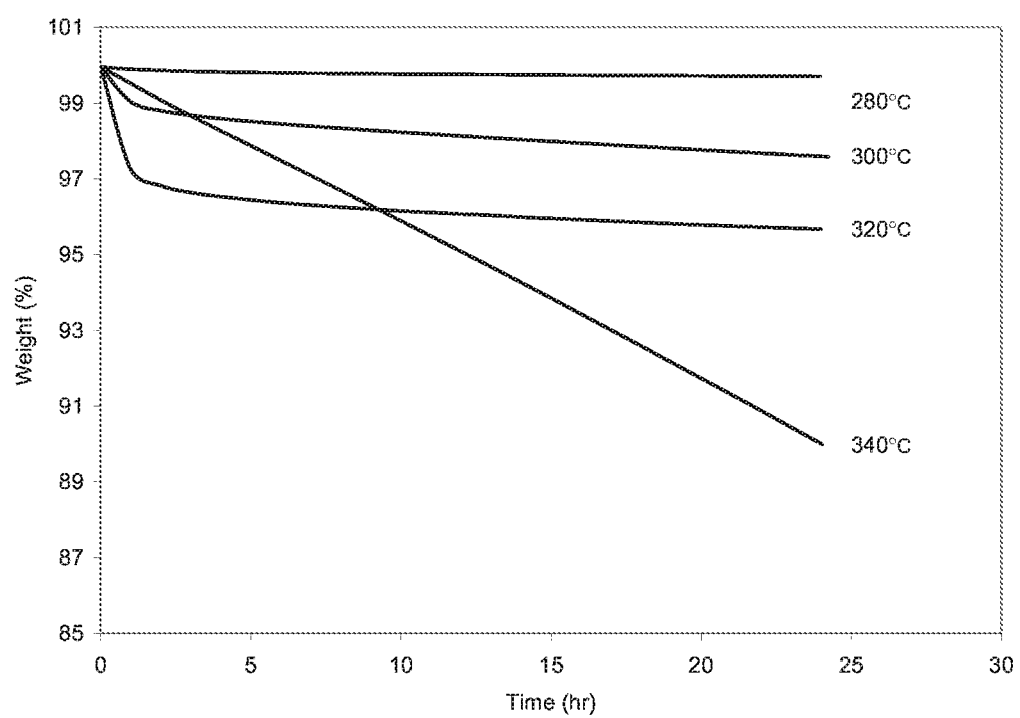
FIG. 38 shows weight loss of 100-kGy irradiated UHMWPE melted at 280, 300, 320, and 340° C. as a function of time.

The weight loss as a function of temperature at the very high temperatures of melting was measured by using a thermal gravimetric analyzer (Q500, TA Instruments, New Castle, DL), heating to temperature at 20° C./min and staying isothermal at the high temperature for the desired duration. This experiment was performed on unirradiated UHMWPE, 65-kGy and 100-kGy e-beam irradiated UHMWPEs at 280, 300, 320 and 340° C. for 24 hours. The weight loss curve most often displayed an initial weight loss within the heating period (first 10 minutes), then either equilibrated or continued at a steady pace (FIGS. 36, 37, and 38).

The initial weight loss during the heating period is attributed as the loss of volatiles and small molecular weight impurities in UHMWPE. After this initial period, both unirradiated and 13 irradiated UHMWPEs showed faster weight loss and higher overall weight loss at the end of the 24 hour period with increasing temperature. This suggests that there is increasing degradation of the polymer with increasing temperature.

Example 4. High Temperature Melting of Vitamin E-Blended UHMWPE

Slab compression molded (CM) UHMWPE blended with 0.15 wt % vitamin E (GUR1050, Orthoplastics, Lancashire, UK) and 0.2 wt % vitamin E (Zimmer, Inc.) were placed each in a stainless steel pouch, which was closed but not sealed. The pouch was placed in contact with the platens of a molding press (3895, Carver, Wabash, Ind.). Argon gas was constantly purged through the pouch while the platens were heated. The samples were brought to 300° C. and kept at this temperature under argon purge for 5 hours. Then, they were cooled under argon purge to about room temperature by shutting the heater off.

TABLE 7

Ultimate tensile strength (UTS), elongation to break (EAB), Young's Modulus (E) and yield strength (YS) of HTM vitamin E-blended UHMWPE.

| | UTS (MPa) | EAB (%) | E (GPa) | YS (MPa) |
|---|---|---|---|---|
| 0.15 wt % | 54.0 ± 6.4 | 386 ± 20 | 1.5 ± 0.3 | 21 ± 1 |
| 0.15 wt % HTM | 52.0 ± 3.6 | 462 ± 39 | 1.0 ± 0.3 | 20 ± 1 |
| 0.2 wt % HTM | 56.4 ± 4.9 | 546 ± 94 | 0.9 ± 0.1 | 20 ± 1 |

Elongation of vitamin E-blended UHMWPEs increased through HTM without significant loss of strength (Table 7).

Example 5. High Temperature Melting Followed by Radiation Cross-Linking and Post-Irradiation Melting Slab compression molded (CM) blocks of UHMWPE (GUR1050, Orthoplastics, Lancashire, UK) were placed each in a stainless steel pouch, which was closed but not sealed. The pouch was placed in contact with the platens of a molding press (3895, Carver, Wabash, Ind.). Argon gas was constantly purged through the pouch while the platens were heated. The sample was brought to 300° C. and kept at this temperature under argon purge for 5 hours. Then, it was cooled under argon purge to about room temperature by shutting the heater off. The cooled blocks were irradiated by electron beam irradiation (2.5 MeV, High voltage research laboratories, MIT, Cambridge, Mass.) to 25, 50, 100 and 150 kGy. Thin sections (3.2 mm-thick) were machined from the high temperature melted and subsequently irradiated UHMWPE. A separate irradiated block of each radiation dose was melted at 170° C. in a vacuum oven; yet another separate block of each radiation dose was melted as described above at 300° C. under argon purge.

Tensile testing was performed on dog-bones (Type V, ASTM D-638) stamped out of 3.2 mm-thick sections machined from high temperature melted UHMWPEs. Testing was performed at 10 mm/min (MTS Insight, Eden Prairie, Minn.). Elongation to break (EAB) was determined by using a laser extensometer. Work to failure was determined as the area under the engineering stress-strain curves. The IZOD single-notch impact tests were done according to ASTM F648 (Orthoplastics, Lancashire, UK). Ultimate tensile strength (UTS) and elastic modulus (E) were also measured.

Wear rates were determined by pin-on-disc wear testing on a custom-designed bidirectional wear tester (see Bragdon C R, O'Connor D O, Lowenstein J D, Jasty M, Biggs S A, Harris W H. A new pin-on-disc wear testing method for simulating wear of polyethylene on cobalt-chrome alloy in total hip arthroplasty. *Journal of Arthroplasty* 2001: 41(2): 795-808). Testing was performed in undiluted, preserved bovine serum at 2 Hz for 2 million cycles (MC) with gravimetric assessment of wear at approximately every 500,000 cycles. Wear rate was determined as a linear regression of weight loss as a function of number of cycles from 0.5 to 2 MC.

Crosslink density measurements of cross-linked UHMWPE (n=3 each) were performed on small samples (approximately 3×3×3 mm). The samples were weighed before swelling in xylene at 130° C. and they were weighed immediately after swelling in xylene. Therefore, the amount of xylene uptake was determined gravimetrically, then converted to volumetric uptake by dividing by the density of xylene; 0.75 g/cc. By assuming the density of polyethylene to be approximately 0.99 g/cc, the volumetric swell ratio of crosslinked UHMWPE was then determined. The cross-link density was calculated using the swell ratio as described previously (Muratoglu et al. Biomaterials 20:1463-1470 (1999)) and is reported as mol/m$^3$.

The elongation of high temperature melted and irradiated UHMWPE was increased compared to irradiated UHMWPE (Table 8).

TABLE 8

Ultimate tensile strength (UTS), elongation to break (EAB), Young's Modulus (E) and yield strength (YS) of HTM + Irradiation + HTM UHMWPE.

|  | UTS (MPa) | EAB (%) | E (GPa) | Cross-link density (mol/m$^3$) |
|---|---|---|---|---|
| No irr. | 51 ± 3 | 442 ± 20 | 1.3 ± 0.3 | — |
| 25 kGy | 46 ± 2 | 376 ± 20 | 3.0 ± 0.0 | 95 ± 0 |
| 50 kGy | 45 ± 6 | 321 ± 25 | 3.1 ± 0.9 | 120 ± 2 |
| 100 kGy | 38 ± 5 | 249 ± 13 | 3.4 ± 0.3 | 152 ± 3 |
| 150 kGy | 36 ± 1 | 202 ± 11 | 4.3 ± 0.4 | 186 ± 2 |
| 25 kGy + HTM | 43 ± 4 | 878 ± 96 | 2.0 ± 0.8 | 6 ± 0 |
| 50 kGy + HTM | 46 ± 3 | 717 ± 115 | 1.7 ± 1.1 | 21 ± 1 |
| 100 kGy + HTM | 48 ± 1 | 686 ± 109 | 1.4 ± 0.5 | 43 ± 1 |
| 150 kGy + HTM | 37 ± 3 | 417 ± 44 | 2.6 ± 0.5 | 68 ± 1 |
| HTM | 47 ± 4 | 654 ± 36 | 2.4 ± 0.6 | 24 ± 10 |
| HTM + 25 kGy | 54 ± 3 | 487 ± 60 | 1.9 ± 0.3 | NT |
| HTM + 50 kGy | NA | NA | NA | 116 ± 5 |
| HTM + 100 kGy | 47 ± 2 | 326 ± 56 | 2.2 ± 0.4 | 125 ± 36 |
| HTM + 150 kGy | 48 ± 2 | 280 ± 17 | 2.6 ± 0.5 | 169 ± 5 |
| HTM + 25 kGy + HTM | 43 ± 4 | 878 ± 96 | 2.0 ± 0.8 | 6 ± 0 |
| HTM + 50 kGy + HTM | 46 ± 3 | 717 ± 115 | 1.7 ± 1.1 | 11 ± 1 |
| HTM + 100 kGy + HTM | 48 ± 1 | 686 ± 109 | 1.4 ± 0.5 | 22 ± 1 |
| HTM + 150 kGy + HTM | 36 ± 3 | 416 ± 44 | 2.6 ± 0.5 | 50 ± 2 |
| HTM + 25 kGy + 170° C. | 48 ± 2 | 389 ± 9 | 1.0 ± 0.2 | 85 ± 5 |
| HTM + 50 kGy + 170° C. | 47 ± 1 | 446 ± 12 | 1.3 ± 0.1 | NT |
| HTM + 100 kGy + 170° C. | 43 ± 1 | 320 ± 7 | 1.5 ± 0.1 | NT |
| HTM + 150 kGy + 170° C. | 36 ± 1 | 276 ± 4 | 1.8 ± 0.1 | 169 ± 5 |

100-kGy irradiated and 150-kGy irradiated UHMWPEs were similarly melted in a pre-heated inert gas convection oven (LLD1-16N-3, Despatch Inc., MN) at 300 or 320° C. The samples were kept at temperature under nitrogen flow for 5 hours, after which the samples were cooled under nitrogen flow to below approximately 60° C. before taking the samples out of the oven.

The cross-link density of 100 kGy irradiated UHMWPE was 152±5 mol/m$^3$ and its wear rate was −2.7±0.8 mg/million cycle. The cross-link density of virgin UHMWPE melted at 300° C. for 5 hours and subsequently irradiated to 150 kGy was 124±7 mol/m$^3$ and its wear rate was −1.9±0.3 mg/million-cycle. Current understanding of wear reduction in UHMWPE dictates that decreased cross-link density results in increased wear rate. In this material which was high temperature melted before radiation cross-linking, the wear rate was decreased despite a decrease in cross-link density.

In addition, the IZOD impact strength of 100 kGy irradiated UHMWPE was 77±3 kJ/m$^2$ and that of 150 kGy irradiated UHMWPE was 62±3 kJ/m$^2$. These values represented a decrease from that of unirradiated UHMWPE, whose IZOD impact strength was 127±7 kJ/m$^2$ as a function of increasing radiation dose. For UHMWPE melted at 300° C. for 5 hours and subsequently irradiated to 150 kGy, the impact strength was 83±2 kJ/m$^2$. Therefore, high temperature melting the UHMWPE before radiation cross-linking not only increased its wear resistance but also its fracture toughness.

Example 6. High Temperature Melting of Vitamin E-Blended UHMWPE Followed by Radiation Cross-Linking Vitamin E-blended UHMWPE (0.1 wt % and 0.2 wt %) was prepared by mixing GUR1050 UHMWPE powder with a 10 wt % isopropyl alcohol solution of vitamin E and subsequently drying the powder at 60° C. Then the powder was consolidated into pucks (10 cm diameter, 1 cm thickness) using a laboratory press (3895, Carver, Wabash, Ind.). The pucks were then high temperature melted in a convection oven equipped with a nitrogen purge (LLD1-16N-3, Despatch Inc., MN) at 300° C. or 320° C. for 5 hours and were cooled down under nitrogen purge to room temperature. Then, the high temperature melted pucks were packaged in vacuum and irradiated by electron-beam irradiation (Iotron, Vancouver, BC) to 150 kGy at 50 kGy/pass.

Crosslink density measurements of cross-linked UHMWPE (n=3 each) were performed on small samples (approximately 3×3×3 mm). The samples were weighed before swelling in xylene at 130° C. and they were weighed immediately after swelling in xylene. Therefore, the amount of xylene uptake was determined gravimetrically, then converted to volumetric uptake by dividing by the density of xylene; 0.75 g/cc. By assuming the density of polyethylene to be approximately 0.99 g/cc, the volumetric swell ratio of crosslinked UHMWPE was then determined. The cross-link density was calculated using the swell ratio as described previously (Muratoglu et al. Biomaterials 20:1463-1470 (1999)) and is reported as mol/m$^3$.

Tensile mechanical properties were tested using Type V dog-bone-shaped samples stamped out of these thin sections at 10 mm/min according to ASTM D-638. The elongation to break was measured using a laser extensometer. The work to failure (WF) was calculated as the area under the engineering stress-strain curve. Ultimate tensile strength (UTS) and elastic modulus (E) were also measured. The IZOD single-notch impact tests were done according to ASTM F648 (Orthoplastics, Lancashire, UK).

Crystallinity (n=3 each) was measured by differential scanning calorimetry from −20° C. to 180° C. at a heating rate of 10° C./min. The crystallinity was determined by normalizing the enthalpy of fusion by the enthalpy of fusion of 100% crystalline polyethylene; 291 J/g.

Thin sections (150 μm-thick) were microtomed and analyzed using Fourier Transform Infrared Spectroscopy (FTIR). A vinyl index was calculated using the area under 880-920 $cm^{-1}$ and normalizing it to the area under 1895 $cm^{-1}$.

TABLE 9

Crystallinity and peak melting point of high temperature melted irradiated vitamin E-blend UHMWPEs.

| | Crystallinity (%) | Peak melting point (° C.) | Vinyl index |
|---|---|---|---|
| 0.1 wt % + 150-kGy | 60 ± 0 | 139.4 | 0.01 |
| 0.1 wt % + 300° C., 5 hr + 150 kGy | 60 ± 1 | 138.8 | 0.01 |
| 0.1 wt % + 320° C., 5 hr + 150 kGy | 67 ± 0 | 137.3 | 0.03 |
| 0.2 wt % + 150-kGy | 60 ± 1 | 139.3 | 0.01 |
| 0.2 wt % + 300° C., 5 hr + 150 kGy | 62 ± 1 | 138.9 | 0.01 |
| 0.2 wt % + 320° C., 5 hr + 150 kGy | 66 ± 1 | 137.8 | 0.02 |

High temperature melting prior to irradiation of vitamin E-blended UHMWPE resulted in a material with increased elongation to break (EAB). At 300° C., 5 hours of melting gave a material with comparable ultimate tensile strength to irradiated UHMWPE without high temperature treatment with much improved elongation to break and decreased modulus. In contrast, at 320° C., crystallinity and modulus were increased but not accompanied by an increase in strength, suggesting that there was increased chain scissioning and re-crystallization in these samples (Tables 9 and 10).

TABLE 10

Ultimate tensile strength (UTS), elongation to break (EAB), Young's Modulus (E) and yield strength (YS) of HTM vitamin E-blended UHMWPE.

| | UTS (MPa) | EAB (%) | E (GPa) | YS (MPa) | IZOD Impact strength (KJ/m²) |
|---|---|---|---|---|---|
| 100 kGy | 50 ± 4 | 303 ± 12 | 1.8 ± 0.2 | 21 ± 1 | 74 ± 3 |
| 150 kGy | 48 ± 2 | 266 ± 19 | 2.0 ± 0.5 | 21 ± 1 | 62 ± 3 |
| 0.1 wt % + 150-kGy | 45 ± 2 | 244 ± 11 | 2.6 ± 0.4 | 21 ± 1 | 66 ± 2 |
| 0.1 wt % + 300° C., 5 hr + 150 kGy | 49 ± 2 | 303 ± 14 | 1.8 ± 0.1 | 22 ± 1 | 76 ± 2 |
| 0.1 wt % + 320° C., 5 hr + 150 kGy | 47 ± 2 | 404 ± 21 | 3.6 ± 0.4 | 24 ± 1 | 94 ± 3 |
| 0.2 wt % + 150-kGy | 51 ± 3 | 278 ± 15 | 2.6 ± 0.2 | 21 ± 1 | 77 ± 2 |
| 0.2 wt % + 300° C., 5 hr + 150 kGy | 48 ± 5 | 319 ± 24 | 2.0 ± 0.4 | 21 ± 1 | 87 ± 6 |
| 0.2 wt % + 320° C., 5 hr + 150 kGy | 40 ± 1 | 369 ± 17 | 4.5 ± 0.3 | 24 ± 1 | 96 ± 5 |

The IZOD impact strength of vitamin E-blended, high temperature melted and irradiated UHMWPEs were all significantly higher than non-melted, irradiated UHMWPEs (Table 10). Most importantly, despite a severe decrease in cross-link density, vitamin E-containing, high temperature melted, radiation cross-linked UHMWPEs had remarkably low wear (Table 11). Therefore, these materials have improved fracture resistance and wear resistance compared to virgin irradiated and vitamin E-containing irradiated UHMWPEs. Due to the presence of the antioxidant, they are rendered oxidatively stable.

TABLE 11

Cross-link density and wear rate of vitamin E-containing, high temperature melted, radiation cross-linked UHMWPE

| | Cross-link density (mol/m³) | Wear rate (mg/MC) |
|---|---|---|
| 100-kGy irradiated | 152 ± 5 | −2.69 ± 0.80 |
| 0.1 wt % + 150-kGy | 164 ± 4 | −1.96 ± 0.75 |
| 0.1 wt % + 300° C., 5 hr + 150 kGy | 140 ± 4 | −1.69 ± 0.50 |
| 0.1 wt % + 320° C., 5 hr + 150 kGy | 83 ± 2 | −2.62 ± 0.18 |
| 0.2 wt % + 150-kGy | 148 ± 4 | −2.62 ± 0.89 |
| 0.2 wt % + 300° C., 5 hr + 150 kGy | 129 ± 1 | |
| 0.2 wt % + 320° C., 5 hr + 150 kGy | 83 ± 2 | |

Example 7. Chain Diffusion and Grain Boundary Profile of High Temperature Melted UHMWPE A puck of GUR1050 UHMWPE was high temperature melted in a convection oven equipped with a nitrogen purge (LLD1-16N-3, Despatch Inc., MN) at 300° C. for 5 hours and were cooled down under nitrogen purge to room temperature. It was freeze fractured in liquid nitrogen and coated with gold using a sputter coater. A puck of GUR1050 UHMWPE that had not been high temperature melted was used as control.

The microscopy images were taken on a FEI-Phillips environmental scanning electron microscope equipped with a backscatter electron detector.

Figure 39A:
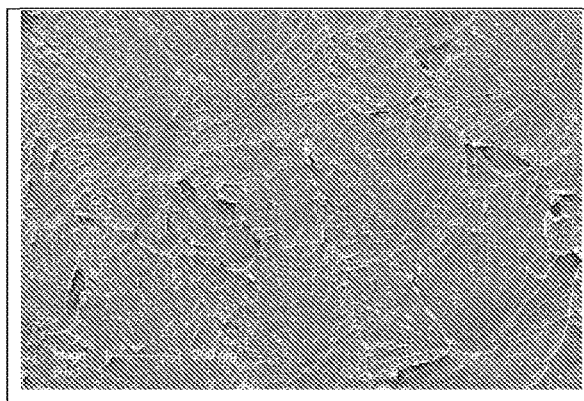
FIGS. 39A-39B depict freeze fractures surfaces of slab compression molded GUR1050 UHMWPE (FIG. 39A) and compression molded UHMWPE after melting at 300° C. in nitrogen for 5 hours (FIG. 39B).

The grain boundaries of the high temperature melted sample (FIG. 39B) were much less discernable than the conventional slab compression molded UHMWPE sample (FIG. 39A). This suggested that there were diffusion of the polymer chains across the grain boundary.

Example 8. High Temperature Melting of Vitamin E-Blended and Radiation Cross-Linked UHMWPEs Vitamin E-blended UHMWPE (0.1 wt % and 0.2 wt %) was prepared by mixing GUR1050 UHMWPE powder with a 10 wt % isopropyl alcohol solution of vitamin E and subsequently drying the powder at 60° C. Then the powder was consolidated into pucks (10 cm diameter, 1 cm thickness) using a laboratory press (3895, Carver, Wabash, Ind.). The pucks were then packaged in vacuum and irradiated by electron-beam irradiation (Iotron, Vancouver, BC) to 150 kGy at 50 kGy/pass. After irradiation, they were high temperature melted in a convection oven equipped with a nitrogen purge (LLD1-16N-3, Despatch Inc., MN) at 300° C. for 5 hours and were cooled down under nitrogen purge to room temperature.

Tensile testing was performed on dog-bones (Type V, ASTM D-638) stamped out of 3.2 mm-thick sections machined from high temperature melted UHMWPEs. Testing was performed at 10 mm/min (MTS Insight, Eden Prairie, Minn.). Elongation to break (EAB) was determined by using a laser extensometer. Work to failure was determined as the area under the engineering stress-strain curves. The IZOD single-notch impact tests were done according to ASTM F648 (Orthoplastics, Lancashire, UK). Ultimate tensile strength (UTS) and elastic modulus (E) were also measured.

Wear rates were determined by pin-on-disc wear testing on a custom-designed bidirectional wear tester (see Bragdon C R, O'Connor D O, Lowenstein J D, Jasty M, Biggs S A, Harris W H. A new pin-on-disc wear testing method for simulating wear of polyethylene on cobalt-chrome alloy in total hip arthroplasty. *Journal of Arthroplasty* 2001: 41(2): 795-808). Testing was performed in undiluted, preserved bovine serum at 2 Hz for 2 million cycles (MC) with gravimetric assessment of wear at approximately every 500,000 cycles. Wear rate was determined as a linear regression of weight loss as a function of number of cycles from 0.5 to 2 MC.

Crosslink density measurements of cross-linked UHMWPE (n=3 each) were performed on small samples (approximately 3×3×3 mm). The samples were weighed before swelling in xylene at 130° C. and they were weighed immediately after swelling in xylene. Therefore, the amount of xylene uptake was determined gravimetrically, then converted to volumetric uptake by dividing by the density of xylene; 0.75 g/cc. By assuming the density of polyethylene to be approximately 0.99 g/cc, the volumetric swell ratio of crosslinked UHMWPE was then determined. The cross-link density was calculated using the swell ratio as described previously (Muratoglu et al. Biomaterials 20:1463-1470 (1999)) and is reported as mol/m$^3$.

Thin sections (150 μm-thick) were microtomed and analyzed using Fourier Transform Infrared Spectroscopy (FTIR). A vinyl index was calculated using the area under 880-920 cm$^{-1}$ and normalizing it to the area under 1895 cm$^{-1}$.

TABLE 12

Crystallinity and peak melting point of irradiated, high temperature melted vitamin E-blended UHMWPEs.

| | Crystallinity (%) | Peak melting point (° C.) | Vinyl index |
|---|---|---|---|
| 0.1 wt % + 150-kGy | 60 ± 0 | 139.4 | |
| 0.1 wt % + 300° C., 5 hr | 55 ± 0 | 134.5 | 0.019 |
| 0.1 wt % + 150 kGy + 300° C., 5 hr | 52 ± 1 | 131.3 | 0.012 |
| 0.2 wt % + 150-kGy | 60 ± 1 | 139.3 | |
| 0.2 wt % + 300° C., 5 hr | | | |
| 0.2 wt % + 150 kGy + 300° C., 5 hr | 51 ± 1 | 131.1 | 0.012 |

TABLE 13

Tensile mechanical properties of irradiated, high temperature melted vitamin E-blended UHMWPEs.

| | UTS (MPa) | EAB (%) | WF (KJ/m$^2$) |
|---|---|---|---|
| 0.1 wt % + 150-kGy | 45 ± 2 | 244 ± 11 | 1344 ± 97 |
| 0.1 wt % + 300° C., 5 hr | | | |
| 0.1 wt % + 150 kGy + 300° C., 5 hr | 43 ± 2 | 329 ± 16 | 1794 ± 160 |
| 0.2 wt % + 150-kGy | 51 ± 3 | 278 ± 15 | 1784 ± 174 |
| 0.2 wt % + 300° C., 5 hr | | | |
| 0.2 wt % + 150 kGy + 300° C., 5 hr | 48 ± 2 | 356 ± 9 | 2210 ± 138 |

TABLE 14

Cross-link density and wear of irradiated, high temperature melted vitamin E-blended UHMWPEs.

| | Cross-link density (mol/m$^3$) | Wear rate (mg/MC) |
|---|---|---|
| 0.1 wt % + 150-kGy | 164 ± 4 | −2.0 ± 0.8 |
| 0.1 wt % + 300° C., 5 hr | — | |
| 0.1 wt % + 150 kGy + 300° C., 5 hr | 131 ± 3 | −2.42 ± 0.46 |
| 0.1 wt % + 150 kGy + 300° C., 12 hr | 99 ± 1 | −3.16 ± 0.97 |
| 0.2 wt % + 150-kGy | 148 ± 4 | −2.62 ± 0.89 |
| 0.2 wt % + 300° C., 5 hr | — | |
| 0.2 wt % + 150 kGy + 300° C., 5 hr | 119 ± 3 | |

Example 9. High Temperature Melting of Vitamin E-Blended and Radiation Cross-Linked UHMWPEs at Different Temperatures Vitamin E-blended UHMWPE (0.1 wt % and 02 wt %) was prepared by mixing GUR1050 UHMWPE powder with a 10 wt % isopropyl alcohol solution of vitamin E and subsequently drying the powder at 60° C. Then the powder was consolidated into pucks (10 cm diameter, 1 cm thickness) using a laboratory press (3895, Carver, Wabash, Ind.). The pucks were then packaged in vacuum and irradiated by electron-beam irradiation (Iotron, Vancouver, BC) to 150 kGy at 50 kGy/pass. After irradiation, they were high temperature melted in a convection oven equipped with a nitrogen purge (LLD1-16N-3, Despatch Inc., MN) at 280° C. for 5 hours or at 300° C. for 1, 5 or 12 hours and were cooled down under nitrogen purge to room temperature.

Tensile testing was performed on dog-bones (Type V, ASTM D-638) stamped out of 3.2 mm-thick sections machined from high temperature melted UHMWPEs. Testing was performed at 10 mm/min (MTS Insight, Eden Prairie, Minn.). Elongation to break (EAB) was determined by using a laser extensometer. Work to failure was determined as the area under the engineering stress-strain curves. The IZOD single-notch impact tests were done according to ASTM F648 (Orthoplastics, Lancashire, UK). Ultimate tensile strength (UTS) and elastic modulus (E) were also measured.

Wear rates were determined by pin-on-disc wear testing on a custom-designed bidirectional wear tester (see Bragdon C R, O'Connor D O, Lowenstein J D, Jasty M, Biggs S A, Harris W H. A new pin-on-disc wear testing method for simulating wear of polyethylene on cobalt-chrome alloy in total hip arthroplasty. *Journal of Arthroplasty* 2001: 41(2): 795-808). Testing was performed in undiluted, preserved bovine serum at 2 Hz for 2 million cycles (MC) with gravimetric assessment of wear at approximately every 500,000 cycles. Wear rate was determined as a linear regression of weight loss as a function of number of cycles from 0.5 to 2 MC.

High temperature melting of vitamin E-blended UHMWPE after radiation cross-linking resulted in decreased cross-link density as a function of increasing duration at the same temperature (Table 15). In addition, the elongation to break and work to failure increased with duration while ultimate tensile strength was largely not affected. Increasing the temperature of the high temperature melting process at the same duration decreased cross-link density, increased elongation at break and work to failure while did not affect ultimate tensile strength significantly.

TABLE 15

Cross-link density and tensile mechanical properties of vitamin E-blended, radiation cross-linked and subsequently high temperature melted UHMWPEs.

| | Cross-link density (mol/m³) | UTS (MPa) | EAB (%) | WF (KJ/m²) |
|---|---|---|---|---|
| 0.1 wt % + 150 kGy | 164 ± 4 | 45 ± 2 | 244 ± 11 | 1344 ± 97 |
| 0.1 wt % + 150 kGy + 280° C., 5 hr | 156 ± 8 | 43 ± 4 | 290 ± 12 | 1578 ± 216 |
| 0.1 wt % + 150 kGy + 300° C., 1 hr | 152 ± 2 | 44 ± 2 | 302 ± 12 | 1669 ± 122 |
| 0.1 wt % + 150 kGy + 300° C., 5 hr | 131 ± 3 | 43 ± 2 | 329 ± 16 | 1794 ± 160 |
| 0.1 wt % + 150 kGy + 300° C., 12 hr | 99 ± 1 | 48 ± 3 | 387 ± 15 | 2401 ± 267 |
| 0.2 wt % + 150 kGy | 148 ± 4 | 51 ± 3 | 278 ± 15 | 1784 ± 174 |
| 0.2 wt % + 150 kGy + 280° C., 5 hr | 132 ± 2 | 45 ± 7 | 321 ± 22 | 1883 ± 484 |
| 0.2 wt % + 150 kGy + 300° C., 1 hr | 130 ± 2 | 46 ± 2 | 326 ± 8 | 1902 ± 143 |
| 0.2 wt % + 150 kGy + 300° C., 5 hr | 119 ± 3 | 46 ± 3 | 356 ± 9 | 2210 ± 138 |
| 0.2 wt % + 150 kGy + 300° C., 12 hr | 101 ± 5 | 45 ± 5 | 381 ± 16 | 2149 ± 377 |

Example 10. Wear as a Function of Cross-Link Density in High Temperature Melted UHMWPEs Vitamin E-blended UHMWPE (0.1 wt %) was prepared by mixing GUR1050 UHMWPE powder with a 10 wt % isopropyl alcohol solution of vitamin E and subsequently drying the powder at 60° C. Then the powder was consolidated into pucks (10 cm diameter, 1 cm thickness) using a laboratory press (3895, Carver, Wabash, Ind.). The pucks were then high temperature melted in a convection oven equipped with a nitrogen purge (LLD1-16N-3, Despatch Inc., MN) at 300° C. 5 hours and were cooled down under nitrogen purge to room temperature. Then they were packaged in in vacuum and irradiated by electron-beam irradiation (Iotron, Vancouver, BC) to 150 kGy at 50 kGy/pass. Virgin UHMWPE consolidated without vitamin E was used as control.

Cylindrical pins (n=3 each, 9 mm diameter, 13 mm length) were machined from high temperature melted and irradiated UHMWPEs. Wear rates were determined by pin-on-disc wear testing on a custom-designed bidirectional wear tester (see Bragdon C R, O'Connor D O, Lowenstein J D, Jasty M, Biggs S A, Harris W H. A new pin-on-disc wear testing method for simulating wear of polyethylene on cobalt-chrome alloy in total hip arthroplasty. *Journal of Arthroplasty* 2001: 41(2): 795-808). Testing was performed in undiluted preserved bovine serum at 2 Hz for approximately 1.2 million cycles (MC) with gravimetric assessment of wear at approximately every 250,000 cycles. Wear rate was determined as a linear regression of weight loss as a function of number of cycles from 0.5 to 1.2 MC.

Figure 40:
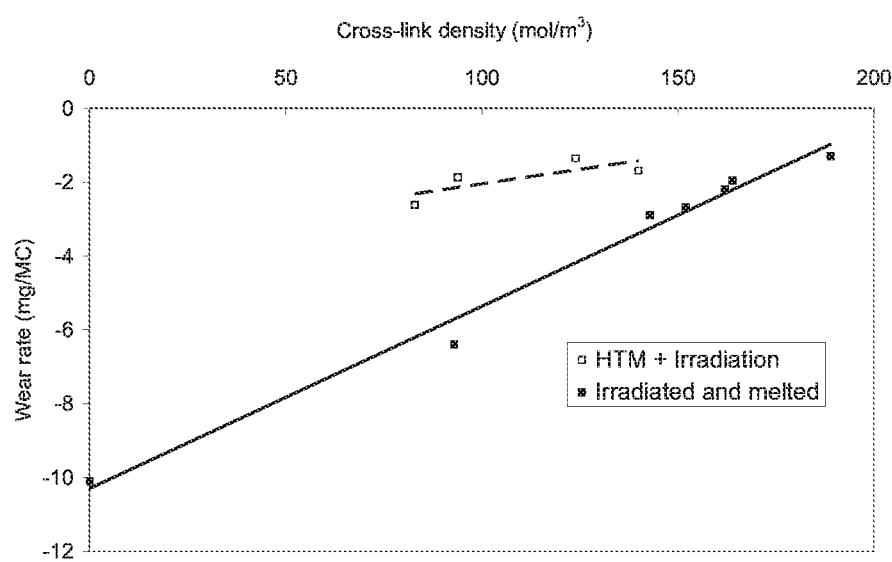
FIG. 40 shows wear rate as a function of cross-link density for high temperature melted and irradiated UHMWPE compared to irradiated UHMWPEs and UHMWPEs irradiated and melted below 200° C.
Figure 41A:
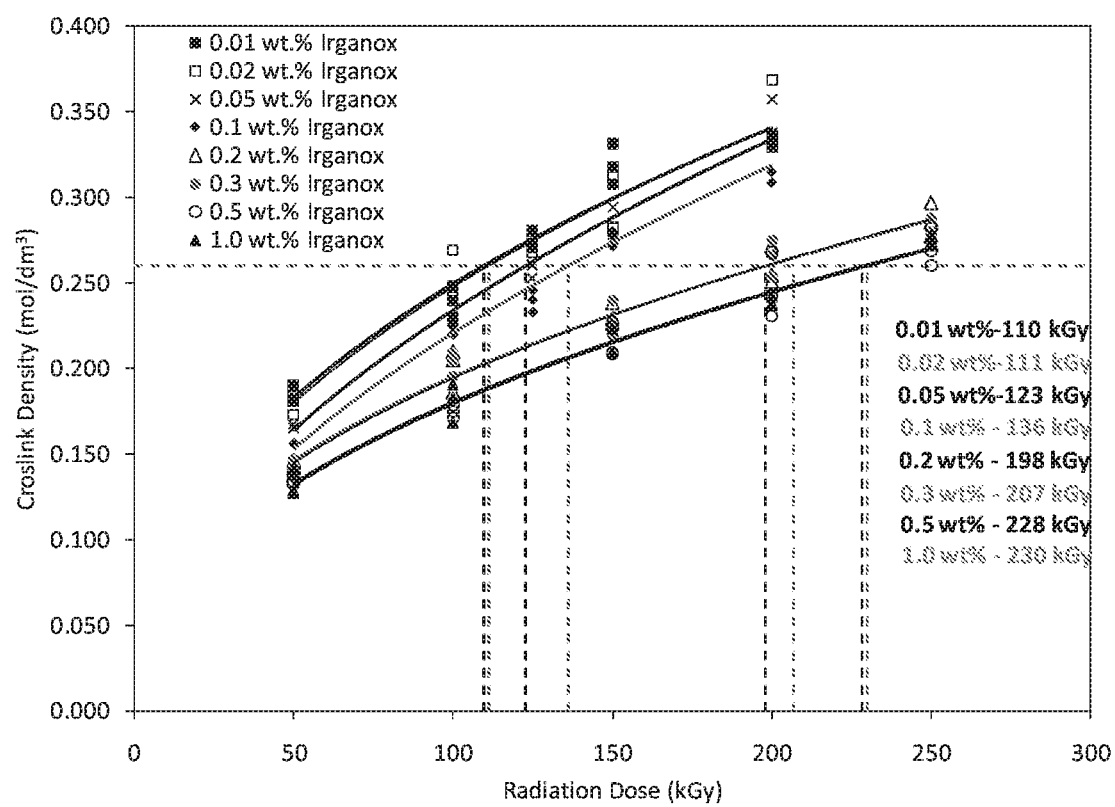
FIG. 41A illustrates cross-link density as a function of radiation dose in UHMWPE blends of Irganox® 1010. The dashed lines indicate the radiation dose required to obtain a cross-link density of 0.260 mol/dm$^3$; the crosslink density of 100-kGy irradiated virgin UHMWPE. The numbers at the right side of the graph are the radiation dose values required to obtain this level of crosslinking in Irganox® 1010 blended UHMWPE as a function of concentration.
Figure 41B:
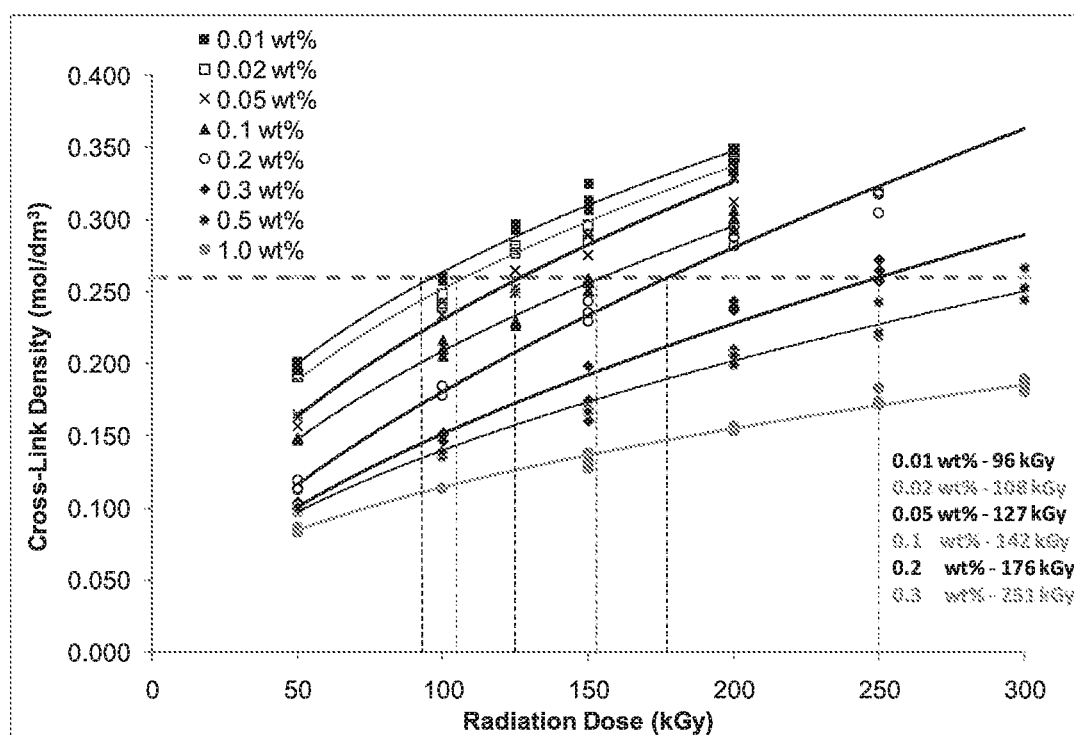
FIG. 41B illustrates cross-link density as a function of radiation dose in UHMWPE blends of Irganox® 1076. The dashed lines indicate the radiation dose required to obtain a cross-link density of 0.260 mol/dm$^3$; the crosslink density of 100-kGy irradiated virgin UHMWPE. The numbers at the right side of the graph are the radiation dose values required to obtain this level of crosslinking in Irganox® 1076 blended UHMWPE as a function of concentration.

The other samples in Table 16 and FIG. 40 were irradiated as consolidated blocks and melted in a vacuum oven at the designated temperature in partial vacuum/argon. They were tested similarly at 2 Hz for 2 MC with gravimetric assessment at every 500,000 cycles. Wear rate was determined as a linear regression of weight loss as a function of number of cycles from 0.5 to 2 MC.

TABLE 16

Wear rate of samples shown in FIG. 40

| | Wear rate (mg/MC) |
|---|---|
| Virgin, 300° C. 5 hours + 150 kGy | −1.4 |
| Virgin, 320° C. 5 hours + 150 kGy | −1.9 |
| 0.1 wt % + 300° C. 5 hours + 150 kGy | −1.7 |
| 0.1 wt % + 320° C. 5 hours + 150 kGy | −2.6 |
| 0.1 wt % + 150 kGy | −2.0 |
| 25 kGy | −6.4 |
| Unirradiated virgin | −10.1 |
| Unirradiated 0.1 wt % vitamin E-blended | −7.8 |
| 65 kGy gamma irradiated and melted at 200° C. | −2.9 |
| 65 kGy e-beam irradiated and melted at 170° C. | −2.2 |
| 100 kGy gamma irradiated and melted at 200° C. | −0.9 |
| 100 kGy e-beam irradiated and melted at 150° C. | −1.3 |

The high temperature treated samples showed wear rates of less than −3.5 mg/MC for cross-link density of approximately less than 140 mol/m³, while irradiated and irradiated and melted UHMWPEs required at least this much cross-linking.

It is clearly shown in FIG. 40 that samples which were treated by high temperature melting prior to irradiation had lower wear rates despite lower cross-link density. For example, at a cross-link density of about 90 mol/m³, simply irradiated UHMWPE had a wear rate of around −6 mg/MC while high temperature melted and irradiated UHMWPE had a wear rate of approximately −2.0 mg/MC. From another data point, for example, a wear rate of less than 3.5 mg/MC for cross-link density lower than 140 mol/m3 is achieved by high temperature melting and subsequently irradiating the UHMWPE, a much higher wear resistance, which is not achievable with radiation cross-linked or cross-linked and melted UHMWPE.

Example 11. High Temperature Melting of Irradiated and Melted UHMWPE

A puck of GUR 1020 or GUR1050 UHMWPE is irradiated to 25, 50, 100, 150, 200, and 500 kGy by ionizing radiation. Similarly, GUR1020 or GUR1050 blended with 0.05, 0.1, 0.2, 0.3, 0.5, 1.0, 2.0 and 5.0 wt % vitamin E is irradiated to 25, 50, 100, 150, 200 and 500 kGy by ionizing radiation. The samples are further melted at 170° C. until transparent in air or in vacuum, then they are cooled down to about room temperature. Further, they are melted at 280, 300, 320, and 340° C. for about 5 hours in inert gas, then cooled down under inert gas to about room temperature. In this manner, the wear resistance and toughness of irradiated and melted UHMWPEs is increased.

Example 12. Warm and Cold Irradiation of High Temperature Melted, Radiation Cross-Linked UHMWPEs Vitamin E-blended UHMWPE (0.1 wt %, 0.2 wt %, 1 wt %, 2 wt %, 5 wt %) are prepared by mixing GUR1050 UHMWPE powder with a 10 wt % isopropyl alcohol solution of vitamin E and subsequently drying the powder at 60° C. Then the powder is consolidated into pucks (10 cm diameter, 1 cm thickness) using a laboratory press (3895, Carver, Wabash, Ind.). The pucks are then packaged in vacuum and irradiated by electron-beam irradiation (Iotron, Vancouver, BC) to 25, 50, 100, 150, 200 and 500 kGy at 50 kGy/pass starting at room temperature (cold irradiated). Alternatively, they are pre-heated in a convection oven at approximately 120° C., then warm irradiated. After irradiation, they are high temperature melted in a convection oven equipped with a nitrogen purge (LLD1-16N-3, Despatch Inc., MN) at 300° C. for 1, 5 or 12 hours and were cooled down under nitrogen purge to room temperature.

Example 13. Warm and Cold Irradiation of Radiation Cross-Linked, High Temperature Melted UHMWPEs Vitamin E-blended UHMWPE (0.1 wt %, 0.2 wt %, 1 wt %, 2 wt %, 5 wt %) are prepared by mixing GUR1050 UHMWPE powder with a 10 wt % isopropyl alcohol solution of vitamin E and subsequently drying the powder at 60° C. Then the powder is consolidated into pucks (10 cm diameter, 1 cm thickness) using a laboratory press (3895, Carver, Wabash, Ind.)—The pucks are then high temperature melted in a convection oven equipped with a nitrogen purge (LLD1-16N-3, Despatch Inc., MN) at 300° C. for 1, 5 or 12 hours and were cooled down under nitrogen purge to room temperature. Then they are packaged in vacuum and irradiated by electron-beam irradiation (Iotron, Vancouver, BC) to 25, 50, 100, 150, 200 and 500 kGy at 50 kGy/pass starting at room temperature (cold irradiated). Alternatively, they are pre-heated in a convection oven at approximately 120° C., then warm irradiated.

Example 14. The Effect of Irganox® 1010, Irganox® 1076 and Irganox® 1035 on the Cross-Link Density of UHMWPE Consolidated blends of GUR1050 UHMWPE were made with Irganoxes using solvent (IPA) blending of Irganox® 1010, Irganox® 1076 and Irganox® 1035 with UHMWPE resin powder, evaporating the solvent and compression molding the blended powder in a press. Blended powder was either made at the desired concentration or made at a higher concentration of antioxidant and diluted down with UHMWPE powder. In this manner, UHMWPE containing 0.01 wt %, 0.02 wt %, 0.05 wt %, 0.1 wt %, 0.2 wt %, 0.3 wt %, 0.5 wt % and 1.0 wt % Irganox® 1010, Irganox® 1076, and Irganox® 1035 were made.

Compression molded pucks (diameter ~10 cm, thickness ~1 cm) were irradiated to 50, 100, 150 and 200 kGy using electron beam irradiation.

Cross-link density was measured by swelling ~3 mm cubes in xylene at 130° C. for 2 hours and immediately sealing in pre-weighed vials for weighing. A volumetric expansion ratio was determined by converting the weight swelling ratio using the density of the dry polymer (0.95 g/cm$^3$) and of xylene at 130° C. (0.75 g/cm$^3$). Cross-link density (in mol/m$^3$) was calculated as described using the following equation:

$$v_d = -\left( \frac{\ln\left(1 - \frac{1}{\rho}\right) + \frac{1}{\rho} + \frac{1}{\rho^2}\left(0.33 + \frac{0.55}{\rho}\right)}{136 \times \left(\frac{1}{\rho^{\frac{1}{3}}} - \frac{1}{2\rho}\right)} \right) \times 1000$$

It was observed that increasing antioxidant concentration decreased cross-linking in UHMWPE and thus, the radiation dose required to obtain 260 mol/m$^3$ of cross-link density (equivalent to that of 100-kGy irradiated virgin UHMWPE) in antioxidant-blended UHMWPEs increased with increasing antioxidant concentration (FIGS. 41A-42C and Table 17).

TABLE 17

Radiation doses required to obtain a crosslink density of 0.260 mol/dm$^3$ in antioxidant blended GUR1050 UHMWPEs for different single antioxidant blends.

|  | Irganox ® 1010 | Irganox ® 1035 | Irganox ® 1076 | Vitamin E |
|---|---|---|---|---|
| 0.01 | 110 | 112 | 96 | 110 |
| 0.02 | 111 | 115 | 108 | 110 |
| 0.05 | 122 | 144 | 127 | 118 |
| 0.1 | 136 | 168 | 142 | 123 |
| 0.2 | 199 | 293 | 176 | 150 |
| 0.3 | 199 | 330 | 251 | 189 |
| 0.5 | 228 | 464 | 321 | 245 |
| 1.0 | 230 | 627 | 651 | 540 |

This result also implies that by having different spatial concentration of these Irganoxes and mixtures of these antioxidants with each other in UHMWPE, the cross-link density distribution can be controlled and manipulated.

Example 15. Surface Cross-Linking with Irganox® 1010

Figure 42A:
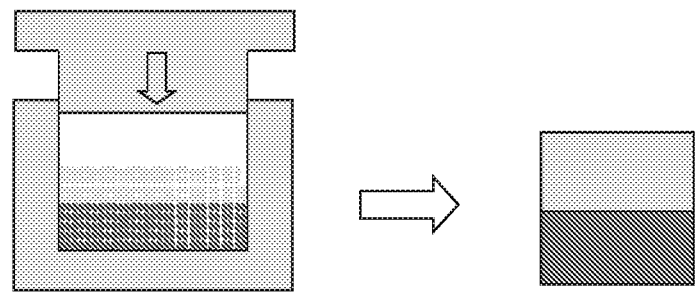
FIGS. 42A-42B illustrate layered molding of UHMWPE with different concentrations of Irganox® 1010 (FIG. 42A); Irganox® profile of layered molded UHMWPE (FIG. 42B).
Figure 42B:
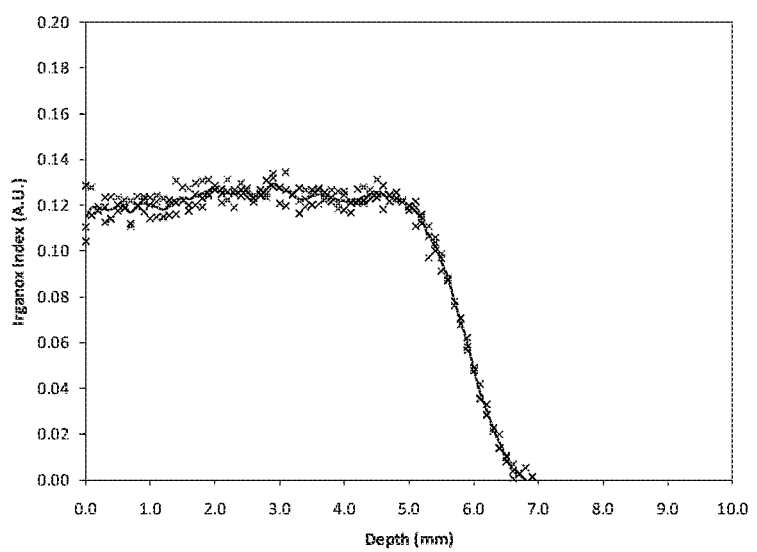

A consolidated puck containing 1 wt % Irganox® 1010-blended GUR1050 UHMWPE on one side and virgin UHMWPE on the other side was prepared by layering of 1 wt % Irganox® 1010-blended UHMWPE powder and virgin UHMWPE powder followed by compression molding (FIG. 42A).

To determine the spatial variation of the antioxidant concentration throughout the samples, 150 µm-thick sections that were microtomed from an inner surface (FIGS. 43A-43D; n=3 each) were analyzed using Fourier Transform Infrared Spectroscopy (FTIR). An Irganox® index was calculated as a function of depth away from the surface as the ratio of the areas under 1223 cm$^{-1}$-1245 cm$^{-1}$ to the absorbance over 1875 cm$^{-1}$-1905 cm$^{-1}$.

The Irganox® concentration in the sample was constant for part of the sample after which it decreased gradually to undetectable limits where the 1 wt % Irganox® 1010-blended UHMWPE had been consolidated with the virgin UHMWPE (FIG. 43B). When this material is irradiated, the surface will be highly cross-linked and the bulk will have lower cross-link density.

Example 16. Antioxidant Bleeding During Layered Molding

A consolidated puck containing 1 wt % Irganox® 1010-blended UHMWPE on one side and virgin UHMWPE on the other side was prepared by layering of 1 wt % Irganox® 1010-blended UHMWPE powder and virgin UHMWPE powder followed by compression molding (FIG. 42A). A similar puck containing 1 wt % vitamin E-blended UHMWPE on one side and virgin UHMWPE on the other side was also prepared.

To determine the spatial variation of the antioxidant concentration throughout the samples, 150 µm-thick sections were microtomed from an inner surface (FIGS. 43A-43D; n=3 each) were analyzed using FTIR. An Irganox® index were calculated as a function of depth away from the surface as the ratio of the areas under 1223 cm$^{-1}$-1245 cm$^{-1}$ to the absorbance over 1875 cm$^{-1}$-1905 cm$^{-1}$. A vitamin E index was calculated as the ratio of the areas under 1245 cm$^{-1}$-1275 cm$^{-1}$ to the absorbance over 1875 cm$^{-1}$-1905 cm$^{-1}$.

Figure 44:
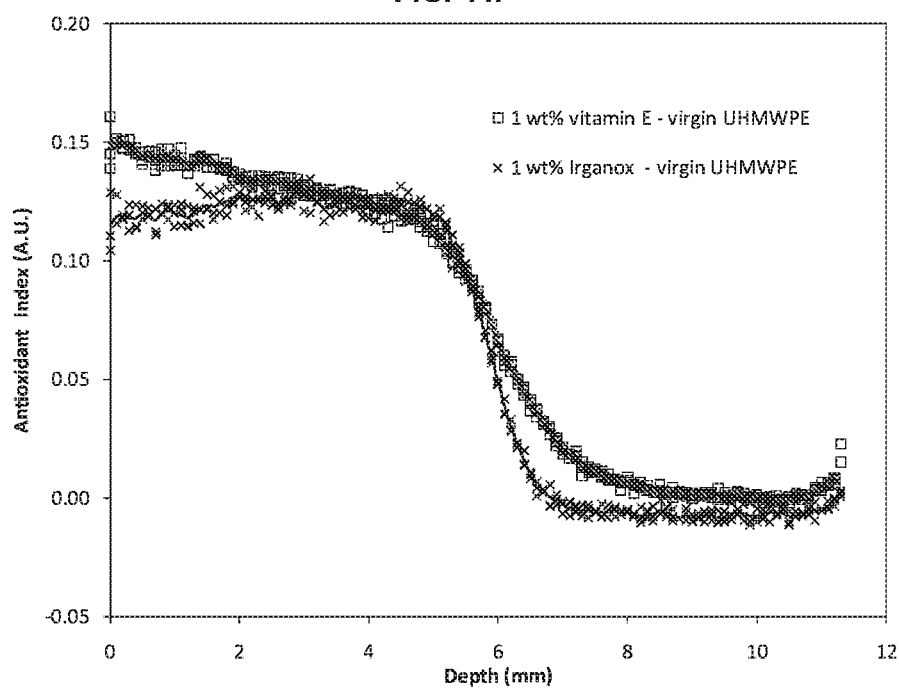
FIG. 44 shows Irganox® 1010 and vitamin E profiles as a function of depth in layered molded UHMWPE. Profiles are splined averages of three sections.

The gradient interface width of the Irganox® 1010-virgin layered puck was approximately 3 mm (with a low threshold of Irganox® index of 0.02) whereas the gradient width of the vitamin E-virgin layered puck was approximately 2 mm (FIG. 44).

Example 17. Surface Cross-Linking with More than One Antioxidant

A consolidated puck containing 1 wt % vitamin E blended UHMWPE on one side and 0.1 wt % Irganox® 1010 blended UHMWPE on the other side was prepared by layering of 1 wt % vitamin E-blended UHMWPE powder and 0.1 wt % Irganox®-blended UHMWPE powder followed by compression molding (FIG. 42A).

To determine the spatial variation of the antioxidant concentration throughout the samples, 150 µm-thick sections that were microtomed from an inner surface (FIGS. 43A-43D; n=3 each) were analyzed using FTIR. Irganox® index were calculated as a function of depth away from the surface as the ratio of the areas under 1223 $cm^{-1}$-1245 $cm^{-1}$ to the absorbance over 1875 $cm^{-1}$-1905 $cm^{-1}$. Vitamin E index was calculated as the ratio of the areas under 1245 $cm^{-1}$-1275 $cm^{-1}$ to the absorbance over 1875 $cm^{-1}$-1905 $cm^{-1}$.

Figure 45:
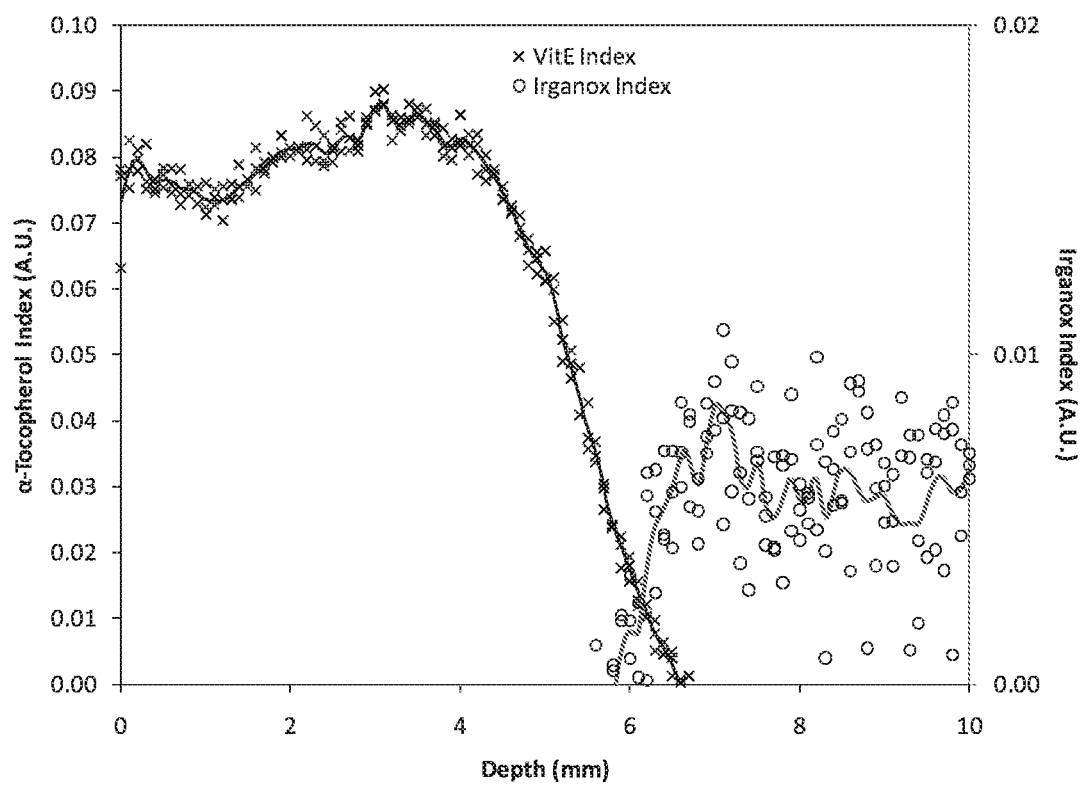
FIG. 45 shows vitamin E (alpha-tocopherol) and Irganox® indices as a function of depth for a layered molded puck containing 1 wt % vitamin E on one side and 0.1 wt % Irganox® on the other side.

Vitamin E and Irganox® 1010 profiles showed that one side of the puck (7-10 mm) contained only Irganox® 1010 and the other side (0-5.8 mm) contained only vitamin E (FIG. 45).

The gradient interface containing both antioxidants was approximately 1.2 mm. When this puck is irradiated, it has different cross-link density in the bulk and surface.

Example 18. Preferential Surface Cross-Linking by Machining

A UHMWPE puck containing a spatial distribution of high and low concentrations of at least one antioxidant is made by layered molding as described in Example 15 and FIG. 42A. Antioxidants can be chosen from but not limited to glutathione, lipoic acid, vitamins such as ascorbic acid (vitamin C), vitamin B, vitamin D, vitamin-E, tocopherols (synthetic or natural, alpha-, gamma-, delta-), acetate vitamin esters, water soluble tocopherol derivatives, tocotrienols, water soluble tocotrienol derivatives; melatonin, carotenoids including various carotenes, lutein, pycnogenol, glycosides, trehalose, polyphenols and flavonoids, quercetin, lycopene, lutein, selenium, nitric oxide, curcuminoids, 2-hydroxytetronic acid; cannabinoids, synthetic antioxidants such as tertiary butyl hydroquinone, 6-amino-3-pyrodinoles, butylated hydroxyanisole, butylated hydroxytoluene, ethoxyquin, tannins, propyl gallate, other gallates, Aquanox family; Irganox® and Irganox® B families including Irganox® 1010, Irganox® 1076, Irganox® 1035, Irganox® 1330; Irgafos® family; phenolic compounds with different chain lengths, and different number of OH groups; enzymes with antioxidant properties such as superoxide dismutase, herbal or plant extracts with antioxidant properties such as St. John's Wort, green tea extract, grape seed extract, rosemary, oregano extract, mixtures, derivatives, analogues or conjugated forms of these. They can be primary antioxidants with reactive OH or NH groups such as hindered phenols or secondary aromatic amines, they can be secondary antioxidants such as organophosphorus compounds or thiosynergists, they can be multifunctional antioxidants, hydroxylamines, or carbon centered radical scavengers such as lactones or acrylated bis-phenols. The antioxidants can be selected individually or used in any combination. Further, antioxidants can be used in combination with other compounds such as hydroperoxide decomposers.

The layered molded puck has two layers of containing UHMWPE wherein one side will be more crosslinked than the other after irradiation. The surface of an implant or preform fabricated from this layered molded material can be further manipulated by machining (FIGS. 46A-46H). For example, the surface is machined such that the articular surface is concave and the outside part of the surface is machined down to the UHMWPE containing high antioxidant concentration (FIG. 46C). Alternatively, the surface can have a contour after machining such that part of the surface contains more than another part (FIGS. 46A-46H). Such surfaces are then radiation crosslinked, yielding an implant or preform surface with preferentially crosslinked regions.

Example 19. Preferential Crosslinking by Using Different Molding Configurations

Figure 47A:
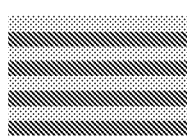
FIGS. 47A-47F show examples of different antioxidant blend configurations during molding. Darker color shows regions with higher antioxidant concentration blended into the polymer.

A UHMWPE puck containing a spatial distribution of high and low concentrations of at least one antioxidant is made by layered molding by using layering in different configurations. For example, there can be more than two layers having different concentrations of at least one antioxidant (FIG. 47A).

Figure 47B:
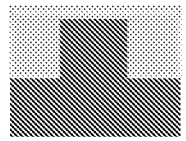
Figure 47C:
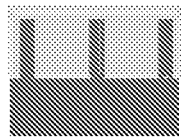
Figure 47D:
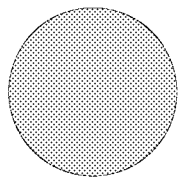
Figure 47E:
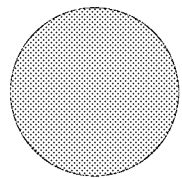
Figure 47F:
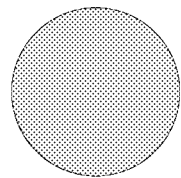

Alternatively, the blends are layered in such a way to allow for high concentration regions within the low concentration regions (FIG. 47B and FIG. 47C). The mold is topped with a low concentration layer which is machined away as desired.

Example 20. Preferential Surface Crosslinking by Masking

A method of creating a spatial distribution of antioxidant concentration through UHMWPE is to extract some antioxidant from a compression molded antioxidant blend of UHMWPE. In this way, the antioxidant concentration is lowered at the surface of the blended piece, and irradiation of such a piece yields a highly cross-linked surface and a less cross-linked bulk region. In another method, the surface is crosslinked preferentially by using masking of parts of the surface during extraction, followed by irradiation (FIGS. 48A-48F). The masking will serve the purpose of preventing antioxidant extraction from masked regions and limit the extraction to unmasked regions. This method will allow one to achieve an implant with crosslinking only in the regions where it is desired; for instance on the articular surfaces but not where the locking mechanisms are located.

Example 21. Irganox® Blends (Powder Vs. Solution Blends)

Irganox® 1010 was blended with UHMWPE powder using two methods: solvent blending and dry blending. In the solvent blend, the Irganox® 1010 was dissolved first in isopropyl alcohol (IPA) at room temperature or at a slightly elevated temperature around 40° C., then the solution was mixed with UHMWPE powder at the desired concentration. The solvent was dried off in a vacuum oven at 60° C. for at least one week. In the powder blend, Irganox® powder was mixed directly with UHMWPE powder at the desired concentration.

To determine the spatial variation of the antioxidant concentration throughout the samples, 150 µm-thick sections that were microtomed from an inner surface (FIGS.

43A-43D; n=3 each) were analyzed using FTIR. Irganox® index were calculated as a function of depth away from the surface as the ratio of the areas under 1223 cm$^{-1}$-1245 cm$^{-1}$ to the absorbance over 1875 cm$^{-1}$-1905 cm$^{-1}$.

Figure 49:
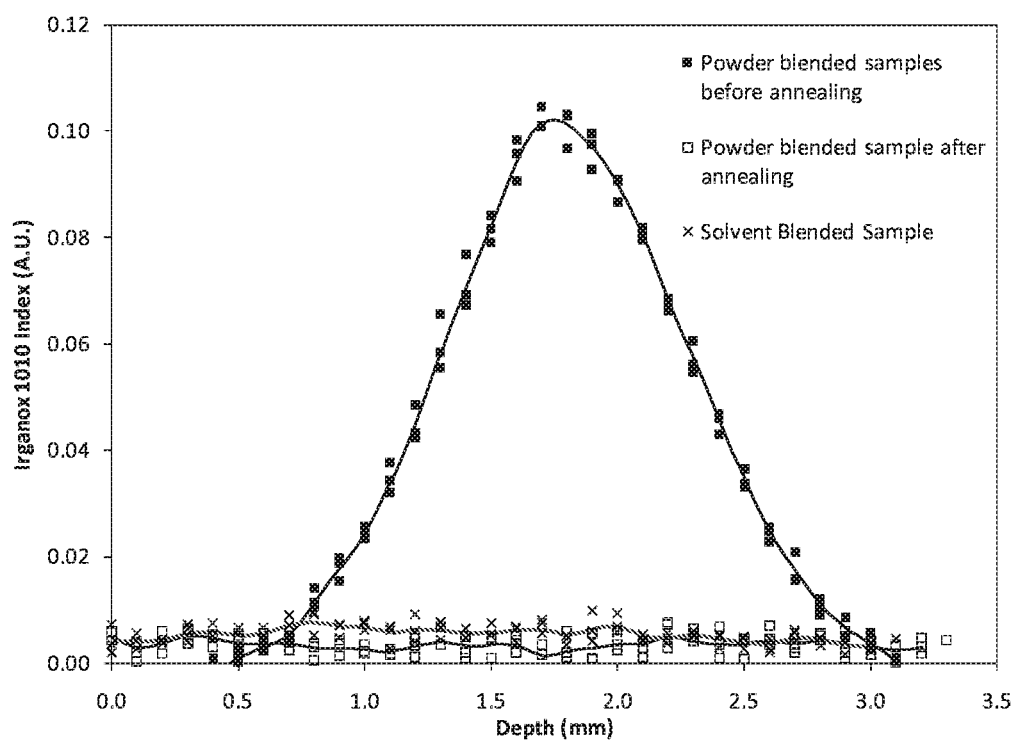
FIG. 49 shows concentration profile of powder and solvent blends of Irganox® 1010 with UHMWPE.

The concentration profile of Irganox® 1010 through the compression molded UHMWPE pucks fabricated from solvent blend and powder blend of Irganox® 1010 with UHMWPE before annealing are shown in FIG. 49. The solvent blend was more homogenous after molding. But, the concentration profile of the powder blend was also homogenized by annealing the puck at 130° C. for 64 hours (FIG. 49).

Example 22. Oxidative Stability of Irradiated Irganox® 1010 Blends of UHMWPE UHMWPE pucks containing a uniform concentration of 0.1 wt % Irganox® 1010 were prepared by solvent blending Irganox® 1010 with UHMWPE powder (Example 21) and compression molding (FIG. 42A). Pucks were used untreated or were irradiated to 150 kGy for cross-linking. Control was virgin UHMWPE irradiated to 150 kGy.

Two accelerated aging methods were used: 14 days at 70° C. under 5 atm. of oxygen (ASTM F2003) and 14 days at 70° C. under 5 atm. of oxygen after squalene doping. Squalene is an unsaturated lipid, which initiated severe oxidation in irradiated and melted UHMWPE. Cubes (1 cm) were machined from Irganox® 1010 blended pucks and irradiated blended pucks. Squalene doping was done in pre-heated squalene at 120° C. for 2 hours in air.

After accelerated aging, the 150 μm-thick sections were microtomed from an inner surface (FIGS. 43A-43D; n=3 each). These sections were boiled in hexane overnight and then dried in vacuum at room temperature for 24 hours. They were then analyzed by FTIR. An oxidation index was calculated as a function of depth away from the surface as the ratio of the areas under 1680 cm$^{-1}$-1780 cm$^{-1}$ to the absorbance over 1370 cm$^{-1}$ per ASTM F2003.

Figure 50A:
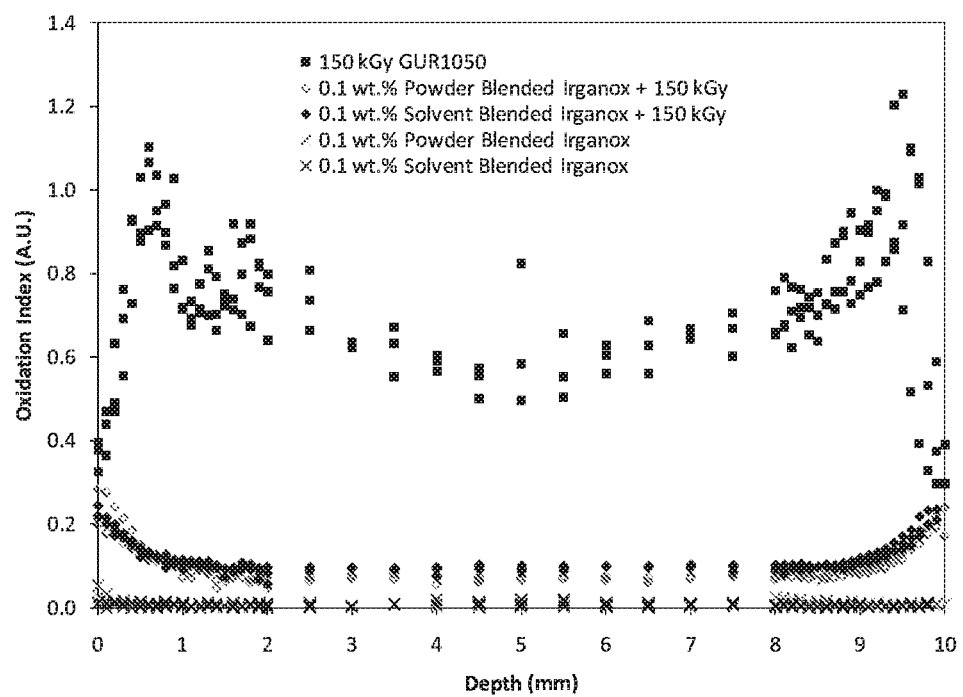
FIG. 50A and FIG. 50B show oxidation profiles of accelerated aged irradiated Irganox®1010 blends.
Figure 50B:
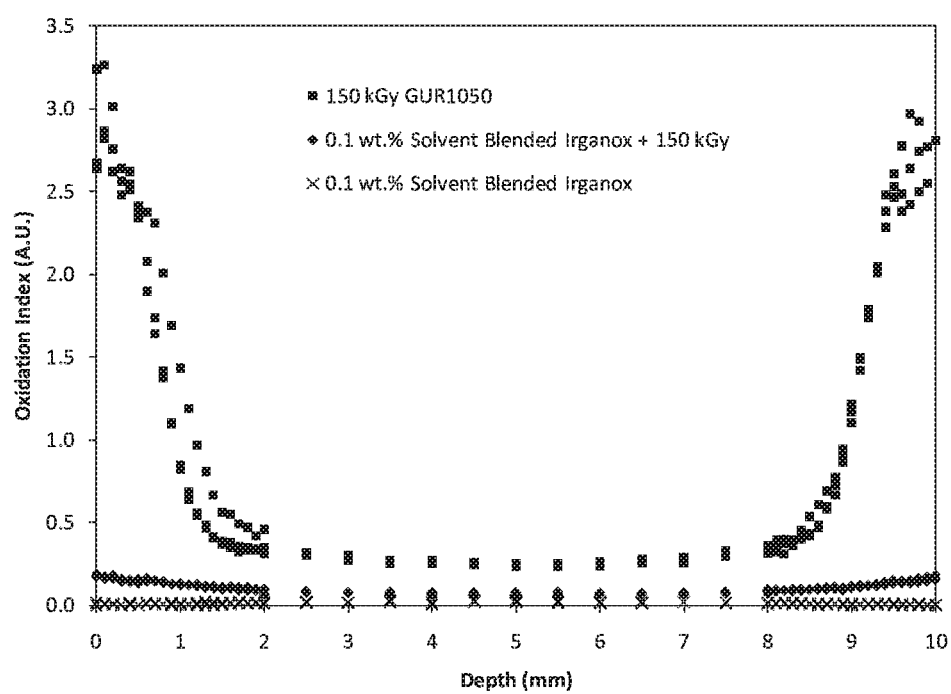

After accelerated aging both with (FIG. 50B and without lipids (FIG. 50A), irradiated virgin UHMWPE oxidized heavily, whereas irradiated Irganox® 1010 blends showed substantially lower oxidation. The non-irradiated Irganox® 1010 blends showed no detectable oxidation, those that were irradiated showed very small oxidation near the surface.

These results showed that Irganox® 1010 increased the oxidative stability of UHMWPE substantially after irradiation.

Example 23. Wear Resistance of Irradiated Irganox® 1010 Blends of UHMWPE

The wear rate (mg/million cycles) of irradiated blends of Irganox® 1010 with UHMWPE was measured using a bidirectional pin-on-disc wear tester (AMTI Orthopod, Watertown. Mass.). Cylindrical pins (diameter 9 mm, length 13 mm) were articulated against medical grade polished CoCr discs in a rectangular pattern ($R_a$=0.03-0.05 μm) at 2 Hz in bovine serum at room temperature. Wear was assessed by gravimetric measurements at 0.5 MC and at every subsequent 0.15 million-cycle (MC) and the wear rate was determined as the linear regression of wear vs. number of cycles from 0.5 MC to the end of the test (1.2 MC).

TABLE 18

POD wear rates of irradiated Irganox ® 1010 blends of UHMWPE.

| Material | Wear rate (mg/MC) |
|---|---|
| Virgin + 150 kGy | −0.8 ± 0.2 |
| 0.1 wt % solvent blend of Irganox ® 1010 | −13.6 ± 1.1 |
| 0.1 wt % solvent blend of Irganox ® 1010 + 150 kGy | −0.5 ± 0.0 |
| 0.1 wt % powder blend of Irganox ® 1010 + 150 kGy | −0.94 ± 0.4 |

The wear rates of irradiated 0.1 wt % Irganox® 1010 blends of UHMWPE were comparable to or less than that of 150 kGy irradiated virgin UHMWPE (Table 17).

Example 24. Extraction of Irganox® with Hexane

One UHMWPE puck each containing a uniform concentration of Irganox® 1010 (0.1 wt %) was prepared by solvent blending or dry powder blending Irganox® 1010 with UHMWPE powder (Example 21) and compression molding (FIG. 42A).

To determine the spatial variation of the antioxidant concentration throughout the samples, 150 μm-thick sections were microtomed from an inner surface (FIGS. 43A-43D; n=3 each) were analyzed using FTIR. Irganox® index were calculated as a function of depth away from the surface as the ratio of the areas under 1223 cm$^{-1}$-1245 cm$^{-1}$ to the absorbance over 1875 cm$^{-1}$-1905 cm$^{-1}$.

Microtomed sections were boiled in hexane overnight (~16 hours) and were dried in vacuum at room temperature for 24 hours. Irganox® content was measured before and after hexane extraction as a function of depth away from the surface of the molded puck.

Figure 51:
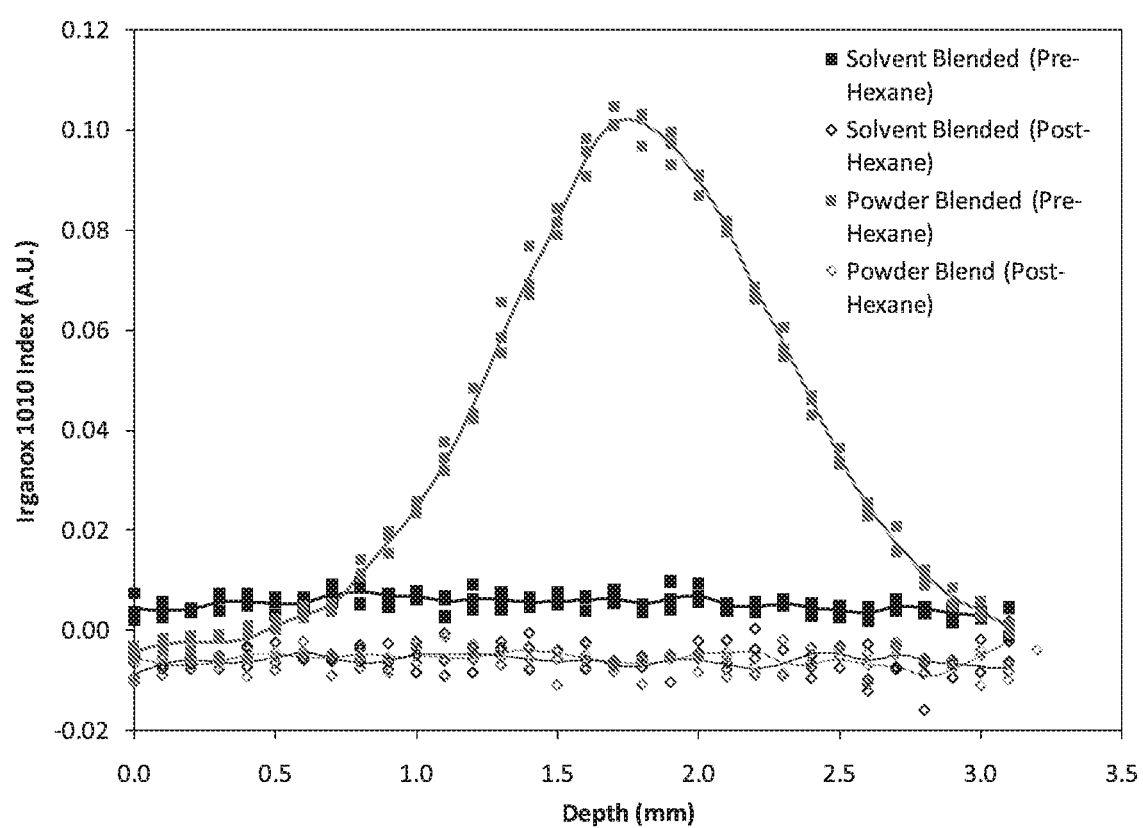
FIG. 51 shows Irganox® 1010 concentration profiles of molded Irganox® blends of UHMWPE before and after extraction by boiling hexane.

The concentration profiles after hexane extraction in both samples was close to undetectable (FIG. 51), suggesting efficient extraction of Irganox® from the UHMWPE.

Example 25. Annealing for Redistribution of Antioxidants

A UHMWPE puck with high and low concentrations of Irganox® 1010 is made by layering blend powder in any configuration, for example as described in Example 6. Or, a UHMWPE puck with a high concentration of vitamin E in the bulk and a low concentration of an Irganox® antioxidant is made by layering blend powder. Then, it is radiation crosslinked. After radiation cross-linking it is annealed below, at or above the melting temperature at 100, 110, 120, 130, 140, 150, 170, or 300° C. for 1 hour, 2 hours, 4 hours, 8 hours, 24 hours, 36 hours, 64 hours or 300 hours or 1000 hours. In this manner, the antioxidant in the regions containing high antioxidant concentration is redistributed to the regions with low antioxidant concentration. Annealing is alternatively done in a supercritical carbon dioxide environment.

Example 26. Blending with More than One Antioxidant

A consolidated blend of GUR1050 UHMWPE was made using solvent (IPA) blending of Irganox® 1010 and vitamin E with UHMWPE resin powder, evaporating the solvent and compression molding the blended powder in a press. Blended powder was made containing 0.1 wt % of each antioxidant.

Compression molded pucks (diameter ~10 cm, thickness ~1 cm) were irradiated to 50, 100, 150 and 200 kGy using electron beam irradiation.

Figure 52:
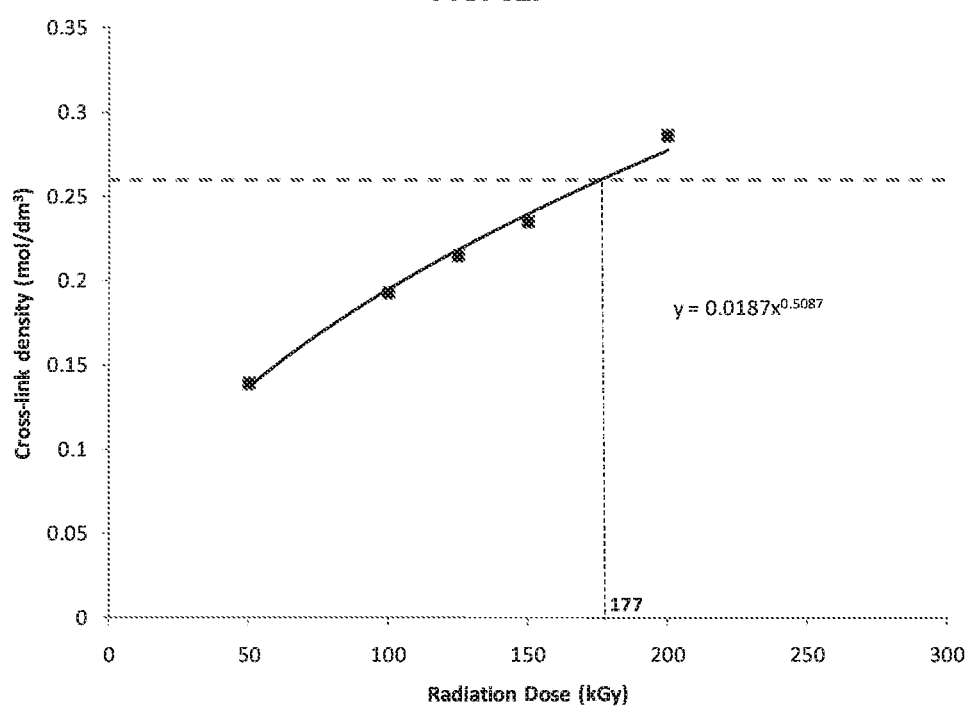
FIG. 52 shows cross-link density as a function of radiation dose in UHMWPE blend of 0.1 wt % Irganox® 1010 and 0.1 wt % vitamin E. The dashed line indicates the radiation dose required to obtain a cross-link density of 0.260 mol/dm$^3$; the crosslink density of 100-kGy irradiated virgin UHMWPE. The number at the bottom of the dashed line is the radiation dose required to obtain this level of crosslinking in this blended UHMWPE.

Cross-link density was measured and calculated as described in Example 14 and are shown in FIG. 52.

Example 27. Blending with Vitamin E

Consolidated blends of GUR1050 UHMWPE were made with vitamin E using solvent (IPA) blending of vitamin E with UHMWPE resin powder, evaporating the solvent and compression molding the blended powder in a press. Blended powder was either made at the desired concentration or made at a higher concentration of antioxidant and diluted down with UHMWPE powder. In this manner, UHMWPE containing 0.01 wt %, 0.02 wt %, 0.05 wt %, 0.1 wt %, 0.2 wt %, 0.3 wt %, 0.5 wt % and 1.0 wt % vitamin E were made.

Compression molded pucks (diameter ~10 cm, thickness ~1 cm) were irradiated to 50, 100, 150 and 200 kGy using electron beam irradiation. Cross-link density was measured and calculated as described in Example 14.

Figure 53:
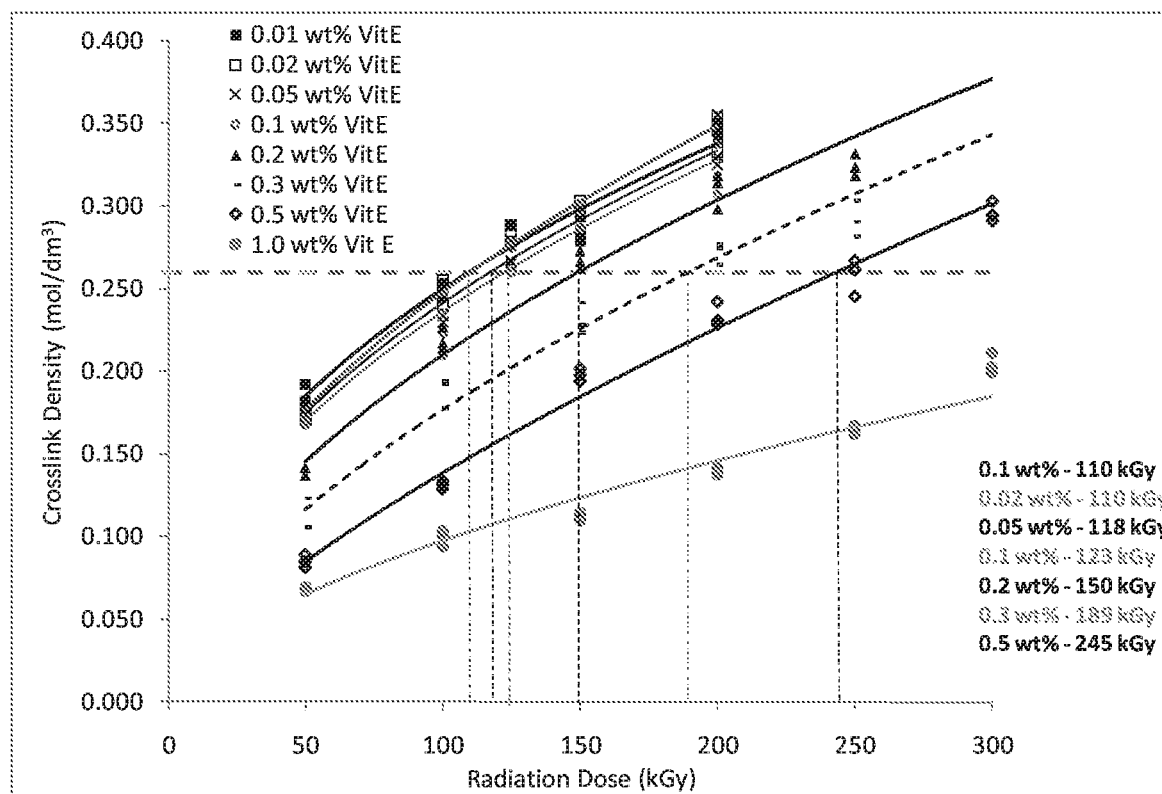
FIG. 53 shows cross-link density as a function of radiation dose in UHMWPE blend of vitamin E. The vertical dashed lines indicate the radiation dose required to obtain a crosslink density of 0.260 mol/dm$^3$; the crosslink density of 100-kGy irradiated virgin UHMWPE. The numbers at the right side of the graph are the radiation dose values required to obtain this level of crosslinking in vitamin E-blended UHMWPE as a function of concentration.

It was observed that increasing antioxidant concentration decreased cross-linking in UHMWPE and thus, the radiation dose required to obtain 260 mol/m$^3$ of cross-link density (equivalent to that of 100-kGy irradiated virgin UHMWPE) in antioxidant-blended UHMWPEs increased with increasing antioxidant concentration (FIG. 53).

Example 28. Oxidative Stability of Irradiated Antioxidant Blends

UHMWPE pucks containing a uniform concentration of 0.01 wt %, 0.02 wt %, 0.05 wt % and 0.1 wt % Irganox® 1010 were prepared by solvent blending Irganox® 1010 with UHMWPE powder (Example 21) and compression molding FIG. 42A). UHMWPE pucks containing a uniform concentration of 0.01 wt %, 0.02 wt %, 0.05 wt %, 0.1 wt %, 0.2 wt %, 0.3 wt % and 0.5 wt % vitamin E were prepared by solvent blending vitamin E with UHMWPE powder (Example 27) and compression molding FIG. 42A). Pucks were irradiated to different doses to achieve 0.260 mol/dm$^3$ of crosslink density (Table 17). Control was virgin UHMWPE irradiated to 150 kGy.

A severe accelerated aging method was used: 14 days at 70° C. under 5 atm. of oxygen after squalene doping. Squalene is an unsaturated lipid, which initiated severe oxidation in irradiated and melted UHMWPE. Cubes (1 cm) were machined from blended pucks and irradiated blended pucks. Squalene doping was done in pie-heated squalene at 120° C. for 2 hours in air.

After accelerated aging, the 150 μm-thick sections were microtomed from an inner surface (FIGS. 43A-43D; n=3 each). These sections were boiled in hexane overnight and then dried in vacuum at room temperature for 24 hours. They were then analyzed by FTIR. An oxidation index was calculated as a function of depth away from the surface as the ratio of the areas under 1680 cm$^{-1}$-1780 cm$^{-1}$ to the absorbance over 1370 cm$^{-1}$ per ASTM F2003.

Figure 54:
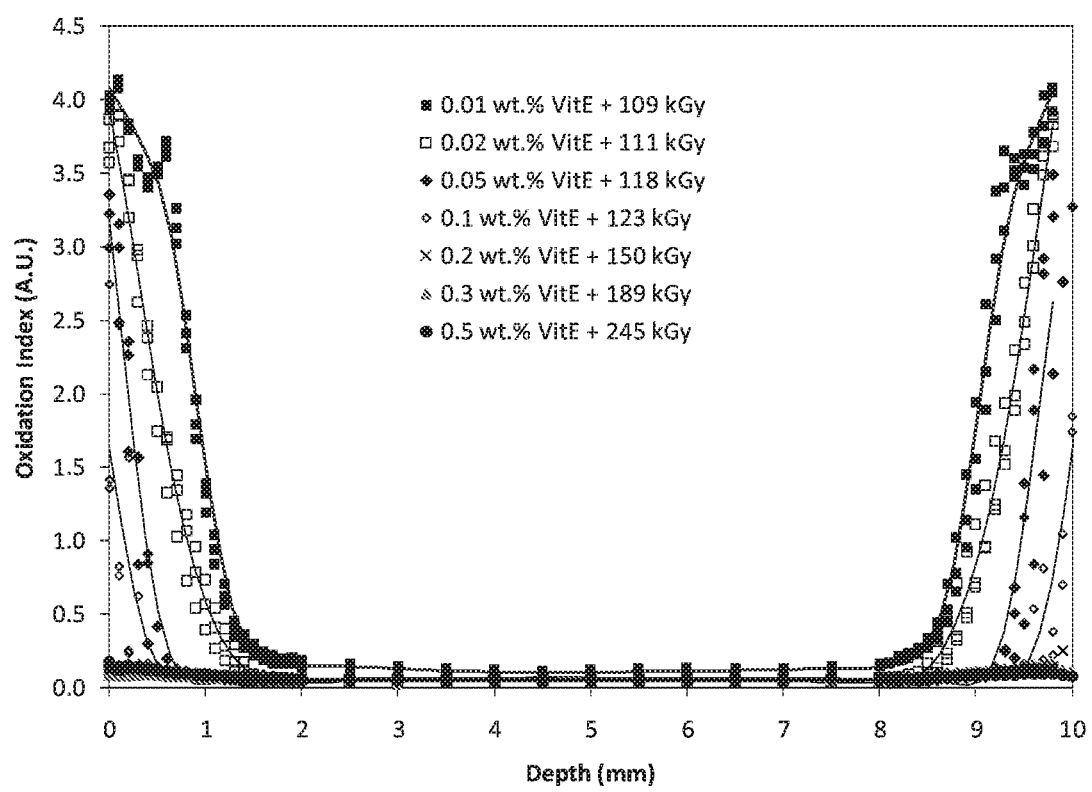
FIG. 54 shows oxidation index as a function of depth after squalene challenge and bomb aging of irradiated vitamin E blends.
Figure 55:
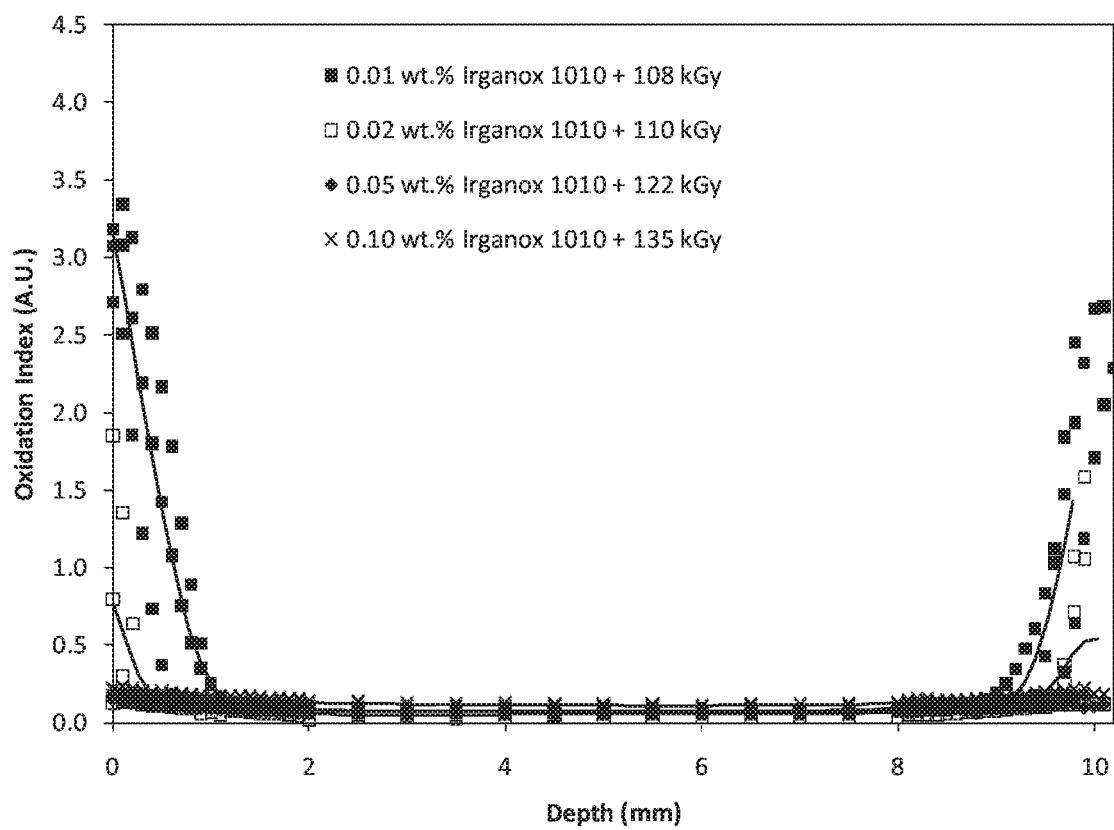
FIG. 55 shows oxidation index as a function of depth after squalene challenge and bomb aging of irradiated vitamin E blends.

After squalene challenge and bomb aging under elevated oxygen partial pressure, irradiated vitamin E blends containing less than 0.1 wt % vitamin E oxidized (FIG. 54). In contrast, under the same conditions, irradiated Irganox® 1010 blends containing less than 0.05 wt % Irganox® 1010 oxidized (FIG. 55). Therefore, Irganox® 1010 appeared to be more effective towards oxidation induced by squalene during accelerated aging than vitamin E.

Example 29. Diffusion and Homogenization of Irganox® in UHMWPE

Virgin UHMWPE was machined into blocks (1 cm$^3$). Irganox® 1010 was pre-heated to 130° C. in a convection oven. Cubes were doped in this pre-heated Irganox® 1010 for 6 hours at 130° C. The cubes were then removed from Irganox® 1010 and the excess antioxidant on the surface was wiped off. Then they were placed in homogenization for 64 hours at 130° C. To determine the spatial variation of the antioxidant concentration throughout the samples, 150 μm-thick sections were microtomed from an inner surface (FIGS. 43A-43D; n=3 each) were analyzed using FTIR. Irganox® index were calculated as a function of depth away from the surface as the ratio of the areas under 1223 cm$^{-1}$-1245 cm$^{-1}$ to the absorbance over 1875 cm$^{-1}$-1905 cm$^{-1}$.

Figure 56:
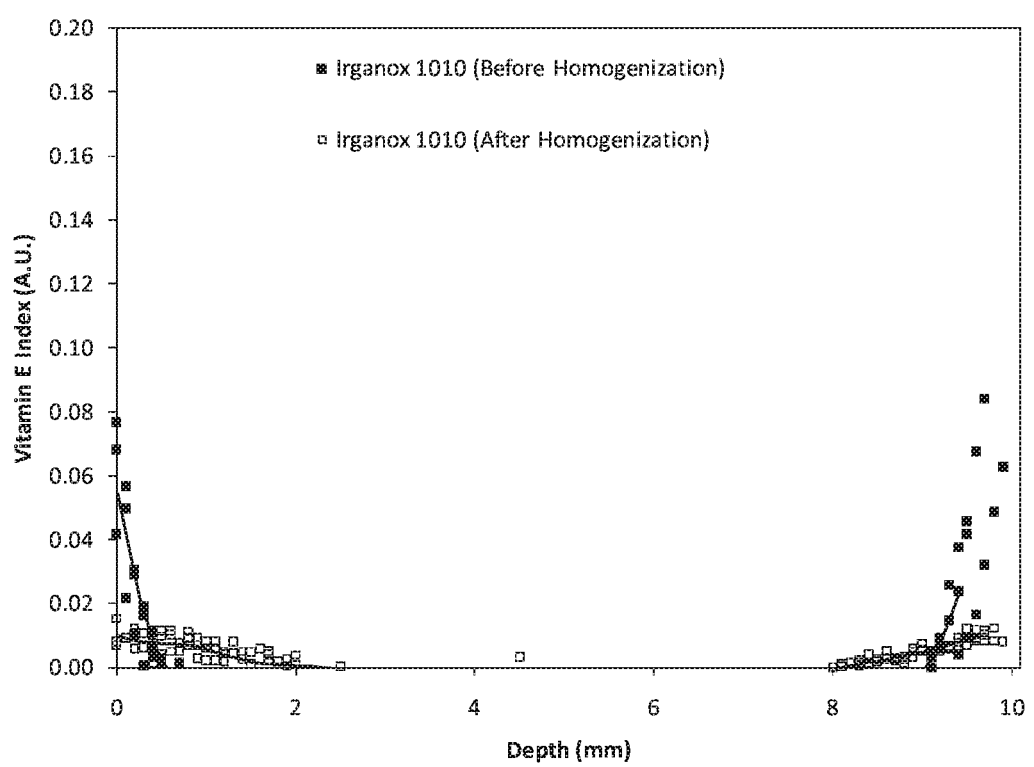
FIG. 56 shows Irganox® 1010 index as a function of depth after doping and doping/homogenization.
Figure 57:
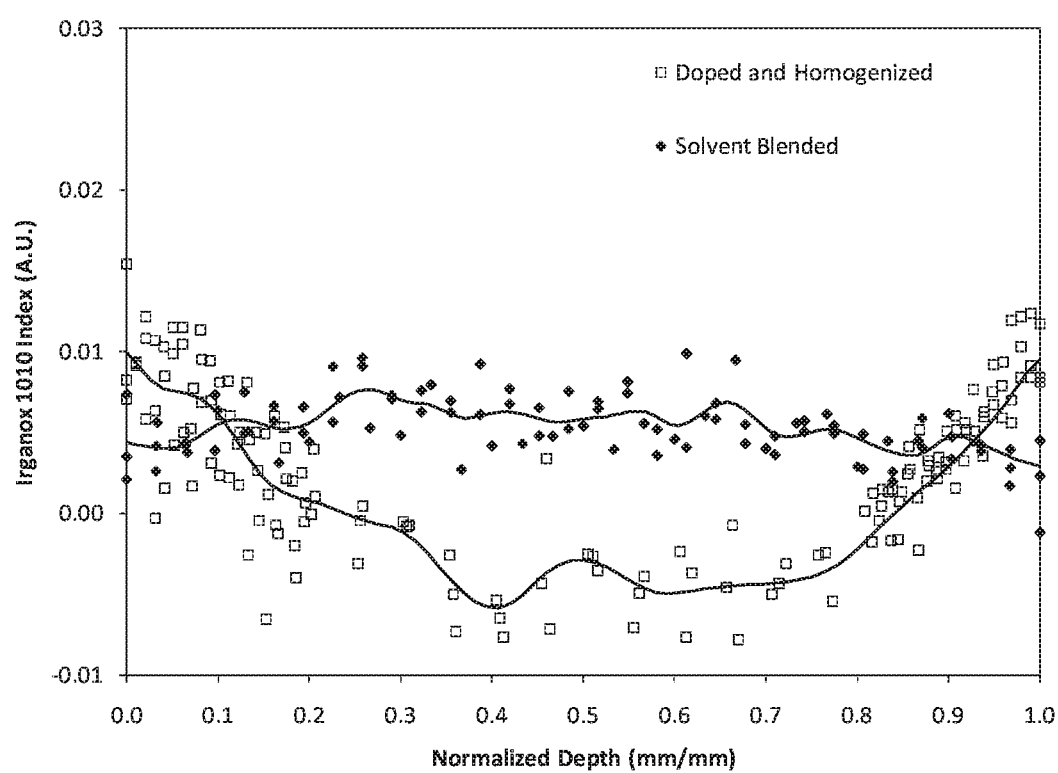
FIG. 57 illustrates Irganox® 1010 index as a function of depth after doping and doping/homogenization.

A more uniform Irganox® 1010 profile was obtained by using doping of UHMWPE in Irganox® 1010 followed by homogenization of the high surface concentration obtained by doping (FIG. 56). The obtained concentration was similar to that obtained by solvent blending of Irganox®1010 in UHMWPE and compression molding of the blend (FIG. 57).

Example 30. Mechanical Properties of Surface Crosslinked UHMWPE

GUR1050 UHMWPE pucks were prepared as described in FIG. 42A by layered compression molding of 1 or 2 wt % vitamin E-blended UHMWPE in one layer and 0.05 wt % vitamin E-blended UHMWPE resin powder in the other layer. Blending of the antioxidant into the powder was made by dissolving in IP A, mixing the solution with UHMWPE powder, and evaporating the solvent by vacuum drying at 60° C. The thickness of the layer molded with low vitamin E concentration was approximately 2 mm and the rest contained the higher concentration of vitamin E.

One puck each (10 cm diameter, ~6.4 mm thickness) was vacuum packaged and irradiated to 75, 100 and 150 kGy by electron beam irradiation (2.5 MeV generator, MIT) at 25 kGy/pass. The irradiated pucks were machined into IZOD impact testing coupons (ASTM F648) without machining away the surface layer and notched and tested according to ASTM F648 at Orthoplastics Ltd, UK.

TABLE 19

Impact strength of surface crosslinked UHMWPEs containing 1 wt % and 0.05 wt % vitamin E.

| | IZOD Impact strength (kJ/m$^2$) | |
|---|---|---|
| Radiation Dose (kGy) | Surface crosslinked | No surface crosslinking |
| 75 | 109 ± 3 | 124 ± 2 |
| 100 | 97 ± 3 | 118 ± 1 |
| 150 | 83 ± 4 | 93 ± 4 |

TABLE 20

Impact strength of surface crosslinked UHMWPEs containing 2 wt % and 0.05 wt % vitamin E.

| | IZOD Impact strength (kJ/m$^2$) | |
|---|---|---|
| Radiation Dose (kGy) | Surface crosslinked | No surface crosslinking |
| 75 | 113 ± 3 | 130 ± 1 |

The IZOD impact strength of 100-kGy irradiated virgin UHMWPE was 72±2 kJ/m$^2$ and that of unirradiated UHMWPE was 127±8 kJ/m$^2$. The IZOD impact strength of surface crosslinked UHMWPE containing a surface of 30% of the entire thickness was 10-20% less than the 1 or 2 wt % vitamin E blended and irradiated UHMWPE without a crosslinked surface (Tables 19 and 20). In addition, the impact strength of these UHMWPEs was 15 to 57% higher than that of 100-kGy irradiated UHMWPE.

Figure 58:
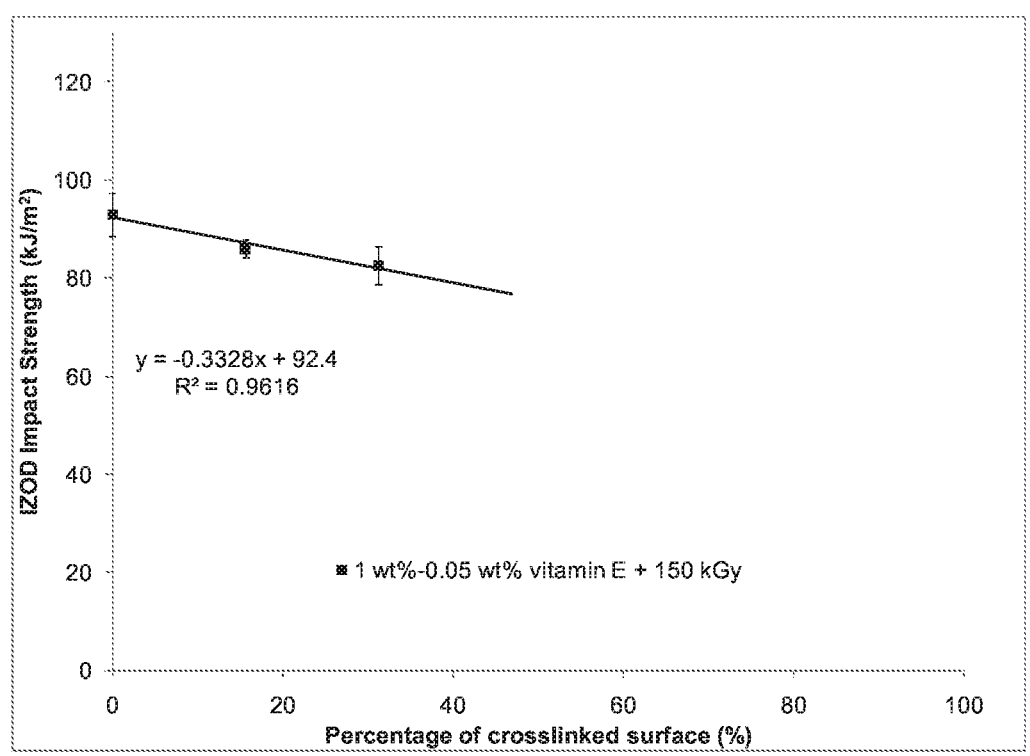
FIG. 58 illustrates Impact strength as a function of the percentage of the thickness of the surface crosslinked layer in surface crosslinked UHMWPE.

To elucidate the thickness effect on the surface crosslinked layer on the mechanical properties on the material, 3 UHMWPE pucks were prepared by layering and compression molding 1, 2 or 3 mm of 0.05 wt % vitamin E blended GUR1050 UHMWPE powder with 1 wt % vitamin E blended UHMWPE powder into 6.4 mm-thick sample. The pucks were then vacuum packaged and irradiated to 150 kGy. IZOD testing was done as described above. The results are shown in FIG. 58. The impact strength decreased with increasing thickness of the highly crosslinked layer irradiated in the presence of a lower vitamin E concentration.

Example 31. Homogenization of Antioxidants after Surface Crosslinking

GUR1050 UHMWPE pucks were prepared as described in FIG. 42A by layered compression molding of 1 wt % vitamin E-blended UHMWPE powder in one layer and 0.05 wt % vitamin E-blended UHMWPE resin powder in the other layer. Blending of the antioxidant into the powder was made by dissolving in IPA, mixing the solution with UHMWPE powder, and evaporating the solvent by vacuum drying at 60° C. The thickness of the layer molded with low vitamin E concentration was approximately 2 mm and the rest contained the higher concentration of vitamin E.

One puck each (10 cm diameter, ~6.4 mm thickness) was vacuum packaged and irradiated to 75, 100 and 150 kGy by electron beam irradiation (2.5 MeV generator, MIT) at 25 kGy/pass. After irradiation, the pucks were machined into 1 cm by 1 cm by 6.4 mm blocks. One block each was annealed in argon at 135° C. for 16, 40, 64, 88 and 185 hrs. The vitamin E profiles were determined by FTIR spectroscopy before and after annealing.

To determine the spatial variation of the antioxidant concentration throughout the samples, 150 μm-thick sections were microtomed from an inner surface (FIGS. 43A-43D; n=3 each) were analyzed using FTIR. Vitamin E index was calculated as the ratio of the areas under 1245 cm$^{-1}$-1275 cm$^{-1}$ to the absorbance over 1875 cm$^{-1}$-1905 cm$^{-1}$.

Figure 59A:
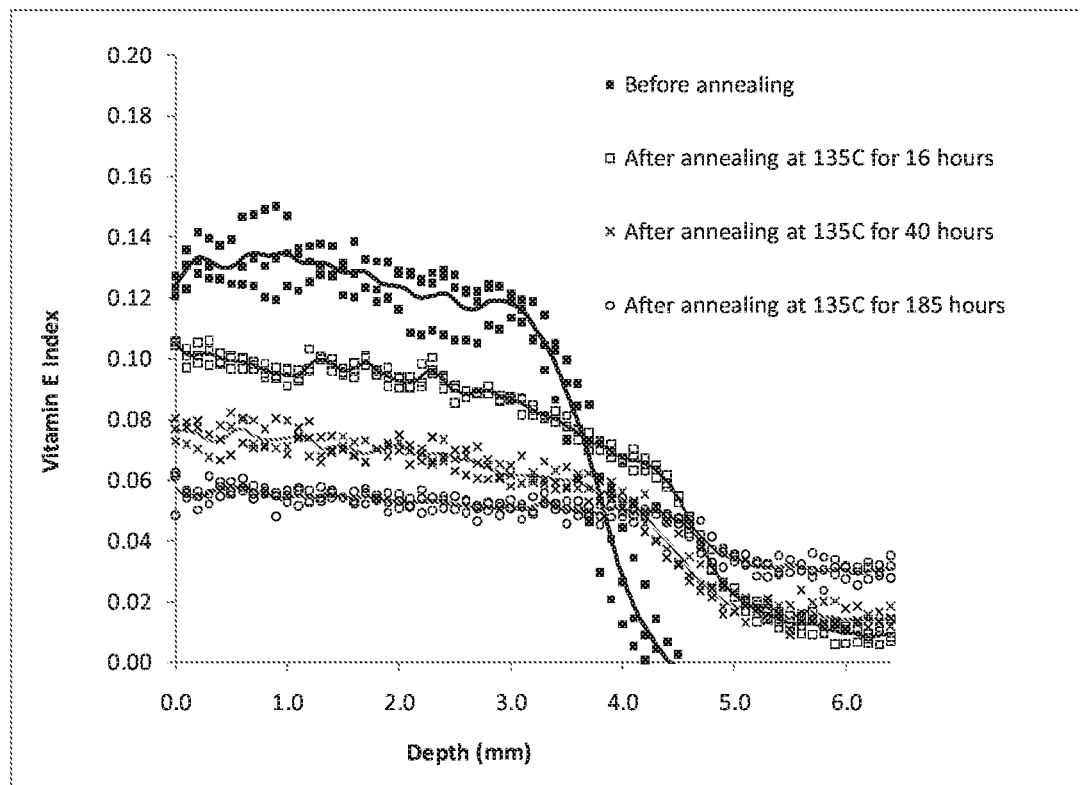
FIG. 59A and FIG. 59B illustrate the vitamin E profiles of homogenized surface crosslinked UHMWPE containing 1 wt %-0.05 wt % vitamin E blends irradiated to 100 kGy (FIG. 59A) and 150 kGy (FIG. 59B).
Figure 59B:
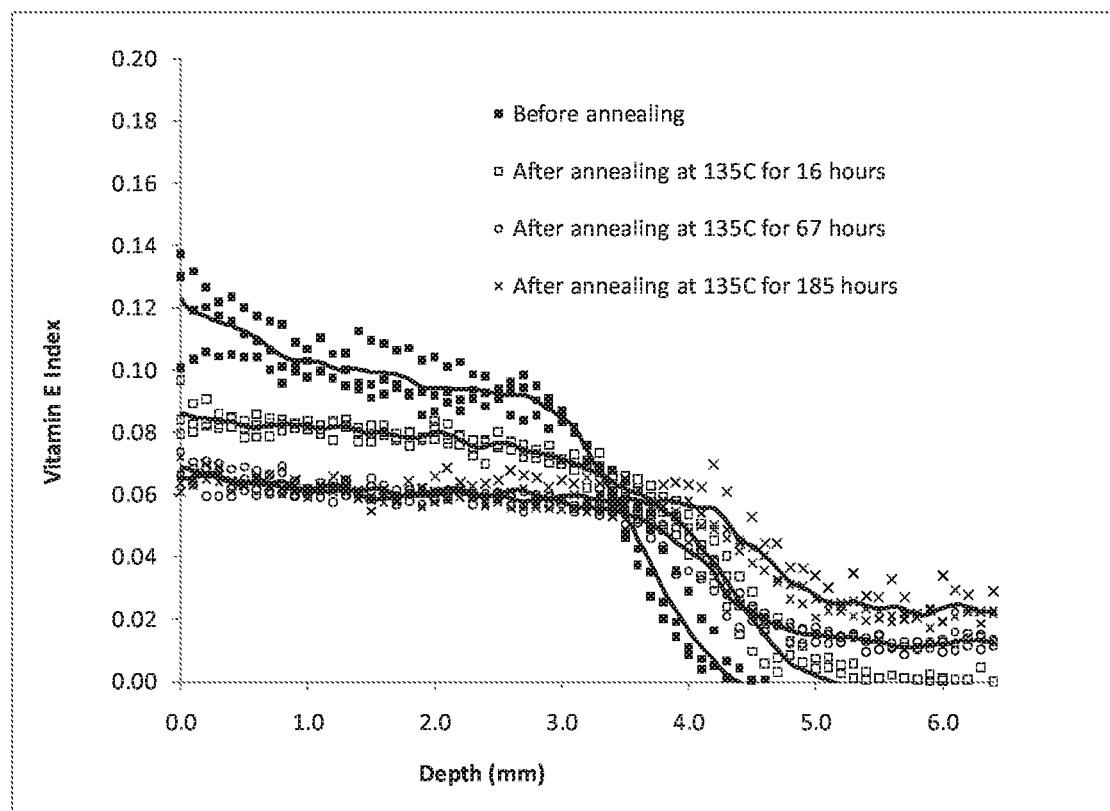

FIGS. 59A-59B show the vitamin E profiles of homogenized surface crosslinked UHMWPE containing 1 wt % and 0.05 wt % vitamin E blends of UHMWPE irradiated to 100 kGy (59a) and 150 kGy (59b). Homogenization was done after irradiation in argon at 135° C. for 16-185 hours. The vitamin E index on the surface crosslinked side, which was undetectable before homogenization increased substantially (FIGS. 59A-59B). Thus, the oxidation resistance of this side increases as well.

Example 32. Homogenization of Surface Crosslinked UHMWPE in a Supercritical Medium GUR1050 UHMWPE pucks are prepared as described in FIG. 42A by layered compression molding of 1 wt % vitamin E-blended UHMWPE in one layer and 0.05 wt % vitamin E-blended UHMWPE resin powder in the other layer. Blending of the antioxidant into the powder is made by dissolving in IPA, mixing the solution with UHMWPE powder, and evaporating the solvent by vacuum drying at 60° C. The thickness of the layer molded with low vitamin E concentration is approximately 2 mm and the rest contains the higher concentration of vitamin E.

One puck each (10 cm diameter, ~6.4 mm thickness) is vacuum packaged and irradiated to 50, 75, 100, 150, 200, 250, 300, 350, 400 kGy by electron beam irradiation (2.5 MeV generator, MIT) at 25 kGy/pass. After irradiation, the pucks are annealed in inert gas or supercritical carbon dioxide at 45, 50, 60, 80, 100, 120, 130, 135, 150, 180, 200, 250, 280, 300, 320° C. for 16, 40, 64, 88, 185 or 1000 hrs.

Example 33. Diffusion of Antioxidant in Surface Crosslinked UHMWPE

GUR1050 UHMWPE pucks are prepared as described in FIG. 42A by layered compression molding of 1 wt % vitamin E-blended UHMWPE in one layer and 0.05 wt % vitamin E-blended UHMWPE resin powder in the other layer. Blending of the antioxidant into the powder is made by dissolving a solvent (such as an alcohol or alcohol mixture such as IPA, ethanol, methanol), mixing the solution with UHMWPE powder, and evaporating the solvent by vacuum drying at 60° C. The thickness of the layer molded with low antioxidant concentration is approximately 2 mm and the rest contains the higher concentration of antioxidant.

One puck each (10 cm diameter, ~6.4 mm thickness) is vacuum packaged and irradiated to 50, 75, 100, 150, 200, 250, 300, 350, 400 kGy by electron beam irradiation (2.5 MeV generator, MIT) at 25 kGy/pass. After irradiation, the pucks are doped in antioxidant at 100, 120, 130, 150, 180, 200, or 300° C. for 16, 40, 64, 88, 185 or 1000 hrs. After doping, they are homogenized in inert gas or supercritical carbon dioxide at 100, 120, 130, 150, 180, 200, or 300° C. for 16, 40, 64, 88, 185 or 1000 hrs.

Example 34. Warm Irradiation of Irganox® Blends

GUR1050 UHMWPE pucks are prepared as described in FIG. 42A by layered compression molding of 1 wt % vitamin E-blended UHMWPE in one layer and 0.05 wt % Irganox® 1010-blended UHMWPE resin powder in the other layer. Blending of the antioxidants into the powder is made by dissolving in IPA, mixing the solution with UHMWPE powder, and evaporating the solvent by vacuum drying at 60° C. The thickness of the layer molded with low Irganox® concentration is approximately 2 mm and the rest contains the higher concentration of vitamin E.

The layered compression molded puck is pre-heated to an elevated temperature below the melting point of UHMWPE, for example 25, 50, 70, 100, 120, 125, or 135° C. Then the pre-heated material is irradiated to 25, 50, 100, 150, and 200 kGy by electron-beam or gamma irradiation. The e-beam irradiation is carried out in either one pass for the total desired dose or in multiple passes. In some embodiments the dose applied in each pass is ¼, ½, ⅓, ⅕, ⅙, or 1/7$^{th}$ of the total desired dose. The pucks are either packaged in inert gas or irradiated in air.

Control samples are prepared by compression molding pucks with uniform concentrations of vitamin E and Irganox® using 1 wt % vitamin E-blended UHMWPE and 0.05 wt % Irganox® blended UHMWPE. These controls are irradiated with and without pre-heating to the same temperatures as listed above.

Example 35. Decomposition of UHMWPE as a Function of Temperature

In order to assess the thermal stability of UHMWPE at high temperatures, TGA was performed by using a Q-500 Thermogravimetric analyzer (TA Instruments Inc., Newark, Del.). One sample (about 10 mg) was loaded on the pan and heated up to a target temperature (280, 300, 320, 340, and 400° C.) at 20° C./min and held at the temperature for 1440 min under nitrogen flow at 60 ml/min. The weight over time was sampled every 30 seconds. The remaining weight percentage was plotted against time to compare the thermal stability of UHMWPE at different temperatures.

Figure 60:
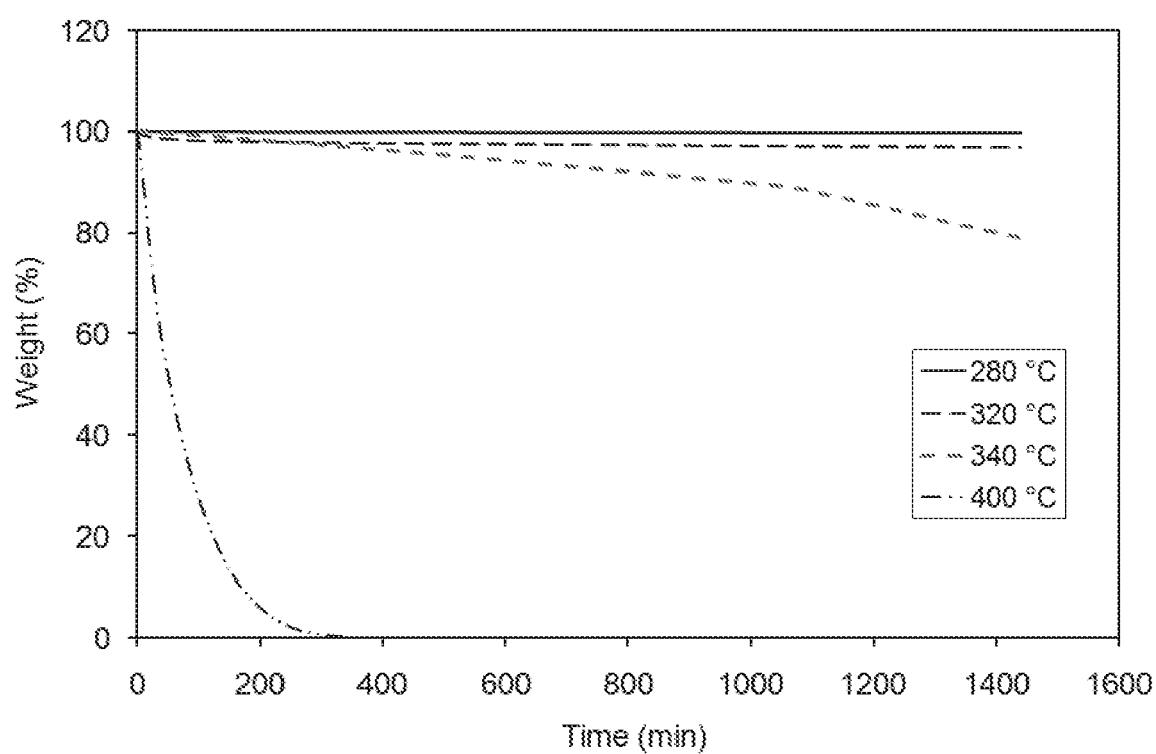
FIG. 60 illustrates thermogravimetric curves of UHMWPE melted at 280, 300, 320, 340 and 400° C. for 24 hours.

There was no significant decomposition of UHMWPE within 24 hours when it was heated to below 340° C. (FIG. 60).

Example 36. High Temperature Melting of GUR1050 UHMWPE in an Inert Gas Convection Oven Compression molded GUR 1050 UHMWPE (CM UHMWPE) (Orthoplastics, Bacup Lancashire, UK) with dimensions of 250×60×45 mm³ (length×width×height) were melted in a programmable inert gas convection oven (Despatch Industries, Minneapolis, Minn.) under continuous nitrogen flow (flow rate was ~2 m³/min). The oven was preheated to a preset temperature with nitrogen purge. Then, the UHMWPE blocks were placed in the oven and purged again. Three temperatures (280, 300, and 320° C.) were used to melt the UHMWPE. At each temperature, the UHMWPE was held for 2, 5, or 12 h and then cooled down to 40° C. within 2 h (or an average cooling rate of 2.5° C./min or less). The samples were held at 40° C. for 20 min in the oven before retrieval. Such melted UHMWPE was denoted as HTM UHMWPE. Specifically, the HTM UHMWPE samples were denoted as UH T-t, where T is the melting temperature and t is the melting duration; for example UH 280-2, UH 280-5, and UH 280-12 represent UHMWPE melted at 280° C. for 2, 5, and 12 h, respectively.

Thin sections (thickness=3.2 mm) were machined (Eastern Tool Inc, Medford, Mass.) from HTM UHMWPE and CM UHMWPE. Tensile testing specimens (Type V, n=5) were stamped from these thin sections according to ASTM D638. Uni-axial tensile testing was conducted by using an MTS machine (Eden Prairie, Minn.) at a crosshead speed of 10 mm/min. The axial displacement and force were sampled at a rate of 100 Hz. The extension of a specific gauge on the specimen was measured by a laser extensometer, which was used to determine the elongation at break (EAB).

True stress-true strain curves were converted from the engineering stress-strain results by using the extension readings from the laser extensometer. The ultimate tensile strength (UTS), yield strength (YS), work to failure (area under the engineering stress-strain curve; WF), and elastic modulus (E) were calculated. Statistical analysis was performed by using a Student's t-test for two-tailed distributions with unequal variance where applicable.

The strain-hardening modulus (G) is regarded as the intrinsic property of an entangled amorphous network. According to the Gaussian model by Haward and Thackray, (Haward R N. Macromolecules 1993; 26:5860-5869) the true stress (σ) and G are related by $$\sigma = G(\lambda^2 - 1/\lambda) + Y \tag{1}$$

where λ is the extension ratio and $\lambda = \exp(\varepsilon_t)$ with $\varepsilon_t$ as true strain, and Y is the flow stress exerted by the crystalline phase including intra- and interlamellar coupling. In order to calculate the strain-hardening modulus of the amorphous phase in this semi-crystalline polymer, we deduced the Haward plots from the true stress-strain curves and extracted the slope of the fitted line after yielding.

Double-notched Izod impact strength measurements were conducted at Orthoplastics Inc. (Bacup Lancashire, UK). The specimens (n=5 for each material) were machined to 63.5×12.7×6.35 mm³ bars and double notched to a depth of 4.57±0.08 mm according to ASTM F648. The specimens were conditioned after notching for not less than 16 h at 23±2° C. and tested in accordance with ASTM F648. The energy absorbed by the specimens was recorded for the calculation of the impact strength in kJ/m².

In order to evaluate the chain scission in UHMWPE by high temperature melting, the melted samples were microtomed into thin slices (thickness=150 μm) by using an LKB Sledge Microtome (Sweden). FTIR absorption spectra of these thin slices were collected by using a UMA-500 infrared microscope (Bio-Rad Laboratories, Natick, Mass.) scanning from 400 to 4000 cm$^{-1}$ (step width 2 cm$^{-1}$) in transmission mode. Chain scissioning taking place in UHMWPE at high temperatures led to the formation of terminal vinyl groups with absorbance at 909 and 990 cm$^{-1}$. The content of these terminal vinyl groups was indexed by normalizing the integral of the peak at 909 cm$^{-1}$ against that of the polyethylene skeleton peak at 1895 cm$^{-1}$. These vinyl indices were taken as an indication to the extent of chain scission occurring in UHMWPE under high temperatures.

The bi-directional POD wear test was performed on an MTS machine (Eden Prairie, Minn.) in bovine serum. Pins of 13-mm length and 9-mm diameter (n=3 for each material) were machined and mounted on the MTS wear tester to undergo bi-directional motions on polished CoCr discs at 2 Hz and a step length of 5×10 mm under a maximum load of 1.9 kN. The pins were weighed at every 157 kilo-cycle until a total of 1 million cycles (MC) and the weight loss from 0.5 to 1 MC were used to evaluate the gravimetric wear rate in milligram per million cycles (mg/MC).

Figure 61A:
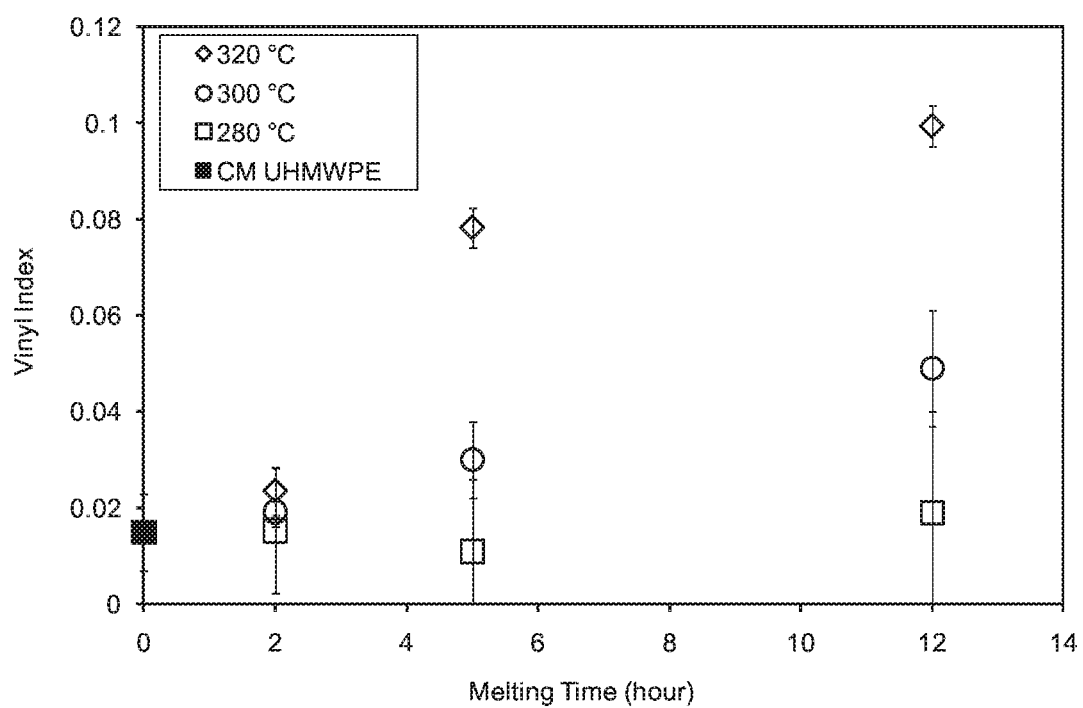
FIG. 61A, FIG. 61B, and FIG. 61C show the terminal vinyl index as a function of melting time at 280, 300 and 320° C., in comparison with CM UHMWPE that was not subjected to high temperature melting (FIG. 61A). The dependence of elongation-at-break on the terminal vinyl group index (FIG. 61B). The dependence of the strain-hardening modulus, G, on the vinyl index (FIG. 61C).
Figure 61B:
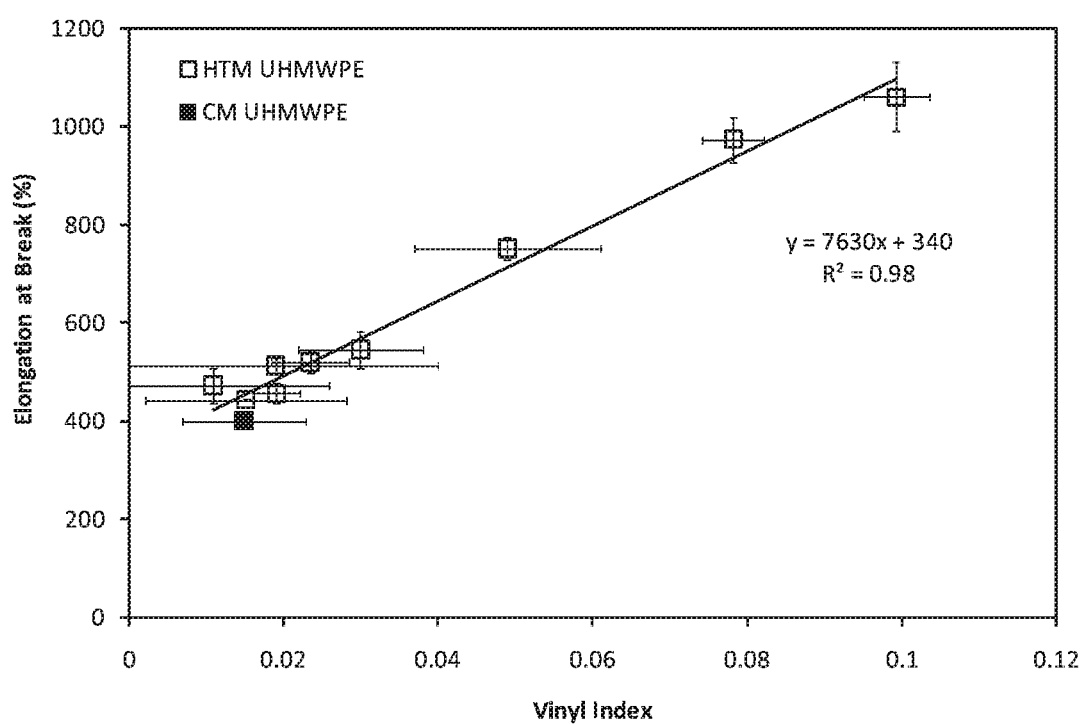
Figure 61C:
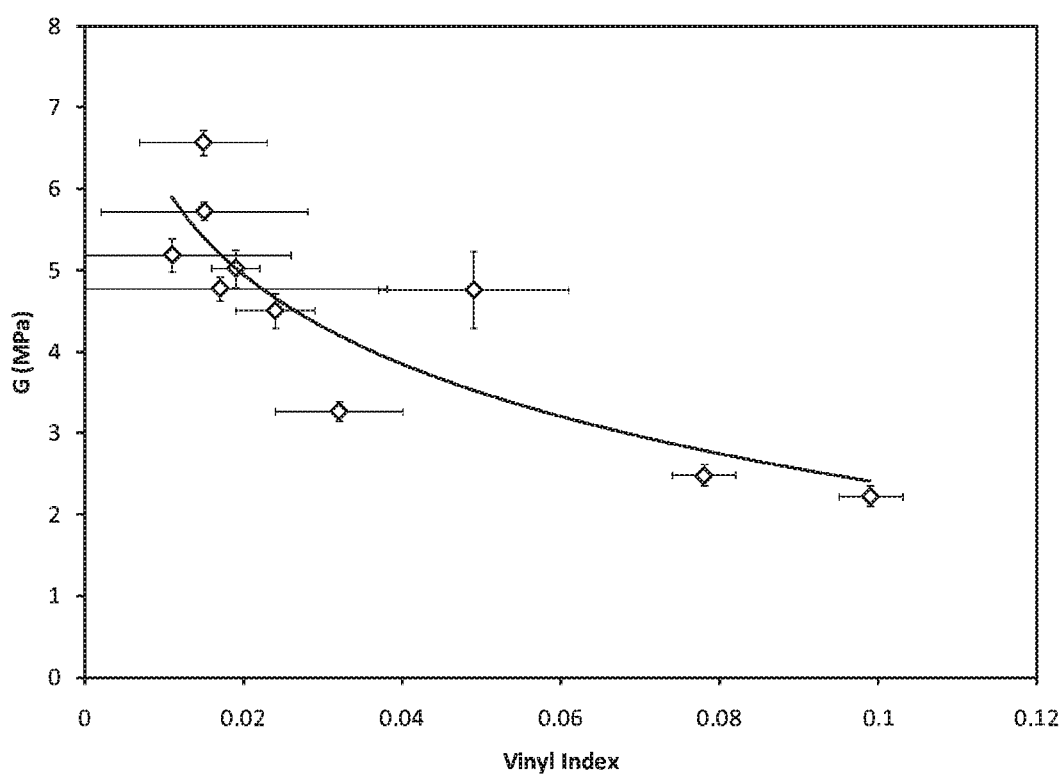

Increasing temperature and increasing duration during high temperature melting increased the vinyl index, suggesting increased chain scissioning (FIG. 61A). Increasing chain scissioning was directly correlated to increasing elongation-at-break (FIG. 61B) and a non-linear decrease in the strain-hardening modulus (FIG. 61C).

Figure 62A:
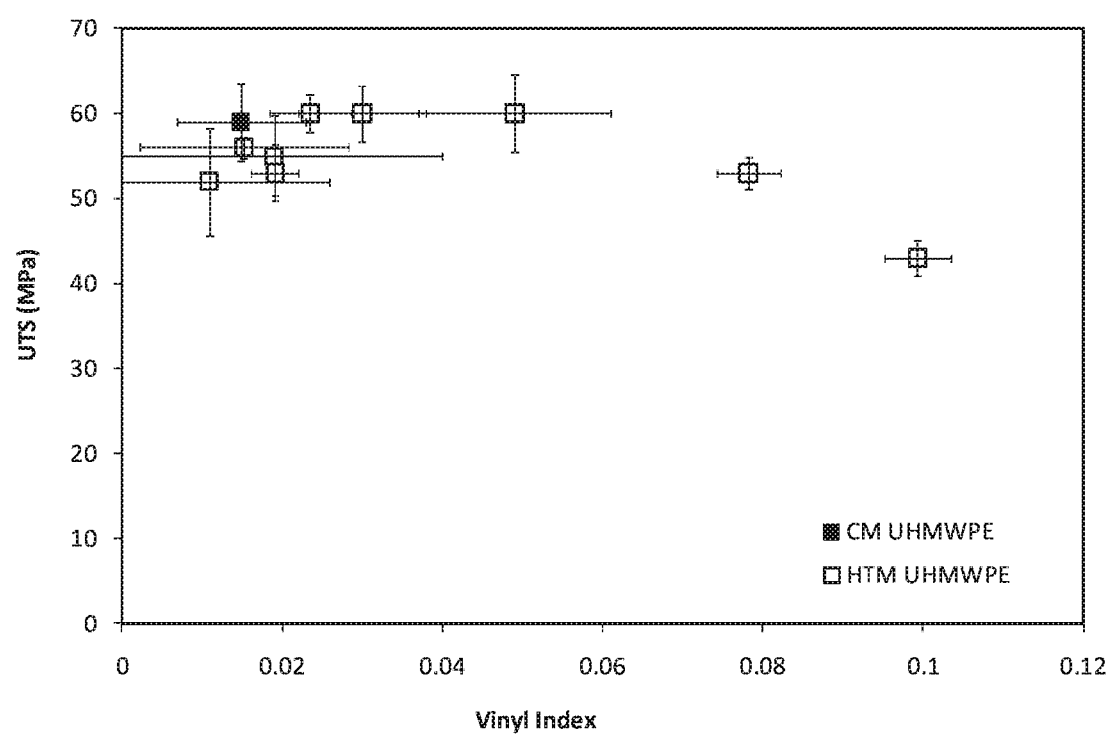
FIG. 62A, FIG. 62B, FIG. 62C, and FIG. 62D show mechanical and wear properties of high temperature melted GUR1050 UHMWPEs compared to compression molded (CM) GUR1050 UHMWPE without high temperature melting as a function of vinyl index.
Figure 62B:
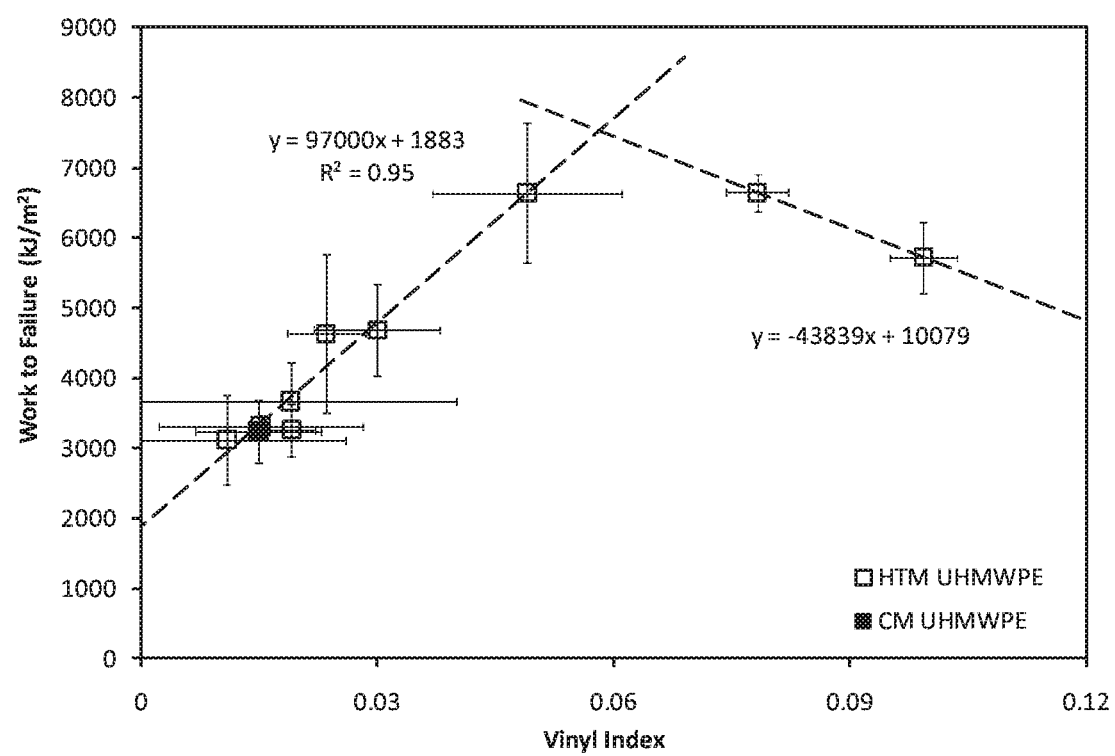
Figure 62C:
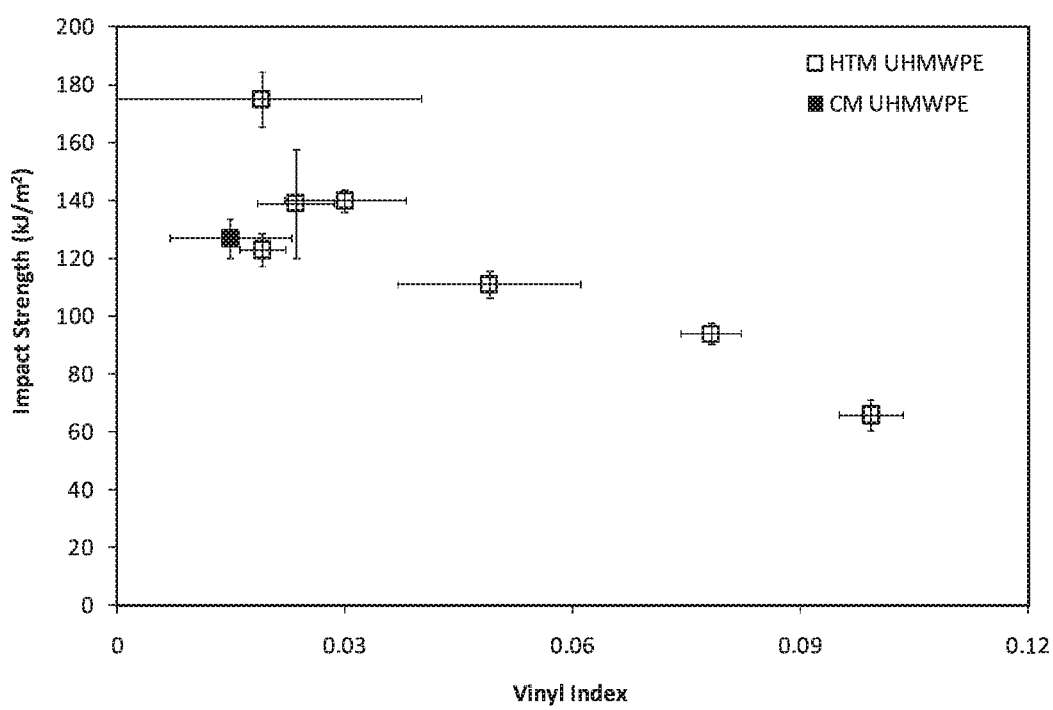
Figure 62D:
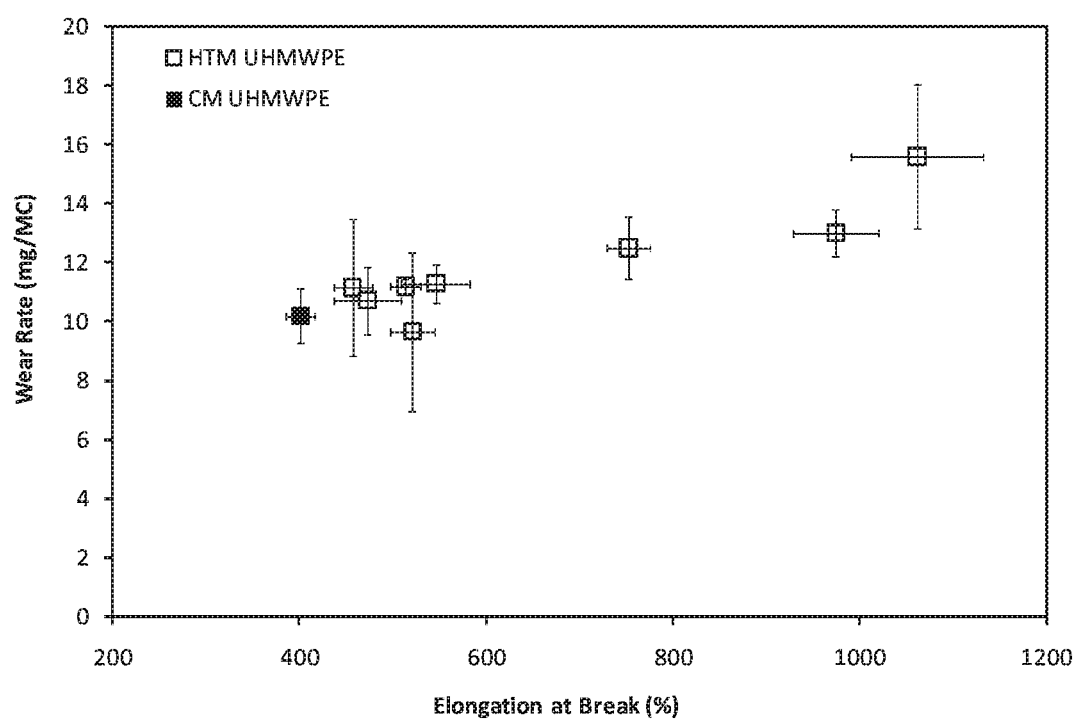

The ultimate tensile strength (UTS) was not significantly changed until the vinyl index reached approximately 0.06, after which there was a significant decrease in the UTS (FIG. 62A). Similarly, the tensile work-to-failure (WF) increased until the vinyl index reached approximately 0.06, after which there was a significant decrease in the WF (FIG. 62B). There was a slight increase in the IZOD impact strength as a function of vinyl index at a vinyl index of 0.02-0.04, after which there was a decrease, significantly after a vinyl index of 0.06 (FIG. 62C). Nevertheless, there was not a significant increase in the wear rate of UHMWPE as a function of increasing elongation-at-break (EAB) until an EAB of over 1000% (FIG. 62D).

Figure 39B:
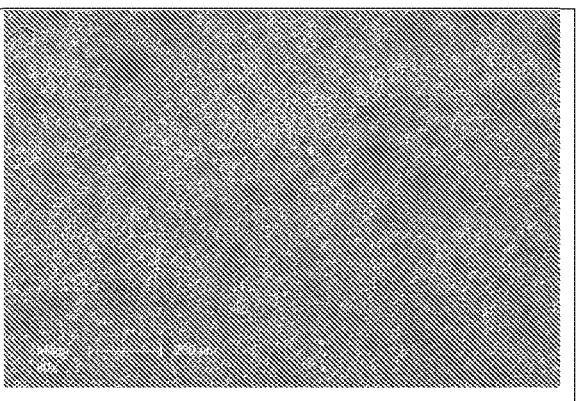

The mechanical properties, wear rates and significance values are shown in Table 21. We attribute the elimination of structural defects through the self-diffusion of the UHMWPE chains for the increase in the tensile toughness (WF) and the impact strength. At conventional molding temperatures ($T_p$<200° C.), self-diffusion is very slow and the time required for the UHMWPE chains to reptate (De Gennes P-G. Scaling concepts in polymer physics, 4 ed. Ithaca: Cornell University Press, 1979) through the highly viscous UHMWPE melt (>15 h) (Rastogi S, Lippits D R, Peters G W M, Graf R, Yao Y, and Spiess H W. Nature Materials 2005; 4: 635) is much longer than the typical molding time (<0.5 h). In particular, it is more difficult for the chains to reptate across the granule boundaries, where there are no entanglements before molding. This explains the presence of the granule with explicit boundaries (FIG. 39A) on the freeze-fractured surface of the as-molded CM UHMWPE. These boundaries could serve as structural defects with low toughness that may lead to the initiation of cracks under cyclic loading. At high temperatures, the melt viscosity is reduced and the chain mobility is enhanced, whereas some UHMWPE chains were cleaved. As a result, self-diffusion via chain reptation through the tube defined by the neighboring chains (Doi M and Edwards S F. The Theory of Polymer Dynamics. Oxford: Clarendon, 1986) is accelerated. Thus, the granules further fused and the chain entanglements were improved, leading to the formation of spherulites without distinct boundaries after recrystallization (FIG. 39B). The structural defects were eliminated and the stress concentration could be largely reduced.

Example 37. Mechanical and Wear Properties of High Temperature Melted and Irradiated UHMWPEs Compression molded GUR 1050 UHMWPE (CM UHMWPE) (Orthoplastics, Bacup Lancashire, UK) with approximate dimensions of 250×60×45 mm³ (length× width×height) were melted by using a programmable convection oven with inert gas capability (LLD1-16N-3, Despatch Industries, Minneapolis, Minn.). The oven was preheated to a preset temperature with nitrogen purge (flow rate 2 m³/min). Then, the UHMWPE was placed in the oven and was held at temperature for different durations. The temperatures used were 280, 300, and 320° C. At each temperature, the UHMWPE was held for 2, 5, or 12 h and then cooled down to 40° C. within 2 h (at an average cooling rate of 2.5° C./min) and held at 40° C. for 20 min in the oven before retrieval. These melted UHMWPEs were denoted as UH T-t, where T is temperature, and t is time. For example, UH 280-2 denotes a UHMWPE stock melted at 280° C. for 2 h.

The HTM UHMWPEs (HTM-PE) were vacuum packed and cross-linked by using a 10 MeV electron beam at room temperature at Iotron Inc. (Vancouver, BC) at a dose rate of 50 kGy/pass. The total doses were 50, 100, and 150 kGy. CM UHMWPE blocks without HTM treatment were irradiated as controls. The control samples were denoted as XL-PE-50, XL-PE-100, and XL-PE-150 and the irradiated HTM-PEs were denoted as UHI T-t-D, where T is temperature, t is time, and D is radiation dose. For example, UHI 280-2-50 denotes a UHMWPE melted at 280° C. for 2 h and then e beam cross-linked with a dose of 50 kGy.

The mechanical testing and wear testing and vinyl index calculations were done as described in the previous example. Crosslink density measurements of cross-linked UHMWPE (n=3 each) were performed on small samples (approximately 3×3×3 mm). The samples were weighed before swelling in xylene at 130° C. and they were weighed immediately after swelling in xylene. Therefore, the amount of xylene uptake was determined gravimetrically, then converted to volumetric uptake by dividing by the density of xylene; 0.75 g/cc. By assuming the density of polyethylene to be approximately 0.99 g/cc, the volumetric swell ratio of crosslinked UHMWPE was then determined. The cross-link density was calculated using the swell ratio as described previously (Muratoglu et al. Biomaterials 20:1463-1470 (1999)) and is reported as mol/m³.

Figure 63:
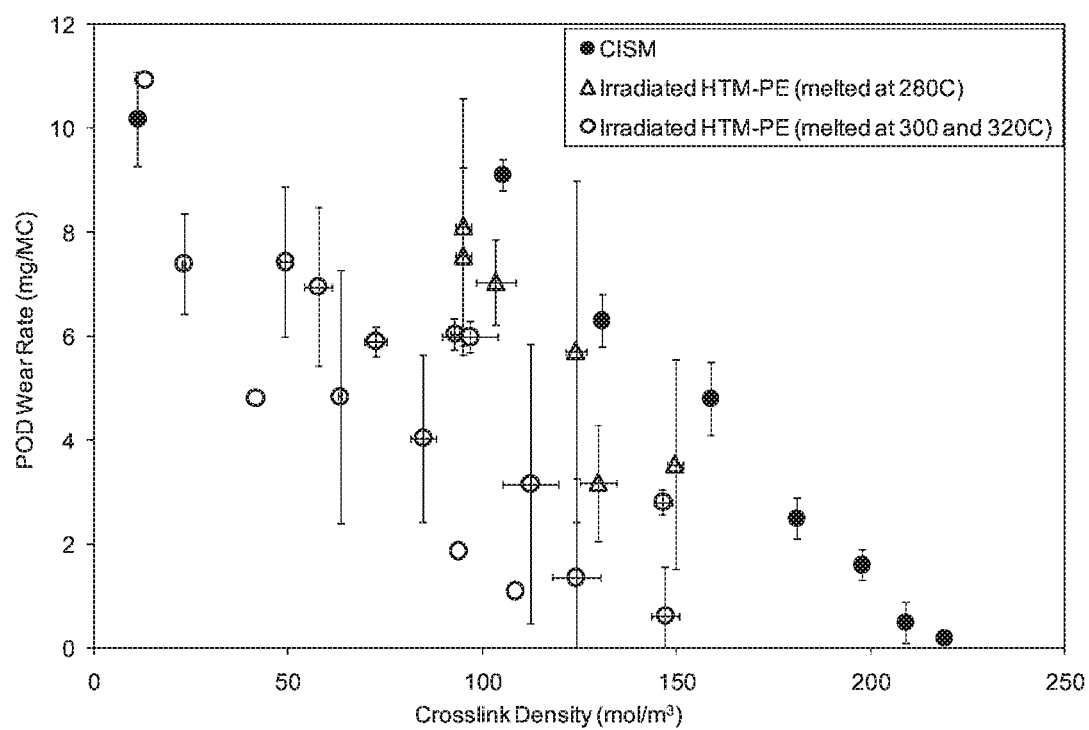
FIG. 63 shows the effect of crosslink density on the POD wear rate of radiation crosslinked UHMWPEs. The solid symbols represent irradiated and melted UHMWPE without high temperature melting (CISM). These samples have been melted at approximately 170° C. after irradiation for less than 5 hours. The open symbols are irradiated UHMWPEs with prior high temperature melting.

At the same crosslink density, high temperature melted, then radiation crosslinked UHMWPEs had lower wear rates than irradiated, then melted UHMWPEs without high temperature treatment (FIG. 63).

Figure 64A:
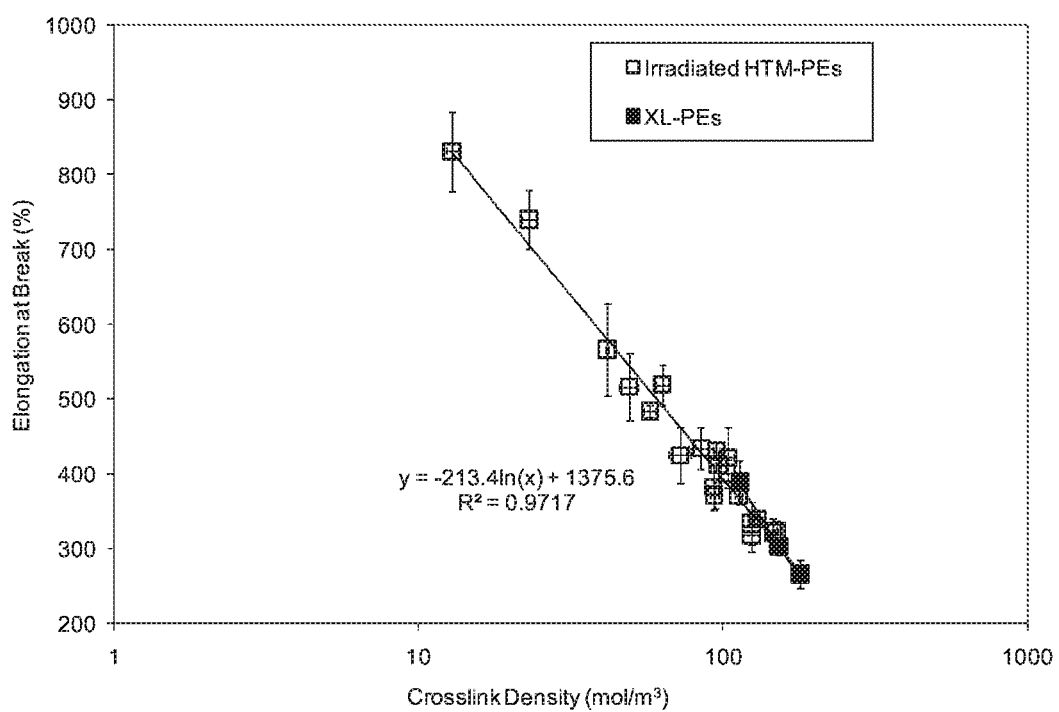
FIG. 64A, FIG. 64B, and FIG. 64C show the effect of crosslink density on the elongation-at-break (FIG. 64A), IZOD impact strength (FIG. 64B) and ultimate tensile strength (FIG. 64C) of radiation crosslinked UHMWPEs. The solid symbols represent irradiated and melted UHMWPE without high temperature melting (CISM). The open symbols are irradiated UHMWPEs with prior high temperature melting.

The elongation-at-break (EAB) of both irradiated high temperature melted (HTM) UHMWPEs and irradiated UHMWPEs without HTM showed the same logarithmic dependence on cross-link density (FIG. 64A). However, irradiated HTM UHMWPEs had lower crosslink density than non-HTM UHMWPE, thus their EAB was higher. Similarly, IZOD impact strength showed a weak linear decrease with increasing crosslink density (FIG. 64B), but the impact strength values for irradiated HTMs were much higher at the same radiation dose due to lower crosslink density (Table 22). The ultimate tensile strength (UTS) of irradiated HTM UHMWPEs were unaffected by changes in crosslink density whereas irradiated UHMWPEs without HTM treatment showed a large decrease with increasing crosslink density (FIG. 64C).

Figure 64B:
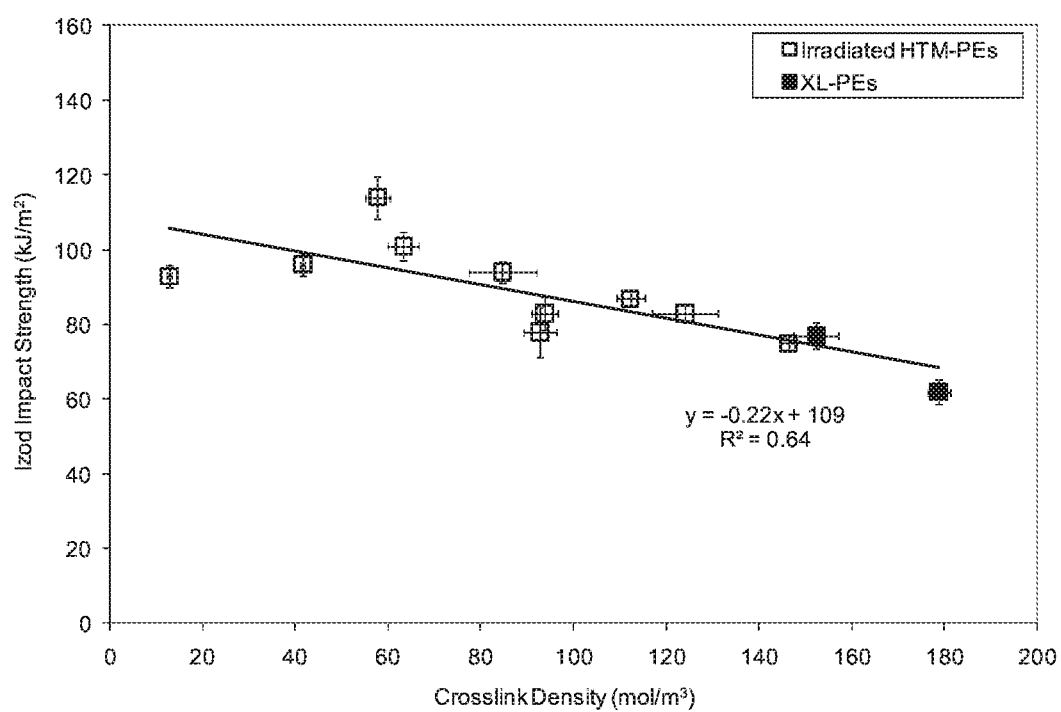
Figure 64C:
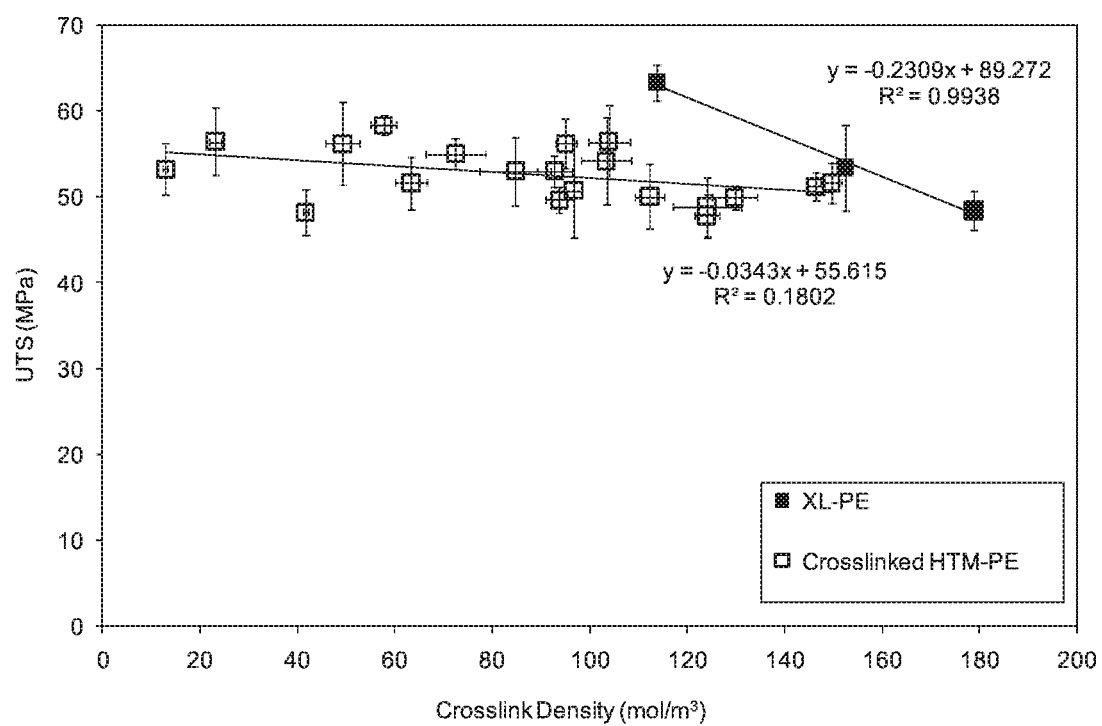

FIGS. 64A-64C illustrates the effect of crosslink density on the elongation-at-break (FIG. 64A), IZOD impact strength (FIG. 64B) and ultimate tensile strength (FIG. 64C) of radiation crosslinked UHMWPEs. Samples were irradiated and melted UHMWPE without high temperature melting (CISM). These samples have been melted at approximately 170° C. after irradiation for less than 5 hours. The open symbols are irradiated UHMWPEs with prior high temperature melting.

The lower crosslink density of irradiated HTM UHMWPEs was correlated to the amount of chain scissioning due to HTM prior to irradiation. The higher the pre-irradiation vinyl index (thus increased chain scissioning), the lower was the crosslink density (FIG. 65). FIG. 65 illustrates the effect of the initial vinyl index before irradiation on the crosslink density of irradiated high temperature melted UHMWPEs. The samples were irradiated and melted UHMWPE without high temperature melting (CISM). These samples also have been melted at approximately 170° C. after irradiation for less than 5 hours.

The physical, mechanical and wear properties of irradiated, high temperature melted UHMWPEs are shown in Table 22.

Example 38. Oxidative Stability of Irradiated, HTM UHMWPE by Antioxidant Incorporation Blends of vitamin E with GUR1050 UHMWPE were prepared by making solutions of vitamin E in isopropyl alcohol (IPA), mixing the solution with UHMWPE powder and vacuum drying the powder at 60° C. until the solvent was evaporated. In this manner, concentrated (2 wt %) blends were made and diluted with UHMWPE powder if desired. Blends of UHMWPE containing 0.1 and 0.2 wt % vitamin E were compression molded into cylindrical pucks (diameter 10 cm, thickness ~1 cm) using an automatic laboratory press. One puck each was melted at 280, 300 or 320° C. for 2, 5 or 12 hours as described in the previous example. Then the HTM pucks were packaged in vacuum and irradiated to 50, 100 and 150 kGy using electron-beam irradiation. Samples were machined into 1 cm cubes.

Two accelerated aging methods were used: 14 days at 70° C. under 5 atm. of oxygen (ASTM F2003) and 14 days at 70° C. under 5 atm. of oxygen after squalene doping. Squalene is an unsaturated lipid, which initiated severe oxidation in irradiated and melted UHMWPE. Cubes (1 cm) were machined from Irganox® 1010 blended pucks and irradiated blended pucks. Squalene doping was done in pre-heated squalene at 120° C. for 2 hours.

After accelerated aging, the 150 µm-thick sections were microtomed from an inner surface (FIGS. 43A-43D; n=3 each). These sections were boiled in hexane overnight and then dried in vacuum at room temperature for 24 hours. They were then analyzed by FTER. An oxidation index was calculated as a function of depth away from the surface as the ratio of the areas under $1680$ $cm^{-1}$-$1780$ $cm^{-1}$ to the absorbance over $1370$ $cm^{-1}$ per ASTM F2003.

Figure 66A:
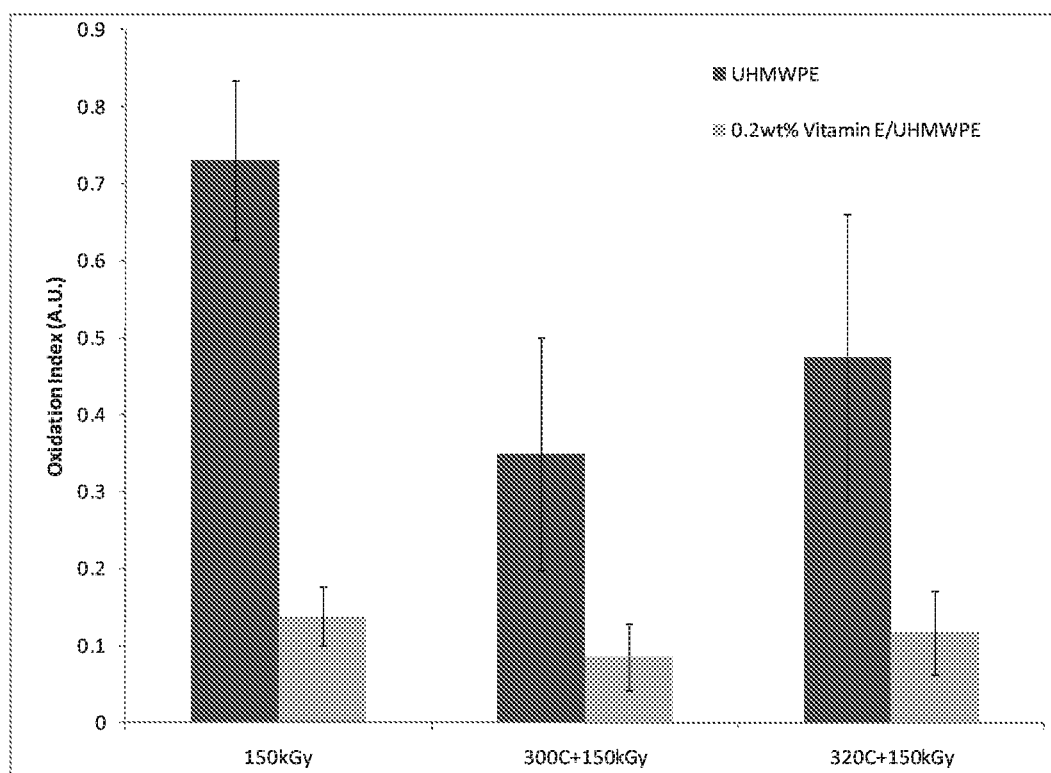
FIG. 66A and FIG. 66B depict post-hexane oxidation of accelerated aged 150-kGy irradiated virgin UHMWPE and 0.2 wt % vitamin E-blended UHMWPE with and without high temperature melting at 300 and 320° C. for 5 hours. Accelerated aging was performed at 70° C. for 14 days at 5 atm. of oxygen (FIG. 66A). Accelerated aging was performed at 70° C. for 14 days at 5 atm. of oxygen after squalene doping at 120° C. for 2 hours (FIG. 66B).
Figure 66B:
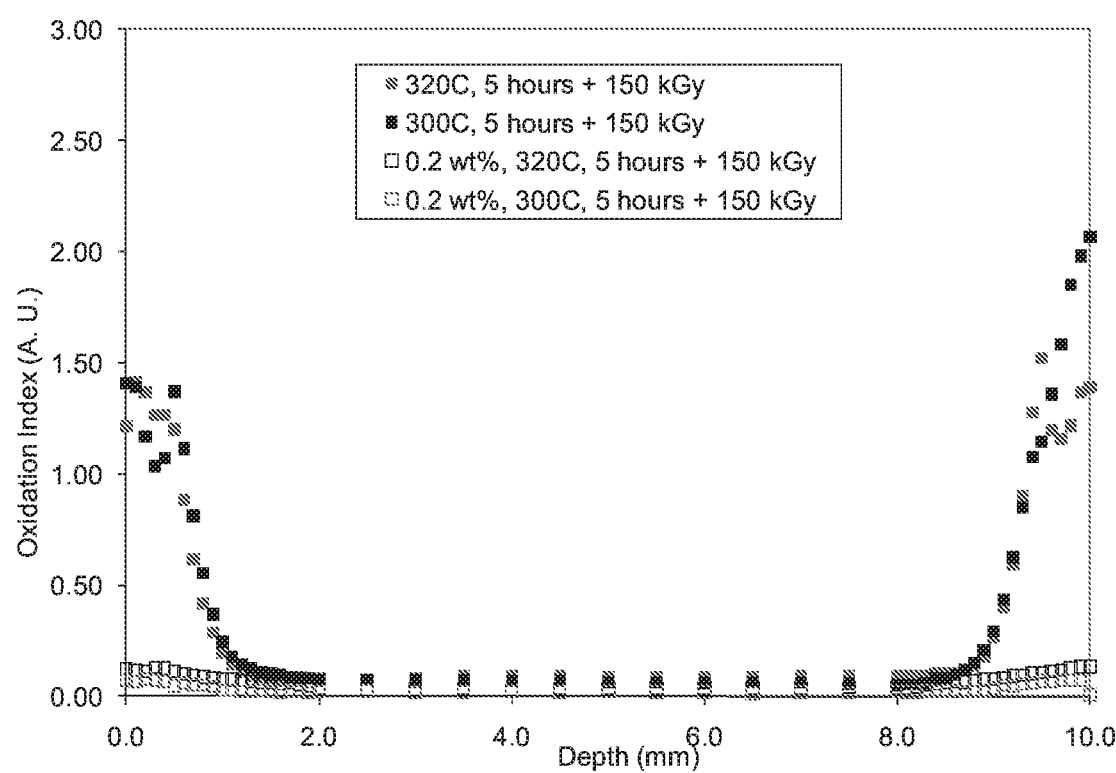

Both high temperature melting before irradiation and vitamin E-blending prior to high temperature melting and irradiation increased the oxidative resistance of UHMWPE under accelerated aging without squalene (FIG. 66A) and in the presence of squalene (FIG. 66B). FIGS. 66A-66B show post-hexane oxidation of accelerated aged 150-kGy irradiated virgin UHMWPE and 0.2 wt % vitamin E-blended UHMWPE with and without high temperature melting at 300 and 320° C. for 5 hours. Accelerated aging was performed at 70° C. for 14 days at 5 atm. of oxygen (FIG. 66A). Accelerated aging was performed at 70° C. for 14 days at 5 atm. of oxygen alter squalene doping at 120° C. for 2 hours (FIG. 66B).

Example 39. Various Methods and Options for Making Surface Crosslinked Joint Implants Various methods of making surface crosslinked joint implants according to the invention are described in more details in the following illustrative examples. Although these examples may represent only selected embodiments of the invention, it should be understood that the following examples are illustrative and not limiting.

FIGS. 67A-67F illustrate schematic of a generic tibial insert with regions containing different concentrations of antioxidant. For example, the shaded regions contain Irganox® 1010 at a low concentration such as 0.05 wt % and the other regions contain higher concentration of antioxidant such as 1 wt % vitamin E. FIGS. 67A-67F depict the top (articular surface) view of a generic tibial insert—the tibial insert could be symmetric on the medial and lateral sides or anti-symmetric.

FIGS. 68A-68H depict the top (articular surface) view of a generic acetabular liner. The shaded regions depict examples of implant surfaces which contain a different concentration of antioxidant than the not shaded regions. The intended purpose of having low concentration of antioxidant in the shaded regions is to obtain high levels of crosslinking in these regions after exposure to irradiation (FIGS. 69A-69B). These types of surfaces can be obtained by layered molding of polymer blends with different antioxidants and different antioxidant concentrations. In the unshaded regions, an anti-crosslinking agent is used. This can be an antioxidant such as vitamin E or a mixture of antioxidants such as Irganox® 1010 and vitamin E. The concentrations are determined depending on the level of crosslinking desired in the shaded and unshaded regions. For example, 1 wt % vitamin E in the unshaded regions and 0.05 wt % Irganox® 1010 in the shaded regions can be used.

Subsequently, the tibial inserts with different layers of polymer blends, examples as shown in FIGS. 67B-67F, can be irradiated to 25, 50, 75, 100, 125, 150, 175, 200, 250 or 300 kGy.

Such shapes can be obtained by direct compression molding of layers of polymer blends with antioxidants/anti-crosslinking agents. Alternatively, these compression molded shapes can be further machined from the articular or backside surfaces or in other parts of the implant for example to machine locking mechanisms.

Another method by which these surfaces can be obtained is by preferentially extracting the antioxidants/anti-crosslinking agents that were blended into the polymer resin and compression molded after molding before exposure to irradiation.

Alternatively, these implants can be machined from a previously consolidated (ram extrusion, compression molding, direct compression molding) UHMWPE/antioxidant blend. The implants are then subjected to an extraction procedure to remove surface antioxidant. The removal from the implants can be preferential by masking areas where extraction is not desired.

Figure 68A:
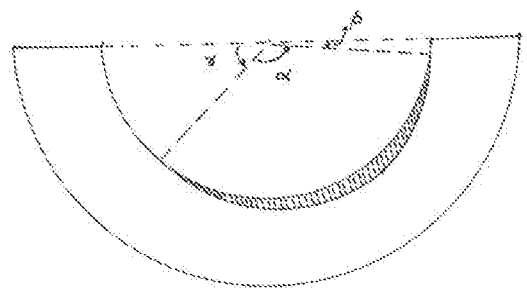
FIG. 68A, FIG. 68B, FIG. 68C, FIG. 68D, FIG. 68E, FIG. 68F, FIG. 68G, and FIG. 68H depict schematic of a generic acetabular liner (crosssectional view) with surface regions containing a low concentration of antioxidant, where the surface region containing a low amount of antioxidant can cover entirely or partially top surface of the implant (FIG. 68A). Low concentration of antioxidant can be contained on both the top and backside surfaces of the implant (FIG. 68B). In addition, low concentration of antioxidant can be contained on the top and/or backside surfaces of the implant such that locking mechanisms can be machined into regions with high concentration of antioxidant (FIG. 68C, FIG. 68D). Examples of surface regions (top view) with varying antioxidant concentration (FIG. 68E, FIG. 68F, FIG. 68G, and FIG. 68H).
Figure 68B:
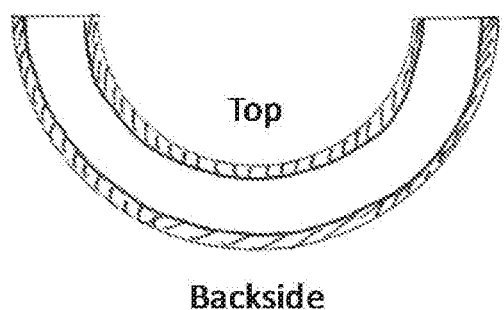
Figure 68C:
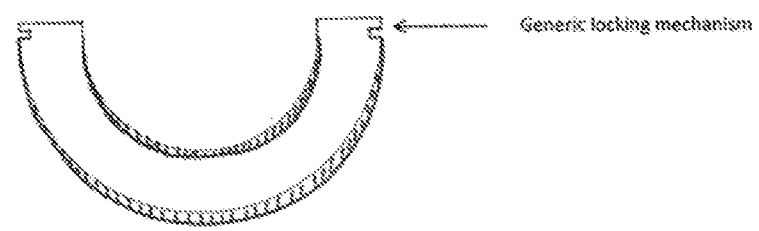
Figure 68D:
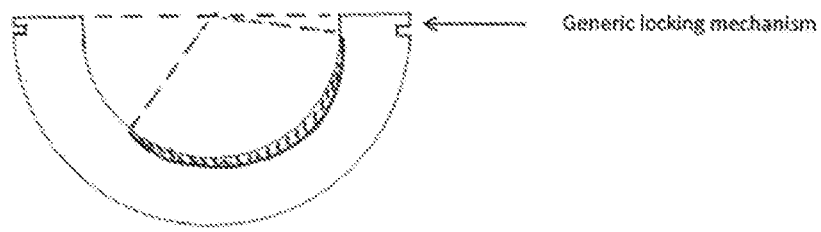
Figure 68E:
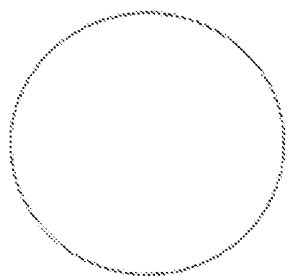
Figure 68F:
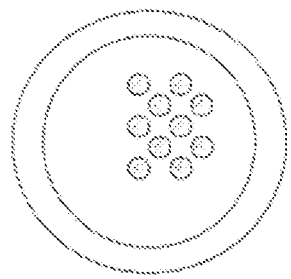
Figure 68G:
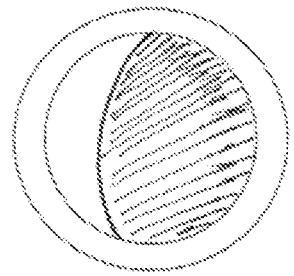
Figure 68H:
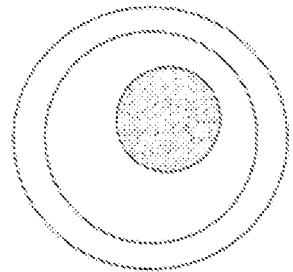
Figure 69A:
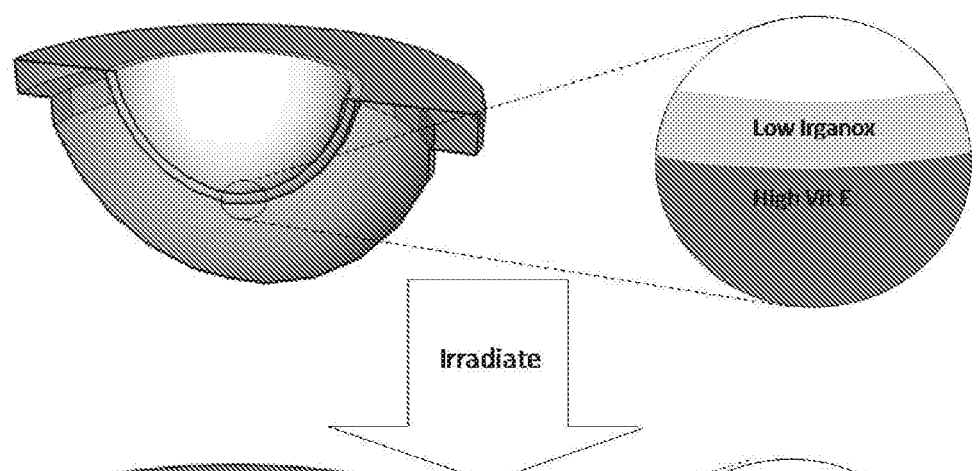
FIGS. 69A-69B depict schematic of a hip implant with a highly crosslinked articular surface made by direct compression molding of layers of a polymer blend with a high concentration of vitamin E and a polymer blend with a low concentration of an antioxidant from the Irganox® family such as Irganox® 1010.
Figure 69B:
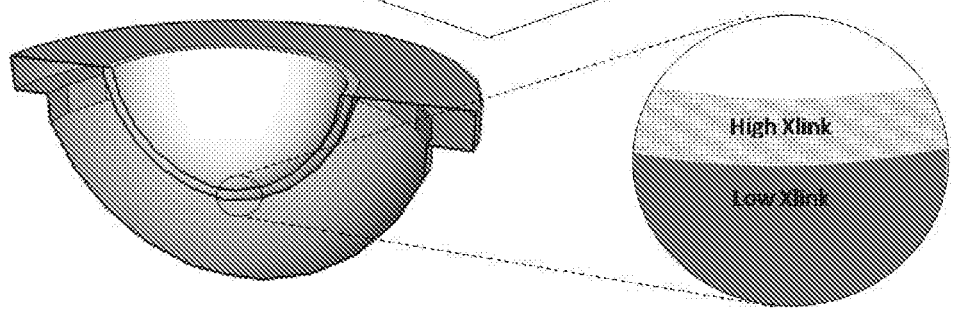

FIGS. 68A-68H show schematic of a generic acetabular liner (crosssectional view) with surface regions containing a low concentration of antioxidant, where the surface region containing a low amount of antioxidant can cover entirely or partially top surface of the implant (FIG. 68A). Low concentration of antioxidant can be contained on both the top and backside surfaces of the implant (FIG. 68B). In addition, low concentration of antioxidant can be contained on the top and/or backside surfaces of the implant such that locking mechanisms can be machined into regions with high concentration of antioxidant (FIG. 68C, FIG. 68D). Examples of surface regions (top view) with varying antioxidant concentration are shown in FIG. 68E, FIG. 68F, FIG. 68G, and FIG. 68H. For example, the shaded regions contain Irganox® 1010 at a low concentration such as 0.05 wt % and the other regions contain higher concentration of antioxidant such as 1 wt % vitamin E.

Extraction of the antioxidants from the surfaces of the implant can be used either on a molded polymer or molded implant with a uniform concentration of antioxidant/anti-crosslinking agent or on a molded polymer or molded implant that already has a gradient of antioxidant/anti-crosslinking agent. In this manner, the concentration of at least one antioxidant/anti-crosslinking agent is lowered in the surface regions. Subsequent exposure to irradiation results in a different crosslink density in these surface regions than if they are not extracted before irradiation. Extraction can be applied uniformly to the surfaces such as in FIG. 68C or it can be applied preferentially such as in FIG. 68E, FIG. 68F, FIG. 68G, and FIG. 68H by masking parts of the surface.

FIGS. 69A-69B show schematic of a hip implant with a highly crosslinked articular surface made by direct compression molding of layers of a polymer blend with a high concentration of vitamin E and a polymer blend with a low concentration of an antioxidant from the Irganox® family such as Irganox® 1010.

Example 40. Wear Rate as a Function of Depth of Surface Crosslinked UHMWPE Prepared by Extraction Blends of vitamin E with GUR1050 UHMWPE were prepared by making solutions of vitamin E in isopropyl alcohol (IPA), mixing the solution with UHMWPE powder and vacuum drying the powder at 60° C. until the solvent was evaporated. In this manner, concentrated (2 wt %) blends were made and diluted with UHMWPE powder if desired. Blends of UHMWPE containing 0.5, 1, 1.5 and 2 wt % vitamin E were compression molded into cylindrical pucks (diameter 10 cm, thickness ~1 cm) using an automatic laboratory press. These pucks were then machined into cylindrical pins (9 mm diameter, 13 mm length) for wear testing.

Figure 70B:
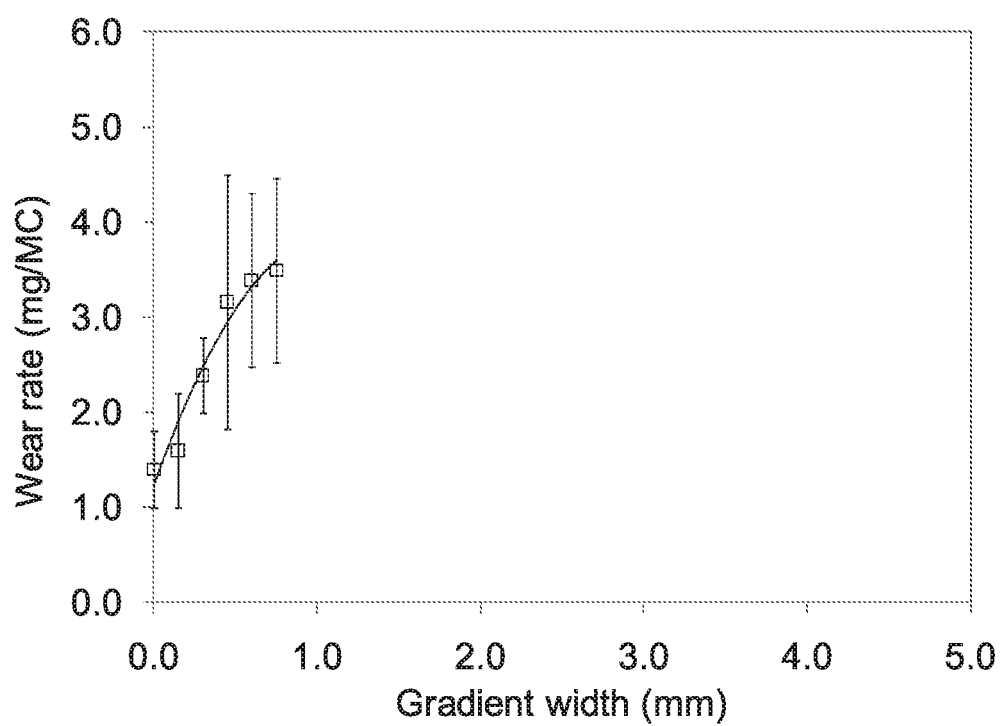

These pins were boiled in a 20 v/v % aqueous solution of Tween 20 under reflux for 40 hours to extract the vitamin E from the surface regions. Then the extracted pins were irradiated by e-beam irradiation to 150 kGy. To determine the spatial variation of the antioxidant concentration throughout the samples, 150 µm-thick sections were microtomed from an inner surface (FIGS. 43A-43D; n=3 each) were analyzed using FTIR. Vitamin E index was calculated as the ratio of the areas under $1245$ $cm^{-1}$-$1275$ $cm^{-1}$ to the absorbance over $1875$ $cm^{-1}$-$1905$ $cm^{-1}$. The vitamin E concentration profiles for 0.5 wt % vitamin E blended and extracted UHMWPE before and after 150 kGy irradiation are shown in FIG. 70A.

Wear rates were determined by pin-on-disc wear testing on a custom-designed bidirectional wear tester (see Bragdon C R, O'Connor D O, Lowenstein J D, Jasty M, Biggs S A, Harris W H. A new pin-on-disc wear testing method for simulating wear of polyethylene on cobalt-chrome alloy in total hip arthroplasty. *Journal of Arthroplasty* 2001: 41(2): 795-808). Testing was performed in undiluted preserved bovine serum at 2 Hz for approximately 1.2 million cycles (MC) with gravimetric assessment of wear at approximately every 250,000 cycles. Wear rate was determined as a linear regression of weight loss as a function of number of cycles from 0.5 to 1.2 MC.

Figure 70C:
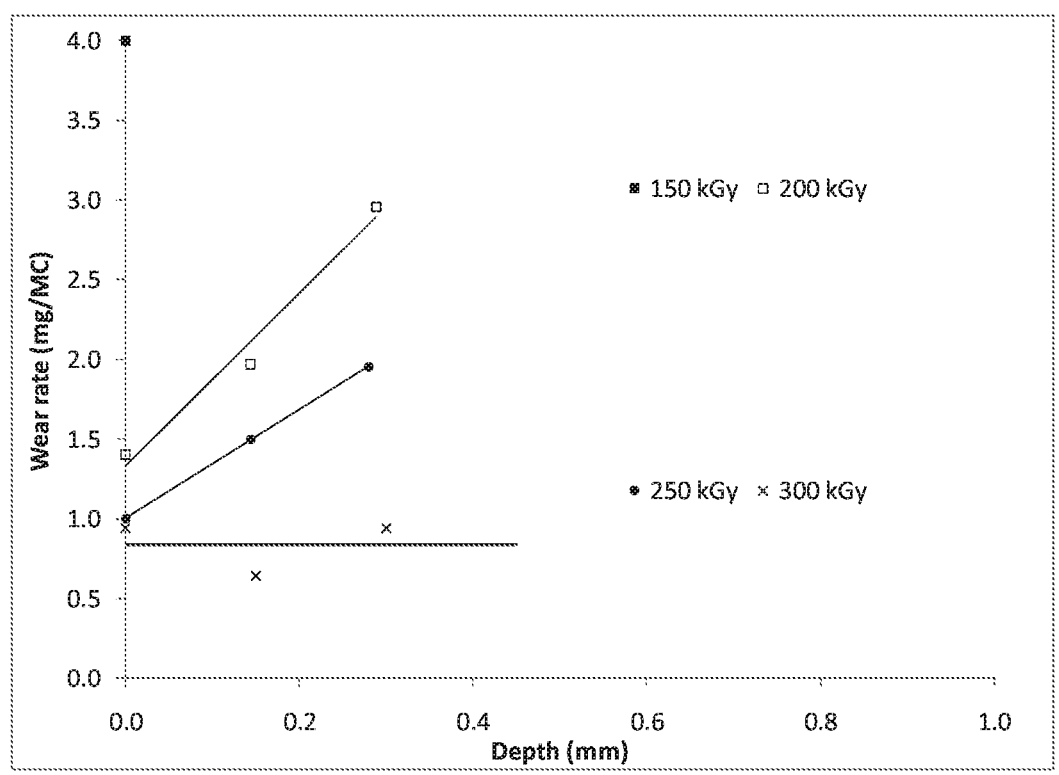

Wear rates were determined as a function of depth by machining away approximately 150 µm from the surface after each wear test was completed and re-testing the samples. The wear rates as a function of depth away from the surface are shown for 0.5 wt % vitamin E-blended, extracted and 150 kGy irradiated UHMWPE in FIG. 70B. The wear rates a function of depth away from the surface are shown for 1.0 wt % vitamin E-blended, extracted and 150, 200, 250 or 300 kGy irradiated UHMWPE in FIG. 70C.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

The invention claimed is:

1. A method of making a layered consolidated UHMWPE for use as a medical implant, wherein the method comprises the steps of:
   blending a first ultrahigh molecular weight polyethylene (UHMWPE) powder, flakes or particles with at least one pharmaceutical agent excluding vitamin-E in a solvent that comprises water and ethanol to provide a first UHMWPE blend;
   drying the first UHMWPE blend;
   consolidating as layers the UHMWPE blend from drying step with a second UHMWPE without blending to a pharmaceutical agent to yield layered consolidated UHMWPE comprising at least one pharmaceutical agent excluding vitamin-E in one layer; and
   machining the layered consolidated UHMWPE.

2. The method according to claim 1, wherein the second UHMWPE is a consolidated UHMWPE.

3. The method according to claim 1, wherein the consolidating step is by direct compression molding.

4. The method of claim 1, wherein the second UHMWPE comprises a peroxide and an antioxidant.

5. The method according to claim 2, wherein the first UHMWPE is cross-linked and oxidation resistant.

6. The method according to claim 3, wherein the second UHMWPE was consolidated and heated to a temperature of at least 200° C.

7. The method according to claim 1, wherein the drying is carried out under vacuum and a temperature below the melting point of the UHMWPE.

8. The method according to claim 1, wherein the medical implant is selected from the group consisting of tibial insert, an acetabular liner, a glenoid liner, a patella, an interpositional device for any joint and a unicompartmental insert.

* * * * *